United States Patent
Yamazaki et al.

(10) Patent No.: US 8,035,082 B2
(45) Date of Patent: Oct. 11, 2011

(54) PROJECTION ELECTRON BEAM APPARATUS AND DEFECT INSPECTION SYSTEM USING THE APPARATUS

(75) Inventors: Yuichiro Yamazaki, Tokyo (JP); Ichirota Nagahama, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 162 days.

(21) Appl. No.: 12/580,505

(22) Filed: Oct. 16, 2009

(65) Prior Publication Data

US 2010/0096550 A1 Apr. 22, 2010

Related U.S. Application Data

(62) Division of application No. 11/817,763, filed on Dec. 8, 2008.

(30) Foreign Application Priority Data

| Mar. 3, 2005 | (JP) | ................................. 2005-059504 |
| Mar. 28, 2005 | (JP) | ................................. 2005-092297 |
| Mar. 28, 2005 | (JP) | ................................. 2005-092314 |

(51) Int. Cl.
*H01J 37/244* (2006.01)
(52) U.S. Cl. .............. 250/310; 250/396 R; 250/396 ML
(58) Field of Classification Search .................. 250/310, 250/396 R, 396 ML
See application file for complete search history.

(56) References Cited

U.S. PATENT DOCUMENTS

| 3,472,997 A | 10/1969 | El-Kareh et al. |
| 4,779,046 A | 10/1988 | Rouberoi et al. |
| 4,962,313 A | 10/1990 | Rose |
| 5,084,622 A | 1/1992 | Rose |
| 5,763,893 A | 6/1998 | Nakasuji |
| 5,864,142 A | 1/1999 | Muraki et al. |
| 6,043,491 A | 3/2000 | Ose et al. |
| 6,111,253 A | 8/2000 | Tsuno |
| 6,191,423 B1 | 2/2001 | Krijn et al. |
| 6,310,341 B1 | 10/2001 | Todokoro et al. |
| 6,329,659 B1 | 12/2001 | Krijn et al. |
| 6,462,474 B1 | 10/2002 | Symons |

(Continued)

FOREIGN PATENT DOCUMENTS

JP 62-31933 A 2/1987

(Continued)

OTHER PUBLICATIONS

International Search Report of PCT/JP2006/305688 dated Jul. 4, 2006.

(Continued)

*Primary Examiner* — Kiet T Nguyen
(74) *Attorney, Agent, or Firm* — Westerman, Hattori, Daniels & Adrian, LLP

(57) ABSTRACT

A sample is evaluated at a high throughput by reducing axial chromatic aberration and increasing the transmittance of secondary electrons. Electron beams emitted from an electron gun 1 are irradiated onto a sample 7 through a primary electro-optical system, and electrons consequently emitted from the sample are detected by a detector 12 through a secondary electro-optical system. A Wien filter 8 comprising a multipole lens for correcting axial chromatic aberration is disposed between a magnification lens 10 in the secondary electro-optical system and a beam separator 5 for separating a primary electron beam and a secondary electron beam, for correcting axial chromatic aberration caused by an objective lens 14 which comprises an electromagnetic lens having a magnetic gap defined on a sample side.

2 Claims, 58 Drawing Sheets

U.S. PATENT DOCUMENTS

| | | |
|---|---|---|
| 6,465,797 B2 | 10/2002 | Okunuki |
| 6,479,819 B1 | 11/2002 | Hamashima et al. |
| 6,509,569 B1 | 1/2003 | Frosien |
| 6,563,114 B1 | 5/2003 | Nagahama |
| 6,580,073 B2 | 6/2003 | Plies et al. |
| 6,608,308 B1 | 8/2003 | Takagi et al. |
| 6,635,891 B1 | 10/2003 | Nakano et al. |
| 6,661,008 B2 | 12/2003 | Takagi et al. |
| 6,770,887 B2 | 8/2004 | Krivanek et al. |
| 6,784,437 B2 | 8/2004 | Rose |
| 6,844,548 B2 | 1/2005 | Lopez et al. |
| 6,855,929 B2 | 2/2005 | Kimba et al. |
| 6,924,488 B2 | 8/2005 | Matsuya et al. |
| 6,992,290 B2 | 1/2006 | Watanabe et al. |
| 7,012,262 B2 | 3/2006 | Rose |
| 7,223,973 B2 | 5/2007 | Kimba et al. |
| 7,282,727 B2 | 10/2007 | Retsky |
| 7,321,124 B2 | 1/2008 | Rose |
| 7,351,969 B2 | 4/2008 | Watanabe et al. |
| 7,408,175 B2 | 8/2008 | Kimba et al. |
| 7,465,939 B2 | 12/2008 | Frosien |
| 7,569,838 B2 | 8/2009 | Watanabe et al. |
| 2002/0024013 A1 | 2/2002 | Gerlach et al. |
| 2002/0148961 A1 | 10/2002 | Nakasuji et al. |
| 2003/0085353 A1 | 5/2003 | Almogy et al. |
| 2003/0098415 A1 | 5/2003 | Matsuya et al. |
| 2003/0122076 A1 | 7/2003 | Matsuya et al. |
| 2003/0189181 A1 | 10/2003 | Ohta et al. |
| 2003/0207475 A1 | 11/2003 | Nakasuji et al. |
| 2004/0108457 A1 | 6/2004 | Kienzle et al. |
| 2004/0159787 A1 | 8/2004 | Nakasuji et al. |
| 2004/0188635 A1 | 9/2004 | Kawasaki et al. |
| 2005/0253066 A1 | 11/2005 | Watanabe et al. |
| 2006/0169910 A1 | 8/2006 | Frosien et al. |
| 2007/0228922 A1 | 10/2007 | Nakasuji |
| 2008/0173814 A1 | 7/2008 | Watanabe et al. |
| 2008/0308729 A1 | 12/2008 | Kimba et al. |
| 2008/0315090 A1 | 12/2008 | Nakasuji et al. |
| 2009/0014649 A1 | 1/2009 | Nakasuji et al. |
| 2009/0212213 A1 | 8/2009 | Nakasuji et al. |
| 2009/0218506 A1* | 9/2009 | Nakasuji et al. ....... 250/396 ML |

FOREIGN PATENT DOCUMENTS

| | | |
|---|---|---|
| JP | 09-270241 A | 10/1997 |
| JP | 11-067139 A | 3/1999 |
| JP | 11-233062 A | 8/1999 |
| JP | 11-238484 A | 8/1999 |
| JP | 2000-228162 A | 8/2000 |
| JP | 2001-148227 A | 5/2001 |
| JP | 2001-513254 A | 8/2001 |
| JP | 2001-291482 A | 10/2001 |
| JP | 2002-367552 A | 12/2002 |
| JP | 2003-157785 A | 5/2003 |
| JP | 2003-173756 A | 6/2003 |
| JP | 2003-187731 A | 7/2003 |
| JP | 2003-234078 A | 8/2003 |
| JP | 2004-87460 A | 3/2004 |
| JP | 2004-165146 A | 6/2004 |
| JP | 2004-214044 A | 7/2004 |
| JP | 2004-214156 A | 7/2004 |
| JP | 2004-235225 A | 8/2004 |
| JP | 2004-303547 A | 10/2004 |
| JP | 2004-335190 A | 11/2004 |
| JP | 2004-342341 A | 12/2004 |
| JP | 2005-197121 A | 7/2005 |
| WO | 99-33085 A1 | 7/1999 |
| WO | 02/37527 A1 | 5/2002 |
| WO | 2005/024890 A1 | 3/2005 |

OTHER PUBLICATIONS

International Search Report of PCT/JP2006/314571, date of mailing Oct. 10, 2006.
Japanese Office Action dated Jul. 12, 2010, issued in corresponding Japanese Patent Application No. 2006-065143.
Japanese Office Action dated Dec. 10, 2010, issued in corresponding Japanese Patent Application No. 2006-065143.
International Search Report of PCT/JP2006/304088, date of mailing May 30, 2006.
Rose, H.; "Inhomogeneous Wien filter as a corrector compensating for the chromatic and spherical aberration of low-voltage electron microscopes."; Optik, (1990), pp. 91-107, vol. 84, No. 3.
Tsuno, K.; "Negative aberrations generated by a Wien-type multipole corrector"; Japan Society for the Promotion of Science, Jul. 29, 2005, pp. 39-46.
Ioanoviciu, D. et al.; "Third order aberration theory of double Wien filters"; Review of Scientific Instruments, Nov. 2004, pp. 4434-4441, vol. 75, No. 11.
Tsuno K. et al.; "Third-order aberration theory of Wien filters for momchromators and aberration correctors"; Journal of Microscopy, Mar. 2005, pp. 205-215, vol. 217, Pt. 3.

* cited by examiner (B)

Fig.13
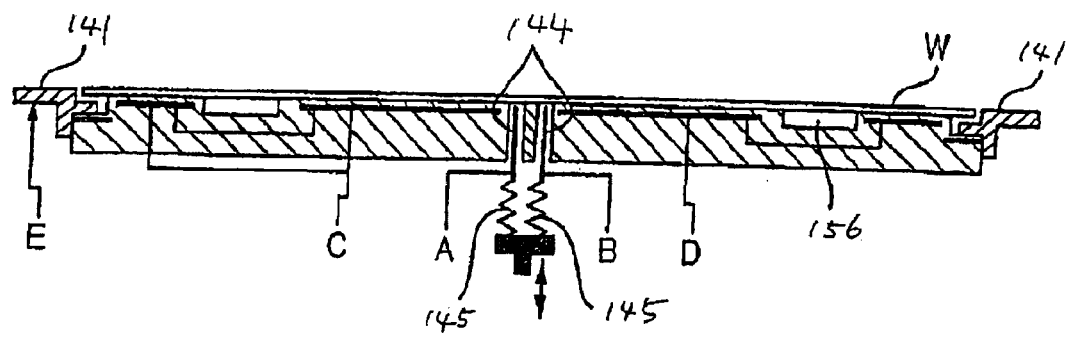
(A)
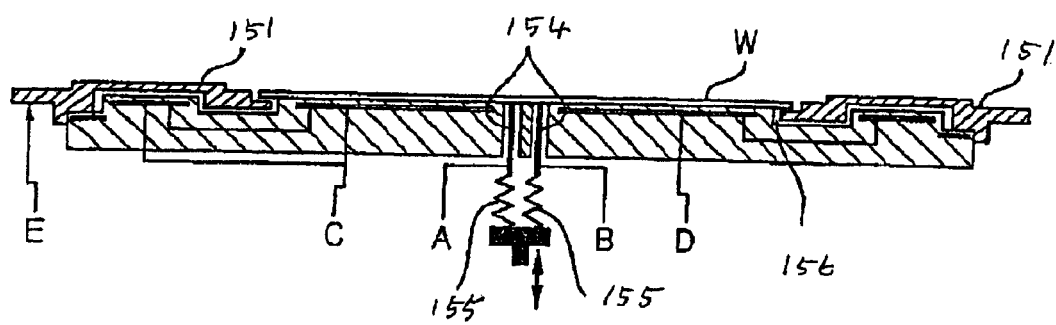
(B)

Fig. 18
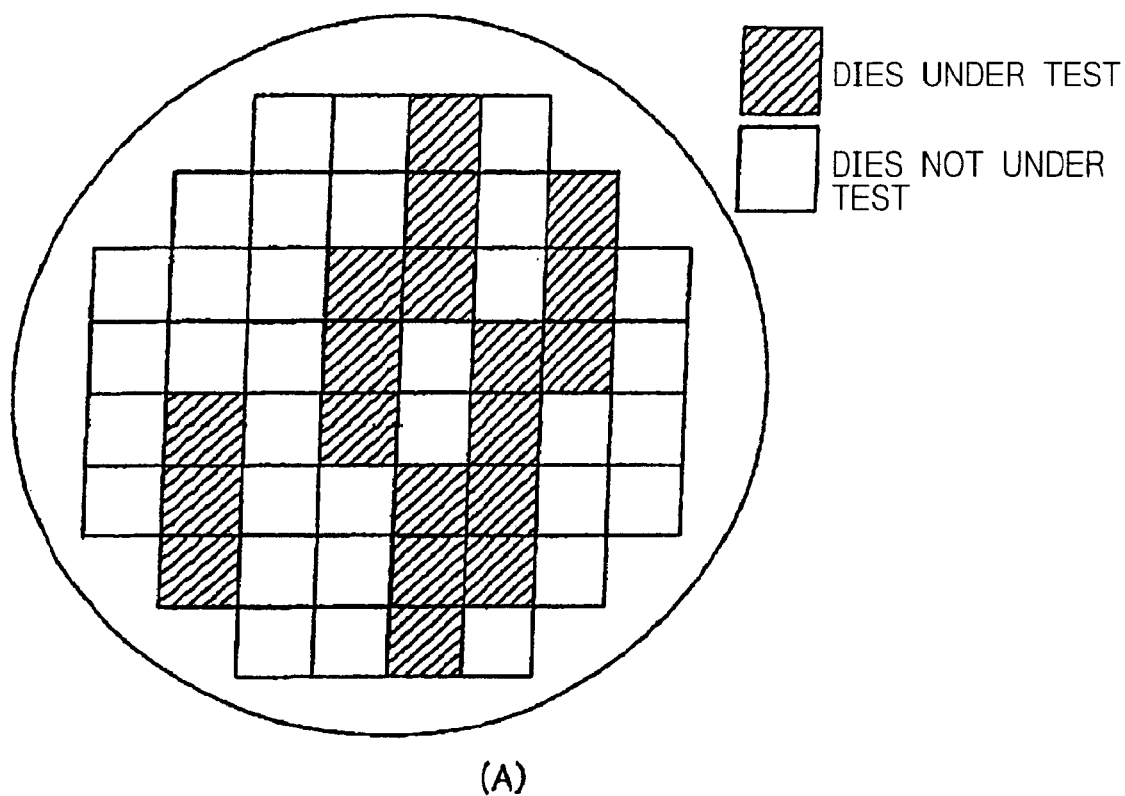
(A)
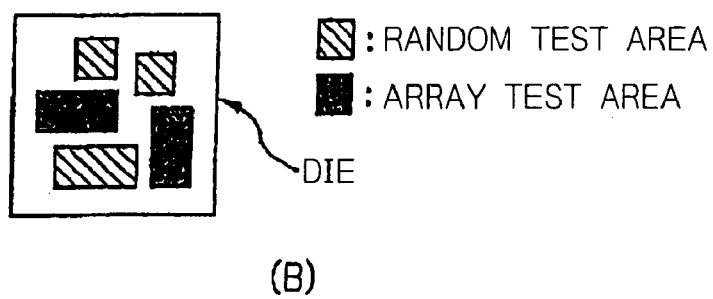
(B)

Fig. 20
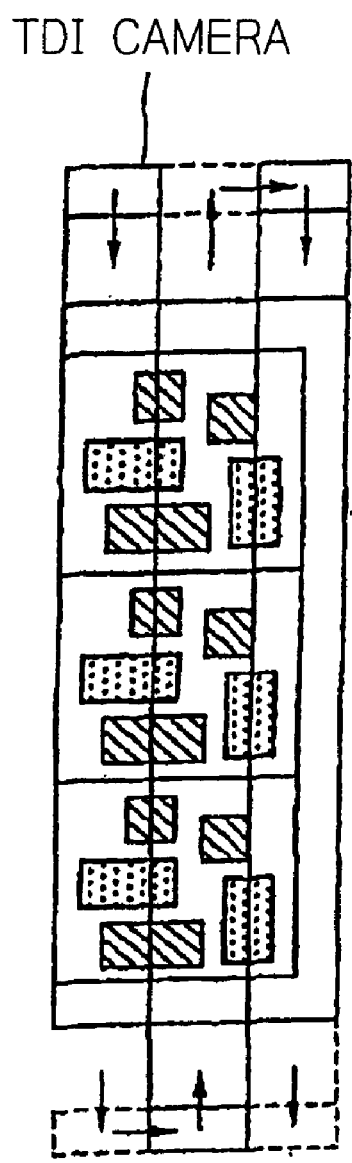
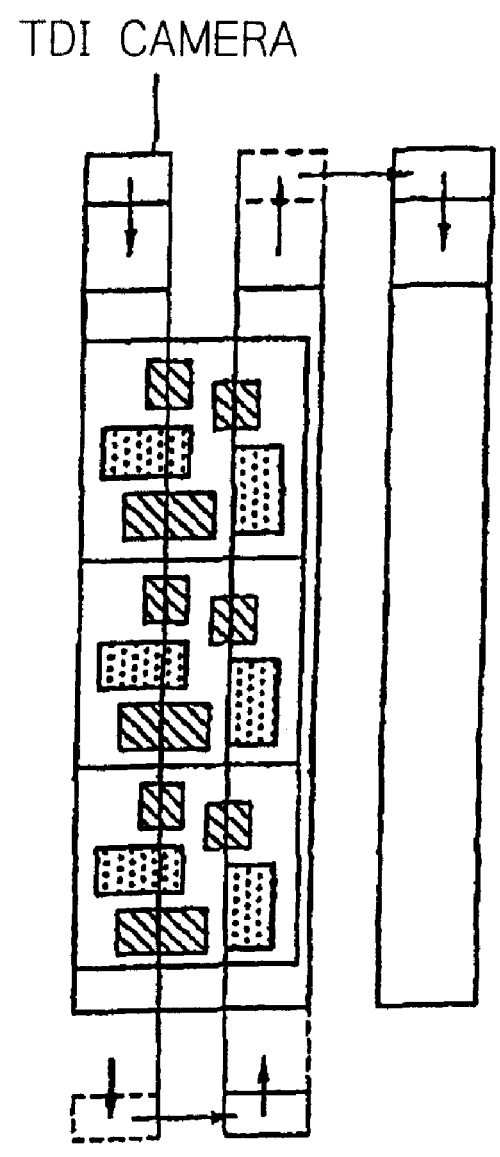

THIRD SEARCHED DIE IMAGING AREA

SECOND SEARCHED DIE IMAGING AREA

FIRST SEARCHED DIE IMAGING AREA

Y-DIRECTION PATTERN MATCHING (TRANSITIONS OF PATTERN SEARCH POSITION FOR CALCULATING θ ROTATION CORRCTION AMOUNT)

[도35]

DIE MAP SCREEN

Fig. 38
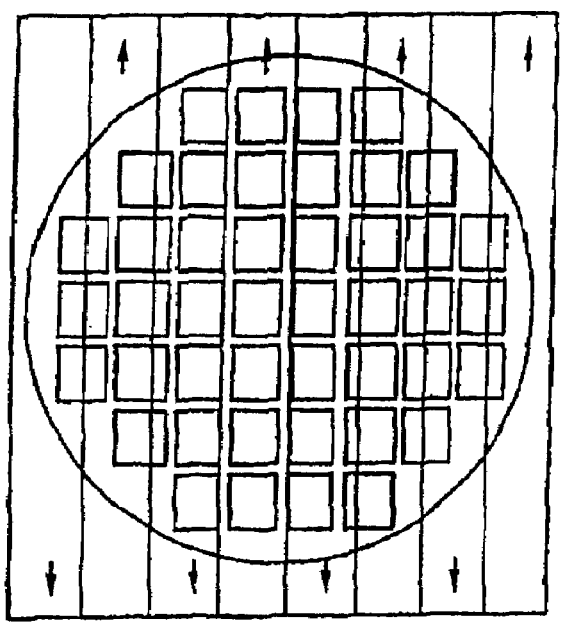
A OPERATION
(A)
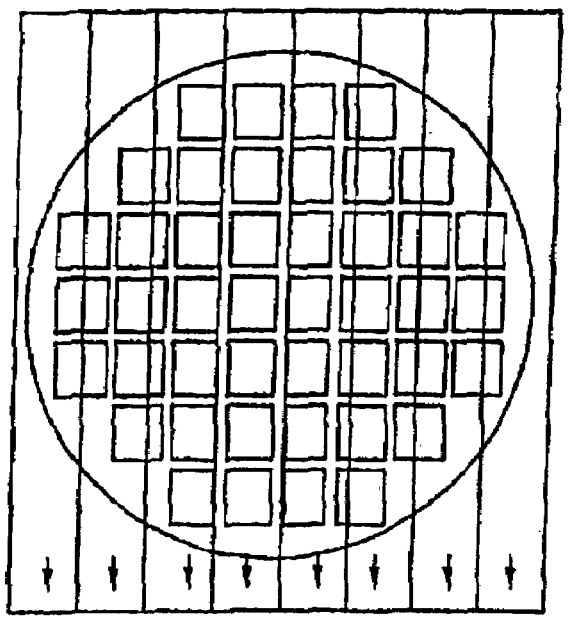
B OPERATION
(B)

Fig.39
(A)
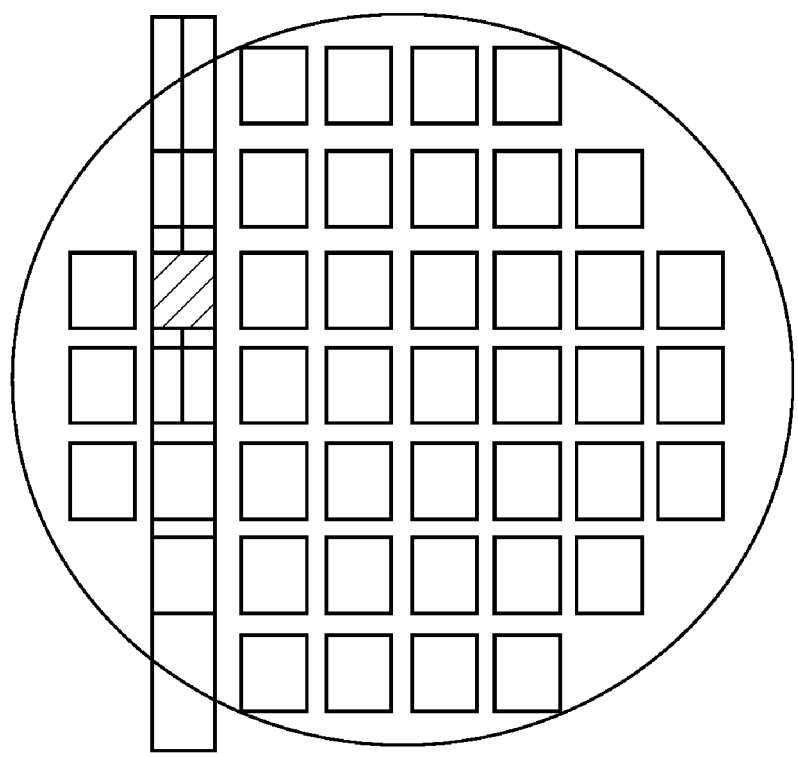
(B)
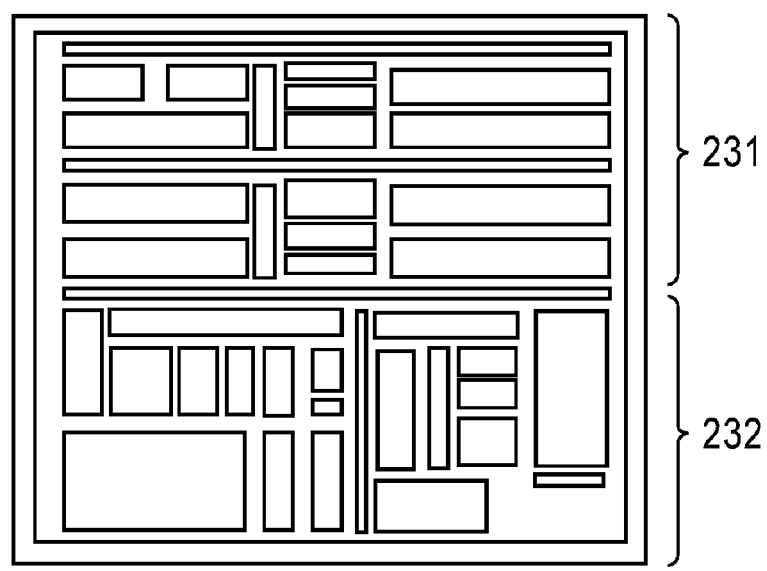

(A)　　　　　(B)

Fig.65
(A)
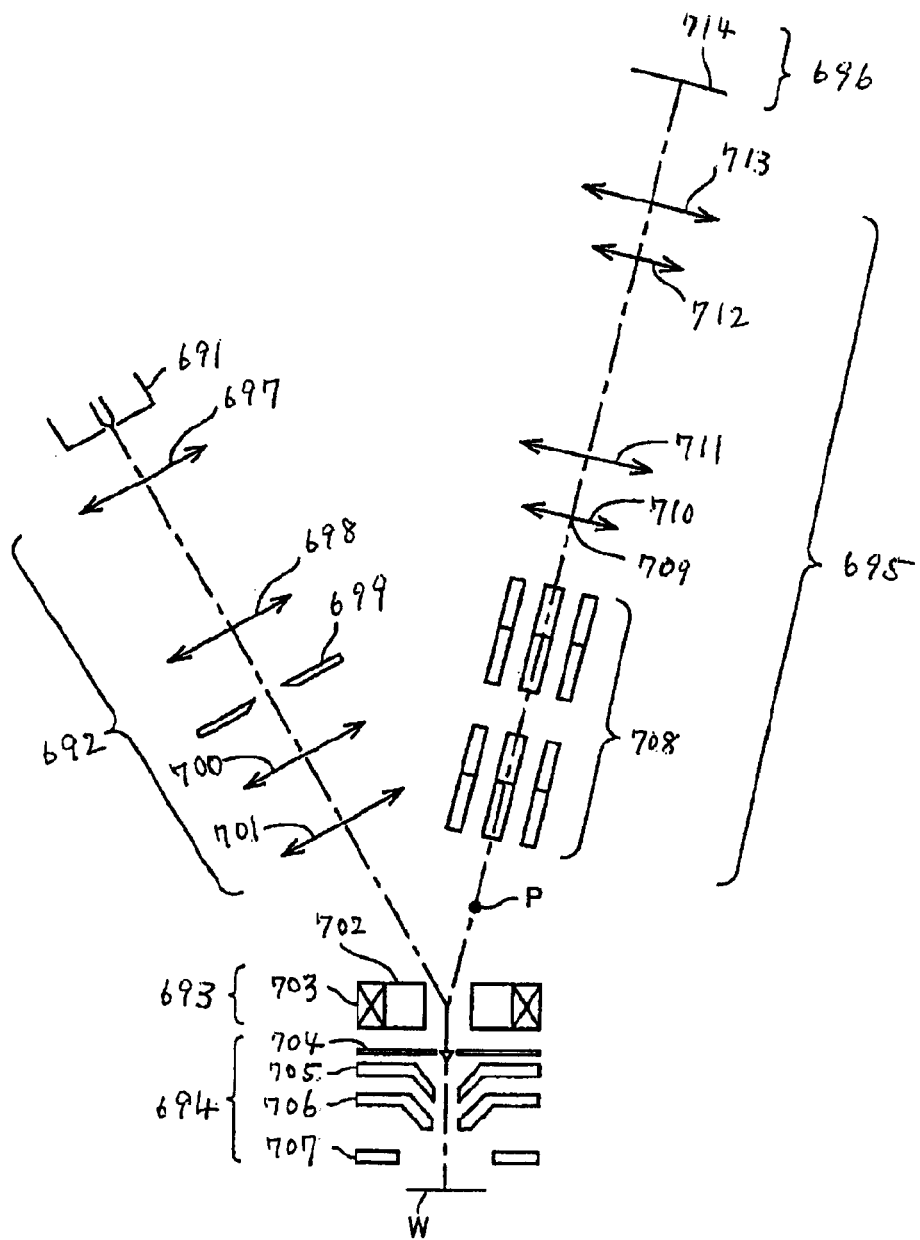
(B)
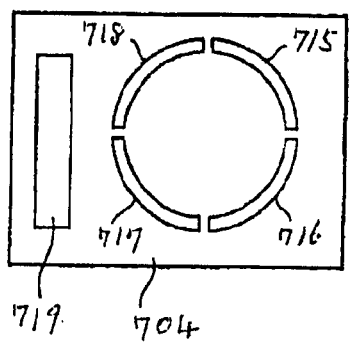

Fig.66
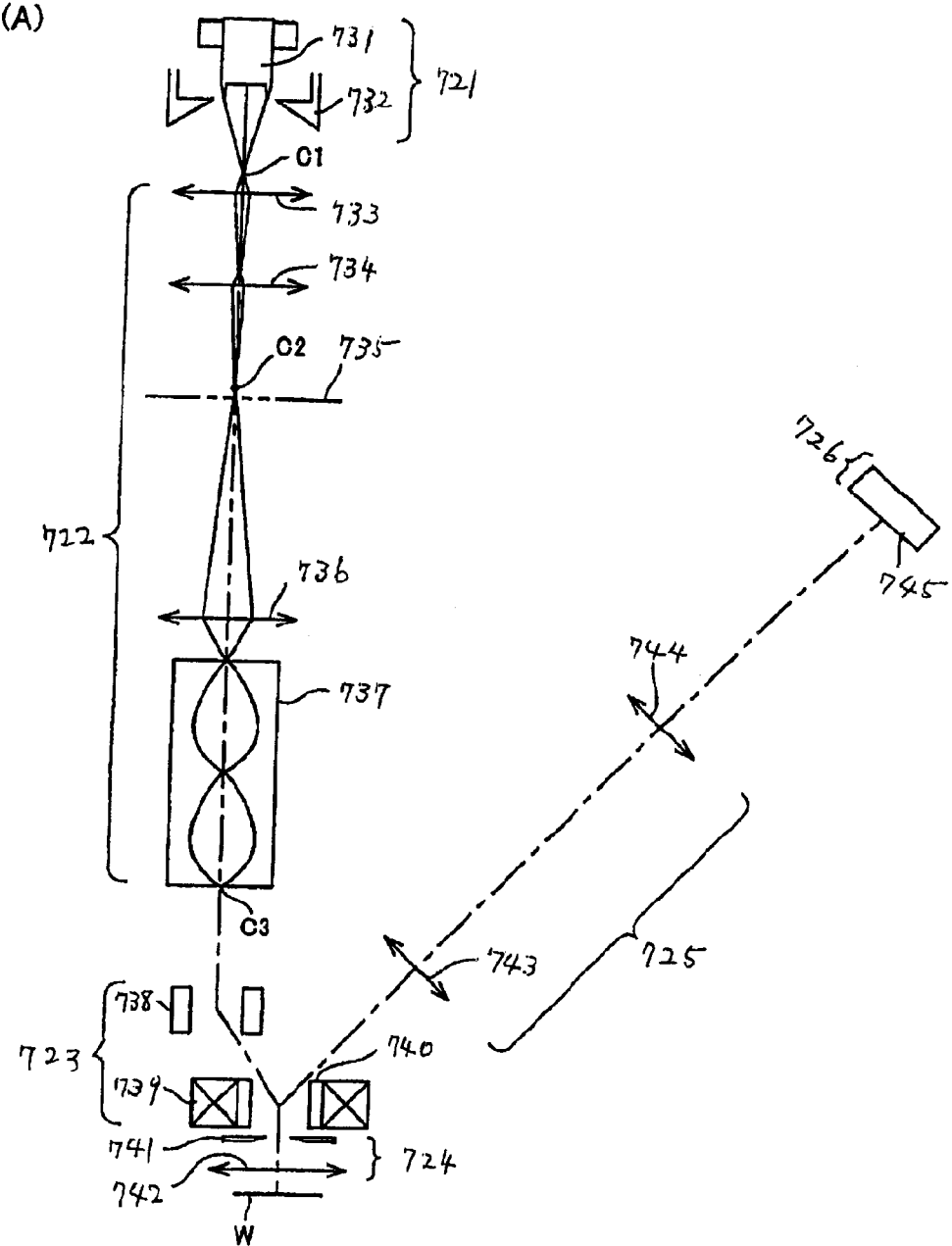
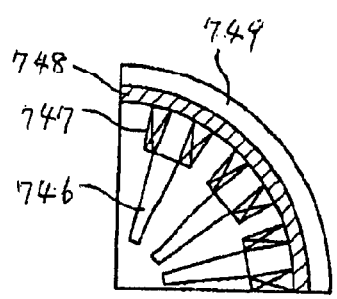

PROJECTION ELECTRON BEAM APPARATUS AND DEFECT INSPECTION SYSTEM USING THE APPARATUS

CROSS-REFERENCE TO RELATED APPLICATIONS

This application is a division of U.S. application Ser. No. 11/817,763, filed on Dec. 8, 2008 which is based on Japanese Patent Application No. 2004-306641 filed on Oct. 21, 2004 and Japanese Patent Application No. 2005-032157 filed on Feb. 8, 2005, and which is based on and claims priority of Japanese Patent Application No. 2005-059504 filed on Mar. 3, 2005, Japanese Patent Application No. 2005-092297 filed on Mar. 28, 2005, and Japanese Patent Application No. 2005-092314 filed on Mar. 28, 2005, the entire contents of which are incorporated herein by reference.

TECHNICAL FIELD

The present invention relates to a projection electron beam apparatus and a defect inspection system using the apparatus, and more particularly, to an electron beam apparatus which has a projection electro-optical system to have the abilities to conduct a defect inspection and the like for semiconductor wafer and the like at a high throughput, and a defect inspection apparatus using the apparatus. For example, the present invention relates to an electron beam apparatus which evaluates a sample having a pattern with a minimum line width of 0.25 μm or less and preferably 0.20 μm or less at high accuracy and high throughput, and a device manufacturing method using the apparatus.

BACKGROUND ART

Generally, in an electron beam apparatus which is configured to irradiate a sample applied with a retarding voltage with a primary electron beam and detect secondary electrons emitted from an irradiated spot to produce an image of the sample, a larger electric field must be applied between the surface of the sample and an objective lens in order to reduce axial chromatic aberration. However, as the electric field strength is increased on the surface of the sample with the intention to reduce the axial chromatic aberration, a discharge will occur between the sample and objective lens. For this reason, the electric field strength must be set to be relatively small, resulting in a problem of relatively large axial chromatic aberration.

Also, an electron beam apparatus is known (see, for example, JP-A-2004-214044) for shaping an electron beam emitted from an electron gun into a rectangular shape, irradiating a sample with the shaped electron beam, producing an enlarged image from secondary electrons emitted from the sample using a projection optical lens, and detecting the sample image using a detector such as a TD1 detector. This apparatus employs an electrostatic lens as an objective lens for irradiating a sample with an electron beam (see, for example, JP-A-11-132975, Republished WO2002/045153). Also, a secondary electron projection optical system is known to employ an electrostatic lens having five electrodes, and further in a lithography apparatus, an electro-optical system which satisfies a MOL (Moving Object Lens) condition is also known.

When an electrostatic lens is employed for an objective lens, a higher voltage applied to a central electrode of the electrostatic lens results in a higher susceptibility to a discharge. Accordingly, when a low voltage is employed, axial chromatic aberration increases. When the electric field strength is increased in order to reduce the axial chromatic aberration, a problem arises in that a discharge occurs between a sample and the lens. Anyway, the transmittance of secondary electrons is difficult to be increased, as a consequence.

The employment of a magnetic lens for an objective lens is also known (for example, see JP-A-2003-168385 and JP-A-2003-173756). In this event, problems lie in that an axial magnetic field is not zero on the surface of a sample, and secondary electron beams emitted from the sample in the normal direction do not intersect with the optical axis or pass through an NA aperture. Also, a MOL scheme has problems that a beam must be scanned, and it is hardly compatible with an inspecting device. Further, in a rectangular visual field, problems are a long distance from the optical axis for the area, and large astigmatism. Another problem lies in that a second electron beam is blurred by space charges of a primary electron beam.

From the foregoing, a need exists for an electron beam apparatus which is free from a discharge occurring between a sample and an electrostatic lens, can reduce axial chromatic aberration and various aberration, can force secondary electrons to intersect with an optical axis and to pass through an NA aperture, can vary the magnification of an image by secondary electrons, can improve the transmittance of the secondary electrons, and can reduce the occurrence of blurs of the secondary electrons due to a space charge effect of primary electrons, and for a semiconductor device manufacturing method using the apparatus.

Conventionally, when an $LaB_6$ cathode is operated in a space charge limiting region, there is an advantage of small shot noise, but on the contrary, there is a problem of large chromatic aberration due to a large energy width. A technology for correcting an objective lens for axial chromatic aberration using a plurality of quadrupole lenses in order to accomplish a high resolution of several nm to one nm has been practically used in SEM and transmission electron microscope.

On the other hand, with the trend of higher integration of semiconductor devices and increasing miniaturization of patterns, inspection apparatuses have been required to provide higher resolution and higher throughput. In order to examine a wafer substrate of 100-nm design rule for defects, it is necessary to view the presence/absence of pattern defects and particles in wires having a line width of 100 nm or less, defective vias, and electric defects thereof. Accordingly, a resolution of 100 nm is required, and a higher throughput is also required because the amount of inspects is increased due to an increase in manufacturing steps resulting from higher integration of devices.

As devices are formed of a larger number of layers, an inspection apparatus is also required to provide a function of detecting defective contacts (electric defects) of vias which connect wires between layers. It is anticipated that an electron beam based defect inspection apparatus will go mainstream in place of an optical defect inspection apparatus in regard to the resolution and defective contact inspection. However, the electron beam based defect inspection apparatus is disadvantageously inferior to the optical one in regard to the throughput. As such, a need exists for the development of an electron beam based inspection apparatus which is capable of a high resolution, a high throughput, and detecting electric defects.

It is said that the resolution of the optical inspection apparatus is limited to one half of the wavelength of used light, and the resolution is approximately 0.2 μm in a practiced example. On the other hand, in a scheme based on electron beams, a scanning electron beam scheme (SEM scheme) has been brought into practical use, where the resolution is 0.1 μm and an inspecting time is eight hours per wafer (200 mm wafer). In addition, the electron beam scheme is largely characterized by its abilities to inspect for electric defects (disconnected wires, defective conduction, defectively connected vias, and the like), but merely provides a very low inspecting speed. Therefore, the development of a defect inspection apparatus which provides a high inspecting speed is expected.

Further, a known electron beam apparatus irradiates a sample with an electron beam having a rectangular cross-section, enlarges secondary electrons emitted from the sample, focuses the enlarged secondary electrons onto a detection plane, and inspects the surface of the sample (see, for example, JP-2002-216694). However, since this type of electron beam apparatus has large axial chromatic aberration, the throughput must be largely reduced in order to provide an S/N ratio required to evaluate at a high resolution.

Another known electron beam apparatus scans the surface of a sample with a plurality of beams, and detects secondary electrons from the sample using a plurality of detectors to increase the throughput (see, for example, U.S. Pat. No. 5,892,224). However, in scanning a plurality of beams, no clear solution has been provided in regard to how a plurality of beams should be arranged in order to most effectively perform evaluations. Moreover, the electron beam apparatus has a problem in that if a magnetic lens is employed for an objective lens, secondary electrons emitted from a sample in the normal direction to the surface of the sample do not intersect with the optical axis.

Also, while it is known to produce an image at an ultra-high resolution of 1 nm or less by correcting axial chromatic aberration, an increase in beam strength has not been practiced, instead of improving the resolution by the correction of aberration.

DISCLOSURE OF THE INVENTION

Problems to be Solved by the Invention

The present invention has been made to solve a variety of problems described above, and one of its objects is to reduce axial chromatic aberration and increase the transmittance of secondary electrons, thereby permitting an electron beam apparatus to evaluate a sample at a high throughput.

Also, another challenge of the present invention is to provide an electron beam apparatus which shapes an electron beam emitted from an electron gun into a rectangular shape using a condenser lens and an aperture, focusing the electron beam on the surface of a sample using a condenser lens and an objective lens, producing an enlarged image from secondary electrons emitted from the sample using a projection optical lens system, and detects the enlarged image using a TDI (Time Delayed Integration) detector or a CCD detector to capture a sample image, where the electron beam apparatus is capable of reducing blurs of secondary electrons due to a space charge effect of primary electrons, reducing axial chromatic aberration without causing a discharge between the sample and an electrostatic lens, simultaneously reducing various aberrations, allowing secondary electrons or reflected electrons emitted from the sample in the normal direction to intersect with an optical axis and pass through an NA aperture, varying the magnification of an image represented by the secondary electrons or reflected electrons, and improving the transmittance of the secondary electrons, and to provide a method of manufacturing a semiconductor device using the electron beam apparatus.

While the axial chromatic aberration correction technology can be applied to SEM and transmission electronic microscope, it cannot be simply applied to a sample evaluation apparatus and a lithography apparatus for inspecting defects and the like, which have a relatively wide visual field. Specifically, a plurality of quadrupole lenses, if employed, can correct the axial chromatic aberration, but increase off-axis aberration when the visual field is wide. Accordingly, even if a plurality of quadrupole lenses are simply used in a defect inspection apparatus and a lithography apparatus which have relatively wide visual fields, off-axis aberration is produced to blur a resulting image. Also, the lithography apparatus has another problem of a largely limited throughput due to the space charge effect.

Accordingly, it is another object of the present invention to provide an electron beam apparatus which is capable of producing a beam current larger by a factor of 10 or more at a resolution of ten to several tens of nm, as compared with the prior art example, by the action of axial chromatic aberration correction in a defect inspection apparatus and a lithography apparatus which have relatively large visual fields.

Generally, since the inspection apparatus is expensive and provides a throughput lower than other processing apparatuses, the inspection apparatus is currently used after important processes, for example, after etching, deposition, or CMP (chemical mechanical polishing) planarization process, and the like. An electron beam based inspection apparatus narrows down an electron beam (the diameter of which is equivalent to the resolution), and scans the resulting electron beam to irradiate a sample in a linear fashion. On the other hand, a region under observation is irradiated with the electron beam in a planar fashion by moving a stage to a direction perpendicular to an electron beam scanning direction. Generally, the electron beam has a scanning width of several hundred μm. Secondary electrons generated from the sample irradiated with the narrowed electron beam (called the "primary electron beam") are detected by a detector (scintillator and photomultiplier or a semiconductor based detector (PIN diode type) or the like). The coordinates of the irradiated spot and the amount of the secondary electrons (signal strength) are combined to produce an image which is then stored in a storage device or output on a CRT (Braun tube). The foregoing is the principle of SEM (scanning electron microscope), and an image captured by this scheme is used to detect defects on a semiconductor (generally, Si) wafer which is in the middle of processing.

The inspection speed (equivalent to the throughput) is determined by the amount and beam diameter of primary electron beams (current value), and a response speed of a detector. The highest response speed is currently 100 MHz for a detector with a beam diameter of 0.1 μm (considered to be the same as the resolution) and a current value of 100 nA, in which case it is said that the inspection speed is approximately eight hours per wafer of 200 cm diameter. This significantly low inspection speed, as compared with the optical scheme, is a grave problem. Particularly, for a device pattern of a design rule of 100 nm or less created on a wafer, i.e., line width of 100 nm or less, vias of 100 nm diameter or less, and the like, it is necessary to detect defects in shape, electric defect, and debris of 100 nm or less at high speeds.

In the SEM based inspection apparatus described above, the aforementioned inspection speed is considered to be substantially a limit, so that a new scheme is required in order to further increase the speed, i.e., the throughput. To satisfy this requirement, an electron beam apparatus has been proposed for irradiating a sample with an electron beam having a rectangular cross section, and enlarging and detecting secondary electrons emitted from the sample using a projection optical system (see, for example, JP-A-2002-216694). Also, another known electron microscope comprises a multi-pole lens to correct an axially symmetric lens for axial chromatic aberration (see, for example, D. Ioanoviciv, et al., Rev. Sci. Instrum., Vol. 75, No. 11, November 2004).

However, in a conventionally known projection electron beam apparatus, as a primary beam having a large current is fed, a resulting image is largely blurred due to the space charge effect between electrons, thus failing to achieve a high resolution. Accordingly, it is another object of the present invention to provide an electron beam apparatus which is capable of preventing a lower resolution caused by the space charge effect, and a device manufacturing method using the apparatus.

Also, it is another object of the present invention to provide an electron beam apparatus which is capable of evaluating a sample without reducing the throughput even if a pattern under evaluation is finer, and a device manufacturing method using the apparatus.

Means for Solving the Problem

To achieve the various objects mentioned above, the present invention provides an electron beam apparatus having a projection electro-optical system for inspecting a surface of a sample. The electron beam apparatus comprises:

an electron gun for emitting an electron beam;

a primary electro-optical system for guiding the emitted electron beam onto a sample for irradiation;

a detector for detecting electrons;

a secondary electro-optical system for guiding an electron beam bearing information on the surface of the sample, emitted from the sample irradiated with the electron beam, to the detector, wherein at least one of the primary electro-optical system and the secondary electro-optical system includes a multi-pole lens.

In the electron beam apparatus according to the present invention, the multi-pole lens is preferably disposed between a magnification lens of the secondary electro-optical system and beam separating means for separating a primary electron beam and a secondary electron beam. Preferably, in this event, an objective lens closest to the surface of the sample comprises an electromagnetic lens having a gap defined on a sample side, and axial chromatic aberration caused by the electromagnetic lens can corrected by a multi-pole lens disposed in the secondary electro-optical system.

Also, the multi-pole lens is preferably disposed between a reducing lens in the primary electro-optical system and beam separating means for separating a primary electron beam and a secondary electron beam. Preferably, in this event, the primary electro-optical system includes an axially symmetric lens, wherein the axially symmetric lens is set such that off-axis aberration at an end of a visual field is equal to or less than a previously set predetermined value, and comprises an electromagnetic lens, and the lens has a Bohr radius larger by a factor of 50 or more than a maximum diameter of the visual field.

Further preferably, the primary electro-optical system comprises means for converting an electron beam from the electron gun into multiple electron beams, and the detector comprises a detection unit for individually detecting multiple electron beams which make up a secondary electron beam emitted from a point on the sample irradiated with the multiple electron beams. Furthermore, the multi-pole lens preferably comprises quadrupole lenses at four stages.

The present invention also provides a defect inspection system which comprises the electron beam apparatus having a projection electro-optical system, for inspecting a surface of a sample for defects. The defect inspection system comprises image capturing means for generating an image of the surface of the sample based on information on the surface of the sample included in electrons detected by the detector of the electron beam apparatus, and defect evaluating means for testing the presence or absence of a defect on the surface of the sample by comparing the captured image with a reference image.

In the defect inspection system according to the present invention, the system preferably further comprises a sample transfer system for transferring the sample, a sample carrier unit for carrying the sample thereon, an XY stage for two-dimensionally moving the sample carrier unit, a main chamber for containing the sample carrier unit and the XY stage, and holding the same in a vacuum state, and a load lock chamber located between the main chamber and the sample transfer system for holding the vacuum state of the main chamber when the sample is moved from the sample transfer system to the main chamber. In this event, the sample transfer system preferably comprises an electrostatic chuck having a function of preventing particles from sticking to the sample. The XY stage preferably comprises an air bearing having a differential exhaust mechanism at least in one axial direction thereof.

The electron beam apparatus having a projection electro-optical system according to the present invention comprises a lens system at two or more stage configured as described above for reduction, so that a reduction ratio of $1/100$-$1/2000$ can be achieved while the optical path length is kept short, thus making it possible to reduce the space charge effect.

Further, since axial chromatic aberration is corrected using a multi-pole lens, the aperture angle can be increased, thus making it possible to provide electron beams with a large beam current, while the beam diameter is kept small, and consequently improve the throughput.

Also, as described above, since the electron beam apparatus can be improved in throughput, the defect inspection apparatus comprising the electron beam apparatus can also improve the throughput of inspections in a similar manner.

The present invention also found the following aspects and solves the aforementioned problems in the following manner. Specifically, in an electron beam apparatus, wherein an electron beam emitted from an electron gun is shaped into a rectangular shape through an aperture, the electron beam is caused to pass along a trajectory deviated from secondary electrons or reflected electrons emitted from a sample below an objective lens by the action of a deflector, secondary electrons or reflected electrons emitted from the sample are directed into a projection optical lens system, an enlarge view is produced by the lens system, and a sample image is captured by detecting the same using a TD1 or a CCD detector to capture a sample image, the objective lens comprises a magnetic lens, and the distance between the sample and a main surface of the objective lens is set to be larger than a Bohr radius of the objective lens, thereby making it possible to reduce axial chromatic aberration, cause the electron beam to pass along a trajectory deviated from the secondary electrons or reflected electrons emitted from the sample below the ExB separator, avoid a discharge in this event, and permit secondary electrons or reflected electrons emitted from the sample in the normal direction to intersect with the optical axis, and pass through the NA aperture.

In the electron beam apparatus described above, the objective lens comprises a magnetic lens, a magnetic gap is defined on the optical axis side, and the Bohr radius of the objective lens is set larger than the diameter of a visual field by a factor of 80 or more, thereby making it possible to reduce aberration, cause the electron beam to pass along a trajectory deviated from the secondary electrons or reflected electrons emitted from the sample below the ExB separator, and focus on the surface of the sample by the objective lens, and permit secondary electrons or reflected electrons emitted from the sample in the normal direction to intersect with the optical axis, and pass through the NA aperture.

In the electron beam apparatus described above, in regard to the magnetic lens, an axially symmetric cylinder electrode is provided near a magnetic gap of the magnetic lens to apply a positive high voltage, and a sufficient distance is ensured between the cylindrical electrode and the sample to avoid a discharge, thereby making it possible to reduce axial chromatic aberration, cause the electron beam to pass along a trajectory deviated from the secondary electrons or reflected electrons emitted from the sample below the ExB separator, without giving rise to a discharge between the sample and discharge lens, and permit secondary electrons or reflected electrons emitted from the sample in the normal direction to intersect with the optical axis, and pass through the NA aperture.

In the electron beam apparatus described above, the secondary electrons or reflected electrons emitted from the sample are deflected by an ExB separator, and subsequently impinge on the projection optical lens system, wherein the lens system comprises at least one stage of an electromagnetic lens having an NA aperture near a main surface of the lens, thereby improving the transmittance of the secondary electrons or reflected electrons, producing an enlarged image, and capturing two-dimensional image data which is converted to an electric signal.

In the electron beam apparatus described above, the lens system comprises at least one stage of an electromagnetic lens having an NA aperture near a main surface of the lens, and the projection optical lens system comprises an auxiliary electrostatic lens and a magnification electromagnetic lens, wherein the electrostatic lens comprises two or more electrodes which can be applied with a voltage, the lens system is configured to focus a sample image position created by a preceding lens on a main surface of the auxiliary lens, and an electrode is selected for driving the electrostatic lens, thereby reducing aberration, improving the transmittance of the secondary electrons or reflected electrons, making the magnification variable, and capture two-dimensional image data which is converted to an electric signal.

In the electron beam apparatus described above, a lens at a final stage comprises an electrostatic lens having at least five electrodes, and a voltage applied to a central electrode thereof is different in sign from voltages applied to a preceding and a subsequent electrode thereof, thereby making it possible to maximize the magnification, reduce the optical path length at the same magnification, and implement this under a low aberration condition.

In the electron beam apparatus described above, the objective lens comprises a magnetic lens which has a Bohr diameter on a sample side smaller than a Bohr diameter on a detection side, thereby making it possible to cause the secondary electrons or reflected electrons emitted in the normal direction from the surface of the sample to pass through the NA aperture, and improve the transmittance of the secondary electrons or reflected electrons.

In the electron beam apparatus described above, the objective lens comprises a magnetic lens, and electromagnetic coils are provided at two stages before and after a main surface of the objective lens, and these deflectors are configured to substantially satisfy a MOL condition, thereby making it possible to expand the visual field with the axial chromatic aberration being kept small.

In the electron beam apparatus described above, the electron beam apparatus is adjusted to correct field curvature aberration and anastigmatic and reduce a difference in beam resolution between a central area of the visual field and a peripheral area of the visual field, thereby making it possible to reduce aberration over the entire visual field. Further, a ball lens can be used to narrow down a light emission direction to 1/n without causing spherical aberration, anastigmatic, or chromatic aberration in the optical axis direction. Also, the optical lens system can be simplified by correcting the ball lens for chromatic aberration in radial directions and distortions by a subsequent optical lens.

A method of manufacturing a semiconductor device comprises preparing a wafer, preparing a mask substrate and manufacturing a mask, performing a wafer processing step for performing required machining to the wafer, evaluating the resulting wafer using the electron beam apparatus according to any of claims 12 to 20, and repeating the wafer processing step and evaluating steps a required number of times, and cutting the wafer and assembling devices. Here, an improved yield rate of the manufacturing can be expected by using an electron beam apparatus which is capable of accurately evaluating a wafer at a high throughput.

Specifically, according to the present invention, the following inventions are provided.

(1) An electron beam apparatus for producing an enlarge view from secondary electrons or reflected electrons emitted from a sample using a projection optical lens system, and detecting the enlarged view using a TD1 or a CCD detector to capture a sample image, characterized by shaping an electron beam emitted from an electron gun into a rectangular shape through an aperture, causing the electron beam to pass along a trajectory deviated from the secondary electrons or reflected electrons emitted from the sample below an objective lens, the objective lens comprising a magnetic lens, and setting the distance between the sample and a main surface of the objective lens to be larger than a Bohr radius of the objective lens.

(2) The electron beam apparatus described above is characterized in that the Bohr radius of the objective lens is larger than the diameter of a visual field by a factor of 80 or more.

The electron beam apparatus characterized in that, in regard to the magnetic lens, an axially symmetric cylinder electrode is provided near a magnetic gap of the magnetic lens to apply a positive high voltage, and a sufficient distance is ensured between the cylindrical electrode and the sample to avoid a discharge therebetween.

(4) The electron beam apparatus described above is characterized in that the secondary electrons or reflected electrons emitted from the sample are deflected by an ExB separator, and subsequently impinge on the projection optical lens system, wherein the lens system comprises at least one stage of an electromagnetic lens having an NA aperture near a main surface of the lens.

The electron beam apparatus, wherein the projection optical lens system comprises an auxiliary electrostatic lens and a magnification electromagnetic lens, the electrostatic lens comprises two or more electrodes which can be applied with a voltage, the lens system is configured to focus a sample image position created by a preceding lens on a main surface of the auxiliary lens, and the magnification is variable by selecting an electrode for driving the electrostatic lens.

(6) In an electron beam apparatus for producing an enlarge view from secondary electrons or reflected electrons emitted from a sample using a projection optical lens system, and detecting the enlarged view using a TD1 or a CCD detector to capture a sample image, the electron beam apparatus is characterized by shaping an electron beam emitted from an electron gun into a rectangular shape through an aperture, causing the electron beam to pass along a trajectory deviated from the secondary electrons or reflected electrons emitted from the sample below an objective lens, a lens at a final stage comprises an electrostatic lens having at least five electrodes, and a voltage applied to a central electrode thereof is different in sign from voltages applied to a preceding and a subsequent electrode thereof.

The electron beam apparatus described above is characterized in that the objective lens comprises a magnetic lens which has a Bohr diameter on a sample side smaller than a Bohr diameter on a detection side.

(8) The electron beam apparatus described above is characterized in that the objective lens comprises a magnetic lens, and electromagnetic coils are provided at two stages before and after a main surface of the objective lens, and these deflectors are configured to substantially satisfy a MOL condition.

(9) The electron beam apparatus described above is characterized in that the electron beam apparatus is adjusted to correct field curvature aberration and anastigmatic and reduce a difference in beam resolution between a central area of the visual field and a peripheral area of the visual field.

(10) A method of manufacturing a semiconductor device, characterized by comprising (a) preparing a wafer, (b) preparing a mask substrate and manufacturing a mask, (c) performing a wafer processing step for performing required machining to the wafer, (d) evaluating the resulting wafer using the electron beam apparatus, and repeating the steps (c) and (d) a required number of times, and (e) cutting the wafer and assembling devices.

According to the present invention, the electron beam apparatus provided thereby can reduce axial chromatic aberration and other aberration, vary the magnification of an image of secondary electrons or reflected electrons emitted from a sample by a projection optical lens system, without causing a discharge between the sample and an objective lens, and improve the transmittance, and semiconductors can be manufactured using the apparatus.

Also, to achieve the aforementioned objects, the present invention provides a projection electron beam apparatus characterized by comprising:
an electron gun;
axial chromatic aberration correcting means having a multi-pole lens; and
an objective lens for performing a MOL operation,
wherein the electron beam apparatus irradiates a sample with an electron beam while performing a MOL operation in a divided visual field region.

In the electron beam apparatus described above, the electron beam apparatus is a lithography apparatus, and the apparatus further comprises a mask or a reticle having a pattern which should be formed on the sample. In another embodiment, the electron beam apparatus is a sample evaluation apparatus for evaluating a pattern formed on the sample. Also, the electron beam apparatus preferably comprises an objective lens, and a deflector contained in the objective lens for generating a deflection magnetic field which is proportional to a differentiated value with respect to an optical axis direction of an axial magnetic field distribution of the objective lens.

The projection electron beam apparatus of the present invention, configured as described above, can correct chromatic aberration, and increase NA at the same resolution at which the chromatic aberration is corrected, so that a beam current can be increased, and processing can be performed at a high throughput. Particularly, since it is important for a sample evaluation apparatus to increase the inspection speed without degrading the resolution, the present invention can provide extremely pragmatic advantageous effects. Also, when applied to a lithography apparatus, since NA can be increased at the same resolution at which chromatic aberration is corrected, the space charge effect can be reduced to further improve the throughput.

Also, to achieve the aforementioned objects, the present invention provides an electron beam apparatus for irradiating a sample with a rectangular primary beam and enlarging and projecting secondary electrons emitted from the sample by an electro-optical system to detect the secondary electrons, characterized in that:
the electro-optical system comprises an aperture plate having apertures arranged in a ring shape for transforming the secondary electrons into hollow beams.

The ring-shaped apertures preferably have a width small enough to neglect spherical aberration. Also preferably, the electro-optical system further comprises a correction lens for correcting the electron beam for axial chromatic aberration.

Further, to achieve the aforementioned objects, the present invention provides an electron beam apparatus for irradiating a sample with a primary beam emitted from an electron gun through an objective optical system to detect secondary electrons emitted from the sample, characterized by comprising:
an evaluation apparatus for transforming the primary beam into hollow beams when the primary beam passes through the objective optical system to irradiate the sample with the hollow beams, and detecting the secondary electrons to evaluate the sample; and
a correction lens for correcting the primary beam or the secondary electrons for axial chromatic aberration.

The electron gun preferably comprises a cathode which has a ring-shaped edge. Also preferably, the electron beam apparatus further comprises a multi-aperture plate for transforming the primary beam into multiple beams which are irradiated to the sample, wherein the secondary electrons are detected by a plurality of detectors.

The electron beam apparatus is preferably used in a method of manufacturing a device, characterized by comprising the steps of:
a. preparing a wafer;
b. performing a wafer process;
c. evaluating the wafer after undergoing the step b;
d. repeating the steps a-c a required number of times; and
e. cutting the wafer after the step d and assembling devices.

Further, to achieve the aforementioned objects, the present invention provides an electron beam apparatus for scanning a sample using a plurality of primary beams arranged in m rows and n columns, and detecting secondary beams emitted from the sample to evaluate the sample, characterized by:
simultaneously scanning m*n beams in a direction inclined by an angle equivalent to 1/m in a row direction, wherein the raster pitch of the scanning is an integer multiple of a pixel dimension.

The present invention also provides an electron beam apparatus for irradiating a surface of a sample with an electron beam having a rectangular cross-section, enlarging secondary electron beams emitted from the sample using a projection optical system including an NA aperture plate, and capturing an image of the sample, characterized by:

disposing the NA aperture plate or forming an optical conjugate plane of the NA aperture plate at a position at which aberration is minimized. The enlarged image preferably has a square shape.

Also, the present invention provides an electron beam apparatus for irradiating a sample with a plurality of primary beams, separating a plurality of secondary beams emitted from the sample from the primary beams by a beam separator, extending the distances between the plurality of secondary electron beams by a magnification optical system, and directing the secondary electron beams into a detector, characterized by comprising:

a correction lens for correcting the plurality of primary beam for axial chromatic aberration, wherein the beam separator is disposed between the correction lens and the sample.

Also, the present invention provides an electron beam apparatus for forming a primary beam into a beam having a rectangular cross-section, conversing the primary beam by an objective lens, irradiating a sample with the primary beam, accelerating and converging secondary electron beams emitted from the sample by the objective lens, enlarging the secondary electron beams by a magnification optical system including an NA aperture plate, and detecting the secondary electron beams by a sensor, characterized in that:

the objective lens is an electromagnetic lens; and an optical conjugate plane of the NA aperture plate is located at a position which is passed by the secondary electron beams emitted about a specified direction with respect to a normal direction of the sample.

The electron beam apparatus is preferably used in a method of manufacturing a device, characterized by comprising the steps of:

a. preparing a wafer;
b. performing a wafer process;
c. evaluating the wafer after undergoing the step b;
d. repeating the steps a-c a required number of times; and
e. cutting the wafer after the step d and assembling devices.

BRIEF DESCRIPTION OF THE DRAWINGS

FIG. 13
A diagram for describing a further example of the electrostatic chuck used in the inspection system according to the present invention.

FIG. 18
A diagram for describing a defect inspection procedure in an electron beam apparatus according to the present invention.

FIG. 20
A diagram for describing a defect inspection procedure in an electron beam apparatus according to the present invention.

Figure 15:
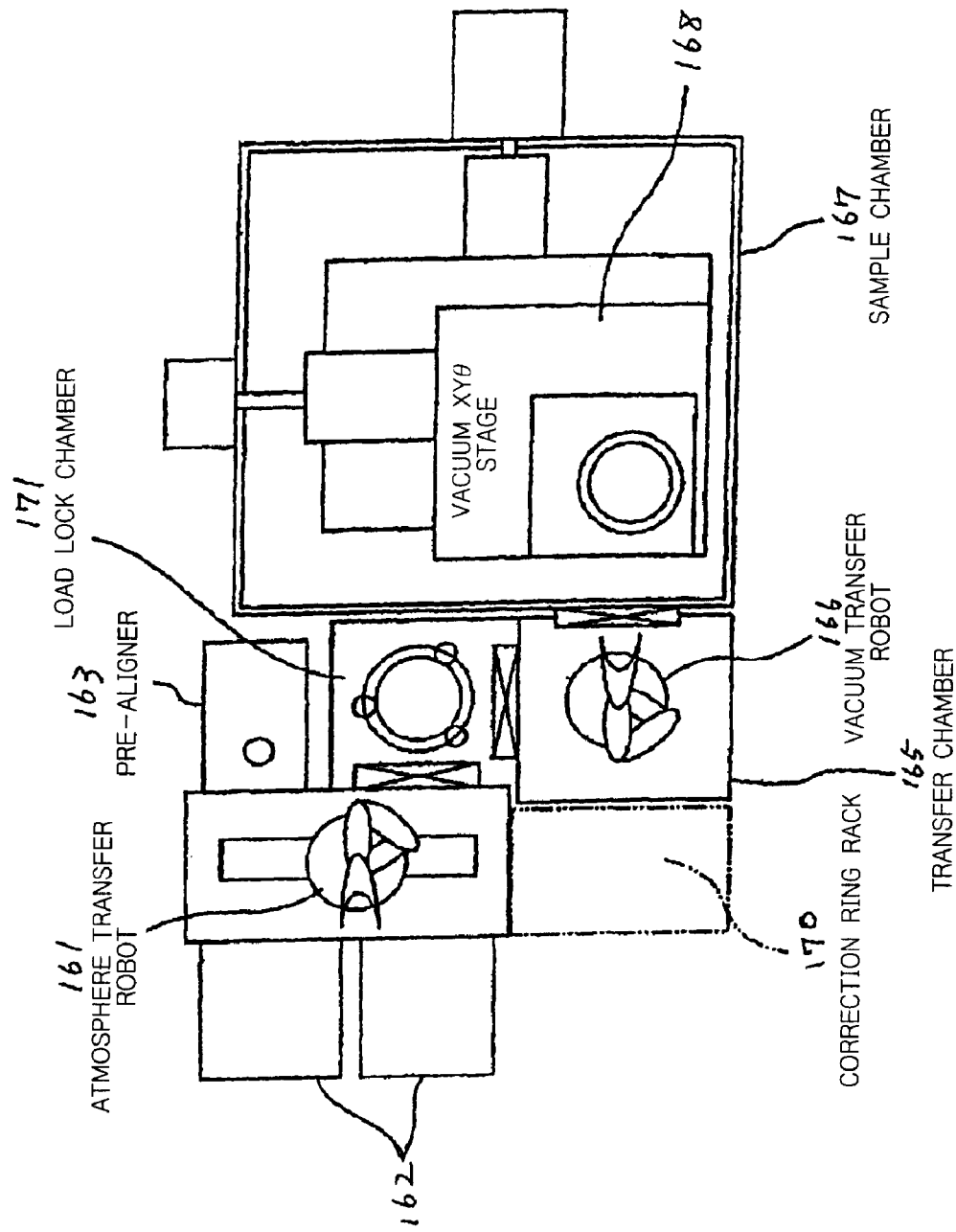
FIG. 15
A diagram for describing another example of the bridge tool used in the inspection system according to the present invention.

A diagram for describing the configuration and an operation procedure of an elevator mechanism in a load lock chamber in FIG. 15.

FIG. 26

A schematic explanatory diagram of a wafer alignment control device which can be applied to the electro-optical system of the inspection system according to the present invention.

FIG. 27

A diagram for describing reasons for which a wafer need be aligned.

FIG. 28

A diagram for describing how a wafer is aligned.

FIG. 29

A diagram illustrating a die map in a die arranged state after the execution of wafer alignment.

FIG. 30

A diagram for describing an update to coordinate values in a wafer alignment procedure.

FIG. 31

A diagram for describing the amount of rotation and a Y-direction size in the wafer alignment procedure.

FIG. 32

A diagram for describing interpolation of a focus value in the creation of focus recipes during the wafer alignment procedure.

FIG. 33

A diagram for describing an error produced during the wafer alignment procedure.

FIG. 34

A diagram for describing a basic flow of a semiconductor device inspection procedure.

FIG. 35

A diagram showing how a die under inspection is set.

FIG. 36

A diagram for describing the setting of an area under inspection within a die.

FIG. 37

A diagram for describing a semiconductor device inspection procedure.

FIG. 38

A diagram for describing a semiconductor device inspection procedure.

FIG. 39

A diagram illustrating exemplary scanning and an exemplary die under inspection when there is one die under inspection.

FIG. 40

A diagram for describing a method of generating a reference image in the semiconductor device inspection procedure.

FIG. 41

A diagram for describing an adjacent die comparison method in the semiconductor device inspection procedure.

FIG. 42

A diagram for describing an adjacent die comparison method in the semiconductor device inspection procedure.

FIG. 43

A diagram for describing an adjacent die comparison method in the semiconductor device inspection procedure.

FIG. 44

A diagram for describing a reference die comparison method in the semiconductor device inspection procedure.

FIG. 45

A diagram for describing focus mapping in the semiconductor device inspection procedure.

FIG. 46

A diagram for describing focus mapping in the semiconductor device inspection procedure.

FIG. 47

A diagram for describing focus mapping in the semiconductor device inspection procedure.

FIG. 48

A diagram for describing focus mapping in the semiconductor device inspection procedure.

FIG. 49

A diagram for describing focus mapping in the semiconductor device inspection procedure.

FIG. 50

A diagram illustrating an embodiment in which an electron beam apparatus according to the present invention is connected to a semiconductor manufacturing line.

FIG. 51

A diagram illustrating a fourth embodiment of the electron beam apparatus according to the present invention.

FIG. 52

A diagram illustrating a fifth embodiment of the electron beam apparatus according to the present invention.

FIG. 53

A flow chart illustrating a process for manufacturing semiconductor devices.

FIG. 54

Figure 53:
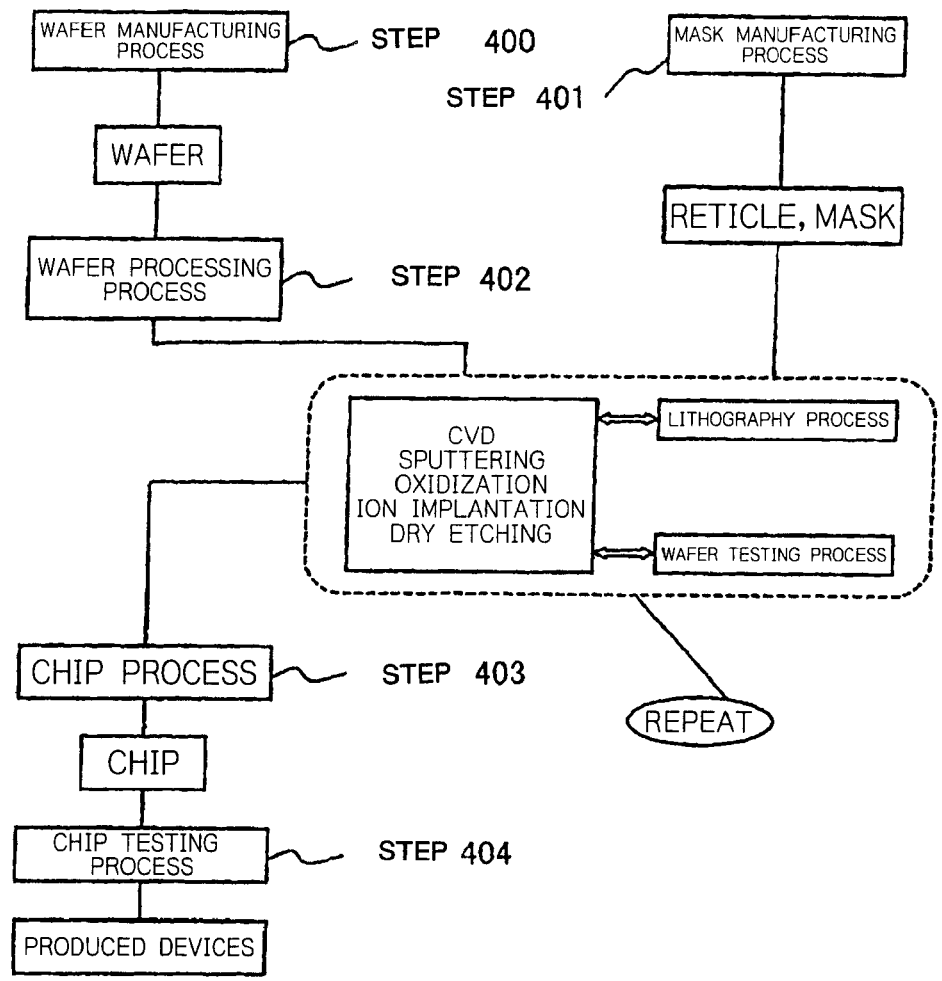

A flow chart illustrating a lithography process in the semiconductor device manufacturing process of FIG. 53.

FIG. 55

Figure 52:
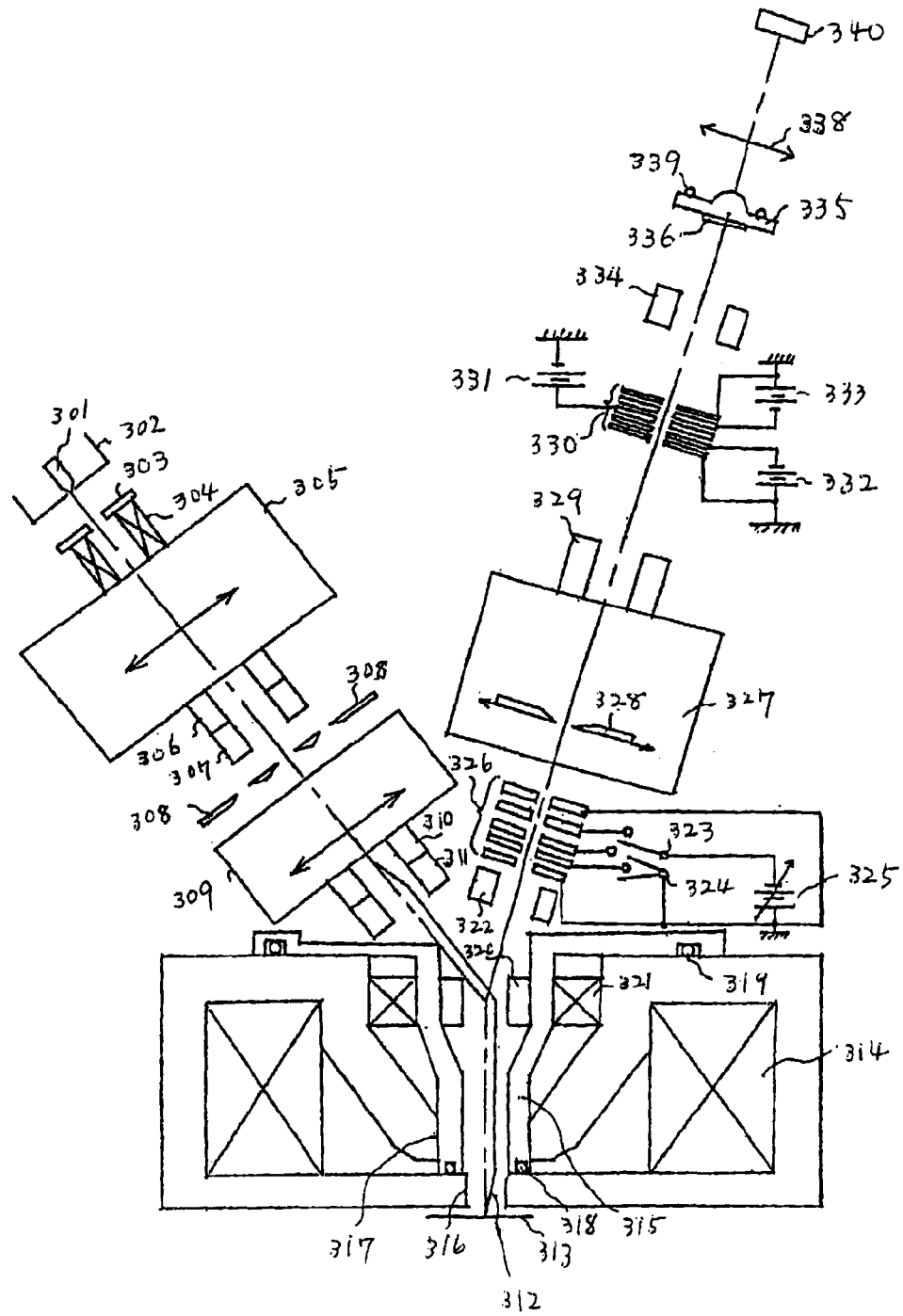

A diagram generally illustrating an objective lens in the electron beam apparatus illustrated in FIG. 52.

FIG. 56

An explanatory diagram illustrating an electro-optical system of a sample evaluation apparatus which is a sixth embodiment of the electron beam apparatus according to the present invention.

FIG. 57

An explanatory diagram illustrating an electro-optical system of an electron beam drawing apparatus which is a seventh embodiment of the electron beam apparatus according to the present invention.

FIG. 58

An explanatory diagram illustrating an electro-optical system of a sample evaluation apparatus which is an eighth embodiment of the electron beam apparatus according to the present invention.

FIG. 59

Figure 58:
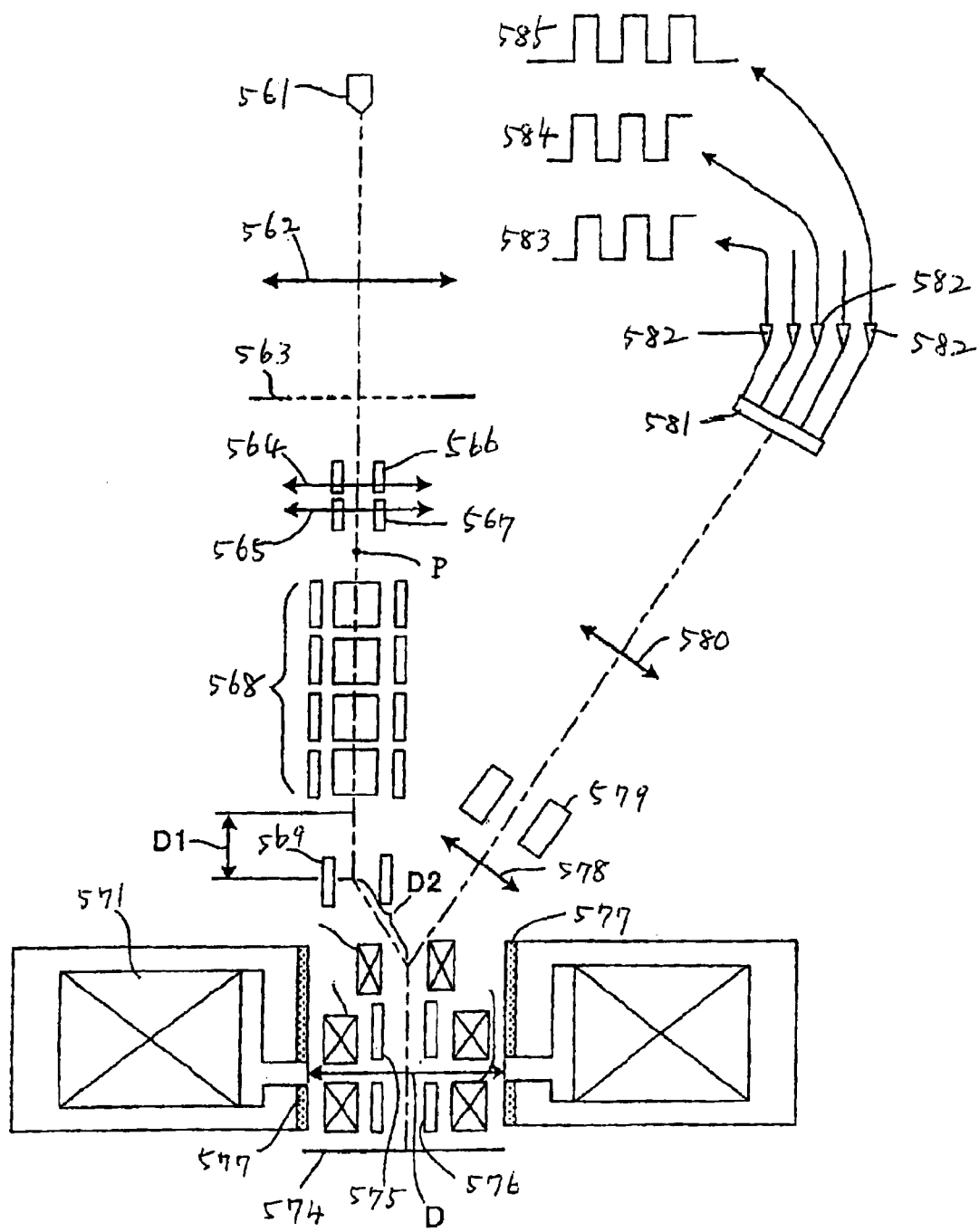

An explanatory diagram illustrating an electron beam scanning method in the sample evaluation apparatus illustrated in FIG. 58.

FIG. 60

An explanatory diagram illustrating an electro-optical system of a sample evaluation apparatus which is a ninth embodiment of the electron beam apparatus according to the present invention.

FIG. 61

An explanatory diagram illustrating an electro-optical system of a transfer apparatus which is a tenth embodiment of the electron beam apparatus according to the present invention.

FIG. 62

(A) and (B) are a plan view and a cross-sectional view of a chromatic aberration corrector which has a plurality of optical axes, which can be employed in a multi-optical-axis sample evaluation apparatus.

FIG. 63

An explanatory diagram illustrating an electro-optical system of a sample evaluation apparatus which is an eleventh embodiment of the electron beam apparatus according to the present invention.

FIG. 64

An explanatory diagram illustrating electro-optical system of a sample evaluation apparatus which is a twelfth embodiment of the electron beam apparatus according to the present invention.

FIG. 65

(A) is a diagram generally illustrating the configuration of a thirteenth embodiment of the electron beam apparatus according to the present invention, and (B) is a plan view of an NA aperture plate in (A).

FIG. 66

(A) a diagram generally illustrating the configuration of a fourteenth embodiment of the electron beam apparatus according to the present invention, and (B) is a diagram for describing the configuration of four axial chromatic aberration correction lenses in (B).

FIG. 67

A diagram generally illustrating the configuration of a fifteenth embodiment of the electron beam apparatus according to the present invention.

FIG. 68

A diagram generally illustrating the configuration of a sixteenth embodiment of the electron beam apparatus according to the present invention.

FIG. 69

Figure 68:
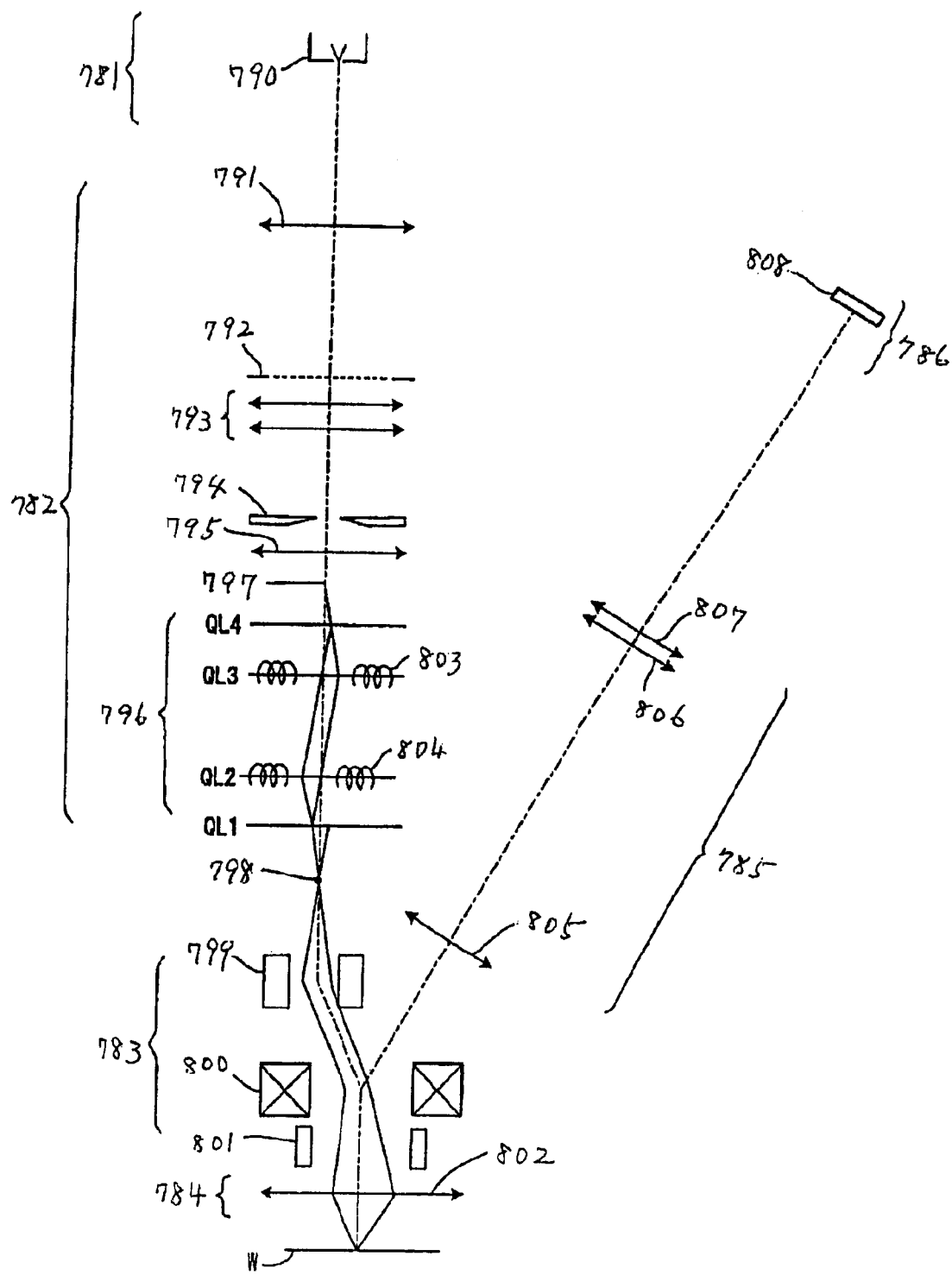

A beam arrangement diagram indicating a position which is irradiated with each beam on the surface of a sample in the electron beam apparatus of FIG. 68.

FIG. 70

A diagram generally illustrating the configuration of a seventeenth embodiment of the electron beam apparatus according to the present invention.

FIG. 71

Figure 70:
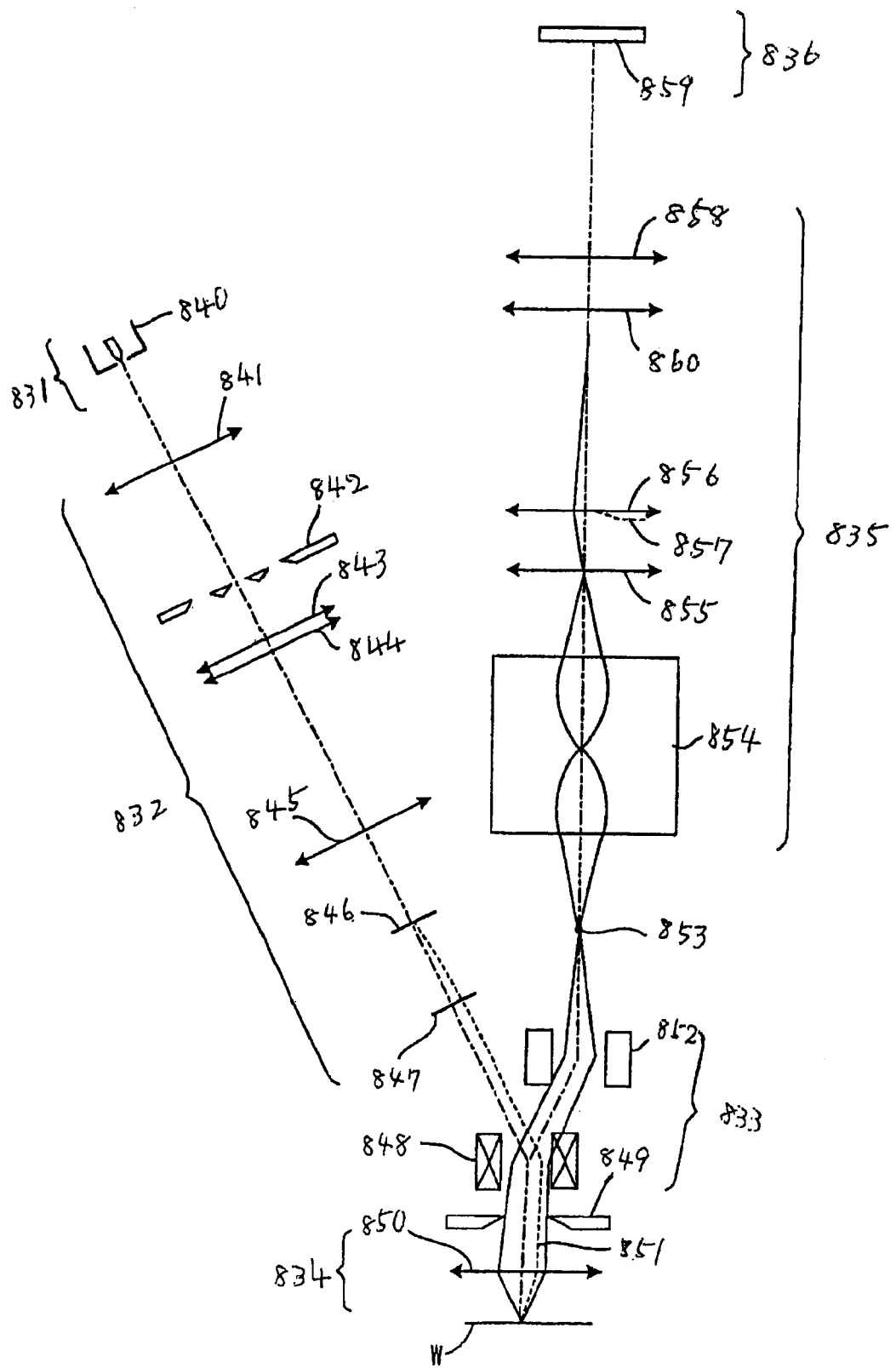

A diagram illustrating an exemplary configuration of an axial chromatic aberration correction lens in FIG. 70.

BEST MODE FOR CARRYING OUT THE INVENTION

Figure 1A:
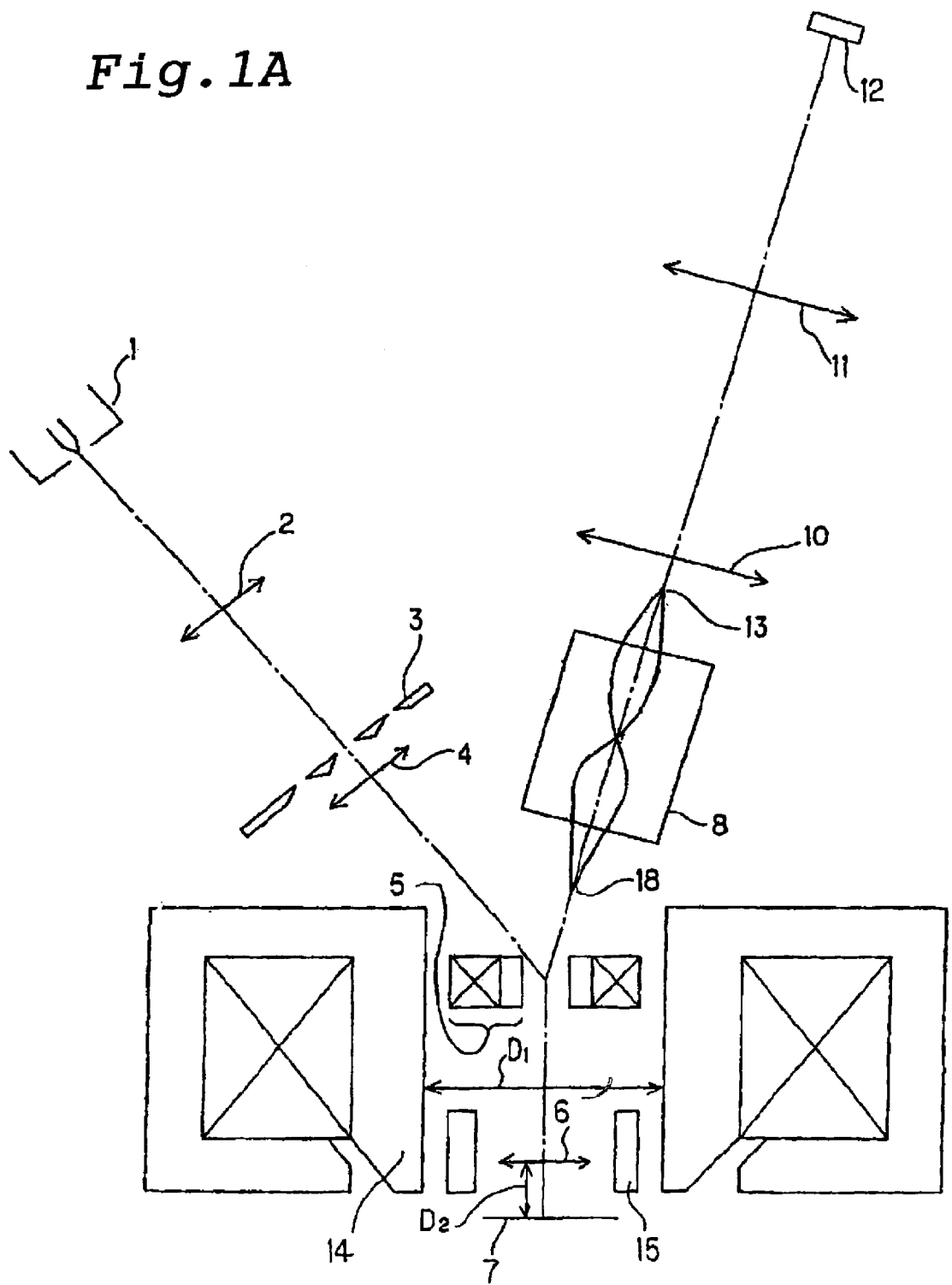
FIG. 1A
An explanatory diagram illustrating an electro-optical system of an electron beam apparatus according to a first embodiment of the present invention.

FIG. 1A is an explanatory diagram illustrating an electro-optical system of an electron beam apparatus which comprises a projection electro-optical system according to a first embodiment of the present invention. As illustrated in FIG. 1A, In this electron beam apparatus, electron beams emitted from an electron gun 1 are formed into a rectangular shape through a condenser lens 2, a forming lens 4, and an aperture plate formed with multiple apertures, and the resulting electron beams are deflected by an ExB separator 5 so as to be perpendicular to the surface of a sample 7, and focused on the surface of the sample 7 by an objective lens 6, such that the surface of the sample is scanned by each electron beam in a rectangular shape. On the other hand, secondary electrons emitted from the surface of the sample 7 by this irradiation create an enlarged image at a position 18 by the objective lens 6, and form an enlarged image at a focal point 13 in front of a magnification lens 10 by a Wien filter 8 including a multi-pole lens.

In this event, axial chromatic aberration can be eliminated at the focal point 13 by the objective lens 6 and Wien filter 8 without changing the position of the focal point 13. Specifically, the objective lens 6, which is an axially symmetric lens, generates positive axial chromatic aberration, while the Wien filter 8 generates negative axial chromatic aberration, where the absolute values of the positive and negative axial chromatic aberration can be made equal by adjusting the positions of these lenses and voltages applied to electrodes. In this way, the positive axial chromatic aberration generated by the objective lens 6 can be canceled out by the negative axial chromatic aberration generated by the Wien filter 8. In this regard, the axial chromatic aberration at the focal point 13 may be adjusted to be a negative value near zero, thereby making it possible to cancel small positive axial chromatic aberration generated by the magnification lenses 10 and 11.

An enlarged image focused at the focal point 13 is further passed through the magnification lens 10 to generate an enlarged image in front of the magnification lens 11. Then, the enlarged image is focused on a detection plane of a detector 12 by the magnification lens 11. The detector 12 generates an optical signal corresponding to the enlarged image formed thereon, and propagates the optical signal to a CMOS image sensor (not shown) of 8×8, 12×12 or the like through an optical fiber (not shown). The CMOS image sensor transduces the optical signal to an electric signal which is then processed by an image data processing unit (not shown).

While axial chromatic aberration accounts for a majority of all aberration in an optical system, the electron beam apparatus illustrated in FIG. 1 can adjust the enlarged image formed at the focal point 13 such that the axial chromatic aberration is substantially zero or a slight negative value, thus making it possible to improve the transmittance of secondary electrons because the aperture angle can be increased while restraining the aberration to a certain value or less.

The electron beam apparatus illustrated in FIG. 1A is configured not only to eliminate or reduce the axial chromatic aberration but also to reduce off-axis aberration. Specifically, the objective lens 6 is composed of a magnetic lens 14 having a magnetic gap close to a sample 7-1, and an axially symmetric lens 15, as illustrated in FIG. 1A, and a Bore diameter D1 of the magnetic lens 14 is set to be larger than the visual field diameter by a factor of 50 or more. Also, the off-axis aberration can be reduced by setting the distance D2 between the main surface of the objective lens 6 and the surface of the sample 7 to be 10 mm or more.

It should be noted that in the electron beam apparatus illustrated in FIG. 1A, alignment deflectors may be provided at two or more stages between the forming lens 4 and ExB separator 5, which form part of a primary electro-optical system.

Figure 1B:
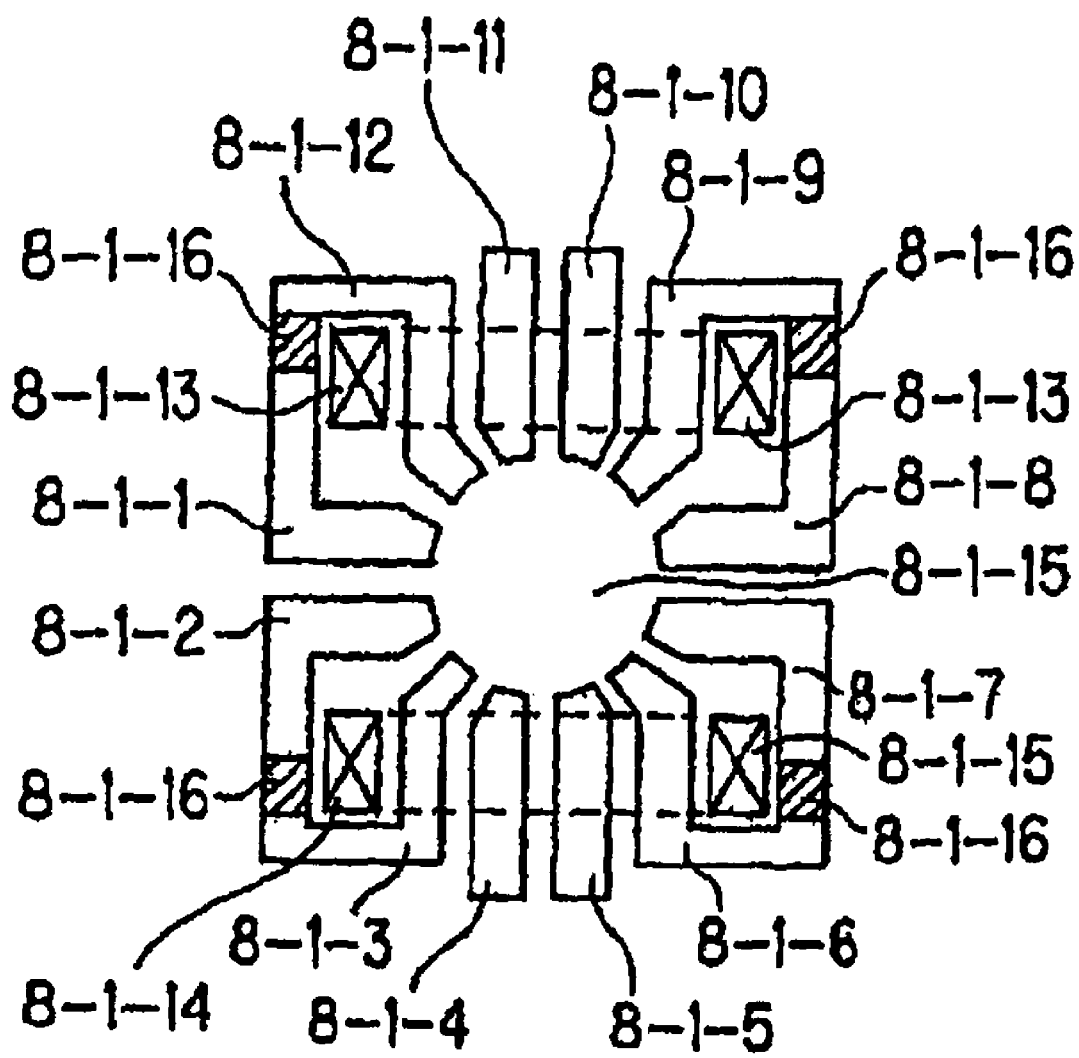
FIG. 1B
A cross-sectional view of a Wien filter in the electron beam apparatus illustrated in FIG. 1A.

FIG. 1B illustrates a cross-sectional view of the Wien filter 8. In this Wien filter, 12 electrodes 8-1-1-8-1-12 are arranged around an optical axis 8-1-15, and can be applied with independent voltages from a power supply, respectively. Reference numeral 8-1-16 designates an insulating spacer for independently supplying voltages to the respective electrodes. Then, by applying currents to coils 8-1-13 and 8-1-14, it is possible to generate a magnetic field which satisfies the Wien condition. Electron beams originating from an image point 18-1 of a secondary electro-optical system is focused at the center 19-1 of the Wien filter 8-1, and again focused at a position 13-1 outside the Wien filter 8 by appropriately setting the magnetic field and the voltages applied to the electrodes. By thus focusing the electron beams twice, the axial chromatic aberration presents a negative value with small tertiary aberration over the visual field. In this regard, a description is found in D. Ionovicin et. al, Rev. Sci. Instrum, Vol. 75, No. 11, November, 2004.

Figure 2:
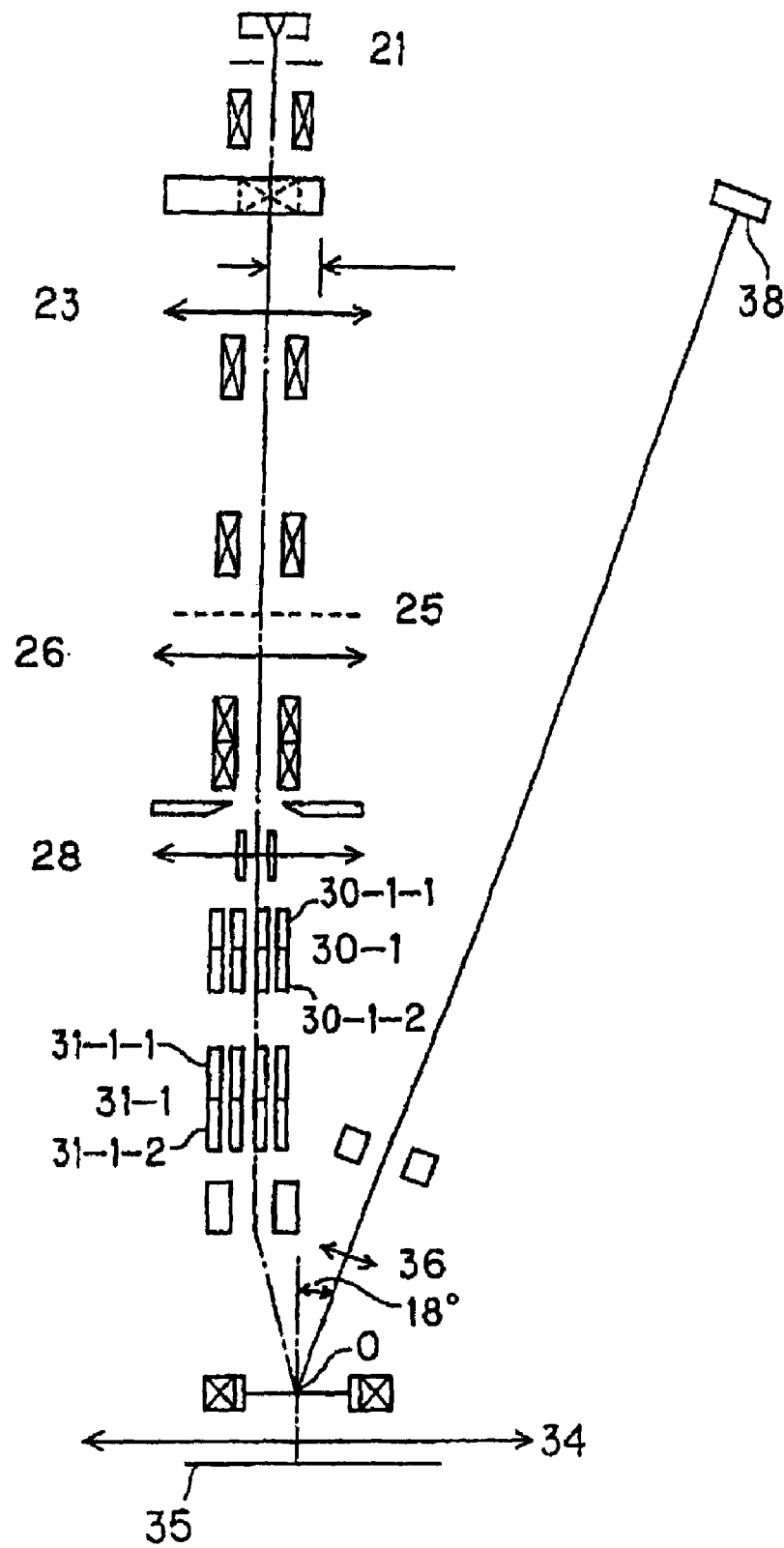
FIG. 2
An explanatory diagram illustrating an electro-optical system of an electron beam apparatus according to a second embodiment of the present invention.

FIG. 2 illustrates an electro-optical system of an electron beam apparatus which comprises a projection secondary electron detection system according to a second embodiment of the present invention. In this electron beam apparatus, electron beams emitted from electron gun 21 are converged by a condenser lens 23, and irradiated to an aperture plate which has multiple apertures. Multiple beams separated and formed by aperture plate 25 form a first reduced image through a forming lens 26 and a reducing lens 28, and further reduced by an objective lens 34 to from a reduced image on a sample 35. In this event, quadrupole lenses 30-1-1, 30-1-2, 31-1-1, 31-12 are provided at four stages between the position at which the first reduced image is formed and the objective lens 34, where these quadrupole lenses can correct axial chromatic aberration caused by the objective lens 34.

Electron beams by secondary electrons emitted from the sample 35 form a first enlarged image in front of a magnification lens 36, and is further enlarged by the magnification lens 36 too form an image which is approximately 100 times larger than the image on the sample 35 on a detection plane of a detector 38. The detector 38 generates an optical signal corresponding to the enlarged image formed thereon, and propagates the optical signal to PMT (not shown) through an optical fiber. The PMT transduces the optical signal to an electric signal which is then processed by an image data processing unit (not shown).

In the electron beam apparatus illustrated in FIG. 2, a Wien filter including a multi-pole lens can be provided in the primary electro-optical system instead of the quadrupole lens.

Figure 3:
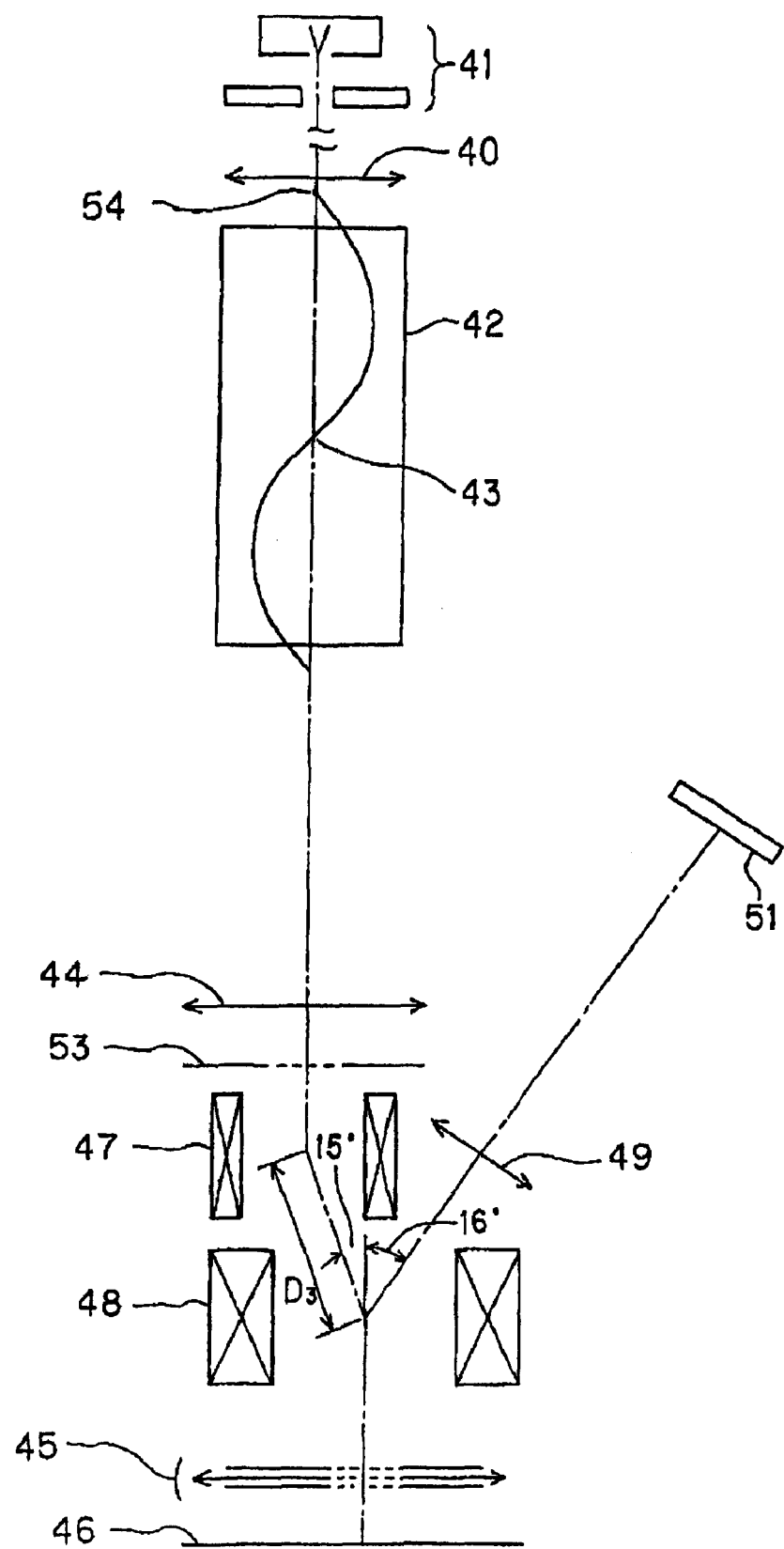
FIG. 3
An explanatory diagram illustrating an electro-optical system of an electron beam apparatus according to a third embodiment of the present invention.

FIG. 3 illustrates an electro-optical system of an electron beam apparatus according to a third embodiment of the present invention. In this electron beam apparatus, electron beams emitted from an electron gun 41 form a reduced image at a position 54 through an axially symmetric lens 40 which is an electromagnetic lens, and electron beams diverged from the position 54 is focused at a position 43 by a Wien filter 42 which converges twice. Further, electron beams diverged from the position 43 are made to be electron beams parallel with the optical axis by an axially symmetric lens 44. In this embodiment, the axially symmetric lens 44 is employed at one stage, but the axially symmetric lenses may be at two or more stages. The electron beams parallel with the optical axis are converged onto a sample 46 through a deflector 47, a beam separator 48 including an electromagnetic deflector, and multi-aperture lens 45 as a plurality of electron beams.

It should be noted that since the electron gun has a cross-over, the size of which is approximately 50 μmφ, a cross-over image of 25 nmφ, must be created for generating electron beams of 50 nmφ, and therefore the diameter φ of the electron beams must be reduced approximately by a factor of 2000. The scaling factor of 1/2000 can be accomplished by reducing the diameter approximately by a factor of 38 by the axially symmetric lens 40 in front of the position 54, and further reducing the diameter approximately by a factor of 60 by the multi-aperture lens 45 at the final stage, so that multiple electron beams of 50 nmφ can be generated including aberration. Also, when a multi-aperture plate 53 is provided behind the axially symmetric lens 44, an aperture angle is reduced to reduce the axial chromatic aberration, with the result that multiple electron beams of 50 nmφ can be generated with a scaling factor of approximately 1/1800. In this event, since the optical path length can be reduced, it is possible to reduce blurs due to the space charge effect.

In addition, the electron beam apparatus of the third embodiment comprises the Wien filter 42 for correcting the axial chromatic aberration between the two axially symmetric lenses 40, 44, as described above. The Wien filter 42 has a configuration similar to the configuration described with reference to FIG. 1B, and the multi-aperture plate 53 can be increased in diameter by correcting the axial chromatic aberration by the Wien filter, so that multiple electron beams can be provided with a large current value. Quadrupole lenses at four stages may be provided instead of the Wien filter.

Figure 4:
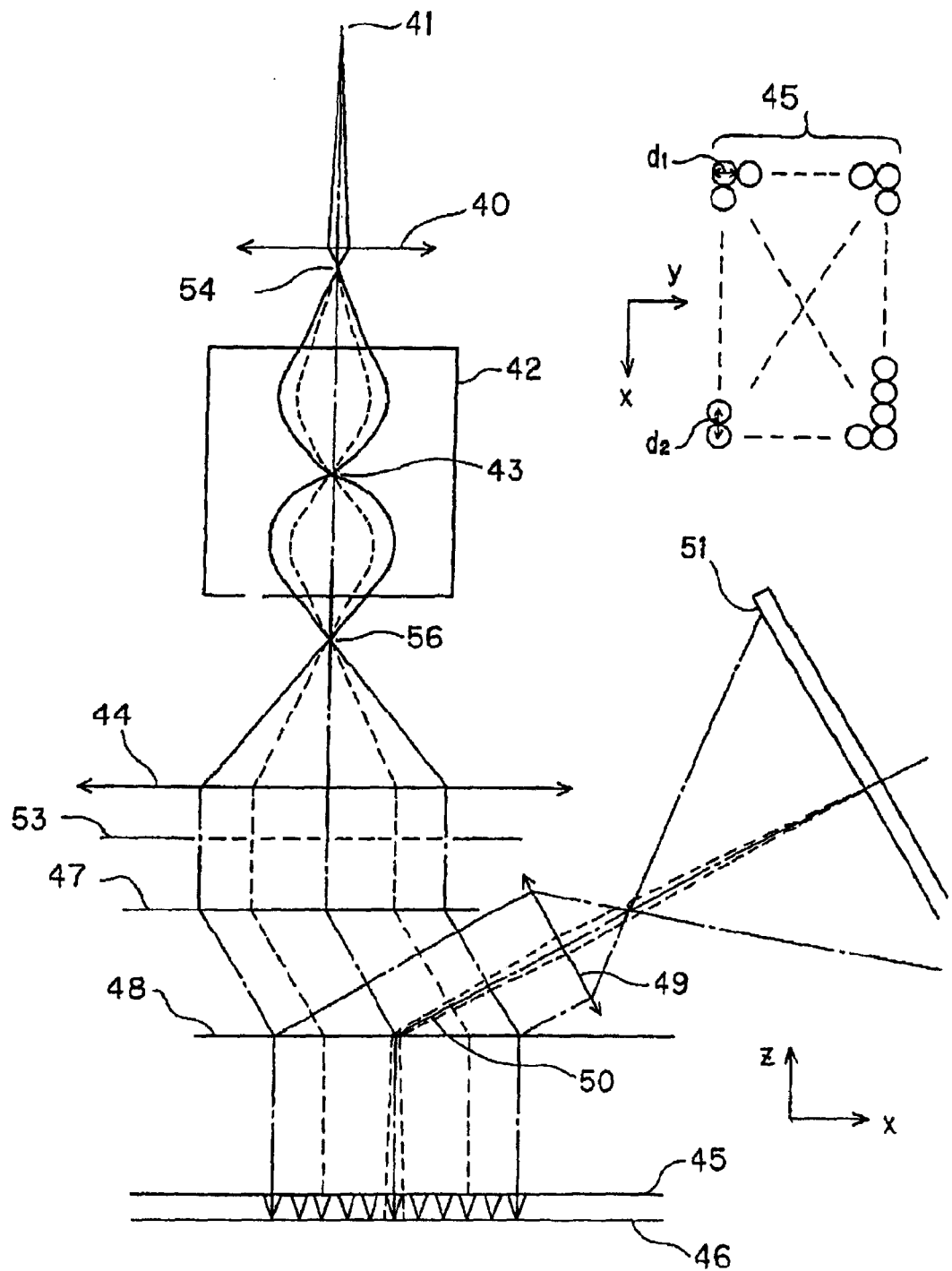
FIG. 4
An explanatory diagram showing an optical path in the electron beam apparatus illustrated in FIG. 3.

The multi-aperture lens 45 is made of three metal plates stacked one on another, and is formed with apertures in m rows×n columns extending through these metal plates, as illustrated in FIG. 4. The central metal plate is applied with a positive high voltage. In the aperture pattern illustrated in FIG. 4, a simulation has shown that the apertures are not affected by their adjacent apertures when the ratio d1/d2 is set to 2/3-4/5, where d1 is the diameter of the apertures, and d2 is the pitch of the apertures (center-to-center distance between two adjacent apertures).

Here, the optical axis from the electron gun 41 to the deflector 47 is intentionally offset from the optical axis of the multi-aperture lens 45, such that they are aligned to the position of the electromagnetic beam separator 48 by the deflector 47. The amount of offset between the two optical axes (distance between the two optical axes) is set to satisfy the relationship:

$$\text{Amount of Offset} = D3 \cdot \tan^{-1} 15°$$

where D3 is the distance between the center of deflection of the deflector 47 and the center of deflection of the electromagnetic beam separator 48. In this example, the amounts of deflection are set by the beam separator 48 comprised of an electromagnetic deflector such that the primary electron beams are deflected by 15°, and the secondary electrons by 16°, but may be set to values other than them.

Since the secondary electrons are deflected by the beam separator 48 comprised of an electromagnetic deflector in a direction opposite to the direction in which the primary electrons are deflected, the secondary electrons propagate in a direction opposite to the direction of the primary electron beams with respect to the right direction, i.e., the optical axis of the lens 45 in the figure, so that the second electrons are separated from the primary electron beams. Since the secondary electron beams form a sample image near the deflection main surface 50 (FIG. 4) of the deflector 47, small deflection chromatic aberration affects on the secondary electrons. The secondary electron beams separated from the primary electron beams by the beam separator 48 form an enlarged image on an area detector 51 through a magnification lens 49, and detected. Then, an image of the surface of the sample is synthesized by an image data processing unit (not shown) with reference to information on spots on the sample 46 irradiated with the multiple primary electron beams. When the magnification is not sufficient, magnification lenses may be provided at a larger number of stages in the secondary optical system.

The electron beam apparatus illustrated in FIG. 3 will be described in greater detail with reference to FIG. 4 which shows the optical path in the apparatus. Electron beams diverged from the cross-over formed by the electron gun 41 are narrowed down and increased in divergence angle by the axially symmetric lens 40 which has a short focal distance, and are directed into the Wien filter 42 and form a cross-over at the center 43 of the Wien filter 42. After exiting the Wien filter 42, the electron beams form a cross-over at a position 56, impinges on the axially symmetric lens 44 which transforms the electron beams into collimated beams parallel with the optical axis.

The collimated beams have their aperture angle controlled by multiple apertures of the multi-aperture plate 53, so that the axial chromatic aberration is kept small. Then, the collimated beams are deflected by 15° by the electromagnetic deflector 47, and deflected by 15° in the opposite direction by the beam separator 48 comprised of an electromagnetic deflector. This is performed by supplying these two deflectors with deflection signals which have the same absolute value but are opposite in deflection direction. In this way, the multiple electron beams are again perpendicular to the z-axis direction, i.e., to the surface of the sample 46. Next, the multiple electron beams are irradiated to the sample 46 through the multi-aperture lens 45, but no deflection chromatic aberration is generated because the deflectors 47, 48 deflect the electron beams by the same angle in the opposite directions to each other. Further, if an alignment signal is multiplexed on the deflector 47 or 48, the alignment of the multi-aperture lens 45 can be maintained to the multiple apertures of the multi-aperture plate 53.

Secondary electrons emitted from the sample 46 are converged into a small beam bunch by an acceleration electric field applied thereto, and pass through the objective lens 45 without substantially causing any loss. Then, the secondary electrons are deflected toward the secondary optical system by the beam separator 48 which is an electromagnetic deflector to impinge on the magnification lens 49. In FIG. 4, while the trajectory of secondary electron beams corresponding to one lens at the center of multi-aperture lens 45, among a plurality of secondary electron beams from the sample 46, is represented by a dotted line, but the secondary electron beams on the trajectory focuses at a position 50 after they have passed through the beam separator 48. Then, they form an enlarged image on the detection plane of the detector 51 by the action of the magnification lens 49. The detector 51 generates an optical signal corresponding to the enlarged image formed thereon, and propagates the optical signal to PMT (not shown) of 8×8, 12×12 or the like through an optical fiber. The PMT transduces the optical signal to an electric signal which is then processed by an image data processing unit (not shown).

A voltage applied to each electrode of the Wien filter and a current applied to a coil of the same may be set with the aid of a simulation such that the axial chromatic aberration is eliminated in consideration of the position 54 of the cross-over, the axial position of the Wien filter 42, the magnitude of the axial chromatic aberration to be corrected, beam energy and the like.

In the electron beam apparatuses of the first to third embodiments described above, the quadrupole lenses may be composed of multi-pole lenses other than the quadrupole ones. Particularly, quadrupole to twelve-pole lenses are preferably used, and when they are configured in four stages, this is optimal because the former half of the beam trajectory can be made point symmetric to the latter half of the same to prevent secondary aberration.

Now, a description will be given of advantageous effects resulting from the elimination of the axial chromatic aberration using multi-pole lenses at a plurality of stages in an electron beam apparatus which comprises a projection electro-optical system.

In the projection electron beam apparatus, a blur σc due to the Coulomb effect can be expressed in the following manner:

$$\sigma c = I \cdot L(\alpha \cdot V^{3/2})$$

where I: Electron Beam Current;
L: Optical Path Length;
α: aperture angle; and
V: electron beam energy.

Figure 5:
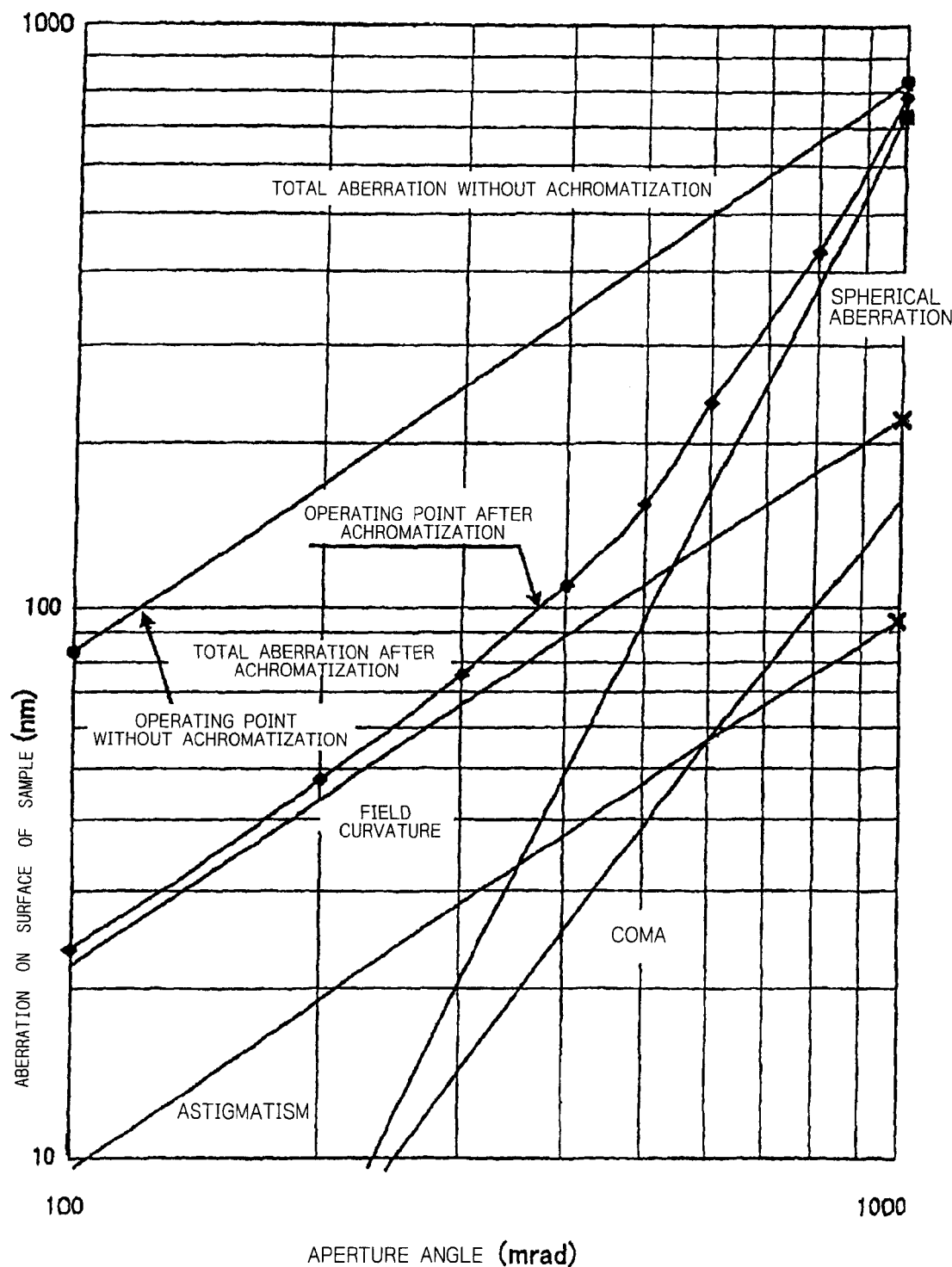
FIG. 5
A graph for describing advantageous effects resulting from removal of axial chromatic aberration in a projection electron beam apparatus.

FIG. 5 shows the result of simulation which was made n the relationship between aberration (nm) on the surface of a sample and the aperture angle α. A lens used in this simulation is a tablet type which employs two stages of electrostatic lenses and eliminates chromatic aberration of magnification. Also, a voltage applied to the lens was set such that the electric field strength is approximately 1.5 kV/mm on the surface of the sample. According to the result of the simulation shown in FIG. 5, the aperture angle α can be improved approximately by a factor of three when axial chromatic aberration is removed. In an electron beam apparatus which comprises a projection electro-optical system, axial chromatic aberration is predominant among aberration on the surface of the sample, and when the aberration on the surface of the sample is assumed to be constant, the aperture angle α can be improved approximately by a factor of three without removing other aberration, if the axial color aberration is removed.

In the aforementioned equation, assuming that the blur δc is constant, the beam current I can also be increased by a factor of three when the aperture angle α is increased by a factor of three, and the transmittance is increased by a factor of nine because it is a square of the aperture angle. Accordingly, since the beam current is three times larger and the transmittance is nine times larger, the throughput, i.e., inspection speed, which is represented by a product of them, can be improved by a factor of 27. The inspection speed can be further improved by employing $LaB_6$ for an electron gun to provide a multi-beam electron beam apparatus as in the second embodiment. A largely improved inspection speed is extremely important in the electron beam apparatus which comprises a projection electro-optical system.

In this regard, since SEM (scanning electron microscope) includes a scanning deflector disposed behind a multi-pole lens, electron beams pass only on the optical axis in the multi-pole lens disposed in front of the deflector irrespective of deflection scanning of the deflector. Accordingly, the axial chromatic aberration can be readily corrected by the multi-pole lens. On the other hand, in the electron beam apparatus which comprises a projection electro-optical system, aberration must be reduced not only for an image on the optical axis but also for an image spaced apart from the optical axis, so that it has been thought that the axial chromatic aberration is hard to correct only by simply using a multi-pole lens. Also, no recognition has been gained that a majority of aberration occurring in the electron beam apparatus comprising a projection electro-optical system is axial chromatic aberration. The inventors found through actual use tests and simulations, which had been made using a variety of parameters, that the axial chromatic aberration can also be favorably corrected using a multi-pole lens even in the electron beam apparatus which comprises a projection electro-optical system, and can thus largely improve the throughput, as described above.

Next, a description will be given of the general configuration of an inspection system for evaluating semiconductor wafers, into which the electron beam apparatus of the present invention can be incorporated for use therewith.

Figure 6:
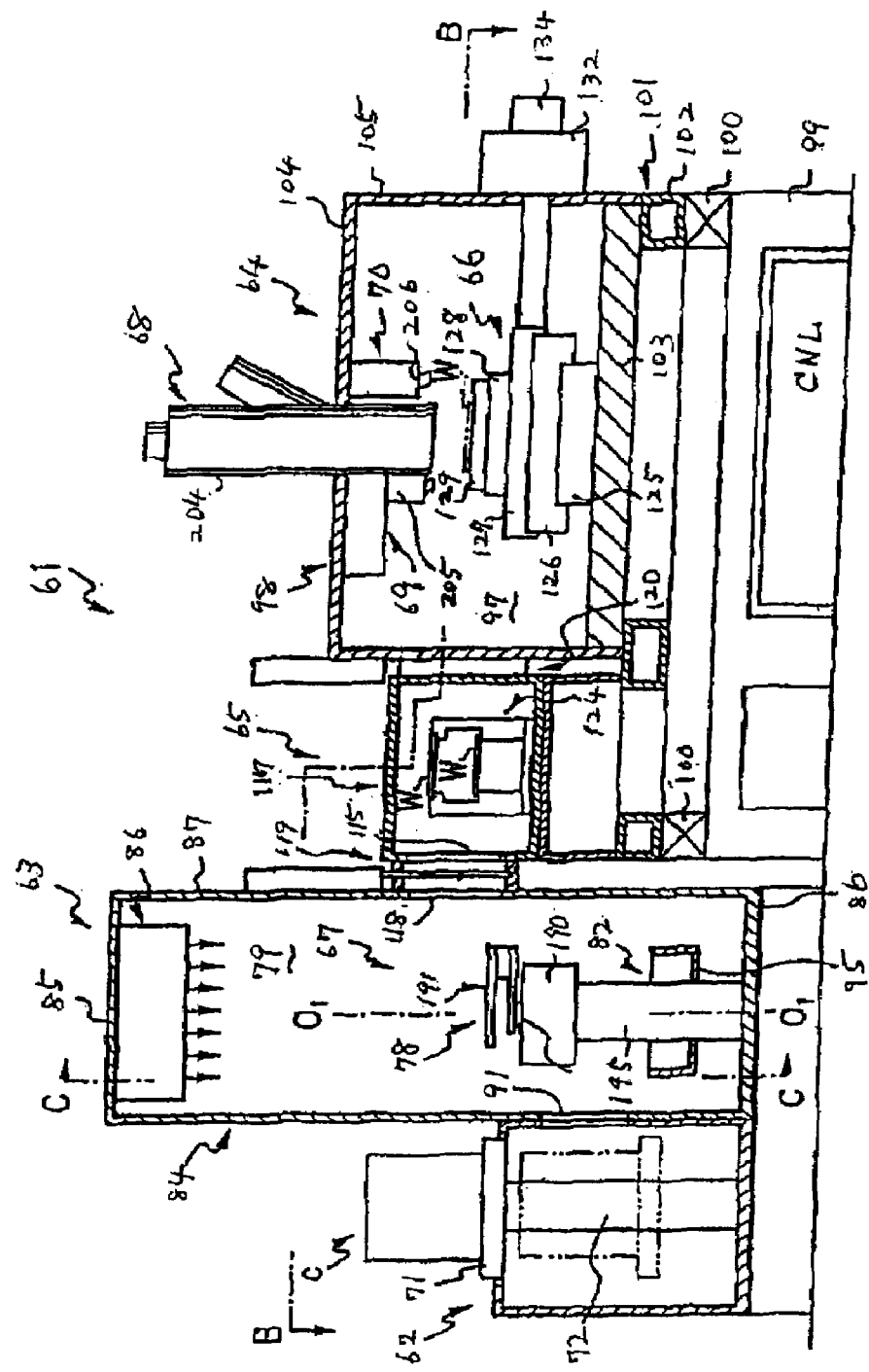
FIG. 6
An explanatory diagram illustrating a sample defect detection system to which the electron beam apparatus of the present invention can be applied.
Figure 7:
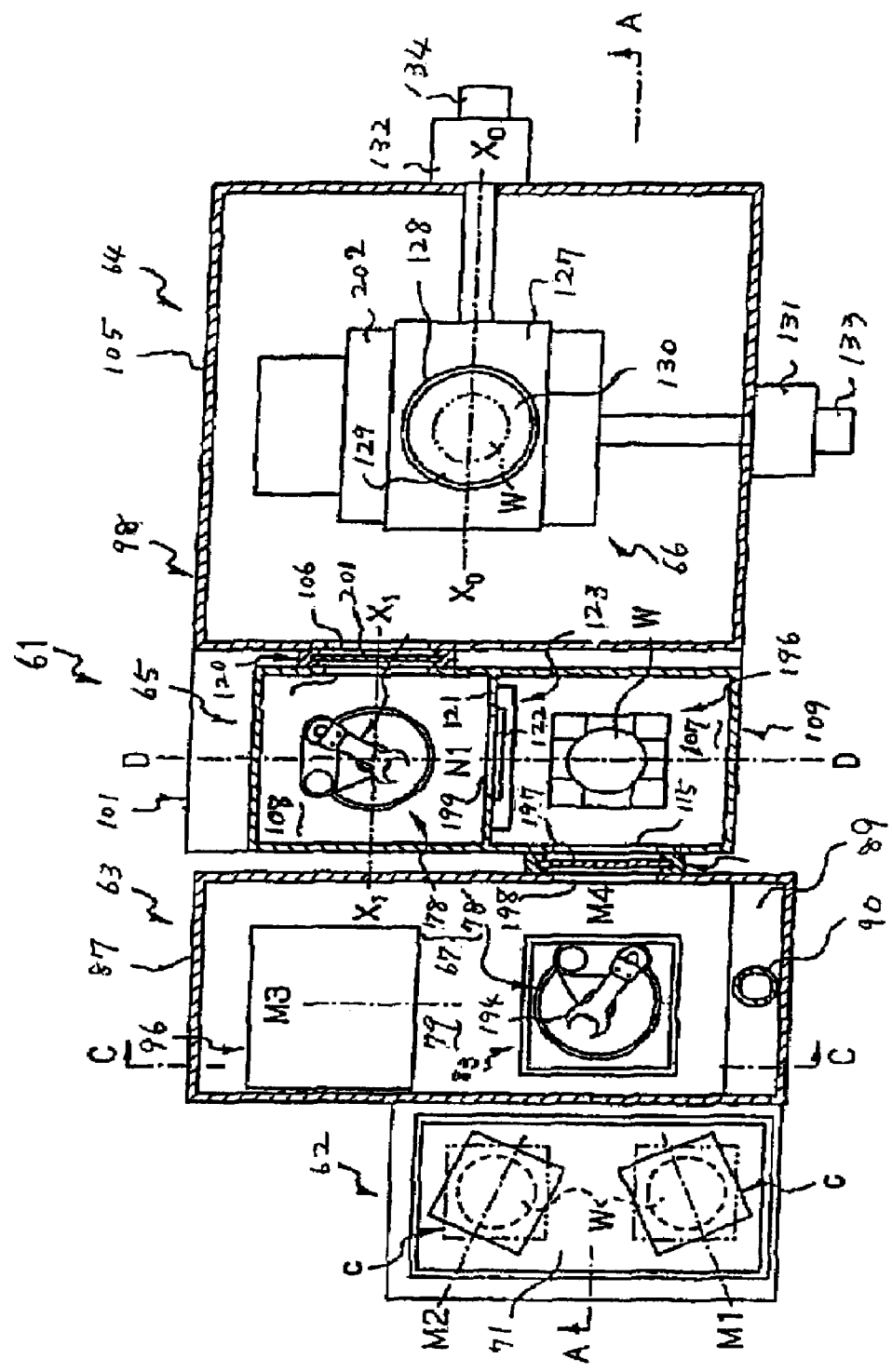
FIG. 7
A plan view of main components of the inspection system illustrated in FIG. 6, taken along a line B-B in FIG. 6.

FIGS. 6 and 7 are a front elevation and a plan view illustrating main components of an inspection system 61. The inspection system 61 comprises a cassette holder 62 for holding a cassette which stores a plurality of wafers; a mini-environment device 63; a main housing 64; a loader housing 65 disposed between the mini-environment device 63 and main housing 64 for defining two loading chambers; a stage apparatus 66 disposed within the main housing 64 for carrying a wafer W which is a wafer thereon for transportation; a loader 67 for loading a wafer from the cassette holder 62 onto the stage apparatus 66 disposed within the main housing 64; and an electro-optical system 68 attached to the main housing 64. These components are laid out in a positional relationship as illustrated in FIGS. 6 and 7. The electron beam apparatus of the present invention described above is incorporated as the electro-optical system 68.

The inspection system 61 also comprises a pre-charge unit 69 disposed in the main housing 64 in vacuum; a potential application mechanism for applying a potential to a wafer; an electron beam calibration mechanism, and an optical microscope 206 which forms part of an alignment controller 70 (shown in FIG. 26) for positioning a wafer on the stage apparatus 66. The inspection system 61 further comprises a control device CNL for controlling operations of these components.

In the following, each of the main components (sub-systems) of the inspection system 61 will be described in detail in regard to the configuration.

Cassette Holder 62

The cassette holder 62 is configured to hold a plurality (two in this embodiment) of cassettes c (for example, closed cassettes such as SMIF, FOUP manufactured by Assist Co.) in which a plurality (for example, twenty-five) wafers are placed side by side in parallel, oriented in the vertical direction. The cassette holder 62 can be arbitrarily selected for installation adapted to a particular loading mechanism. Specifically, when a cassette is automatically loaded into the cassette holder 62 by a robot or the like, the cassette holder 62 having a structure adapted to the automatic loading can be installed. When a cassette is manually loaded into the cassette holder 62, the cassette holder 62 having an open cassette structure can be installed. In this embodiment, the cassette holder 62 is a type adapted to the automatic cassette loading, and comprises, for example, an up/down table 71, and an elevating mechanism 12 for moving the up/down table 71 up and down. The cassette c can be automatically loaded onto the up/down table 71 in a state indicated by chain lines in FIG. 7. After the loading, the cassette c is automatically rotated to a state indicated by solid lines in FIG. 7 so that it is directed to the axis of pivotal movement of a first carrier unit within the mini-environment chamber 20. In addition, the up/down table 71 is moved down to a state indicated by chain lines in FIG. 6.

Figure 8:
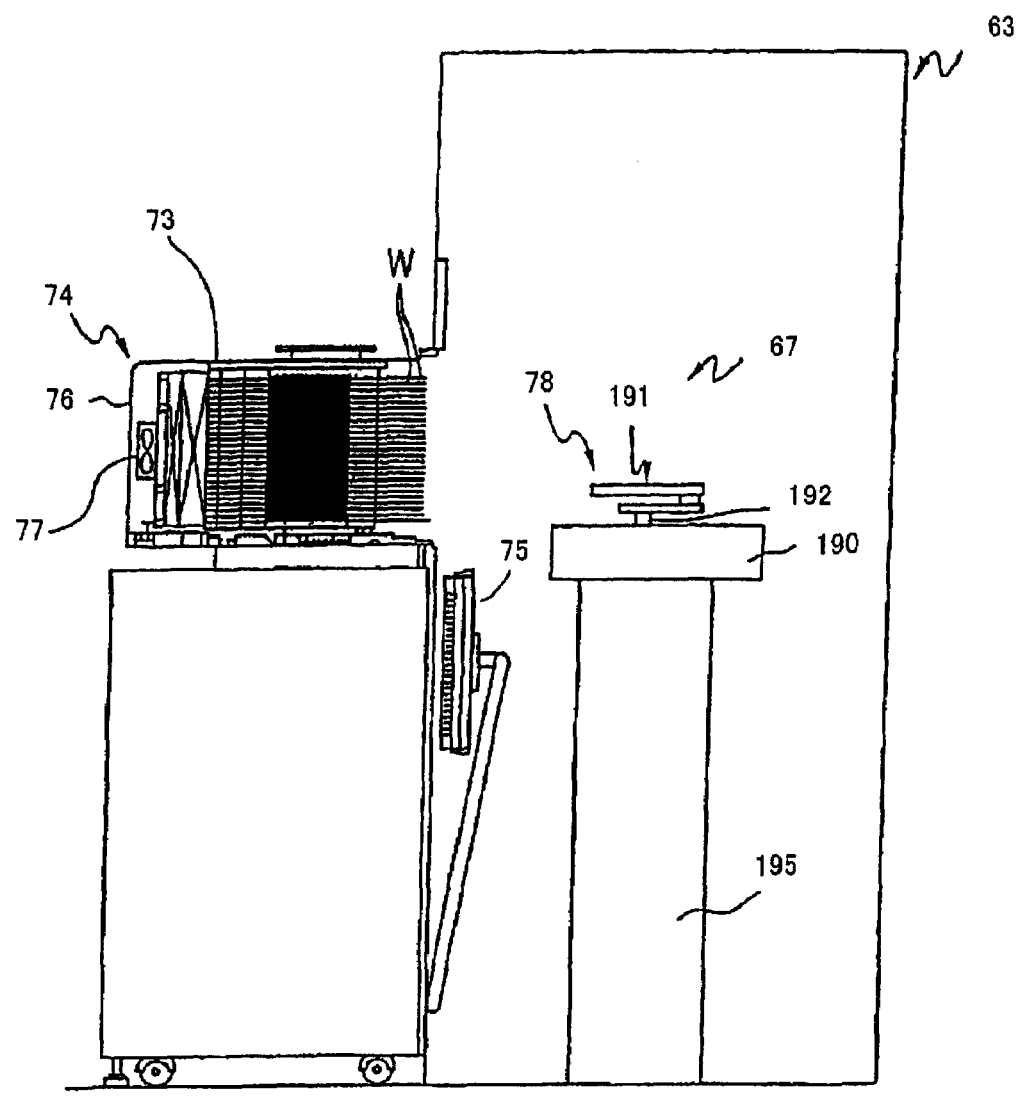
FIG. 8
A diagram showing the relationship between a wafer carrying box and a loader of the inspection system illustrated in FIG. 6.

In another embodiment, as illustrated in FIG. 8, a plurality of 300 mm wafers W are contained in a slotted pocket (not shown) fixed to the inner surface of a box body 73 for carriage and storage. This wafer carrying section 74 comprises a box body 73 of a squared cylinder, a wafer carrying in/out door 75 connected to the box body 73 and an automatic opening apparatus for a door at a substrate carrying in/out aperture positioned at one side of the box body 73 and capable of mechanically opening and closing the aperture, a lid 76 positioned in opposition to the aperture for covering the aperture for the purpose of detachably mounting filers and fan motors, and a slotted pocket 77 for holding a wafer W. In this embodiment, the wafers are carried in and out by means of a robot type carrying unit 78 of the loader 67.

It should be noted that wafers accommodated in the cassette c are subjected to testing which is generally performed after a process for processing the wafers or in the middle of the process within semiconductor manufacturing processes. Specifically, accommodated in the cassette are wafers which have undergone a deposition process, CMP, ion implantation and so on; wafers each formed with wiring patterns on the surface thereof; or wafers which have not been formed with wiring patterns. Since a large number of wafers accommodated in the cassette c are spaced from each other in the vertical direction and arranged side by side in parallel, and the first carrier unit has an arm which is vertically movable, a wafer at an arbitrary position can be held by the first carrier unit which will be described later in detail.

Mini-Environment Device 63

Figure 9:
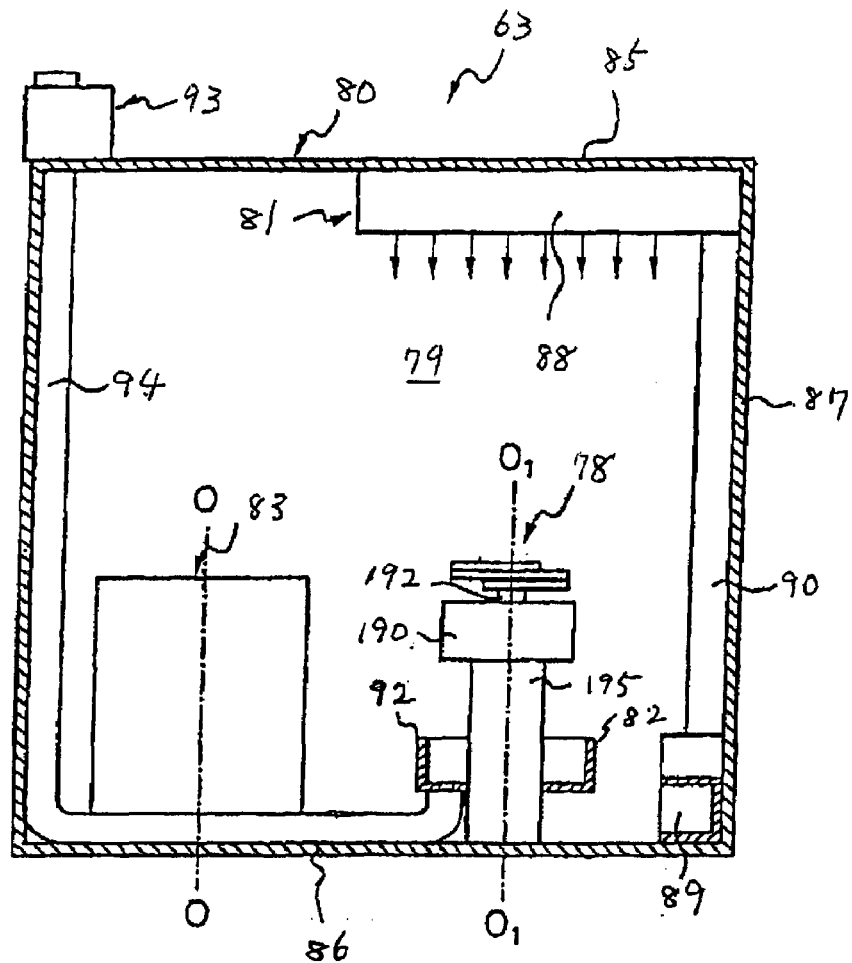
FIG. 9
A cross-sectional view illustrating a mini-environment device of the test system illustrated in FIG. 6, taken along a line C-C in FIG. 6.

FIG. 9 is a front elevation illustrating the mini-environment device 63 in a direction different to that in FIG. 7. As illustrated in FIG. 9 as well as FIGS. 6 and 7, the mini-environment device 63 comprises a housing 80 defining a mini-environment space 79 that is controlled for the atmosphere; a gas circulator 81 for circulating a gas such as clean air within the mini-environment space 79 to execute the atmosphere control; a discharger 82 for recovering a portion of air supplied into the mini-environment space 79 to discharge it; and a prealigner 83 for roughly aligning a sample, i.e., a wafer placed in the mini-environment space 79.

The housing 80 has a top wall 221, bottom wall 222, and peripheral wall 223 which surrounds four sides of the housing 80, to provide a structure for isolating the mini-environment space 79 from the outside. For controlling the atmosphere in the mini-environment space 79, as illustrated in FIG. 9, the gas circulator 23 comprises a gas supply unit 88 attached to the top wall 85 within the mini-environment space 79 for cleaning a gas (air in this embodiment) and delivering the cleaned gas downward through one or more gas nozzles (not shown) in laminar flow; a recovery duct 89 disposed on the bottom wall 96 within the mini-environment space for recovering air which has flown down to the bottom; and a conduit 90 for connecting the recovery duct 89 to the gas supply unit 88 for returning recovered air to the gas supply unit 88.

The laminar downward flow, i.e., down-flow of cleaned air is mainly supplied such that the air passes a carrying surface formed by the first carrier unit, later described, disposed within the mini-environment space 79 to prevent particle particles, which could be produced by the carrier unit, from attaching to the wafer. An access port 91 is formed in a portion of the peripheral wall 87 of the housing 80 that is adjacent to the cassette holder 62.

A discharger 74 comprises a suction duct 92 disposed at a position below the wafer carrying surface of the carrier unit and below the carrier unit; a blower 93 disposed outside the housing 80; and a conduit 94 for connecting the suction duct 92 to the blower 93. The discharger 74 aspires a gas flowing down around the carrier unit and including particle, which could be produced by the carrier unit, through the suction duct 95, and discharges the gas outside the housing 84 through the conduits9 94 and the blower 93.

A prealigner 96 disposed within the mini-environment space 79 optically or mechanically detects an orientation flat (which refers to a flat portion formed along the outer periphery of a circular wafer and hereinafter called as orientation flat) formed on the wafer, or one or more V-shaped notches formed on the outer peripheral edge of the wafer, and previously aligns the position of the wafer in a rotating direction about the axis $O_1$-$O_1$ at an accuracy of approximately ±one degree. The prealigner 96 forms part of a mechanism for determining the coordinates of the wafer which is a wafer, and is responsible for a rough alignment of the wafer.

Main Housing 64

As illustrated in FIGS. 6 and 7, the main housing 64, which defines a working chamber 97, comprises a housing body 98 that is supported by a housing supporting device 101 carried on a vibration blocking device, i.e., vibration isolator 100 disposed on a base frame 99. The housing supporting device 101 comprises a frame structure 102 assembled into a rectangular form. The housing body 98 comprises a bottom wall 103 mounted on and securely carried on the frame structure 102; a top wall 104; and a peripheral wall 105 which is connected to the bottom wall 103 and the top wall 104 and surrounds four sides of the housing body 32. In this embodiment, each of the housing 98 body and the housing supporting device 101 is assembled into a rigid construction, and the vibration isolator 100 blocks vibrations from the floor, on which the base frame 99 is installed, from being transmitted to the rigid structure. A portion of the peripheral wall 105 of the housing 98 that adjoins the loader housing 65 is formed with an access port 106 for introducing and removing a wafer therethrough.

The working chamber 97 is kept in a vacuum atmosphere by a general-purpose vacuum device (not shown). A controller 2 is disposed below the base frame 36 for controlling the operation of the overall inspection system 61.

In the inspection system 61, a variety of housings including the main housing 64 are kept in vacuum atmosphere. A system for evacuating such a housing comprises a vacuum pump, vacuum valve, vacuum gauge, and vacuum pipes, and evaporates the housing such as an electro-optical system portion, detector portion, wafer housing, load lock housing or the like, in accordance with a predetermined sequence. The vacuum valves are adjusted to kept a required vacuum level of the housings. Further, the vacuum levels are always monitored, and when an abnormal vacuum level is detected, an interlock function enables isolation valves to shut dawn the path between chambers or between a chamber and a pumping system to kept the required vacuum level of the housing. As to the vacuum pump, a turbo-molecular pump can be utilized for main evacuation, and a dry pump of a Roots type can be utilized for rough evacuation. The pressure at a test location (electron beam irradiated region) is $10^{-3}$ to $10^{-5}$ Pa. Preferably, pressure of $10^{-4}$ to $10^{-6}$ Pa is practical.

Loader Housing 65

Figure 10:
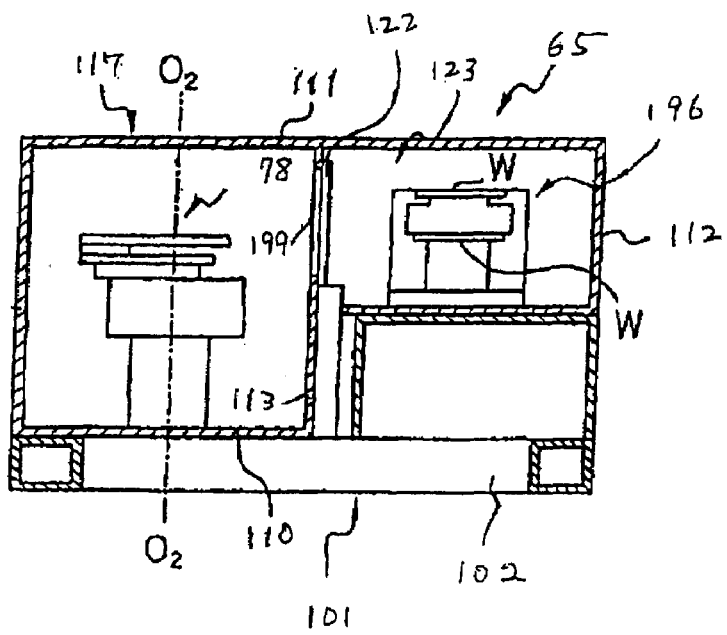
FIG. 10
A diagram illustrating a loader housing of the inspection system illustrated in FIG. 6, taken along a line D-D in FIG. 7.

FIG. 10 shows a front elevation of the loader housing 65, viewed from the direction different to that in FIG. 6. As illustrated in FIG. 10 as well as FIGS. 6 and 7, the loader housing 65 comprises a housing body 109 which defines a first loading chamber 107 and a second loading chamber 108. The housing body 109 comprises a bottom wall 110; a top wall 111; a peripheral wall 1112 which surrounds four sides of the housing body 109; and a partition wall 113 for partitioning the first loading chamber 107 and the second loading chamber 108 to isolate the two loading chambers from the outside. The partition wall 113 is formed with an aperture, i.e., an access port 114 for passing a wafer W between the two loading chambers. Also, a portion of the peripheral wall 112 that adjoins the mini-environment device 63 and the main housing 64, is formed with access ports 115, 116. The housing body 117 of the loader housing 65 is carried on and supported by the frame structure 102 of the housing supporting device 101. This prevents the vibrations of the floor from being transmitted to the loader housing 65 as well.

The access port 115 of the loader housing 65 is in alignment with the access port 118 of the housing 80 of the mini-environment device 63, and a shutter device 119 is provided for selectively blocking a communication between the mini-environment space 79 and the loading chamber 107. Likewise, the access port 116 of the loader housing 65 is in alignment with the access port 106 of the housing body 98, and a shutter device 120 is provided for selectively blocking a communication between the loading chamber 108 and the working chamber 97 in a hermetic manner. Further, the opening formed through the partition wall 121 is provided with a shutter device 123 for closing the opening with the door 122 to selectively block a communication between the first and second loading chambers in a hermetic manner. These shutter devices 119, 120, 122 are configured to provide air-tight sealing for the respective chambers when they are in a closed state.

Within the first loading chamber 107, a wafer rack 124 is disposed for supporting a plurality (two in this embodiment) of wafers spaced in the vertical direction and maintained in a horizontal state.

The first and second loading chambers 107, 108 are controlled for the atmosphere to be maintained in a high vacuum state (at a vacuum degree of $10^{-5}$ to $10^{-6}$ Pa) by a vacuum evacuator (not shown) in a conventional structure including a vacuum pump, not shown. In this event, the first loading chamber 107 may be held in a low vacuum atmosphere as a low vacuum chamber, while the second loading chamber 108 may be held in a high vacuum atmosphere as a high vacuum chamber, to effectively prevent contamination of wafers. The employment of such a loading housing structure including two loading chambers allows a wafer W to be carried, without significant delay from the loading chamber the working chamber. The employment of such a loading chamber structure provides for an improved throughput for the defect testing, and the highest possible vacuum state around the electron source which is required to be kept in a high vacuum state.

The first and second loading chambers 107, 108 are connected to vacuum pumping pipes and vent pipes for an inert gas (for example, dried pure nitrogen) (neither of which are shown), respectively. In this way, the atmospheric state within each loading chamber is attained by an inert gas vent (which injects an inert gas to prevent an oxygen gas and so on other than the inert gas from attaching on the surface).

In the main housing 64 using electron beams, when representative lanthanum hexaboride ($LaB_6$) used as an electron source for an electro-optical system, later described, is once heated to such a high temperature that causes emission of thermal electrons, it should not be exposed to oxygen within the limits of possibility so as not to shorten the lifetime. Since the exposure to oxygen is made less likely by carrying out the atmosphere control as mentioned above at a stage before introducing the wafer W into the working chamber of the main housing 64 in which the electro-optical system 68 is disposed, the lifetime of the electron source is less likely to be shortened.

Stage Apparatus 66

The stage apparatus 66 comprises a fixed table 125 disposed on the bottom wall 103 of the main housing 64; a Y-table 126 movable in a Y direction on the fixed table (the direction vertical to the drawing sheet in FIG. 6); an X-table 127 movable in an X direction on the Y-table 126 (in the left-to-right direction in FIG. 6); a turntable 128 rotatable on the X-table; and a holder 129 disposed on the turntable 128. A wafer W is releasably held on a wafer carrying surface 551 of the holder 129. The holder 129 may be of a general-purpose structure which is capable of releasably chucking a wafer by means of a mechanical or electrostatic chuck feature. The stage apparatus 66 uses servo motors, encoders and a variety of sensors (not shown) to operate the plurality of tables 126-128 mentioned above to permit highly accurate alignment of a wafer W held on the carrying surface 130 by the holder 129 in the X direction, Y direction and Z-direction (the Z-direction is the up-down direction in FIG. 6) with respect to electron beams irradiated from the electro-optical system 68, and in a direction (θ direction) about the axis normal to the wafer supporting surface.

The alignment in the Z-direction may be made such that the position on the carrying surface of the holder 129, for example, can be finely adjusted in the Z-direction. In this event, a reference position on the carrying surface is sensed by a position measuring device using a laser of an extremely small diameter (a laser interference range finder using the principles of interferometer) to control the position by a feedback circuit (not shown). Additionally or alternatively, the position of a notch or an orientation flat of a wafer is measured to sense a plane position or a rotational position of the wafer relative to the electron beam to control the position of the wafer by rotating the turntable 128 by a stepping motor which can be controlled in extremely small angular increments. It may be possible to remove the holder 129 and carry a wafer W directly on the rotatable table 128. In order to maximally prevent particle produced within the working chamber 97, servo motors 131, 132 and encoders 133, 134 for the stage apparatus 66 are disposed outside the main housing 64.

It is also possible to establish a basis for signals which are generated by previously inputting a rotational position, and X-Y-positions of a wafer relative to the electron beams in a signal detecting system or an image processing system, later described.

The wafer chucking mechanism provided in the holder is configured to apply a voltage for chucking a wafer to an electrode of an electrostatic chuck, and the alignment is made by pinning three points on the outer periphery of the wafer (preferably spaced equally in the circumferential direction). The wafer chucking mechanism comprises two fixed aligning pins and a push-type clamp pin. The clamp pin can implement automatic chucking and automatic releasing, and constitutes a conducting spot for applying the voltage.

While in this embodiment, the X-table is defined as a table which is movable in the left-to-right direction in FIG. 7; and the Y-table as a table which is movable in the up-down direction in FIG. 13, a table movable in the left-to-right direction may be defined as the Y-table; and a table movable in the up-down direction as the X-table in the same figures.

Wafer Chucking Mechanism

1) Basic Structure of Electrostatic Chuck:

For accurate and rapid focusing in the electro-optical system, ruggedness on the surface of a sample or a wafer is preferably as small as possible. For this reason, a wafer is absorbed on the surface of an electrostatic chuck which is manufactured with a high flatness (flatness of 5 μm or less is preferable).

The structure for the electrode of the electrostatic chuck is classified into a monopole type and a dipole type. The monopole type electrostatic chuck previously brings a wafer into conduction, and applies a high voltage (generally approximately in a range of several tens to several hundreds of volts) between the single electrode of the electrostatic chuck and the wafer, to absorb the wafer. The dipole type electrostatic chuck need not bring a wafer into conduction, but can absorb a wafer by only applying a positive and a negative voltage to two electrodes of the electrostatic chuck, respectively. However, generally, for ensuring a stable absorption condition, the two electrodes must be formed into an interdigital shape, so that the electrodes are in a complicated shape.

On the other hand, for testing a sample, a wafer must be applied with a predetermined voltage (retarding voltage) in order to establish a focusing condition for the electro-optical system, or in order to facilitate electronic observations on the state of the surface of a sample. The electrostatic chuck must be the monopole type in order to apply the retarding voltage to a wafer and to stabilize the potential on the surface of the wafer. (However, the electrostatic chuck must be operated to be a dipole type until the wafer is brought into conduction with a conduction needle, as will be described later. To meet this requirement, the electrostatic chuck is configured to be switchable between a monopole mode and a dipole mode.) When the potential on the surface of the wafer is not stable at a predetermined value in each test mode, the focusing condition is not satisfied, resulting in a failure of generating a clear image. It is therefore necessary to securely confirm that the wafer is conducting before the application of the retarding voltage.

Therefore, a mechanical contact with the wafer is involved in bringing the wafer into conduction. However, increasingly strict requirements are imposed on wafers for preventing contaminations, and it is therefore requested that a mechanical contact to a wafer be made with the least possible frequency, so that a contact to the edge of a wafer may not be permitted. In this event, the wafer must be brought into conduction through the back thereof.

A wafer is generally formed with a silicon oxide film on its back, so that the conduction cannot be established unless the silicon oxide film is partially removed from the back. To do this, needles are brought into contact with the back of the wafer at two or more locations, and a voltage is applied between the needles to locally break the oxide film, thereby making it possible to successfully bring the wafer into conduction. The voltage applied between the needles may be a DC voltage or an AC voltage of approximately several hundreds of volts. The needles are required to be made of a refractory material which is non-magnetic and wear-resistant, for example, tungsten. Further, for enhancing the durability or for preventing contaminations of wafers, the needles may be effectively coated with TiN or diamond. In addition, for confirming that the wafer is conducting, a voltage is effectively applied between the needles to measure a current with an ampere meter. By applying the retarding voltage after the confirmation of the conduction, the surface of the wafer can be charged with a desired potential, thus conducting a test while satisfying the focusing condition.

Figure 11:
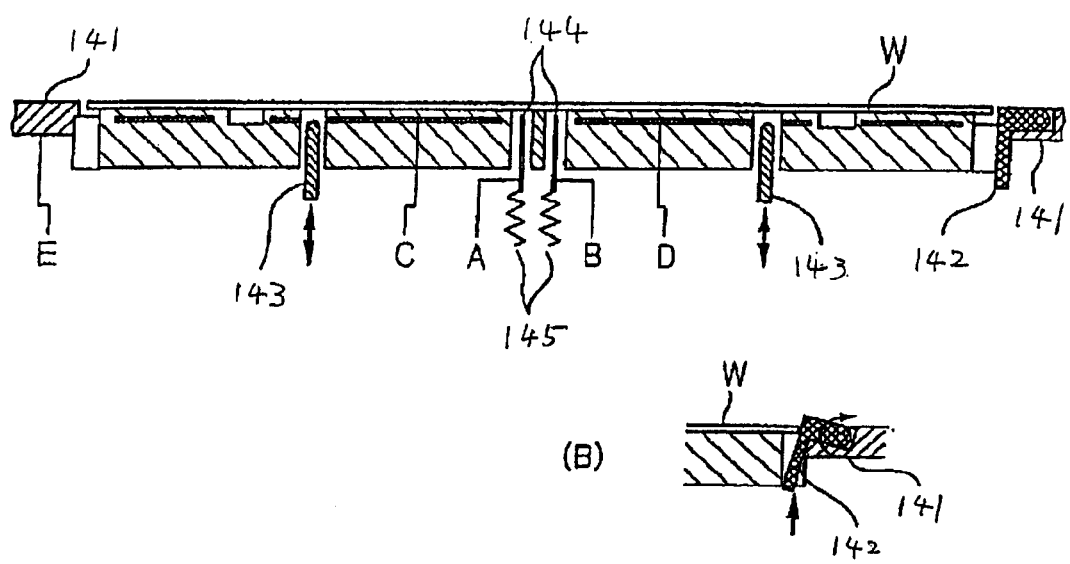
FIG. 11
A diagram for describing an electrostatic chuck used in an inspection system according to the present invention.

A chucking mechanism as illustrated in FIG. 11 has been created from the foregoing background. An electrostatic chuck is provided with electrodes which preferably have an interdigital shape for stably absorbing a wafer W; three pusher pins 143 for passing a wafer; and two or more conduction needles 144 for applying a voltage to a wafer. In addition, a correction ring 141 and a wafer dropping mechanism 142 are disposed around the electrostatic chuck.

The pusher pins 143 previously protrude from the surface of the electrostatic chuck when a sample wafer W is transferred by a robot hand, and slowly move down as the wafer W is placed on the electrostatic chuck by the action of the robot hand to receive the wafer W on the electrostatic chuck. When a wafer W is removed from the electrostatic chuck, the pusher pins 143 perform the reverse actions to pass the wafer W to the robot hand. The pusher pins 143 must be made of a material which contributes to prevention of a shifted position and contamination of the wafer, and silicone rubber, rubber fluoride, ceramics such as SiC, alumina or the like, resin such as teflon, polyimide or the like, are preferably used for the pusher pins 143.

The pusher pins 143 can be driven by several possible methods. A first method involves the installation of a non-magnetic actuator below the electrostatic chuck. Specifically, the pusher pins are directly driven linearly by an ultrasonic linear motor, or the pusher pins are linearly driven by a combination of a rotary ultrasonic motor and a ball screw or a rack-and-pinion gear. With this method, the pusher mechanism can be integrated in compact on the table of the XY-stage on which the electrostatic chuck is mounted, whereas excessively many wires are required for actuators, limit sensors and the like. These wires run from the table on which the XY-stage operates to a wall surface of a sample chamber (main chamber or main housing), and bend in association with the actions of the stage, so that the wires must be routed with large radii of curvature R, resulting in a need for a large space. Also, the wires can be a source of particles, and must be replaced on a periodic basis, so they should be used in a minimally required amount.

An alternative method may supply a driving force from the outside. As the stage is moved to a position at which a wafer W is removed, a shaft protruding into a vacuum through a bellows is driven by an air cylinder disposed outside the chamber to push a shaft of a pusher driving mechanism disposed below the electrostatic chuck. The shaft is connected to a rack-and-pinion gear or a link mechanism within the pusher driving mechanism, such that reciprocal movements of the shaft are associated with up-and-down movements of the pusher pins. When a wafer W is passed to the robot hand, the pusher pins 143 are moved up by adjusting the speed to a proper level by a controller and pushing the shaft out into the vacuum by the air cylinder.

The external shaft driving force is not limited to the air cylinder, but may be implemented by a combination of a servo motor with a rack-and-pinion gear or a ball screw. Alternatively, the external driving source can be a rotary shaft. By this strategy, the rotary shaft is coupled through a vacuum sealing mechanism such as a magnetic fluid seal or the like, and the pusher driving mechanism contains a mechanism for converting rotations into linear motions of pusher pins.

The correction ring 141 has an action of holding a uniform electric field distribution around the edge of a wafer, and is basically applied with the same potential as the wafer. However, the correction ring 141 may be applied with a potential slightly different from the potential at the edge of the wafer in order to cancel out the influence of a narrow gap between the wafer and the correction ring, and of a small difference in height between the surfaces of the wafer and the correction ring. The correction ring 141 has a width of approximately 10-30 mm in a radial direction of the wafer, and can be made of a non-magnetic and conductive material, for example, titanium, phosphor bronze, TiN or Tic coated aluminum, or the like.

Each of the conduction needles 144 is supported by a spring 147, and as a wafer W is placed on the electrostatic chuck, the conduction needles 144 are lightly urged onto the back of the wafer by the forces of the springs. In this state, a voltage is applied in a manner described above to bring the wafer W into electric conduction.

The electrostatic chuck body comprises non-magnetic flat electrodes 19-1, 19-2 made of tungsten or the like, and dielectric films formed on the electrodes. The dielectric films may be made of alumina, aluminum nitride, polyimide or the like. Generally, ceramics such as alumina are perfect insulating materials having a volume resistivity of approximately $10^{14}$ Ωcm, so that no charge migration occurs within the material, and a Coulomb force acts as an absorption force. However, by slightly adjusting the composition of ceramics, the volume resistivity can be reduced to approximately $10^{10}$ Ωcm, permitting charges to migrate within the material to cause a so-called Jonson-Rahbeck force to act as a wafer absorption force which is stronger than the Coulomb force. The stronger the absorption force is, a correspondingly lower voltage can be applied to the wafer, a larger margin can be ensured for breakdown, and a stable absorption force is more likely to be provided. Also, by machining the surface of the electrostatic chuck into a dimple shape, particles or the like, even sticking to the surface of the electrostatic chuck, are likely to drop into valleys of dimples, leading to an expected effect of reducing the possibility of affecting the flatness of the wafer.

Bearing the foregoing discussion in mind, the electrostatic chuck suitable for practical use may be made of such material as aluminum nitride or alumina ceramics which is adjusted to have the volume resistivity of approximately $10^{10}$ Ωcm, and formed with ruggedness such as dimples on the surface which is machined such that a surface formed of a collection of convex portions has a flatness of approximately 5 μm.

Figure 12:
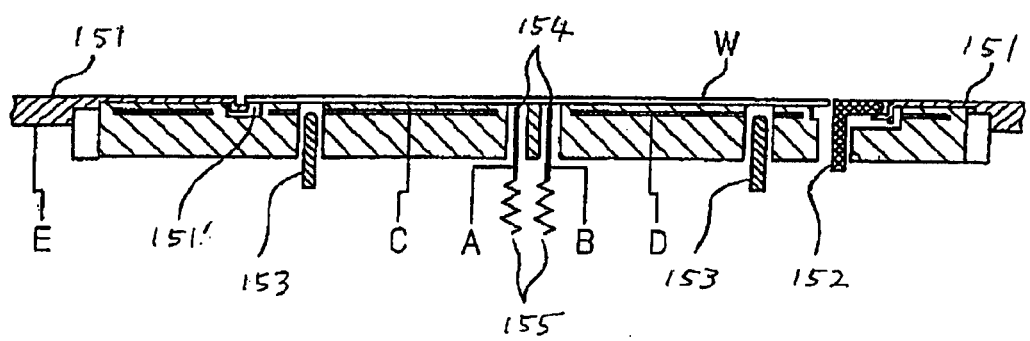
FIG. 12
A diagram for describing another example of the electrostatic chuck used in the inspection system according to the present invention.

2) Chucking Mechanism for 200/300 Bridge Tool:

The inspection apparatus may be required to test two types of wafers of 200 mm and 300 mm diameters without mechanical modifications. In this event, the electrostatic chuck must have the ability to chuck the wafers in two sizes, and a correction ring compatible with the two wafer sizes must be provided along the periphery of the wafer. FIGS. 11(A), 11(B) and FIG. 12 illustrate the structure for meeting the foregoing requirements.

FIG. 11(A) illustrates how a 300-mm wafer W is placed on the-electrostatic chuck. The correction ring 19-1, which has an inner diameter slightly larger than the size of the wafer W (defining a gap of approximately 0.5 mm therebetween), is positioned by and carried on a metal ring part disposed along the outer periphery of the electrostatic chuck with a spigot joint. The correction ring 141 is provided with wafer dropping mechanisms 142 at three locations. Each of the wafer dropping mechanisms 142 is driven by a vertical driving mechanism associated with a mechanism for driving the pusher pins 143, and is supported for rotation about the rotating shaft arranged in the correction ring 141.

When a wafer W is received from a robot hand, the pusher pin driving mechanism operates to push up the pusher pins 143. The wafer dropping mechanisms 142 provided in the correction ring 141 also receive a driving force to rotate at a timing appropriate to the operation of the pusher pin driving mechanism, as illustrated in FIG. 11(B). Consequently, each wafer dropping mechanism 142 forms a tapered surface for guiding the wafer W about the electrostatic chuck. Next, after the wafer W is placed on the pusher pins 143 thus pushed up, the pusher pins 143 are moved down. By adjusting a timing at which the driving force acts on the wafer dropping mechanism 142 to be appropriate to the lowering of the pusher pins 143, the wafer W is placed on the electrostatic chuck such that the center of the wafer W substantially matches the center of the electrostatic chuck while the position of the wafer W is modified by the tapered surfaces of the wafer dropping mechanisms 142.

Desirably, the tapered surface of each wafer dropping mechanism 142 is coated with a low-friction material such as Teflon, or preferably a conductive low-friction material (for example, conductive Teflon, conductive diamond-like carbon, TIN coating). In FIG. 11(A), terminals A, B, C, D and E are applied with respective appropriate voltages (later described), and wafer conduction needles 144 sense that a wafer W is placed on the electrostatic chuck, and are pushed up by associated springs 145.

FIG. 12 illustrates a 200-mm wafer W placed on the same electrostatic chuck. Since the surface of the electrostatic chuck is exposed due to the diameter of the wafer smaller than that of the electrostatic chuck, the electrostatic chuck is mounted with a correction ring 151 which has a size large enough to completely cover the electrostatic chuck. The positioning of the correction ring 151 is performed in a similar manner to the correction ring for 300-mm wafer.

The correction ring 151 is formed with a step along the inner periphery, such that the step fits into an annular groove 151' of the electrostatic chuck. This is a structure for covering the surface of the electrostatic chuck with a conductor (correction ring 151), when a 200-mm wafer W is placed on the electrostatic chuck, such that the surface of the electrostatic chuck is invisible from the gap between the inner periphery of the correction ring 151 and the outer periphery of the wafer W.

If the surface of the electrostatic chuck were visible, charges would be accumulated on the surface of the electrostatic chuck when electron beams are irradiated and would cause disturbance of the potential on the surface of the sample.

For replacing the correction ring 151, a correction ring replacement station has been installed at a predetermined location within the vacuum chamber, and a correction ring of a required size is transferred by a robot from the station, and mounted on the electrostatic chuck (inserted into a spigot joint).

The 200-mm wafer correction ring is also provided with wafer dropping mechanisms 20•2 similar to those of the 300-mm wafer correction ring. The electrostatic chuck is formed with a relief portion for preventing interference with the wafer dropping mechanisms 20-2. A 200-mm wafer is placed on the electrostatic chuck completely in the same manner as the 300-mm wafer. The electrostatic chuck comprises terminals A, B, C, D, E for receiving respective appropriate voltages, push pins 153 similar to the push pins 143, and wafer conduction needles 154 similar to the wafer conduction needles 144.

FIGS. 13(A) and 13(B) generally illustrate the configuration of an electrostatic chuck which can support both of 300-mm wafer and 200-mm wafer, wherein FIG. 13(A) illustrates a 300-mm wafer placed on the electrostatic chuck, and FIG. 13(B) illustrates a 200-mm wafer placed on the electrostatic chuck. As is understood from FIG. 13(A), the electrostatic chuck has an area large enough to accommodate a 300-mm wafer, and as illustrated in FIG. 13(B), a central portion of the electrostatic chuck has an area large enough to accommodate a 200-mm wafer. A groove 156 is formed to surround the central portion of the electrostatic chuck for fitting the inner periphery of the correction ring 151. The electrostatic chuck also comprises terminals A, B, C, D and E for receiving respective appropriate voltages.

In the electrostatic chuck illustrated in FIGS. 13(A) and 13(B), detections may be optically made as to whether or not a wafer is placed on the electrostatic chuck, whether or not a wafer is correctly placed on the electrostatic chuck, whether or not the correction ring is used, and the like. For example, an optical sensor may be disposed above the electrostatic chuck, in which case detection can be made as to whether a wafer is evenly placed or is inclinedly placed by measuring the length of an optical path when light emitted from the optical sensor is reflected back by the wafer to return again to the optical sensor. Also, the presence or absence of the correction ring can be detected by a light emitter which inclinedly emits light to an appropriate point within the area on which the correction ring should be mounted, and a light receiver which receives reflected light from the correction ring. Further, it is possible to detect which of the 300-mm wafer correction ring or 200-mm wafer correction ring is mounted on the electrostatic chuck by providing a combination of a light emitter which inclinedly emits light to an appropriate point in the area on which the 200-mm wafer correction ring should be mounted and a light receiver which receives reflected light from the correction ring, and a combination of a light emitter which inclinedly emits light to an appropriate point in the area on which the 300-mm wafer correction ring should be mounted and a light receiver which receives reflected light from the correction ring, and detects which light receiver receives the reflected light.

3) Wafer Chucking Procedure:

The wafer chucking mechanism which has the structure described above chucks a wafer in the following procedure.

(1) A correction ring suited to a wafer size is transferred by a robot, and mounted on the electrostatic chuck.

(2) The wafer is transferred by a robot hand, and placed on the electrostatic chuck through vertical movements of the pusher pins.

(3) The electrostatic chuck is applied with voltages (a positive and a negative voltage are applied to the terminals C and D, respectively) in the dipole mode to absorb the wafer.

(4) A predetermined voltage is applied across the conduction needles to break the insulating film (oxide film) on the back of the wafer.

(5) A current between the terminals A and B is measured to confirm whether or not the wafer is conducting.

(6) The electrostatic chuck is switched to the monopole absorption mode (a ground potential GRD is applied to the terminals A, B, while the same voltage is applied to the terminals C and D).

(7) The voltage at the terminal A (or B) is reduced while maintaining a potential difference between the terminal A (or B) and the terminal C (or D), and the wafer is applied with a predetermined retarding voltage.

Configuration of Apparatus for $^{200}/_{300}$ Bridge Tool

Figure 14:
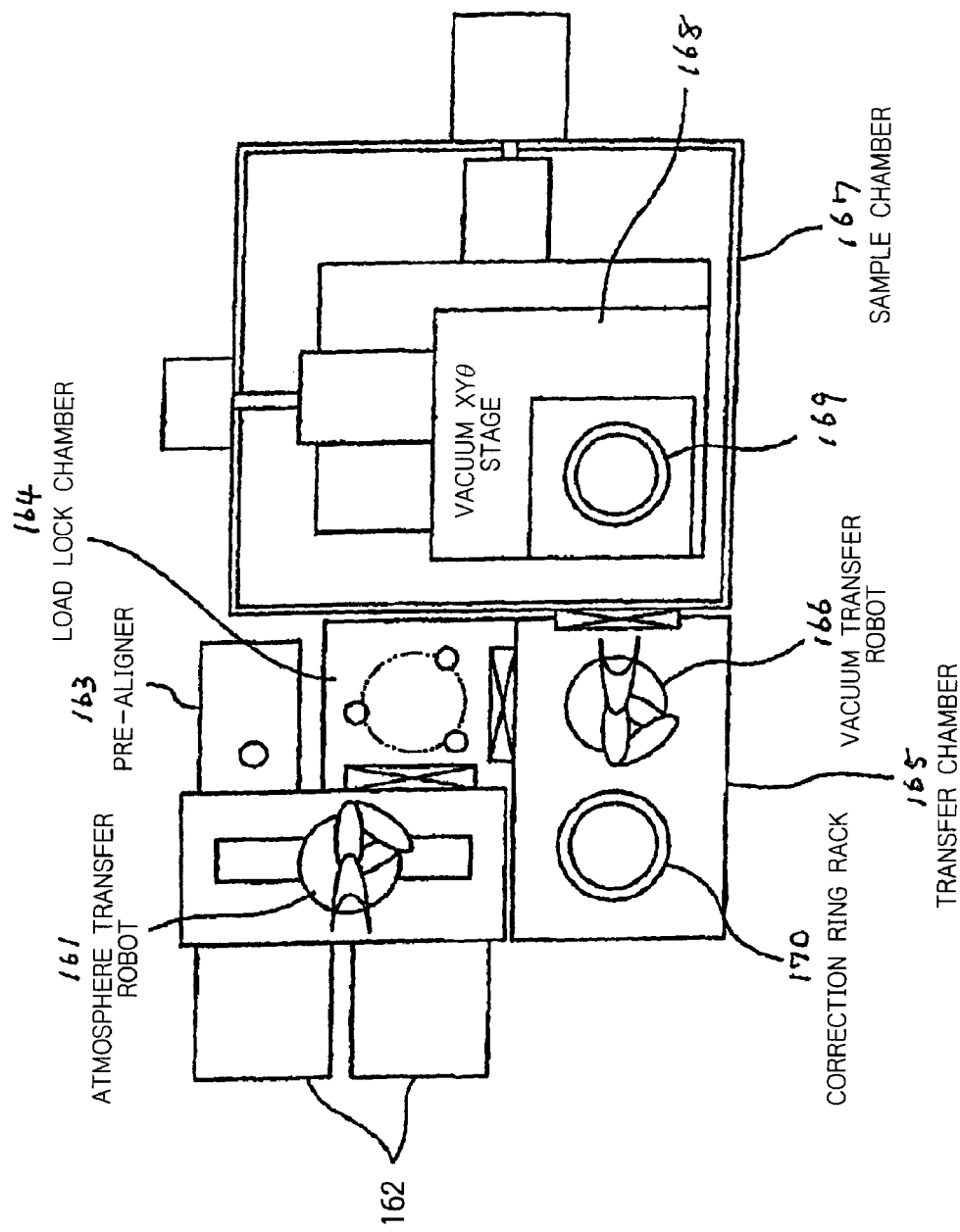
FIG. 14
A diagram for describing a bridge tool used in the inspection system according to the present invention.

FIGS. 14 and 15 illustrate a detection system which is capable of testing either of 200-mm wafers and 300-mm wafers without mechanical modifications. The following description will be centered on aspects different from inspection apparatuses dedicated to 200-mm wafers or 300-mm wafers.

In storage spaces 21•1 for storing wafer cassettes which are picked up in accordance with particular specifications such as $^{200}/_{300}$-mm wafer, FOUP, SMIF, open cassette and the like, a variety of wafer cassettes can be stored in accordance with wafer sizes and types of wafer cassettes determined by specifications determined by the user. An atmosphere transfer robot 21•2 has a hand which can support different sizes of wafers, and more specifically, is formed with a plurality of wafer receiving steps suited to respective wafer sizes, such that a wafer is placed on the hand at a location appropriate to its size. The atmosphere transfer robot 161 transfers wafers from the storage space 162 to a pre-aligner 163 to adjust the orientation of the wafers, and then removes the wafers from the pre-aligner 163 for delivery into a load lock chamber 164.

A wafer rack within the load lock chamber 164, which is also in a similar structure, has a wafer support formed with a plurality of receiving steps suited to respective wafer sizes. The robot hand is adjusted in height such that a group of wafers fit into the receiving step suited to their size. The wafers placed on the hand of the atmosphere transfer robot 161 are loaded into a wafer rack, and then the robot hand is moved down to fit the wafers into a predetermined receiving step of the wafer support.

Each of the wafers placed in the wafer rack within the load lock chamber 164 is next removed from the load lock chamber 163 by a vacuum transfer robot 166 arranged in a transfer chamber 165, and transferred onto a stage 168 within a sample chamber 167. The vacuum transfer robot 166 also has a hand which is formed with a plurality of receiving steps suited to respective wafer sizes, similar to the atmosphere transfer robot 21•2. The wafer fitted into a predetermined receiving step of the robot hand is placed on the electrostatic chuck which has been previously mounted with a correction ring suited to the wafer size, and securely absorbed by the electrostatic chuck on the stage 168. The correction ring 169 is placed on a correction ring rack 170 disposed within the transfer chamber 165. Here, the vacuum transfer robot 166 picks up a correction ring 169 suited to the wafer size from the correction ring rack 170, and mounts the correction ring onto the electrostatic chuck. After fitting the correction ring 169 into a positioning spigot joint formed on the outer periphery of the electrostatic chuck, the wafer is placed on the electrostatic chuck.

When a correction ring is to be replaced with another one, operations reverse to the foregoing are performed. Specifically, the correction ring 169 is removed from the electrostatic chuck by the robot 166, and transferred back into the correction ring rack 170 within the transfer chamber 165. Then, a correction ring suited to the size of a wafer which is to be tested is transferred from the correction ring rack 170 to the electrostatic chuck.

In the inspection apparatus illustrated in FIG. 14, the pre-aligner 163 is positioned near the load lock chamber 164, so that even if a correction ring cannot be mounted in the load lock chamber due to an improperly aligned wafer, the wafer can be readily transferred back to the pre-aligner to again align the wafer, thus advantageously reducing a time loss in the process.

FIG. 15 illustrates an exemplary inspection system in which correction rings are stored at different places. The correction ring rack 170 is omitted. The load lock chamber 171 is formed with a wafer rack and a correction ring lack in a layered structure. These racks are installed on an elevator and can therefore be moved up and down. First, for mounting the electrostatic chuck with a correction ring suited to the size of a wafer which is to be tested, the elevator of the load lock chamber 171 is moved to a position at which the vacuum transfer robot 166 can pick up the correction ring. Then, after the correction ring has been mounted on the electrostatic chuck by the vacuum transfer robot 166, the elevator is operated to carry a wafer to be tested, and the wafer is removed from the wafer rack by the vacuum transfer robot 166, and then placed on the electrostatic chuck. This configuration, though the elevator is required in the load lock chamber 171, can effectively reduce the vacuum transfer chamber 165 held in volume, and also reduce the foot print of the apparatus.

Using the algorithm as described above, an alignment of a wafer on the stage is conducted. While a sensor for sensing whether or not a wafer is placed on the electrostatic chuck is preferably disposed at a position at which the sensor can support any of different wafer sizes, a plurality of sensors which are identical in function may be provided for respective wafer sizes if such a position is not available.

Figure 16:
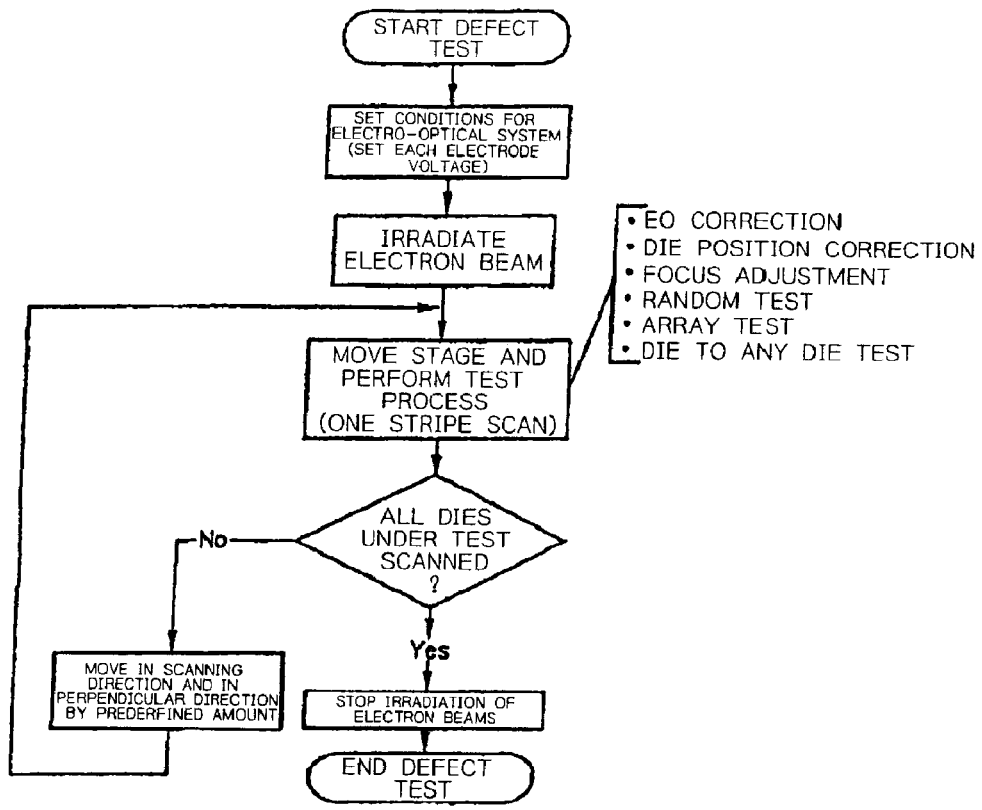
FIG. 16
A diagram for describing a defect inspection procedure in an electron beam apparatus according to the present invention.
Figure 17:
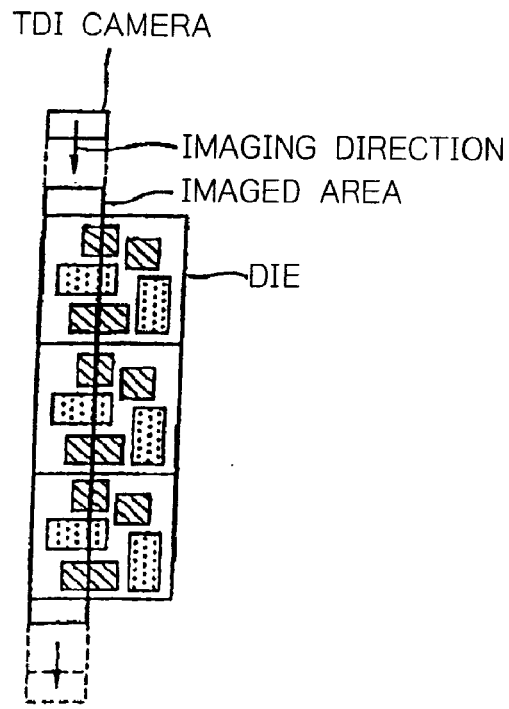
FIG. 17
A diagram for describing a defect inspection procedure in an electron beam apparatus according to the present invention.

Now, description will be made of a whole procedure for a defect test. As illustrated in FIG. 16, the defect test involves moving the stage while irradiating electron beams for TDI scan imaging (FIG. 17), and using a test dedicated processing unit (IPE) in accordance with set inspection conditions (an array inspection condition, a random inspection condition, an area under inspection) for inspecting a sample for defects in real time.

Inspection recipes set conditions for the electro-optical systems, dies under inspection, area under inspection, a inspection method (random/array), and the like (FIGS. 18(A) and 18(B)). For capturing stable images for the defect test, the inspection apparatus simultaneously makes an EO correction for limiting the shaking of captured images due to shifted positions, speed variations and the like; a die position correction for absorbing an error between an ideal placement on a die map and an actual die position; and a focus adjustment for compensating for a focus value of the overall wafer area using a focus value previously measured at a finite measuring point in real time.

Figure 19:
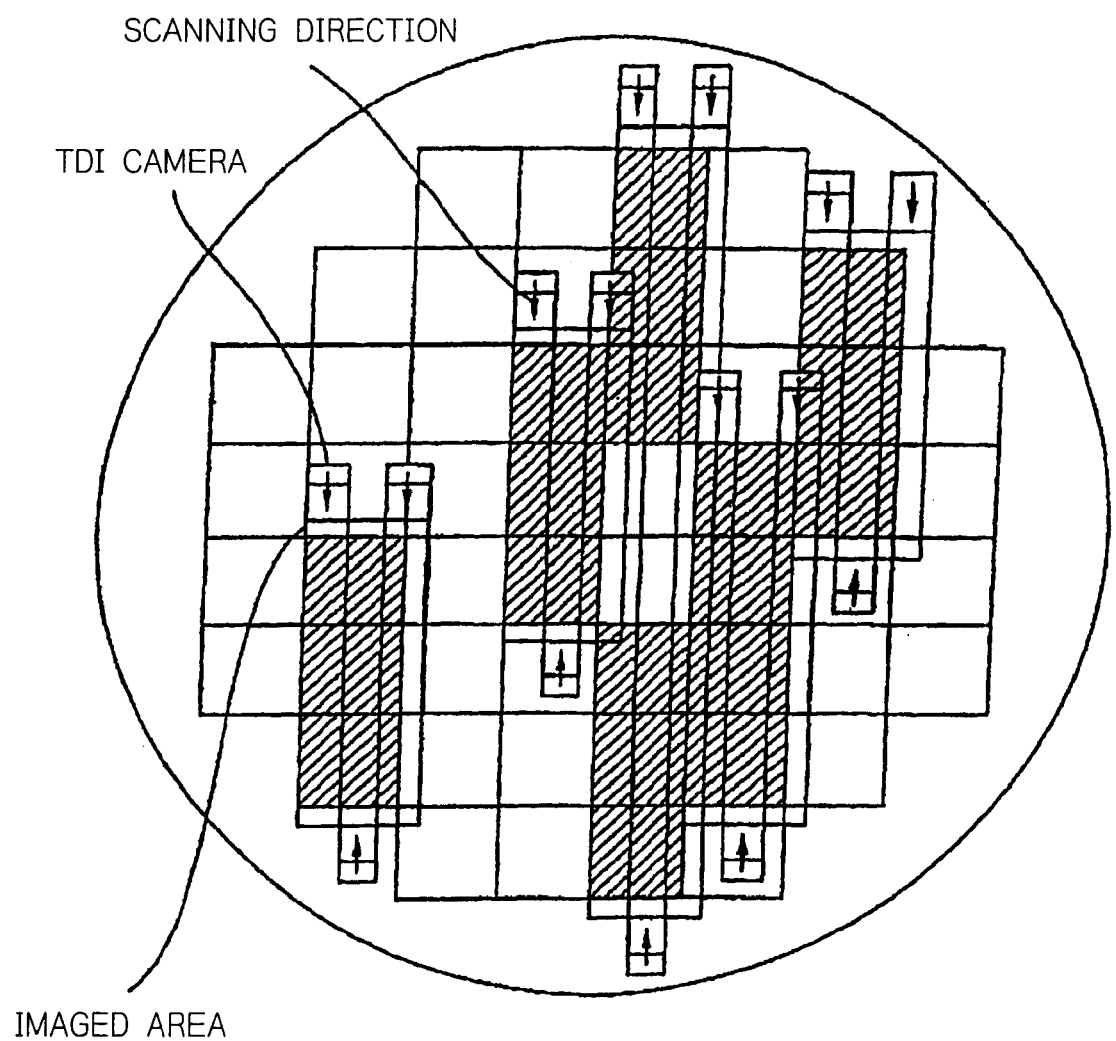
FIG. 19
A diagram for describing a defect inspection procedure in an electron beam apparatus according to the present invention.
Figure 21:
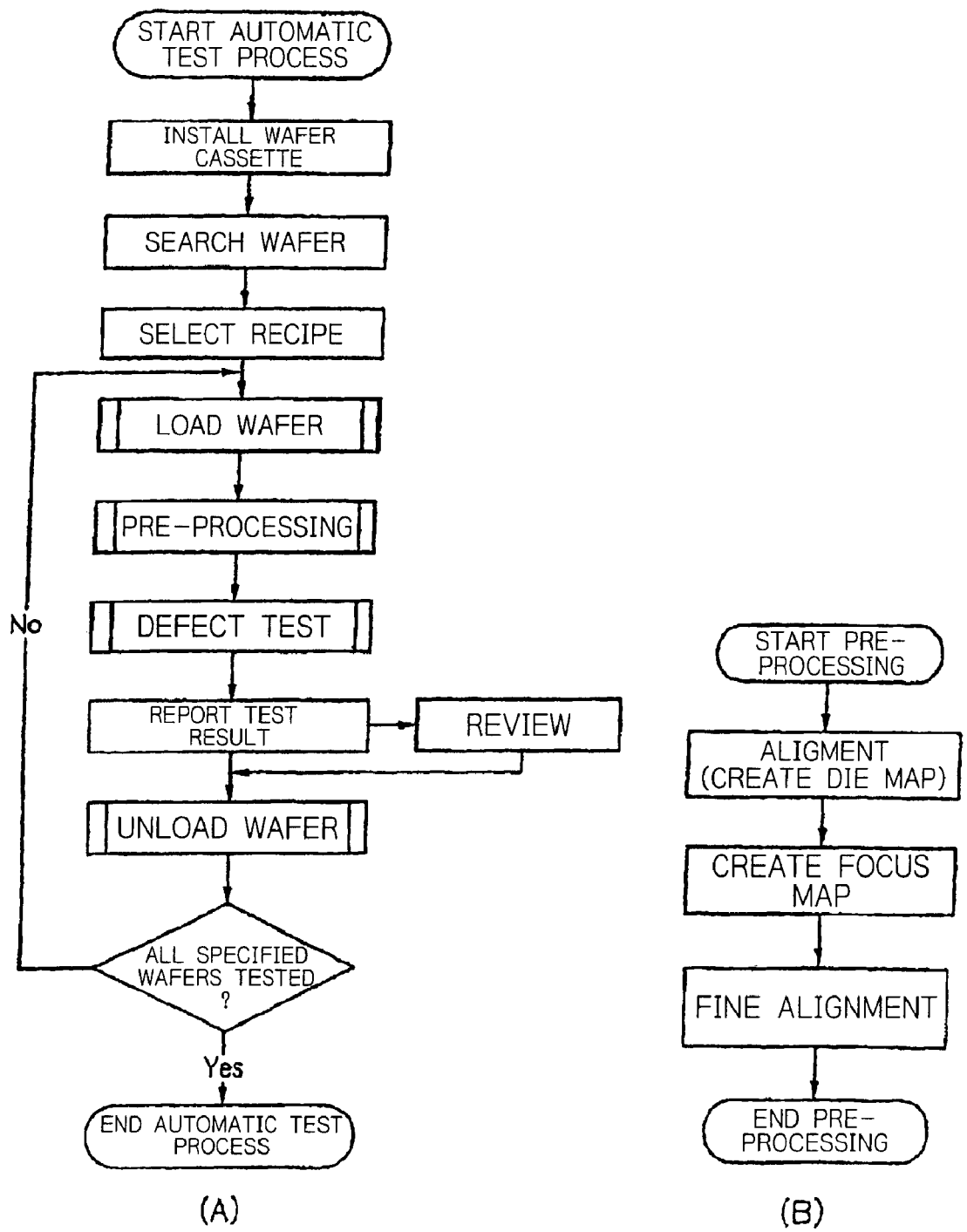
FIG. 21
A diagram for describing a defect inspection procedure in an electron beam apparatus according to the present invention.

In a scanning operation involved in the defect test, instead of testing the entire area of a die under inspection (FIG. 19), an intermittent test can also be made by adjusting step moving increments in a scanning direction and an orthogonal direction, as illustrated in FIG. 20 (for reducing a test time).

After completion of the test, the result of the test is displayed on a display device, including the number of defects, positions of the dies including defects, sizes of the defects, positions of defects within each die, types of defects, images of the defects, and images for comparison. If the foregoing information, recipe information and the like are saved in a file, the results of past tests can be confirmed and reproduced.

During an automatic defect test, a selection of a variety of recipes triggers loading a wafer in accordance with a transfer recipe, aligning the wafer on the stage in accordance with an alignment recipe, setting focus conditions in accordance with a focus map recipe, conducting a test in accordance with a test recipe, and unloading the wafer in accordance with the transfer recipe (FIGS. 20(A) and 20(B)).

Control Device CNL

Figure 22:
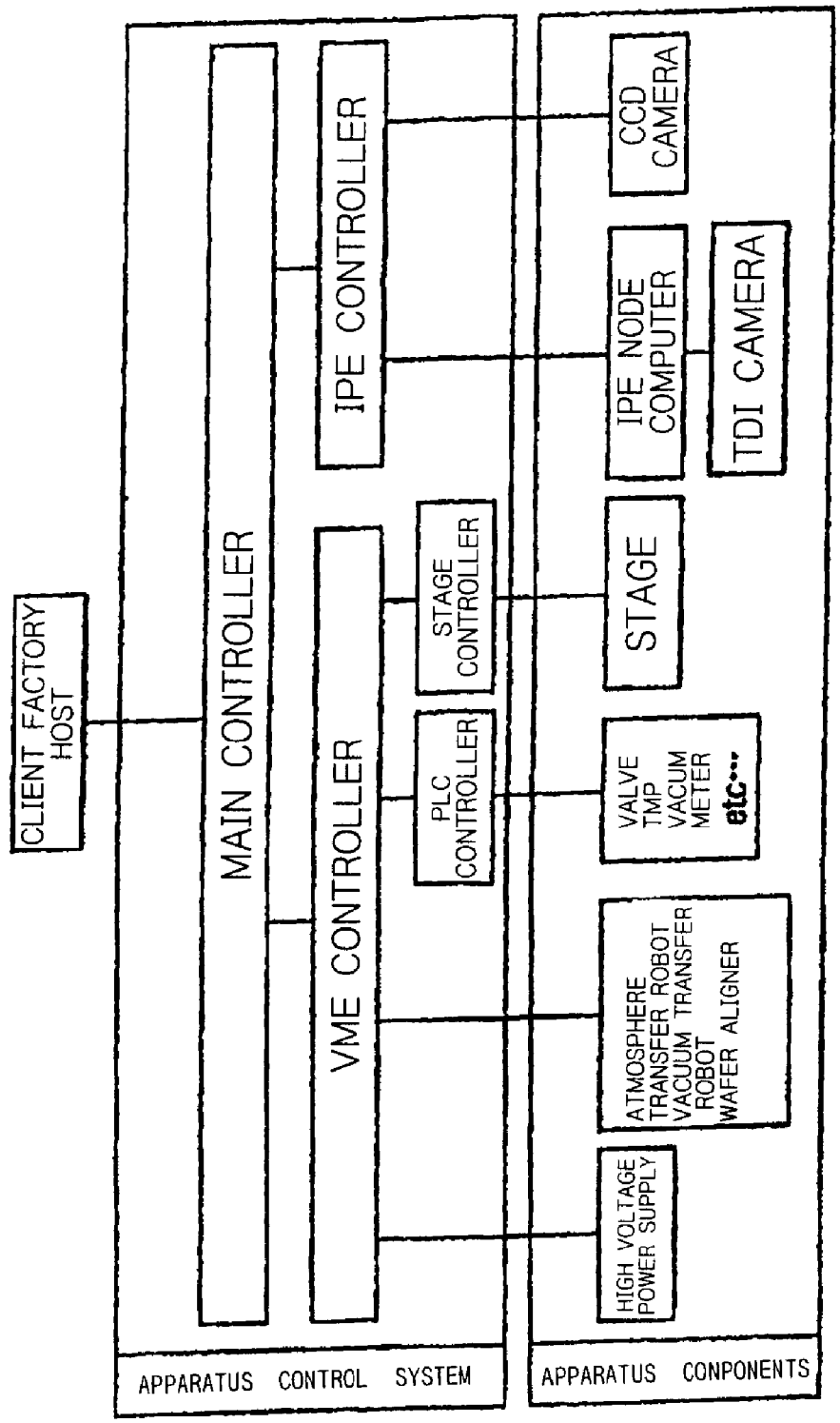
FIG. 22
A diagram for describing the configuration of a control system in an inspection system according to the present invention.

The control device CNL (FIG. 6) for the defect test comprises a plurality of controllers as illustrated in FIG. 22.

A main controller, which governs a GUI unit and sequence operations of the apparatus (EBI), receives operation instructions from a factory host computer or GUI, and gives necessary instructions to a VME controller and an IPE controller. The main controller is provided with a man-machine interface through which the operator performs operations (entering a variety of instructions/commands, recipes and the like, instructing the start of a test, entering all necessary commands for switching between an automatic and a manual test mode, commands involved in the manual test mode, and the like). Otherwise, the main controller is responsible for communications with the host computer in the factory, control of an evacuation system, transfer of wafers, control of positioning, transmission of commands to and reception of information from a stage controller and other controllers, and the like. The main controller also has a stage vibration correcting function for capturing an image signal from an optical microscope and feeding a stage fluctuation signal back to the electro-optical system to correct deteriorated images, and an automatic focus correcting function for detecting a displacement of a wafer observation position in the Z-axis direction (axial direction of the secondary optical system) and feeding the detected displacement to the electro-optical system to automatically correct the focus. The transmission and reception of feedback signals to and from the electro-optical system, as well as the transmission and reception of signals to and from the stage apparatus are performed through the IPE controller and stage controller, respectively.

The VME controller governs the operation of component devices of the apparatus (EBI), and gives instructions to the stage controller and PLC controller in accordance with instructions from the main controller.

The IPE controller acquires defect test information from an IPE node computer, classifies acquired defects, and displays-images of the defects thus classified. The IPE node computer acquires images output from a TDI camera, and conducts a defect test. The IPE node computer also controls the electro-optical system 68, i.e., controls the electron gun, lenses, aligner and the like. The IPE node computer controls automatic voltage setting and the like for the respective lens systems and aligner corresponding to each operation mode (associative control); for example, controlling a power supply such that a constant electron current is irradiated to a target area at all times even if a different scaling factor is selected, and automatically setting voltages to the respective lens systems and aligner corresponding to each scaling factor.

The PLC controller receives instructions from the VME controller, drives devices such as valves, acquires sensor information, and monitors for abnormalities such as an abnormal degree of vacuum which must be monitored at all times.

The stage controller receives instructions from the VME controller, and moves the stage in the X- and Y-directions as well as rotating a wafer placed on the stage. In particular, the stage controller enables precise movements on the order of µm in the X-axis direction and Y-axis direction (with a tolerance of approximately ±0.5 µm), and also enables a control in the rotating direction (θ control) within an error accuracy of approximately ±0.3 seconds.

With the configuration of a distributed control system as described above, even if a component device is changed at an end, no change is required in software and hardware of higher rank controllers, due to maintaining the same interfaces between the respective controllers. Also, even if a sequence operation is added or modified, a flexible support can be provided for a change in configuration by minimizing changes in higher rank software and hardware.

User Interface

Figure 23:
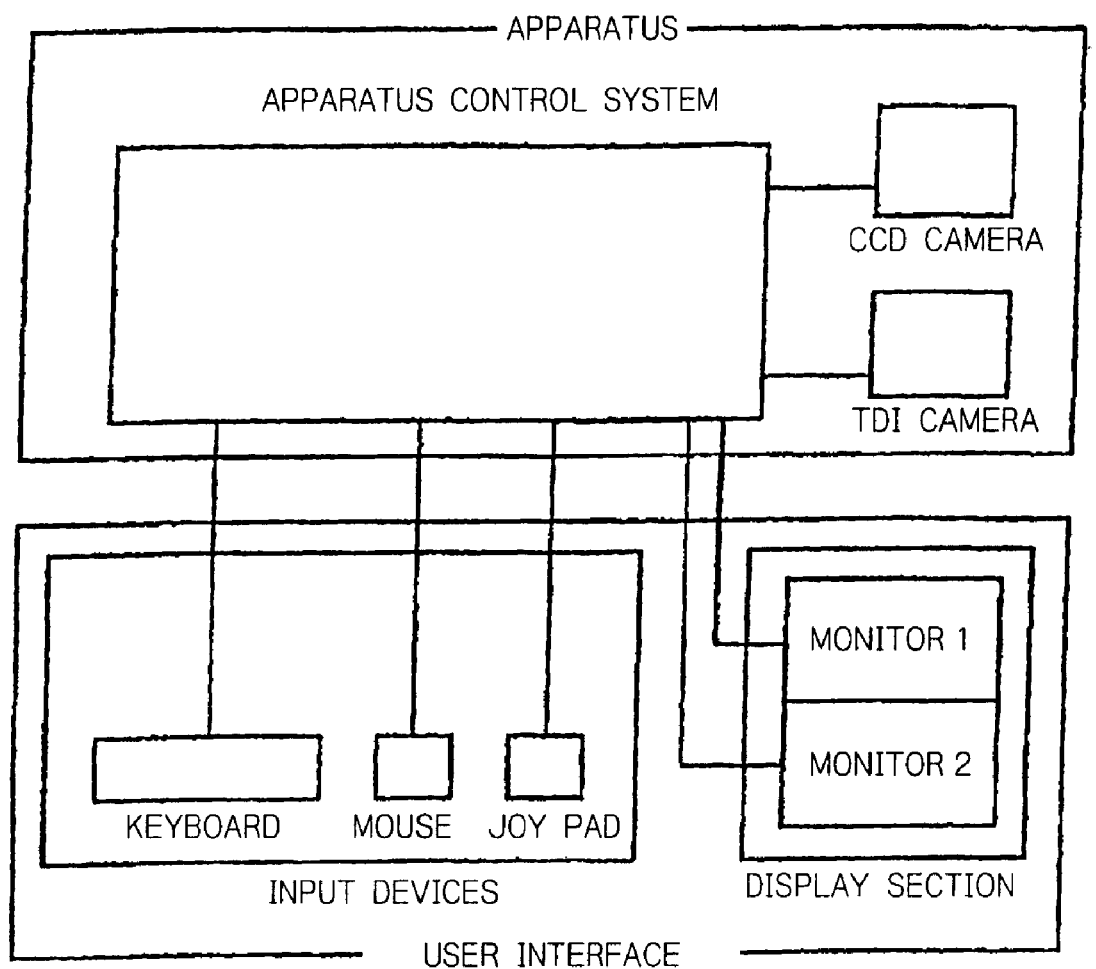
FIG. 23
A diagram for describing the configuration of a user interface in the inspection system according to the present invention.

FIG. 23 illustrates a device configuration in the user interface. An input section shows devices which receive entries from the user, and comprises "keyboard," "mouse," and "JOY pad." A display section shows devices for displaying information to the user, and comprises two monitors. A monitor 1 displays an image captured by a CCD camera or a TDI camera, while a monitor 2 displays a GUI screen.

In this regard, the progress of a test may be displayed on the screen in real time using different colors. The progress of a test will become apparent if different colors are used to display wafer location information indicative of where a certain wafer is found, and information on wafers under inspection such as to which stage the test has been made, where defects are found on each wafer, and the like. Also, dies under inspection may be displayed every swath.

The present apparatus defines the following three coordinate systems.

(1) Stage Coordinate System $[X_S, Y_S]$

This is the reference coordinate system for indicating a position during stage position control, and only one stage coordinate system exists in the apparatus.

The lower left corner of the chamber is defined to be the origin, and the X-coordinate value increases in the right direction, while the Y-coordinate value increases in the upward direction.

A position (coordinate values) represented by the stage coordinate system is the center of the stage (the center of a wafer). In other words, when coordinate values [0, 0] are specified in the stage coordinate system, the center of the stage (center of a wafer) moves to match the origin of the stage coordinate system.

The unit is [µm], but a minimum resolution is defined to be $\lambda/1,024$ (–0.618 [µm]), where λ is the wavelength of a laser used in a laser interferometer (λ·632.991 [µm]).

(2) Wafer Coordinate System $[X_W, Y_W]$

This is a reference coordinate system for indicating a position on a wafer which is to be observed (imaged and displayed), and only one wafer coordinate system exists in the apparatus.

The center of a wafer is defined to be the origin, and the X-coordinate value increases in the right direction, while the Y-coordinate value increases in the upward direction. A position indicated in the wafer coordinate system (coordinate values) is the center of imaging in an imaging device (CCD camera, TDI camera) selected at that time.

The unit is [µm], but a minimum resolution is defined to be $\lambda/1,024$ (–0.618 [µm]), where λ is the same as the foregoing.

(3) Die Coordinate System $[X_D, Y_D]$

This is a reference coordinate system for defining a position on each die which is to be observed (imaged and displayed), and exists on each die.

The lower left corner of each die is defined to be the origin, and the X-coordinate value increases in the right direction, while the Y-coordinate value increases in the upward direction.

The unit is [µm], but a minimum resolution is defined to be $\lambda/1,024$ (–0.618 [µm]), where λ is the same as the foregoing. Dies on a wafer are numbered, and a die which is the basis for the numbering is called the "origin die." By default, the origin die is the one closest to the origin of the wafer coordinate system, but the position of the origin die can be selected in response to a designation of the user.

Figure 24:
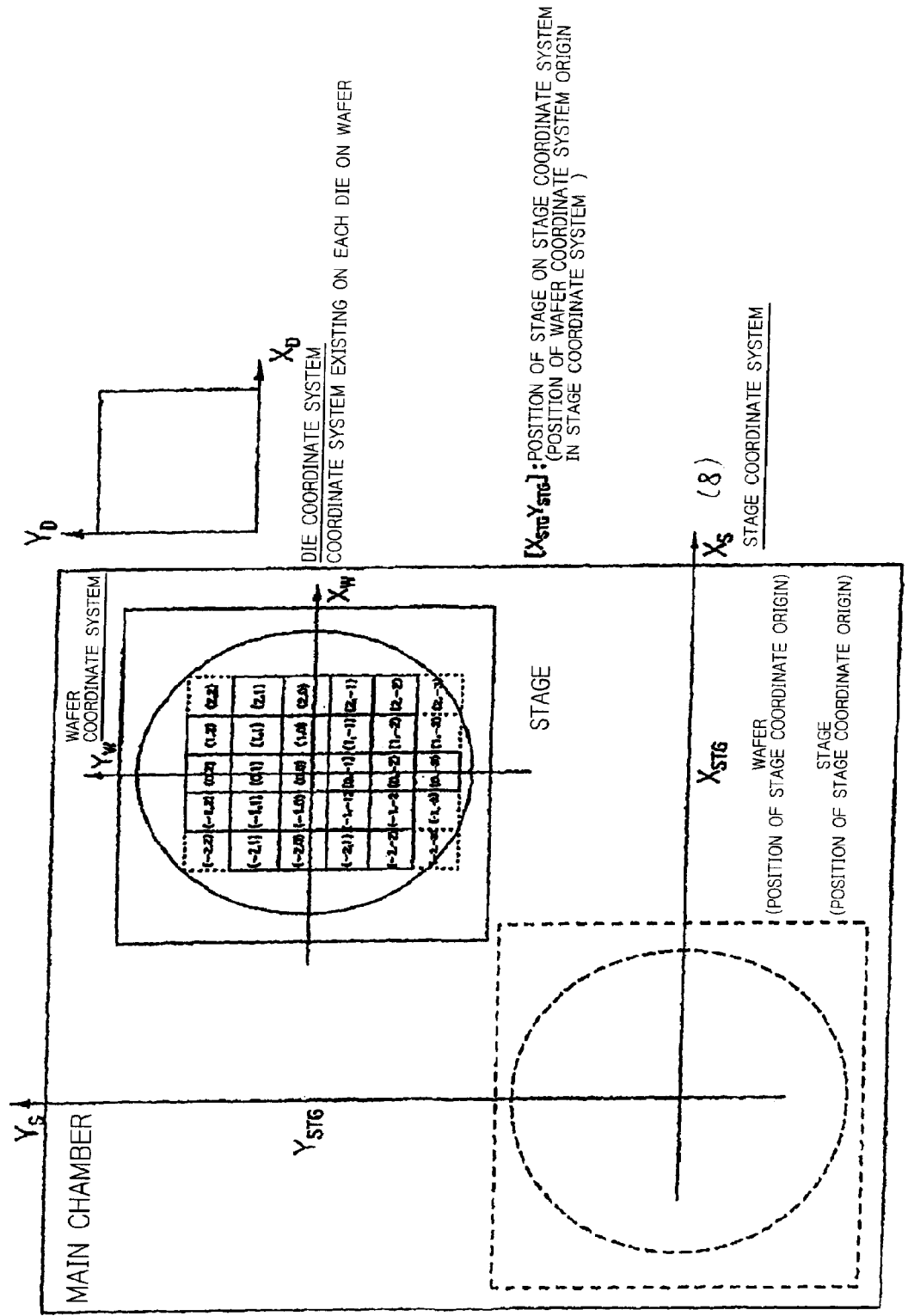
FIG. 24
A diagram for describing the configuration of a user interface in an electron beam apparatus according to the present invention.

The relationship between the coordinate values in the respective coordinate systems and a position at which an observation (display) is made is as shown in FIG. 24.

Also, the relationship between coordinates indicated by the user interface and a direction in which the stage is moved is as described below.

(1) Joy Stick & GUI Arrow Buttons:

A direction indicated by the joy stick and a GUI arrow button is assumed to be a direction in which the operator wishes to view, so that the stage is moved in the direction opposite to the indicated direction.

Example

Indicated Direction: Right . . . Stage Moving Direction: Left (an image moves to the left=the field of view moves to the right)

Indicated Direction: Upward . . . Stage Moving Direction: Downward (an image moves downward=the field of view moves upward)

(2) Direct Entry of Coordinates on GUI:

Coordinates directly entered on the GUI are regarded as a location at which the operator wishes to view on the wafer coordinate system, so that the stage is moved such that the coordinate on a wafer are displayed at the center of a captured image.

Figure 25:
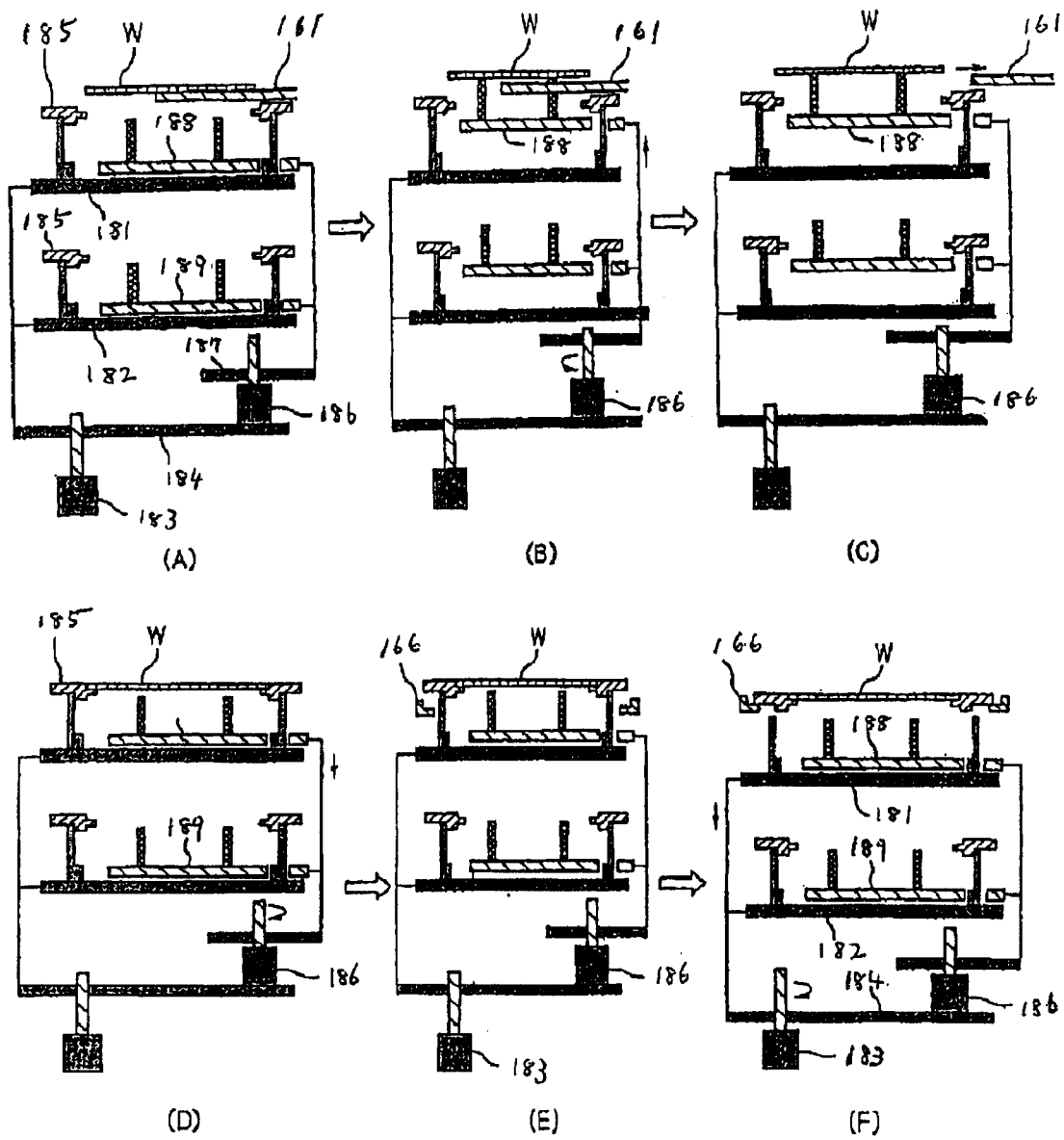
FIG. 25

In the apparatus described in connection with FIG. 14, a procedure is taken to mount a correction ring on the electrostatic chuck, and position a wafer such that the wafer fits in the inner diameter of the correction ring. Therefore, in the inspection apparatus illustrated in FIG. 15, a procedure is taken to mount a correction ring on a wafer in the load lock chamber 22•1, integrally transfer the wafer mounted with the correction ring into the sample chamber 21•7, and place the wafer mounted with the correction ring on the electrostatic chuck on the stage. A feature for implementing the foregoing procedure may be an elevator mechanism for moving up and down an elevator to pass a wafer from the atmosphere transfer robot to the vacuum transfer robot, as shown in FIG. 25. The following description will be focused on a procedure of transferring a wafer using this mechanism.

As illustrated in FIG. 25(A), the elevator mechanism disposed in the load lock chamber has a plurality of stages of correction ring support shelves (two stages in the figure) arranged for movement in the vertical direction. An upper correction ring support shelf 181 and a lower correction ring support shelf 182 are fixed to a first base 184 which is moved up and down through rotations of a first motor 183. Thus, the rotation of the first motor 183 causes the first base 184 and the upper and lower correction ring support shelves 181, 182 to move up or down.

Carried on each correction ring support shelf are correction rings 185 each having an inner diameter suited to a particular size of a wafer. There are two types of correction rings 185 provided for 200-mm wafers and 300-mm wafers, respectively. These correction rings have the same outer diameter. Such use of correction rings having the same outer diameter results in compatibility, allowing correction rings for 200-mm wafers and for 300-mm wafers to be stored in a free combination in the load lock chamber. In other words, for a line on which 200-mm wafers and 300-mm wafers flow in mixture, the upper shelf is dedicated to correction rings for 300-mm wafers, while the lower shelf is dedicated to correction rings for 200-mm wafers, such that a test can be conducted for whichever wafer appears, thus supporting any wafer in a flexible manner. On the other hand, for a line on which wafers of the same size flow, the upper and lower shelves are dedicated to correction rings for 200-mm or 300-mm wafers, so that wafers on the upper and lower shelves can be alternately tested to improve the throughput.

A second motor 186 is carried on the first base 184, while a second base 187 is attached to the second motor 186 such that the second base 187 can be moved up and down. An upper wafer support shelf 188 and a lower wafer support shelf 189 are fixed on the second base 187. With this structure, the rotation of the second motor 186 causes the second base 187 and upper and lower wafer support shelves 188, 189 to integrally move up or down.

Bearing the foregoing in mind, a wafer W placed on the hand of the atmosphere transfer robot 161 is introduced into the load lock chamber 171, as illustrated in FIG. 25(A). Next, as illustrated in FIG. 25(B), the second motor 186 is rotated in a first direction, causing the wafer support shelves 188, 189 to move up. Then, the wafer W is placed on the upper wafer support shelf 188. In this way, the wafer W is moved from the atmospheric transfer robot 161 to the wafer support shelf 188. Subsequently, as illustrated in FIG. 25(C), the atmosphere transfer robot 161 is retracted, and the second motor 186 is rotated in the direction opposite to the first direction, as illustrated in FIG. 25(D), when the atmosphere transfer robot 161 has been retracted, causing the wafer support shelves 188, 189 to move down. In this way, the wafer W is placed on the upper correction ring 185.

Next, as illustrated in FIG. 25(E), the hand of the vacuum transfer robot 161 is introduced into the load lock chamber 171, and stopped below the correction ring 185. In this state, the first motor 183 is rotated to move down the first base 184, upper and lower correction ring support shelves 181, 182, second motor 186, and upper and lower wafer support shelves 188, 189, as illustrated in FIG. 25(F). In this way, the correction ring 185 and wafer W placed on the upper wafer support shelf 188 can be carried on the hand of the vacuum transfer robot 161, and introduced into the sample chamber 167.

The operation for bringing a wafer which has undergone a test in the sample chamber 167 back into the load lock chamber 164 is performed in a procedure reverse to the foregoing. A wafer carried on a wafer support shelf together with a correction ring by the vacuum transfer robot is transferred to a correction ring support shelf, next to the wafer support shelf, and finally on the atmosphere transfer robot. While the foregoing description has been made of the wafer passing operation on the upper shelf with reference to FIG. 25, a similar operation can be accomplished as well on the lower shelf by adjusting the hands of the atmosphere transfer robot 161 and vacuum transfer robot 166 in height. By appropriately switching the heights for the hands of the atmosphere transfer robot 161 and vacuum transfer robot 166 in the foregoing manner, it is possible to alternate the introduction of an untested wafer from one shelf into the sample chamber and the removal of a tested wafer from the sample chamber to the other shelf.

Loader 67

The loader 67 (FIG. 6) comprises a robot-based first transfer unit 78 disposed in the housing 80 of the mini-environment device 63, and a robot-based second transfer unit 78' disposed in the second loading chamber 108.

The first transfer unit 78 has a multi-node arm 191 for rotation about an axis $O_1$-$O_1$ relative to a driver 190. While an arbitrary structure may be applied to the multi-node arm, this embodiment employs the multi-node arm 191 which has three parts attached for rotation relative to each other. A part of the arm 191 of the first transfer unit 78, i.e., a first part closest to the driver 190 is attached to a shaft 192 which can be rotated by a driving mechanism (not shown) in a general-purpose structure arranged in the driver 190. The arm 191 is rotatable about the axis $O_1$-$O_1$ by the shaft 192, and is telescopical in a radial direction relative to the axis $O_1$-$O_1$ as a whole through relative rotations among the parts. At the leading end of the third part furthest away from the shaft 192 of the arm 191, a chuck 194 is attached for chucking a wafer, such as a mechanical chuck in a general-purpose structure, an electrostatic chuck or the like. The driver 190 is vertically movable by an elevating mechanism 195 in a general-purpose structure.

In this first transfer unit 78, the arm 191 extends toward one of two cassettes c held in the cassette holder 10 in a direction M1 or M2 (FIG. 7), and a wafer W stored in the cassette c is carried on the arm, or is chucked by the chuck (not shown) attached at the leading end of the arm for removal. Subsequently, the arm is retracted (to the state illustrated in FIG. 7), and the arm is rotated to a position at which the arm can extend toward the pre-aligner 96 in a direction M3, and is stopped at this position. Then, the arm again extends to the pre-aligner 96 to transfer the wafer held by the arm thereto. After receiving the wafer from the pre-aligner 96 in a manner reverse to the foregoing, the arm is further rotated and stopped at a position at which the arm can extend toward the first loading chamber 107 (in a direction M4), where the wafer is passed to a wafer receiver 196 within the first loading chamber 107. It should be noted that when a wafer is mechanically chucked, the wafer should be chucked in a peripheral zone (in a range approximately 5 mm from the periphery). This is because the wafer is formed with devices (circuit wires) over the entire surface except for the peripheral zone, so that if the wafer were chucked at a portion inside the peripheral zone, some devices would be broken or defects would be produced.

The second transfer unit 78' is basically the same as the first transfer unit 78 in structure, and differs only in that the second transfer unit 78' transfers a wafer W between the wafer rack 124 and the carrying surface of the stage apparatus 66.

The first and second transfer units 78, 78' transfer wafers from the cassette c held in the cassette holder onto the stage apparatus 66 disposed in the working chamber 97 and vice versa while holding the wafer substantially in a horizontal posture. Then, the arms of the transfer units 78, 78' are moved up and down only when a cassette is extracted from the cassette c and loaded into the same, when a wafer is placed on the wafer lack and is extracted from the same, and when a wafer is placed on the stage apparatus 66 and removed from the same. Therefore, the transfer units 78, 78' can smoothly move even a large wafer which may have a diameter of, for example, 30 cm.

Now, a description will be made in order of the transfer of a wafer from the cassette c supported by the cassette holder 62 to the stage apparatus 66 disposed in the working chamber 97 in the inspection system 1 having the configuration described above.

The cassette holder 62 for use in the inspection system 1 may have an appropriate structure either when cassettes are manually set or when cassettes are automatically set, as mentioned above. In this embodiment, as the cassette c is set on the up/down table 71, the up/down table 71 is moved down by the elevating mechanism 72 to bring the cassette c into alignment to the access port 91. As the cassette c is in alignment to the access port 91, a cover (not shown) disposed on the cassette c is opened, whereas a cylindrical cover is arranged between the cassette c and the access port 91 of the mini-environment device 63 to block the cassette c and mini-environment space 63 from the outside. When the mini-environment device 63 is equipped with a shutter device for opening/closing the access port 91, the shutter device is operated to open the access port 91.

On the other hand, the arm 191 of the first transfer unit 78 remains oriented in either the direction M1 or M2 (in the direction M1 in this description), and extends to receive one of wafers stored in the cassette c with its leading end as the access port 91 is opened.

Once the arm 191 has received a wafer, the arm 191 is retracted, and the shutter device (if any) is operated to close the access port 91. Then, the arm 191 is rotated about the axial line $O_1$-$O_1$ so that it can extend in the direction M3. Next, the arm 191 extends to transfer the wafer carried on the leading end thereof or chucked by a chuck onto the pre-aligner 96 which determines a direction in which the wafer is rotated (direction about the center axis perpendicular to the surface of the wafer) within a predetermined range. Upon completion of the positioning, the first transfer unit 78 retracts the arm 191 after the wafer is received from the pre-aligner 96 to the leading end of the arm 191, and takes a posture in which the arm 191 can be extended in the direction M4. Then, the door 197 of the shutter device 119 is moved to open the access ports 226, 436, permitting the arm 191 to place the wafer on the upper shelf or lower shelf of the wafer rack 124 within the first loading chamber 107. It should be noted that before the shutter device 119 opens the access ports to pass the wafer to the wafer rack 124, the opening 199 formed through the partition 121 is hermetically closed by the door 122 of the shutter device 123.

In the wafer transfer process by the first transfer unit 78, clean air flows in a laminar state (as a down flow) from the gas supply unit 231 disposed in the housing body 84 of the mini-environment device 63, for preventing dust from sticking to the upper surface of the wafer during the transfer. Part of air around the transfer unit (in this embodiment, approximately 20% of the air supplied from the gas supply unit 88, which is mainly contaminated) is aspired from the suction duct 95 of the discharger 24 for emission out of the housing body 84. The remaining air is recovered through the recovery duct 89 arranged on the bottom of the housing body 84, and again returned to the gas supply unit 88.

As a wafer is placed on the wafer rack 196 within the first loading chamber 107 of the loader housing 65 by the first transfer unit 78, the shutter device 119 is closed to hermetically close the loading chamber 107. Then, the loading chamber 107 is brought into a vacuum atmosphere by expelling the air within the loading chamber 107, filling an inert gas in the loading chamber 107, and then discharging the inert gas. The vacuum atmosphere in the loading chamber 107 may have a low degree of vacuum. As the degree of vacuum has reached a certain level in the loading chamber 107, the shutter device 123 is operated to open the access port 121, which has been hermetically closed by the door 122, and the arm 200 of the second transfer unit 78' extends to receive one wafer from the wafer receiver 196 with the chuck at the leading end thereof (placed on the leading end or chucked by a chuck attached to the leading end). As the wafer has been received, the arm 200 is retracted, and the shutter device 123 is again operated to close the access port 199 with the door 122. It should be noted that before the shutter device 123 opens the access port 199, the arm 200 has previously taken a posture in which it can extend toward the wafer rack 196 in a direction N1. Also, as described above, before the shutter device 123 opens the access port 199, the shutter device 120 closes the access ports 116, 106 with the door 201 to block communications between the second loading chamber 108 and the working chamber 97, and the second loading chamber 108 is evacuated.

As the shutter device 123 closes the access port 199, the second loading chamber 108 is again evacuated to a degree of vacuum higher than that of the first loading chamber 107. In the meantime, the arm 191 of the second transfer unit 78 is rotated to a position from which the arm 191 can extend toward the stage apparatus 66 within the working chamber 97. On the other hand, in the stage apparatus 66 within the working chamber 97, the Y-table 202 is moved upward, as viewed in FIG. 13, to a position at which the center line $X_0$-$X_0$ of the X-table 203 substantially matches an X-axis line $X_1$-$X_1$ which passes the axis of rotation $O_2$-$O_2$ of the second transfer unit 78'. Also, the X-table 203 has moved to a position close to the leftmost position, as viewed in FIG. 2, and is waiting at this position. When the degree of vacuum in the second loading chamber 108 is increased to a level substantially identical to that of the working chamber 97, the door 201 of the shutter device 120 is moved to open the access ports 116, 106, and the arm extends so that the leading end of the arm, which holds a wafer, approaches the stage apparatus 66 within the working chamber 97. Then, the wafer W is placed on the carrying surface 130 of the stage apparatus 66. Once the wafer W has been placed on the stage apparatus 66, the arm is retracted, and the shutter device 120 closes the access ports 116, 106.

The foregoing description has been made of a sequence of operations until a wafer W in the cassette c is transferred to the working chamber 97 and placed on the carrying surface 130 of the stage apparatus 66. For returning a wafer W which has undergone a test from the stage apparatus 66 to the cassette c, operations reverse to the foregoing are performed. Also, since a plurality of wafers are placed on the wafer rack 196, the first transfer unit can transfer a wafer between the cassette c and the wafer rack 196 while the second transfer unit 78' is transferring a wafer between the wafer rack 196 and the stage apparatus 66. Consequently, operations associated with the test can be efficiently conducted.

Pre-Charge Unit 69

The pre-charge unit 69 is disposed in close proximity to the barrel 204 of the electro-optical system 68 within the working chamber 97, as previously shown in FIG. 6. Since the inspection system 1 of the present invention irradiates a wafer with electron beams for scanning to test a device pattern and the like formed on the surface of the wafer, the wafer can be charged on the surface (charge-up) depending on conditions such as the material of the wafer, energy of irradiated electron beams, and the like. Further, the wafer surface may include a region which is more charged and a region which is less charged. In addition, while information on secondary electrons or the like generated by irradiation of electron beams is used for analyzing the wafer surface, possible variations in the amount of charge on the wafer surface may cause the information on the secondary electrons to include variations as well, thereby failing to provide accurate images.

To prevent such variations in charge, the pre-charge unit 69 is provided in this embodiment. The pre-charge unit 69 includes a charged particle irradiating unit 205 which irradiates charged particles to a wafer before primary electron beams are emitted for testing, thereby eliminating variations in charge. How the wafer surface is charged can be detected by previously forming an image of the wafer surface using the electro-optical system 68, and evaluating the image. Then, the irradiation of charged particles from the charged particle irradiating unit 205 is controlled based on the detected charging state. The pre-charge unit 69 may irradiate blurred primary electron beams.

Alignment Control Unit 70

The alignment control unit 70 aligns a wafer W to the electro-optical system 68 using the stage apparatus 66. The alignment control unit 70 is configured to control a low magnification alignment (alignment with a lower magnification than the electro-optical system 68) which is a rough alignment of a wafer through a wide field observation using the optical microscope 206 (FIGS. 6 and 26); a high magnification alignment for a wafer using the electro-optical system 68; focus adjustment; setting of an area under inspection; pattern alignment; and the like. It should be noted that a wafer is tested at a low magnification as mentioned above because for automatically inspecting patterns on a wafer, an alignment mark must be readily detected by electron beams when the wafer is aligned by observing the patterns on the wafer in a narrow field of view using electron beams.

The optical microscope 206 is installed within the main housing 64, but may be movably disposed within the main housing 64. A light source (not shown) for operating the optical microscope 206 is also disposed within the main housing 64. Further, the electro-optical system involved in observations at high magnification shares components (primary optical system and secondary optical system) of the electro-optical system 68.

Figure 26:
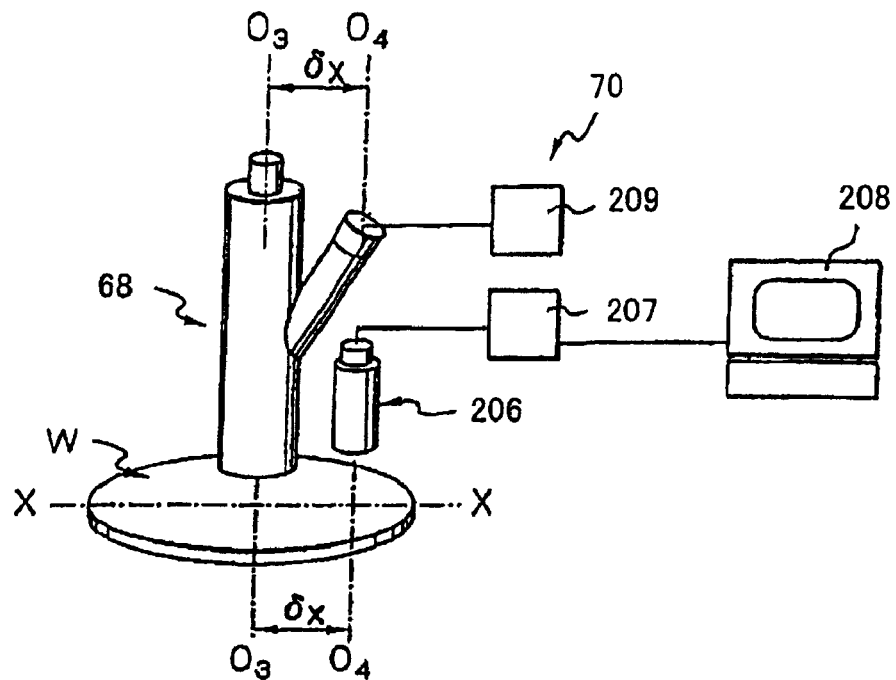

FIG. 26 generally illustrates the configuration of the alignment control unit 70. For observing a site under observation on a wafer W at a low magnification, the site under observation on the wafer W is moved into the field of view of the optical microscope 206 by moving the X-stage or Y-stage of the stage apparatus 66. The wafer W is viewed in a wide field of view using the optical microscope 206, and the site under observation on the wafer W is displayed on a monitor 208 through a CCD 207 to roughly determine where the site under observation is found. In this event, the magnification of the optical microscope 206 may be gradually changed from a low magnification to a high magnification.

Next, the stage apparatus 66 is moved by a distance corresponding to a spacing $\delta x$ between the optical axis of the electro-optical system 68 and the optical axis of the optical microscope 206, thereby moving the site under observation on the wafer W, which has been previously determined using the optical microscope 206, into the field of view of the electro-optical system 68. In this event, since the distance $\delta x$ between the axial line $O_3$-$O_3$ of the electro-optical system 68 and the optical axis $O_4$-$O_4$ of the optical microscope 206 has been previously known (while both are shifted only in the X-direction in this embodiment, they may be shifted in the Y-direction), the site under observation can be moved to a viewing position of the electro-optical system 68 if the wafer W is moved by the distance $\delta x$. After the site under observation has been moved to the viewing position of the electro-optical system 68, the site under observation is imaged at a high magnification by the electro-optical system, and the resulting image is stored or displayed on a monitor 209.

After the site under observation of the wafer is displayed at a high magnification by the electro-optical system 68 as described above, a displacement of the wafer in the rotating direction relative to the center of rotation of the rotatable table 128 of the stage apparatus 66, i.e., a shift $\delta\theta$ of the wafer in the rotating direction relative to the optical axis $O_3$-$O_3$ of the electro-optical system is detected by a known method, and a displacement of a predetermined pattern is detected in the X-axis and Y-axis directions relative to the electro-optical system 68. Then, the operation of the stage apparatus 50 is controlled to align the wafer based on the detected values, data on a test mark separately attached on the wafer, or data related to the shapes of the patterns on the wafer. In the following, an alignment procedure will be described in greater detail.

Figure 27:
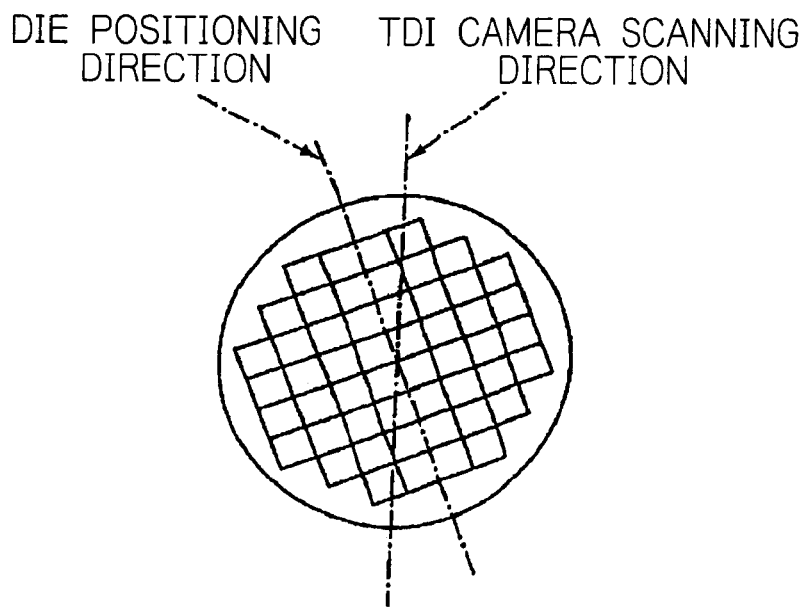
Figures 28, 29:
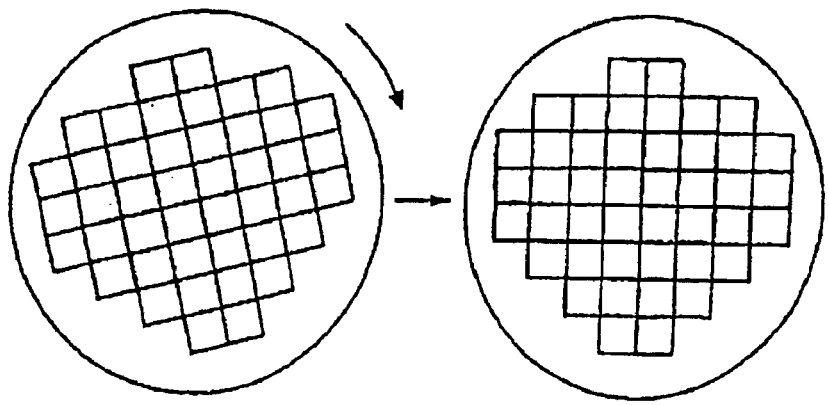

Dies on a wafer loaded on the stage are arranged in a direction which is not necessarily coincident with a scanning direction of a TDI camera (see FIG. 27). To make them coincident, the wafer must be rotated on the θ stage through an operation called "alignment" (FIG. 28). An alignment recipe saves alignment execution conditions after a wafer is loaded on the stage.

In addition, a die map (FIG. 29) is also created for indicating the arrangement of dies upon execution of the alignment, and a die map recipe including the size of dies, the position of an origin die (which serves as the origin for indicating the location of a particular die), and the like is stored.

The alignment (positioning) procedure involves first making a rough alignment at a low magnification with an optical microscope, making a detailed alignment at a high magnification with the optical microscope, and finally making a fine alignment using an EB image.

A. Imaging at Low Magnification Using Optical Microscope:

(1) <Specify First, Second, Third Searched Dies and Template>

(1-1) Specify First Searched Die and Template:

The user moves the stage such that the lower left corner of a die located in a lower region of a wafer is positioned near the center of the camera, and captures a template image for pattern matching after determining the position. This die is referenced for the positioning, and the coordinate at the lower left corner are the coordinate of a characteristic point. From then on, this template image is used for pattern matching to measure the coordinate of the precise location of an arbitrary die on the wafer. An image selected for the template image must be a unique pattern within a search region.

While the lower left corner is defined to be the position at which the template image for pattern matching is captured in this embodiment, the characteristic point is not limited to the lower left corner, but may be an arbitrary location within a die. Generally, however, it is easier to use a corner is to identify the coordinate than a point located within a die or on a side of the die, so that one of the four corners is preferably selected. Likewise, in this embodiment, a template image for pattern matching is captured for a die located in a lower region of a wafer, but it goes without saying that an arbitrary die may be selected to facilitate the alignment.

(1-2) Specify Second Searched Die:

A die next to the first searched die on the right side is chosen to be a second searched die, and the user moves the stage such that the lower left corner of the second searched die is positioned near the center of the camera. After determining the position, the pattern matching is automatically performed using the template image captured in the aforementioned section (1-1) to acquire precise coordinate values for a pattern of the second searched die which is coincident with the template image specified in the first searched die.

While the die adjacent to the first searched die on the right side is chosen to be the second searched die for purposes of description in this embodiment, the second searched die of the present invention is not limited to this die, as a matter of course. In essence, the selection may be made for a point at which a positional relationship of dies in the row direction can be more precisely found from the reference point at which precise coordinate has been found for the position of the characteristic point. Therefore, a die adjacent to the first searched die on the left side may be chosen to be the second searched die.

(1-3) Specify Third Searched Die:

A die immediately above the second searched die is chosen to be a third searched die, and the user moves the stage such that the lower left corner of the third searched die is positioned near the center of the camera. After determining the position, the pattern matching is automatically performed using the template image captured in the aforementioned section (1-1) to acquire precise coordinates for a pattern of the third searched die which are coincident with the template image specified in the first searched die.

While the die immediately above the first searched die on the right side is chosen to be the third searched die for purposes of description in this embodiment, the third searched die of the present invention is not limited to this die, as a matter of course. In essence, the selection may be made such that a positional relationship including a distance to the coordinate of a particular point of a die in the column direction can be found, with reference to the die at which precise coordinate has been found for the position of the characteristic point. Therefore, a die immediately above the second searched die may be chosen to be the third searched die.

(2) <Y-Direction Low Magnification Pattern Matching>

(2-1) Moving amounts (dX, dY) to the immediately above die are calculated from the relationship between the pattern match coordinate (X2, Y2) of the second searched die and the pattern match coordinate (X3, Y3) of the third searched die:

$$dX=X3-X2$$

$$dY=Y3-Y2$$

(2-2) The stage is moved to coordinate (XN, YN) at which a pattern of a die immediately above the first searched die will (be expected to) exist using the calculated moving amount (dX, dY).

$$XN=X1+dX$$

$$YN=Y1+dY$$

where (X1, Y1) are the coordinate values of a pattern of the first searched die.

(2-3) Precise coordinate values (XN, YN) of a pattern currently under observation are captured by imaging at a low magnification with the optical microscope after the stage has been moved and executing the pattern matching using the template image, and one is set to the initial value for the number of detected dies (DN).

(2-4) Moving amount value (dX, dY) are calculated from the coordinate (X1, Y1) of the pattern of the first searched die to the coordinate (XN, YN) of the pattern which is currently being imaged.

$$dX=XN-X1$$

$$dY=YN-Y1$$

(2-5) The stage is moved from the first searched die by moving amounts (2*dX, 2*dY) twice as much as the calculated moving amounts (dX, dY).

Figure 30:
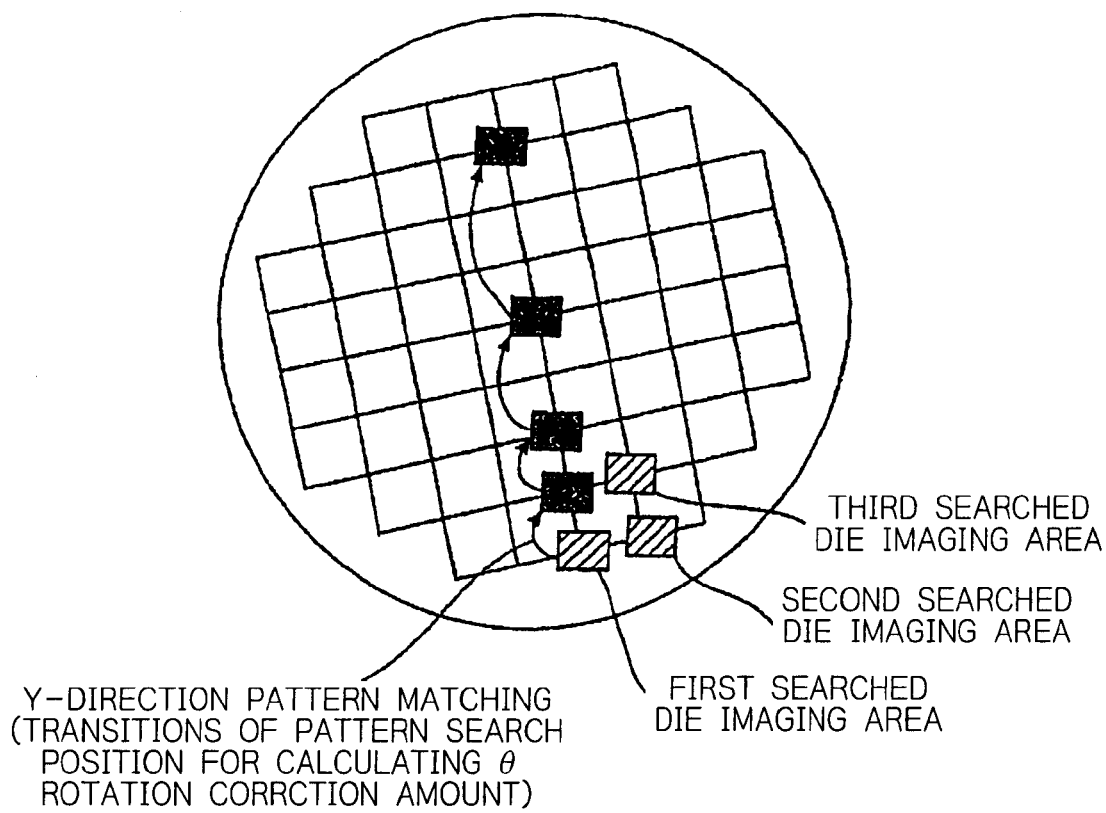

(2-6) The precise coordinate (XN, YN) of the pattern currently under observation are updated by imaging at a low magnification with the optical microscope after the stage has been moved, and executing the pattern matching using the template image, and the number of detected dies is increased by a factor of two. See FIG. 30 for this operation.

(2-7) Steps (2-4) to (2-6) are executed in repetition toward the upward direction on the wafer until a previously specified Y-coordinate value is exceeded.

While this embodiment has been described in connection with an exemplary scenario in which a double moving amount is repeated in order to increase the accuracy, reduce the number of times of processing (number of repetitions), and reduce the processing time, a high integer magnification of more than two, such as three times or four times may be used for execution on the condition that no problem occurs in accuracy and the processing time is preferably further reduced. Conversely, the movement may be repeated with a fixed moving amount for further increasing the accuracy, on the condition that no problem occurs. In either case, it goes without saying that this should be reflected to the number of detected dies.

(3) <θ Rotation at Low Magnification of Optical Microscope>

Figure 31:
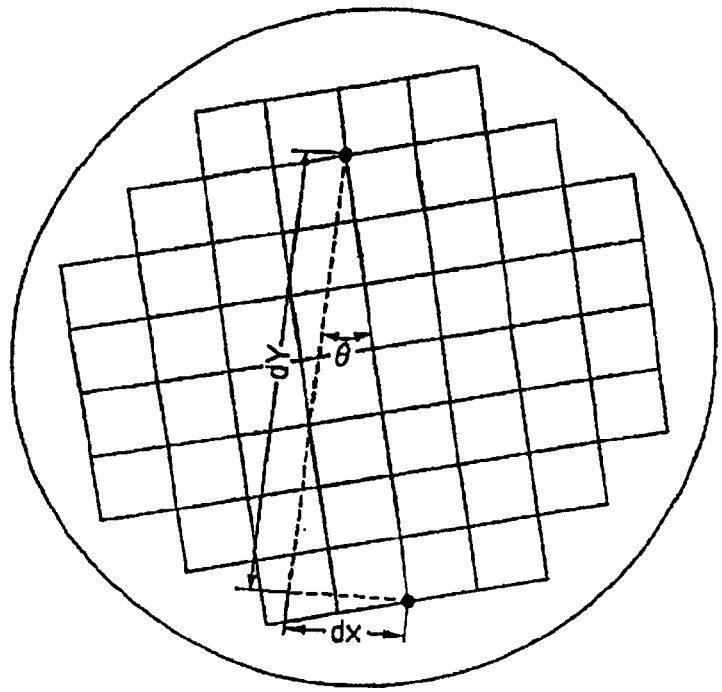

(3-1) A rotating amount (θ) and a Y-direction die size (YD) are calculated using the moving amount from the pattern coordinate (X1, Y1) of the first searched die to the precise coordinate (XN, YN) of the pattern of the finally searched die, and the number (DN) of dies so far detected (see FIG. 31).

$$dX=XN-X1$$

$$dY=YN-Y1$$

$$\theta=\tan^{-1}(dX/dY)$$

$$YD=((dX)^2+(dY)^2)^{1/2}/DN$$

(3-2) The θ Stage is Rotated by the Calculated Rotating Amount (θ).

B. Imaging at High Magnification Using Optical Microscope:

(1) A procedure similar to (1) of the imaging at a low magnification is executed at a high magnification using the optical microscope.

(2) A procedure similar to (2) of the imaging at a low magnification is executed at a high magnification using the optical microscope.

(3) A procedure similar to (3) of the imaging at a low magnification is executed using the optical microscope.

(4) <Check Tolerance After Optical Microscope High Magnification θ Rotation>

(4-1) [Specify First Searched Die and Template for Imaging at High Magnification with Optical Microscope]

The coordinate (X'1, Y'1) of the first searched die after the rotation is calculated from the coordinate (X1, Y1) before the rotation and the rotating amount (θ). The stage is moved to the coordinate (X'1, Y'1). After determining the position, a template image is captured for pattern matching.

$$X'1=x_1*\cos\theta-y_1*\sin\theta$$

$$Y'1=x_1*\sin\theta+y_1*\cos\theta$$

(4-2) Pattern Matching in Y-Direction at High Magnification with Optical Microscope The stage is moved in the-Y-direction by dY from the coordinate (X'1, Y'1) of the first searched die after the rotation, and the pattern matching is executed to acquire precise coordinate (XN, YN) of the pattern currently under observation.

(4-3) From Coordinates (X'1, Y'1) of First Searched Die after Rotation to Coordinate of Pattern Currently under Imaging Moving amounts (dX, dY) to the coordinate (XN, YN) is calculated.

$$dX=XN-X'1$$

$$dY=YN-Y'1$$

(4-4) The stage is moved from the first searched die by moving amounts (2*dX, 2*dY) twice as much as the calculated moving amounts (dX, dY).

(4-5) The precise coordinate (XN, YN) of the pattern currently under observation is updated by imaging at a low magnification with the optical microscope after the stage has been moved, and executing the pattern matching using the template image.

(4-6) Steps (4-3) to (4-5) are executed in repetition in the upward direction on the wafer until a previously specified Y-coordinate value is exceeded.

(4-7) Calculate Rotating Amount of θ:

The rotating amount (θ) is calculated using a moving amount from the coordinate (X'1, Y'1) of the first searched die after the rotation to the precise coordinate (XN, YN) of a pattern of a finally searched die.

$$dX=XN-X1$$

$$dY=YN-Y1$$

$$\theta=\tan^{-1}(dX/dY)$$

(4-8) Optical Microscope High Magnification θ Tolerance Check:

Confirmation is made as to whether the rotating amount (θ) calculated in (4-7) falls within a predefined value. If it does not, steps (4-1) to (4-8) are executed again after the .theta. stage is rotated using the calculated rotating amount (θ). However, when the rotating amount (θ) does not fall within the tolerance even after repeating steps (4-1) to (4-8) a predefined number of times, the processing is aborted, and it is determined that an error has occurred.

C. Alignment Using EB Image (1) <Specify Y Search First Die and EB Template>

A procedure similar to (1) of the imaging at a high magnification with the optical microscope is executed using an EB image.

(2) <EB Y-Direction Pattern Matching>

A procedure similar to (2) of the imaging at a high magnification with the optical microscope is executed using an EB image.

(3) <EB θ Rotation>

A procedure similar to (3) of the imaging at a high magnification with the optical microscope is executed using an EB image.

(4) <EB Tolerance Check After Rotation of θ>

A procedure similar to (4) of the imaging at a high magnification with the optical microscope is executed using an EB image.

(5) Steps (1) to (4) are executed using an EB image at a high magnification as required.

(6) An approximate value for the die size (XD) in the X-direction is calculated from the coordinate (X1, Y1) of the first searched die and the coordinate (X2, Y2) of the second searched die.

$$dX=X2-X1$$

$$dY=Y2-Y1$$

$$XD=((dx)^2+(dy)^2)^{1/2}$$

D. Creation of Die Map Recipe (1) <Specify X-Search First Die and EB Template>

The user moves the stage such that the lower left corner of the die located at the left end of the wafer is positioned near the center of a TDI camera, and acquires a template image for pattern matching after determining the position. Selected for this template image should be an image which is a unique pattern within a search region.

(2) <EB X-Direction Pattern Matching>

(2-1) The stage is moved to the coordinate (X1+XD, Y1) at which a pattern of a die on the right side of the first searched die in the X-direction will (be expected to) exist, using an approximate value (XD) of the die size in the X-direction.

(2-2) After the stage is moved, an EB image is captured by the TDI camera. Precise coordinate (XN, YN) of a pattern currently under observation are acquired by executing the pattern matching using the template image, and one is set to an initial value for the number of detected dies (DN).

(2-3) Moving amounts (dX, dY) are calculated from the coordinate (X1, Y1) of the pattern on the X-search first die to the coordinate (XN, YN) of the pattern which is currently being imaged.

$$dX=XN-X1$$

$$dY=YN-Y1$$

(2-4) The stage is moved from the first searched die in the X-direction by moving amounts (2*dX, 2*dY) which is twice as much as the calculated moving amounts (dX, dY).

(2-5) The precise coordinate (XN, YN) of the pattern currently under observation is updated by capturing an EB image with the TDI camera after the stage has been moved, and executing the pattern matching using the template image, and the number of detected dies is increased by a factor of two.

(2-6) Steps (2-3) to (2-5) are repeatedly executed in the right direction on the wafer until a previously specified X-coordinate value is exceeded.

(3) <Calculation of X-Direction Slope>

A stage straight-going error (Φ) and X-direction die size (XD) are calculated using the moving amount from the coordinate (X1, Y1) of the pattern on the first searched die in the X-direction to the precise coordinate value (XN, YN) of the pattern on the finally searched die, and the number (DN) of dies so far detected.

$$dX=XN-X1$$

$$dY=YN-Y1$$

$$\Phi=\tan^{-1}(dX/dY)$$

$$XD=((dX)^2+(dy)^2)^{1/2}/DN$$

(4) Creation of Die Map

The X-direction die size (XD) thus calculated is combined with a Y-direction die size (YD) found during the calculation of the rotating amount (θ) to create a die map (ideal die arrangement information). The die map permits an ideal arrangement for dies to be found. On the other hand, any die on the substrate is affected, for example, by mechanical errors of the stage (errors in parts such as guides, and errors in assembly), errors of the interferometer (for example, due to the assembly of mirrors and the like), distorted images due to charge-up, so that all dies cannot be observed for an ideal arrangement, but the test should be conducted while finding errors between the actual locations of dies and an ideal arrangement on the die map, and automatically correcting the errors in consideration thereof.

E. Focus Recipe Creation Procedure

Figure 32:
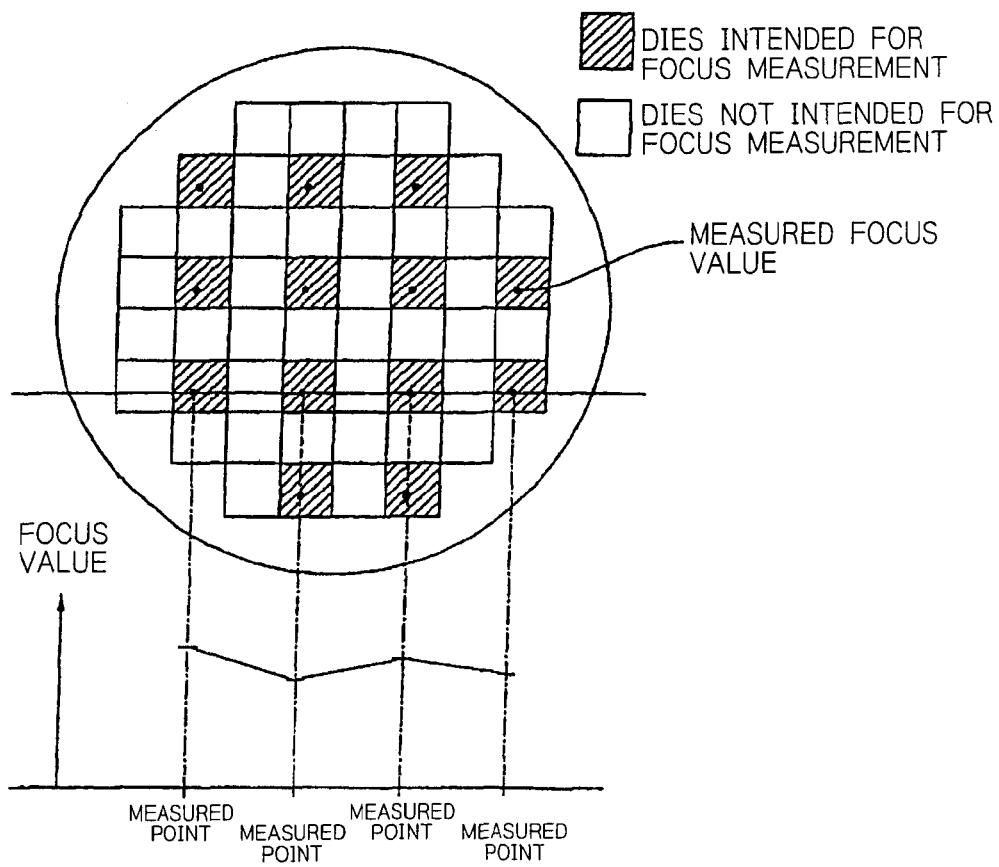

Next, description will be made of a procedure of creating a focus recipe. The focus recipe stores information on an optimal focus position at a position of a mark on a flat surface of a sample such as a substrate, and information on a variety of conditions related to the focus position in a predetermined format such as a table. On a focus map recipe, the focus condition is set only for specified locations on a wafer, and focus values between the specified locations are linearly interpolated (see FIG. 32). The focus recipe creation procedure is as follows.

(1) A die subjected to a focus measurement is selected from the die map.

(2) A focus measurement point is set within a die.

(3) The stage is moved to each point at which the focus value (CL12 voltage) is manually adjusted based on the image and contrast value.

Figure 33:
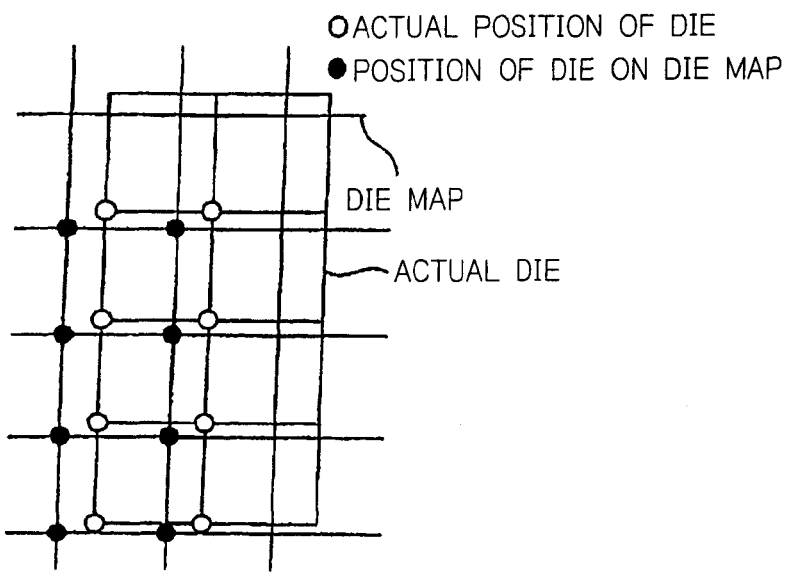

The die map created through the alignment processing shows ideal positional information calculated from the coordinate of the dies at both ends of a wafer, and errors can occur due to a variety of factors between the locations of dies on the die map and actual locations of dies (see FIG. 33). A procedure for creating a parameter for absorbing the errors is called "fine alignment," and a fine alignment recipe error information of the die map (ideal die arrangement information) and actual locations of dies. The information set herein is used during a defect detection. In the fine alignment recipe, errors are measured only for those dies which are specified on the die map, and errors between the specified dies are linearly interpolated.

F. Fine Alignment Procedure (1) Dies subjected to error measurement for fine alignment are specified from the die map.

(2) A reference die is selected from the die subjected to error measurement, and the location of this die is defined to be a point at which there is no error with respect to the die map.

(3) The lower left corner of the reference die is imaged by the TDI camera to capture a template image for pattern matching (however, a unique pattern within a search region is selected as the template image).

(4) Lower left (on the die map) coordinate (X0, Y0) of a nearby die subjected to error measurement are acquired, and the stage is moved thereto. After the movement, the die is imaged by the TDI camera, and precise coordinate (X, Y) is acquired by executing the pattern matching using the template image captured in step (3).

(5) Errors between the coordinate (X, Y) acquired through the pattern matching and coordinate (X0, Y0) on the die map are saved.

(6) Steps (4)-(5) are executed for all the dies subjected to error measurement.

A further detailed description will be made on a defect detecting apparatus for processing data generated by the electro-optical system 70 to acquire image data and for detecting defects on a semiconductor wafer based on the acquired image data in accordance with the present invention. Generally, the inspection apparatus using electron beams, i.e., the electro-optical system 70 is expensive and presents a lower throughput than other process apparatuses. For this reason, the inspection apparatus is currently utilized after important processes which are thought to have the most need of the test (for example, etching, deposition, CMP (chemical mechanical polishing) planarization, and the like) or in part of a wiring process which involves finer wires, i.e., one or two steps of the wiring process, in a gate wiring step in the pre-process, and the like. In particular, it is important to find defective shapes and electric defects of wires having a design rule of 100 nm or less, via holes having diameters of 100 nm or less, and the like, and to feed the found defects back to associated processes.

As described above, a wafer to be tested is transferred by the atmosphere transfer system and vacuum transfer system, aligned on the highly precise stage apparatus (X-Y stage) 66, and then fixed by an electrostatic chucking mechanism or the like. Then, in a defect inspection process, an optical microscope is used to confirm the location of each die and detect the height of each location, as required, and such data is stored. The optical microscope is also used to capture an optical microscopic image of desired sites such as defects and to compare electron beam images. Next, conditions are set for the electro-optical system, and an electron beam image is used to modify the information set by the optical microscope to improve accuracy.

Next, information on recipes is entered to the apparatus depending on the type of wafer (after which process, whether the wafer size is 200 mm or 300 mm, and the like). Subsequently, after specifying a inspection place, setting the electro-optical system, setting inspection conditions, and the like, a defect test is normally conducted in real time while images are captured. A comparison of cells to one another, a comparison between dies, and the like are performed by a high speed information processing system which has associated algorithms installed therein, and the results are output to a CRT or the like, and stored in a memory, as required.

Figure 34:
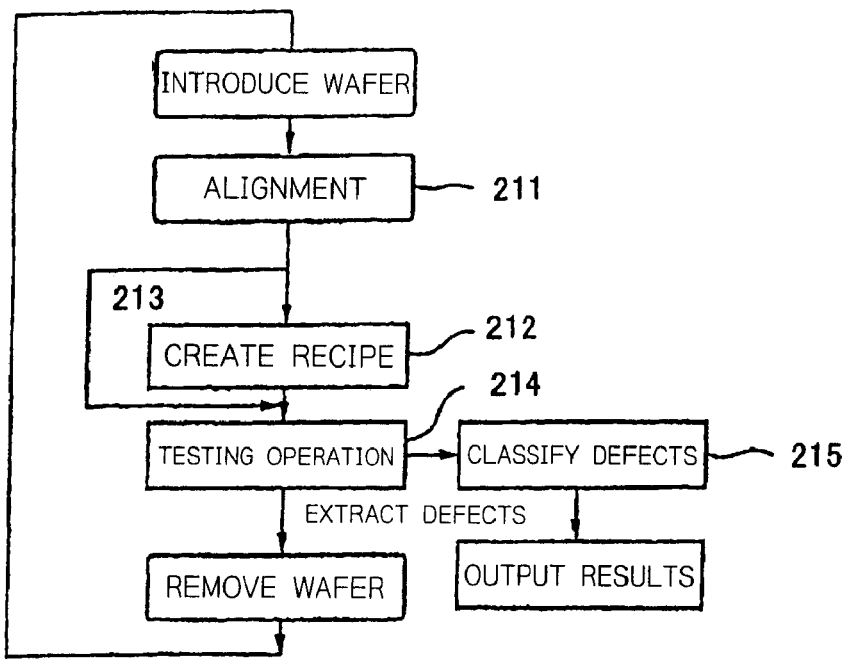

FIG. 34 illustrates a basic flow of the defect test. First, after transfer of wafers including an alignment operation 211, the recipes are created for setting conditions related to the test, and the like (212). While at least one type of recipe is needed for each wafer under inspection, a plurality of recipes may be created for a single wafer under inspection in order to support a plurality of inspection conditions. Also, when there is a plurality of wafers having the same pattern, the plurality of wafers may be tested in accordance with a single recipe. A path 213 in FIG. 34 indicates that when a test is conducted using recipes created in the past, the creation of recipes is not required immediately before the inspection operation.

In FIG. 34, the inspection operation 214 involves a test on a wafer in accordance with the conditions described in the recipe and a sequence. A defect is extracted immediately each time it is found during the inspection operation through the following operations which are executed substantially in parallel.

Defects are classified (215) to add extracted defect information and defect classification information to a result output file.

An extracted defect image is added to a result output file dedicated to images or to a file.

Defect information such as locations of extracted defects is displayed on an operation screen.

Upon completion of the test on a wafer-by-wafer basis, the following operations are next executed substantially in parallel.

The result output file is closed and saved.

When the result of the test is requested through a communication from the outside, the result of the test is sent.

The wafer is removed.

When the inspection system is set to continuously test wafers, the next wafer under inspection is transferred, followed by a repetition of the sequence of operations described above.

In the creation of recipes in FIG. 34, recipes created therein include a file for setting conditions associated with the test, and the like. The recipes can be saved as well, so that the recipes may be used to set conditions at the time of or before a test. The conditions associated with the test described in the recipes include, for example, the following items: dies under inspection;

region to be tested within a die;

inspection algorithm;

detecting conditions (required for extracting defects, such as a test sensitivity); and observation conditions (magnification, lens voltages, stage speed, inspection order, and the like, which are required for observation).

Figure 35:
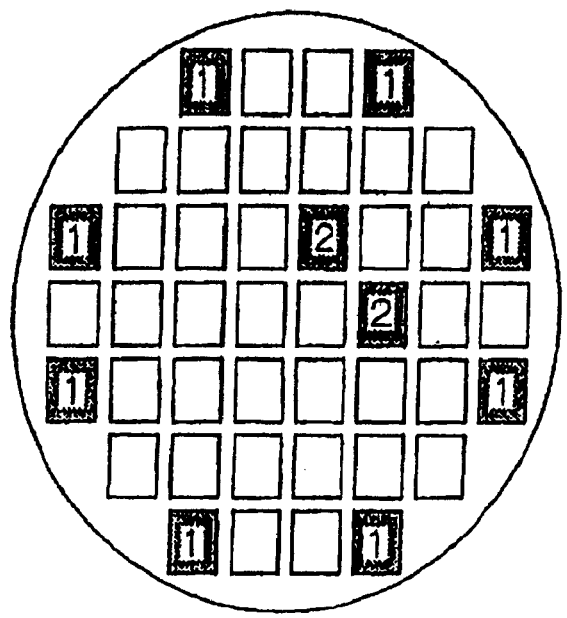

Among the test conditions listed above, the setting of dies under inspection involves an operator specifying dies to be tested on a die map screen displayed on the operation screen, as illustrated in FIG. 35. In the example of FIG. 35, dies 1 near the periphery of the wafer and dies 2 clearly determined as defective in the pre-process are grayed out and removed from dies under inspection, and the remaining dies are subjected to the test. The alignment control unit 2 also has a function of automatically specifying dies under inspection based on the distance from the periphery of the wafer and information on good/fail of dies detected in the pre-process.

Figure 36:
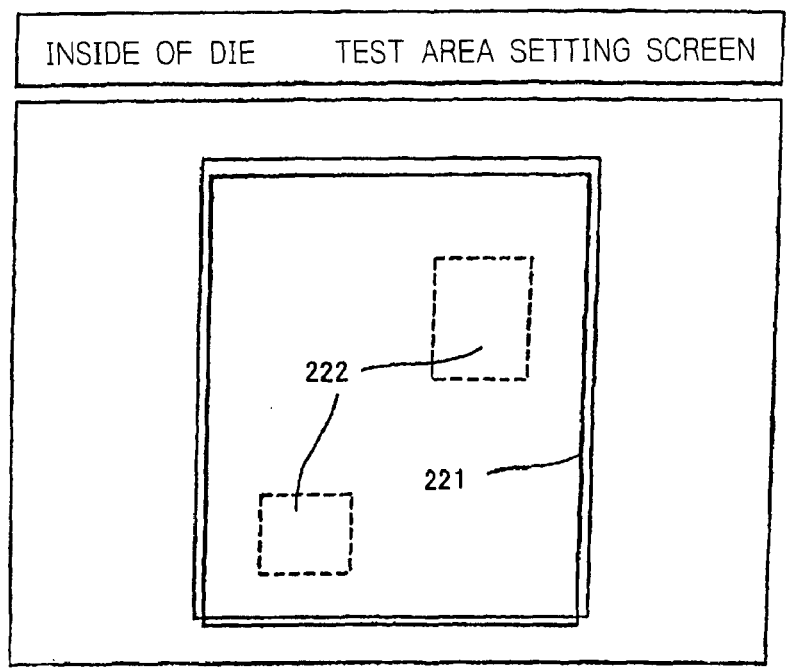

An area under inspection within a die is specified by the operator on a die internal test region setting screen displayed on the operation screen, as illustrated in FIG. 36, using an input device such as a mouse based on an image captured by an optical microscope or an EB microscope. In the example of FIG. 36, an area 221 indicated by a solid line, and an area 222 indicated by a broken line are set to be areas under inspection.

The area 221 includes substantially the entire die which is set to be under inspection. In this event, an adjacent die comparison method is employed for a test algorithm, and detailed detection conditions and observation conditions for this area are separately set. For the area 222, an array test is employed for a test algorithm, and detection conditions and detailed observation conditions for this area are separately set. Thus, a plurality of areas under inspection can be set, and an appropriate test algorithm and test sensitivity can be set for each of the areas. Also, some areas under inspection can be overlapped, so that different test algorithms can be simultaneously executed for the same area.

Figure 37:
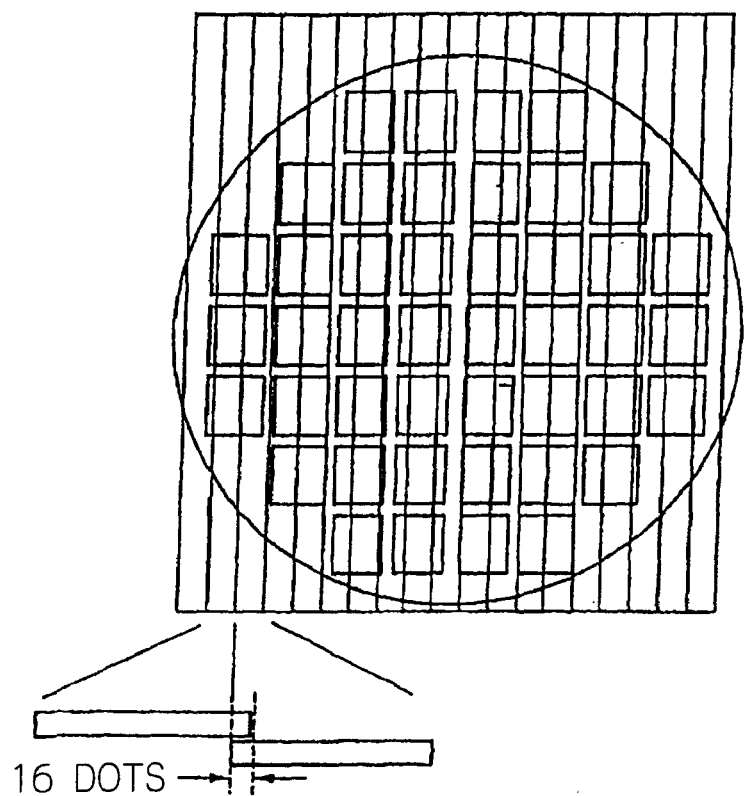

In the inspection operation 214 in FIG. 34, a wafer under inspection is sectioned in scanning widths, as illustrated in FIG. 37. The scanning width is substantially determined by the length of a line sensor, but is set such that adjacent line sensors slightly overlap in their respective edge portions. This is intended to ensure a margin for determining the continuity between lines when detected defects are totally processed at a final stage, and for an alignment of images involved in a comparison test. An overlapping amount is approximately 16 dots for a 2,048-dot line sensor.

FIG. 38 schematically illustrates scanning directions and sequences. Specifically, a bi-directional operation (Operation A) for reducing a test time, and a uni-directional operation (Operation B) due to mechanical restrictions can be selected by the operator. The control unit also has a function of automatically processing and detecting to execute an operation which reduces the amount of scanning for the test based on target die information stored in the recipe. FIG. 39(A) shows an example of scanning which is done when there is only one die under inspection, in which case unnecessary scanning is omitted.

A test algorithm set by the recipe can be classified into a cell test (array test) and a die test (random test).

As illustrated in FIG. 39(B), a die is divided into a cell area 231 which has a periodic structure mainly used for memories, and a random area 232 which does not have the periodic structure. Since the cell area 231 having the periodic structure includes a plurality of cells to be compared within the same die, the cells within the same die can be tested using the cell test by comparing them with one another. On the other hand, since the random area 232 cannot be compared within the same die, dies must be compared using the die test.

The die test method is further classified as follows depending on what is compared:

an adjacent die comparison method (Die-to-Die test);

a reference die comparison method (Die-to-Any Die test); and a CAD data comparison method (Cad Data-to-Any Die test).

A scheme generally called a "golden template scheme" falls under the basic die comparison method and CAD data comparison method. In the reference die comparison method, a reference die is used as a golden template, while in the CAD data comparison method, CAD data is used as a golden template. The following description will be made on the operation of the respective test algorithms.

Cell Test (Array Test)

The cell test is applied to a test of a periodic structure. A DRAM cell is an example which is suitable for the cell test.

The test involves comparing a reference image with an image under inspection, and extracting differences therebetween as defects. The reference image and image under inspection may be digitized images or multi-valued images for improving the detection accuracy.

While defects may be differences themselves between the reference image and the image under inspection, a secondary determination may be made in order to prevent erroneous detections based on difference information such as the amount of detected difference, a total area of pixels which present differences, and the like.

In the cell test, the comparison of the reference image with the image under inspection is made in units of structural periods. Specifically, they may be compared in units of structural periods while reading the images collectively captured by a CCD or the like, or when the reference image comprises n units of structural periods, the n units of structural period can be compared at the same time.

Figure 40:
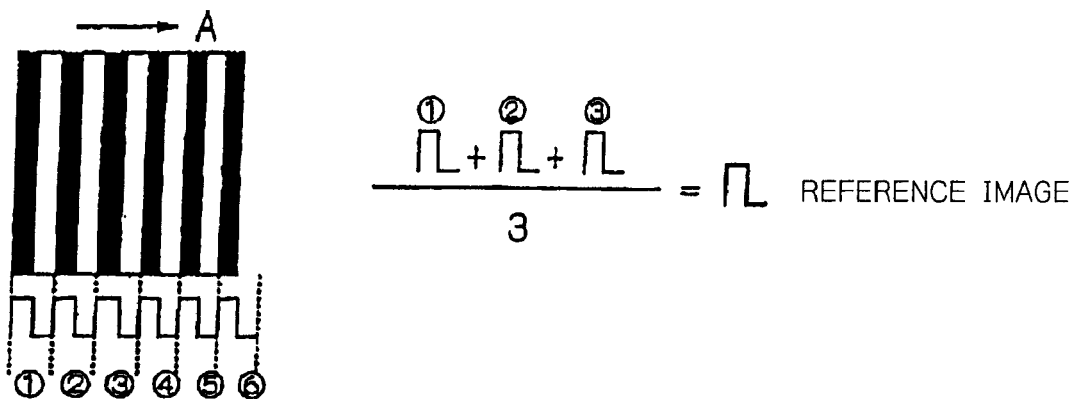

FIG. 40 illustrates an exemplary method of generating a reference image. FIG. 40 illustrates the generation of one structural period unit because the following description will be made on an exemplary comparison which is made on a unit-by-unit basis. The number of periods can be increased to n in the same method.

Assume that a test is conducted in a direction indicated by an arrow A in FIG. 40. Assume also that period 4 is chosen to be a period under inspection. Since the length of the period is entered by the operator while viewing the image, periods 1-6 can be readily recognized in FIG. 40.

The reference period image is generated by adding periods 1-3 immediately before the period under inspection and averaging them in each pixel. Even if a defect is found in any of periods 1-3, the influence is not significant because these periods are averaged. The reference period image thus generated is compared with the period image 4 under inspection to extract defects.

When a period image 5 under inspection is next tested, periods 2-4 are averaged to generate a reference period image. Subsequently, a period image under inspection is generated from images captured before the capturing of the period image under inspection in a similar manner to continue the test.

Die Test (Random Test)

The die test is applied without limited by the structure of die. The test involves comparing a reference image with an image under inspection, and extracting differences therebetween as defects. The reference image and image under inspection may be digitized images or multi-valued images for improving the detection accuracy. While defects may be differences themselves between the reference image and the image under inspection, a secondary determination may be made in order to prevent erroneous detections based on difference information such as the amount of detected difference, a total area of pixels which present differences, and the like. The die test can be classified according to how a reference image is generated. The following description will be made on the operation of an adjacent die comparison method, a reference die comparison inspection method, and a CAD data comparison method which are included in the die test.

A. Adjacent Die Comparison Method (Die-Die Test)

Figure 41:
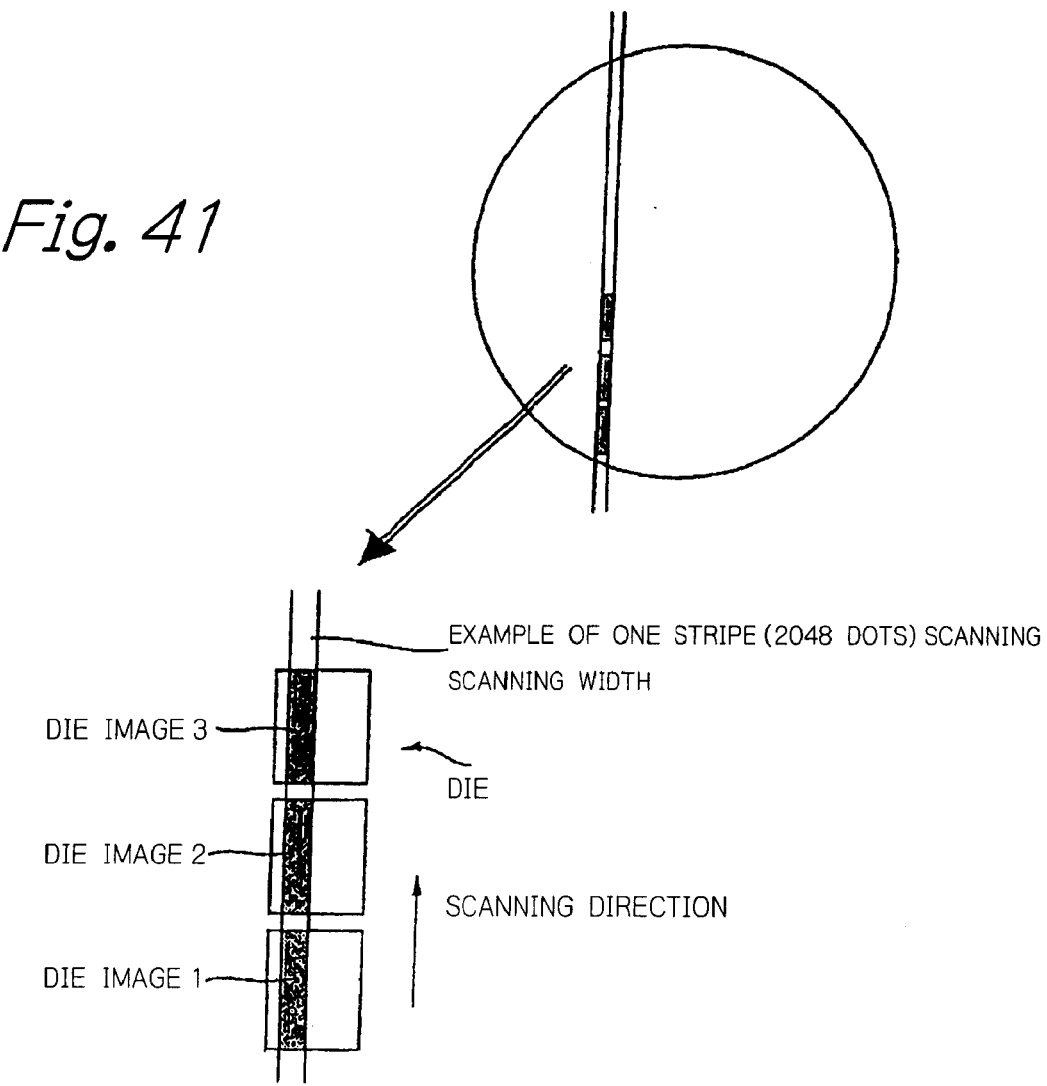

The reference image represents a die adjacent to an image under inspection. Two dies adjacent to the image under inspection are compared to determine a defect. Specifically, referring to FIGS. 41 and 42, the following steps are executed in a situation where switches 245, 246 are set to connect a memory 241 and a memory 242 of an image processing apparatus are connected to a path 244 of a camera 243.

a) A step of storing a die image 1 from the path 244 to the memory 241 in accordance with a scanning direction S.

b) A step of storing a die image 2 from the path 244 to the memory 242.

c) A step of capturing the die image 2 from a path 247 simultaneously with the foregoing step b), while comparing the capture die image 2 with image data stored in the memory 241 which is at the same relative position in the die to find differences.

d) A step of saving the differences found in step c).

e) A step of storing a die image 3 from the path 244 to the memory 241.

f) A step of capturing the die image from the path 247 simultaneously with the foregoing step e), while comparing the captured die image 3 with image data stored in the memory 242 which is at the same relative position in the die to find differences.

g) A step of saving the differences found in step f).

h) A step of determining defects in the die image 2 from the result saved in steps d) and g).

i) A step of subsequently repeating steps a) to h) in consecutive dies.

Settings may be made to correct the two images to be compared such that a position alignment, i.e., a difference in position is eliminated in the two image before the differences are found in steps c) and f). Alternatively, a correction may be made to eliminate density alignment, i.e., a difference density. In some cases, both processes may be required.

B. Reference Die Comparison Method (Die-Any Die Test)

Figure 50:
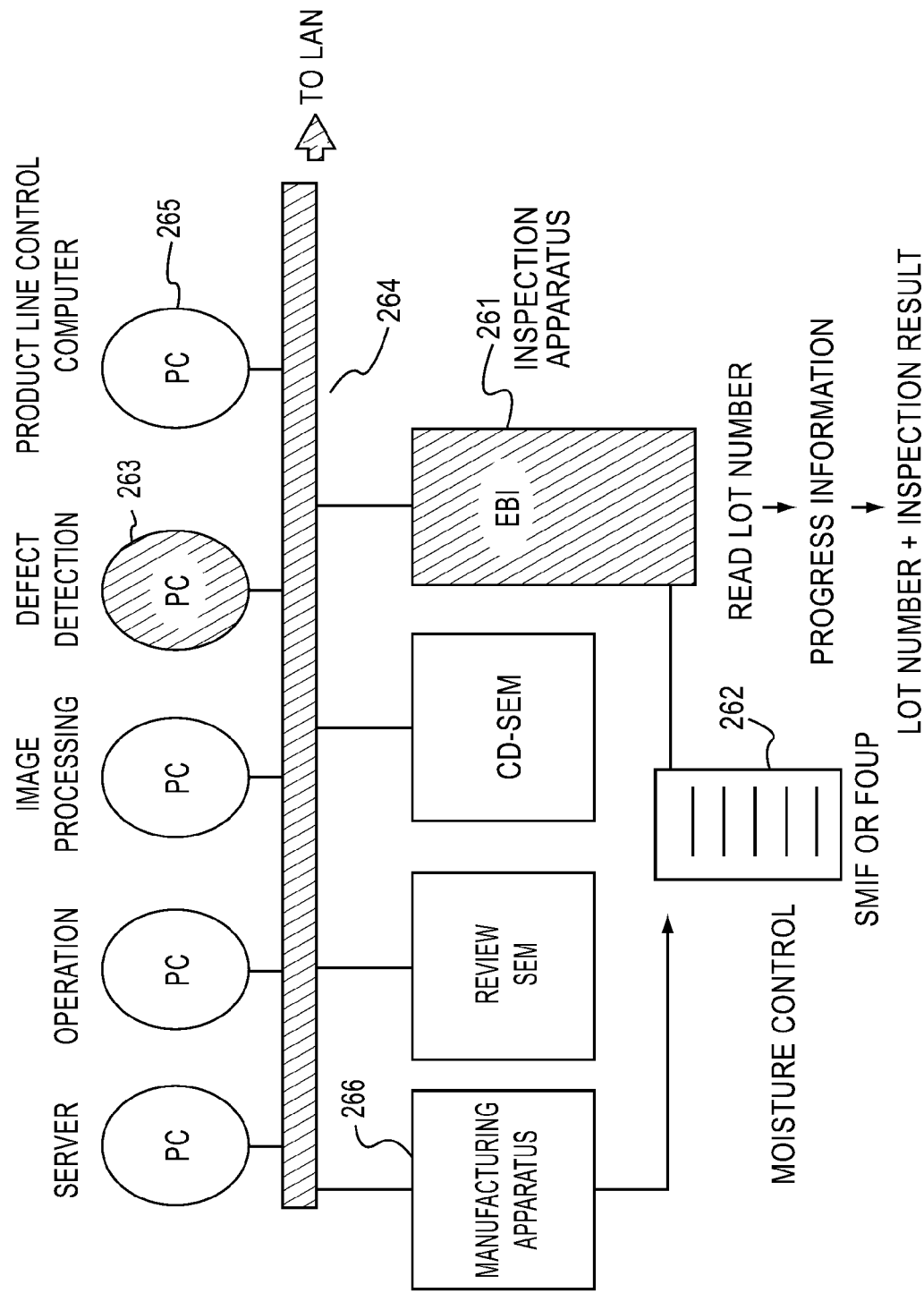

The operator specifies a reference die. The reference die is a die existing on a wafer, or a die image saved before the test. First, the reference die is scanned or transferred to wave its image in a memory for use as a reference image. Specifically, the following steps are executed in FIGS. 42 and 43.

a) A step of selecting the reference die by the operator from a die on a wafer under inspection or die images stored before the test.

b) A step of setting the switch 245 and switch 246 such that at least one of the memory 241 and memory 242 of an image processing apparatus is connected to a path 244 from a camera 243 when a reference die exists on the wafer under inspection.

c) A step of setting the switch 245 and switch 246 such that at least one of the memory 241 and memory 242 of the image processing apparatus is connected to a path 249 from a memory 248 which stores a reference image that is the die image when the reference die is a die image saved before the test.

d) A step of scanning the reference die, when it exists on the wafer under inspection, and transferring a reference image, which is a reference die image, to a memory of the image processing apparatus.

e) A step of transferring a reference image, which is a reference die image, to a memory of the image processing apparatus, without the need for scanning, when the reference die is a die image saved before the test.

f) A step of comparing an image generated by sequentially scanning the image under inspection, the image in the memory to which the reference image, i.e., the reference die image has been transferred, and image data which is at the same relative position in the die to find differences.

g) A step of determining defects from the differences found in the foregoing step f).

h) A step of subsequently testing or inspecting the same portions for a scanning position of the reference die and the die origin of the die under inspection over the entire wafer, as illustrated in FIG. 50, and repeating the foregoing steps d) to g) while changing the scanning position of the reference die until the entire die is tested.

Settings may be made to correct two images to be compared such that a position alignment, i.e., a difference in position is eliminated in the two images before the differences are found in step f). Alternatively, a correction may be made to eliminate density alignment, i.e., a difference density. In some cases, both processes may be required. The reference die image stored in the memory of the image processing apparatus in step d) or e) may be the entire reference die, or a portion of the reference die which is updated.

C. CAD Data Comparison Method (CAD Data-Any Die Test)

A certain image is created for use as a reference image from CAD data which is the output of a CAD-based semiconductor pattern designing process. The reference image may represent an entire die, or part thereof which includes a portion under inspection. Also, this CAD data is typically vector data which cannot be used as the reference image unless the CAD data is converted to raster data equivalent to image data captured by a scanning operation. Thus, the following conversion process is executed in regard to the CAD data processing operation.

a) Vector data, which comprises the CAD data, is converted to raster data.

b) The foregoing step a) is performed in units of image scanning width which is known by scanning the die under inspection during a test.

c) The foregoing step b) converts image data which is at the same relative position in the die as an image which is expected to be captured by scanning the die under inspection.

d) The foregoing step c) is performed while the test scanning is overlapped with the conversion operation.

While the foregoing steps a)-d) are an exemplary sequence of making a conversion in units of image, scanning widths for faster processing, the test can be conducted without fixing the conversion unit to the image scanning width.

As an additional function to the operation for converting vector data to raster data, at least one of the following functions is provided.

a) A function of converting raster data to multi-value data.

b) A function of setting a gradation weight and an offset for the conversion to multi-value data in view of the sensitivity of the inspection apparatus in regard to the foregoing function a).

c) A function of processing an image for modifications such as expansion, reduction and the like after vector data has been converted to raster data.

Figure 42:
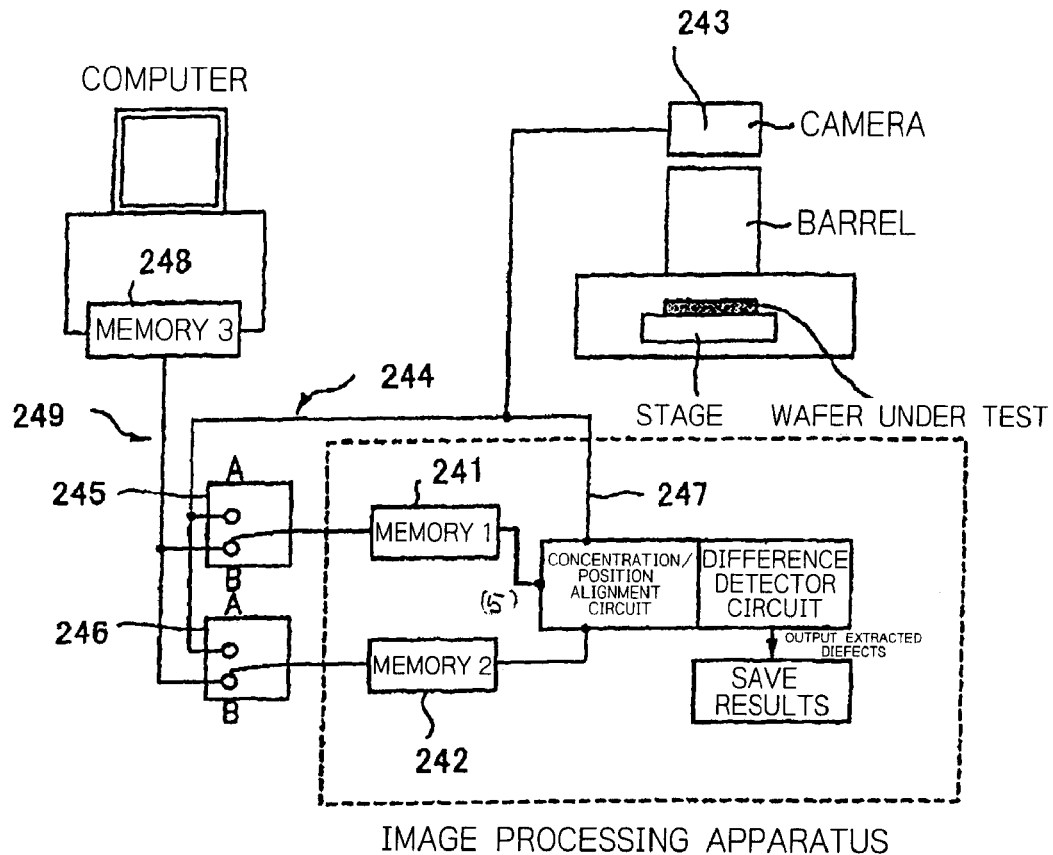
Figure 43:
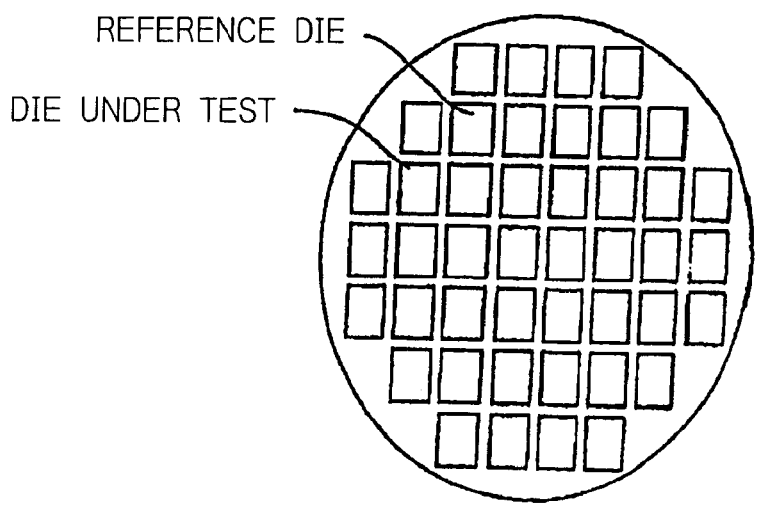
Figure 44:
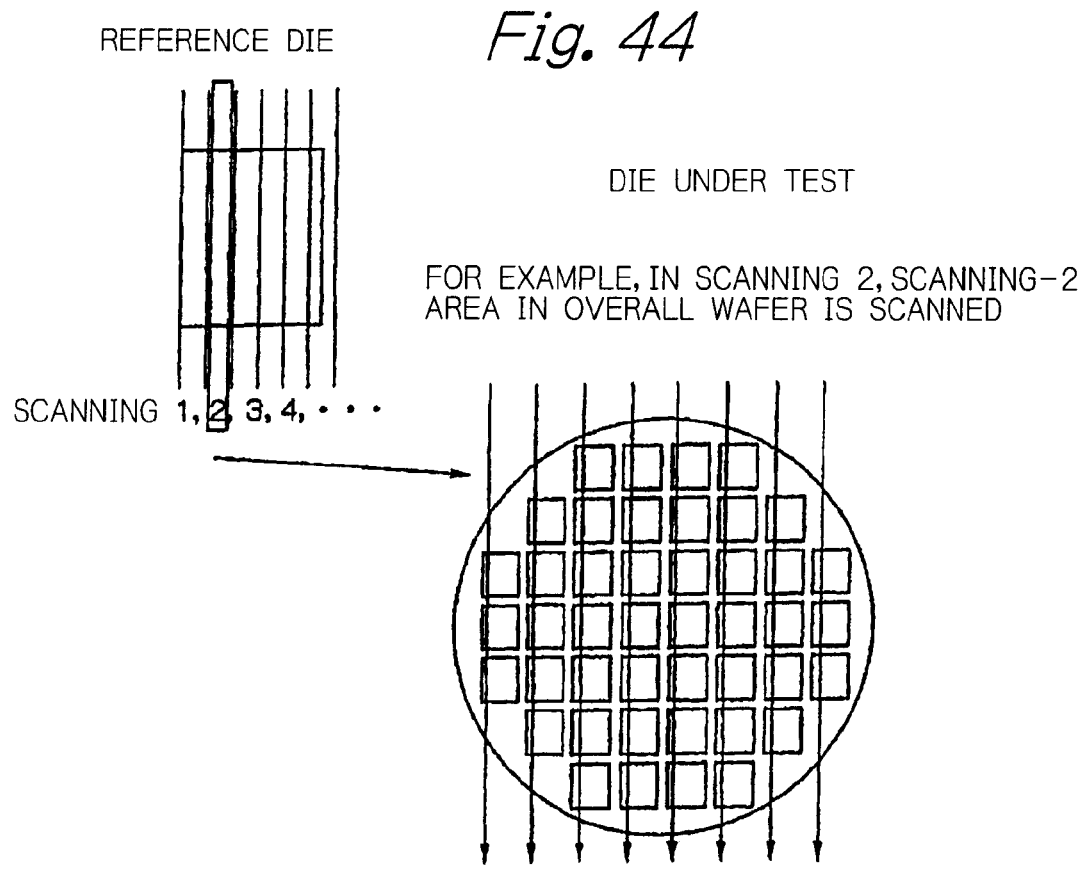

Inspection steps based on the CAD data comparison method executed in the apparatus illustrated in FIG. 42 are as follows:

a) A step of converting CAD data to raster data in a computer 1, and generating a reference image and saving the reference image in the memory 248 with the aid of the foregoing additional function.

b) A step of setting the switch 245 and switch 246 such that at least one of the memory 241 and memory 242 of the image processing apparatus is connected to the path 249 from the memory 248.

c) A step of transferring the reference image in the memory 248 to a memory of the image processing apparatus.

d) A step of comparing an image generated by sequentially scanning the image under inspection, the image in the memory to which the reference image has been transferred, and image data which is at the same relative position in the die to find differences.

e) A step of determining defects from the differences found in the foregoing step d).

f) A step of subsequently testing or inspecting the same portions for a scanning position of the reference die and the die origin of the die under inspection over the entire wafer, as illustrated in FIG. 44, and repeating the foregoing steps a) to e) while changing the scanning position of the reference die until the entire die is tested.

Settings are made to correct two images to be compared such that a position alignment is made, i.e., a difference in position is eliminated in the two images before the differences are found in step d). Alternatively, a correction is made to eliminate density alignment, i.e., a difference density. In some cases, both processes may be required. The reference die image stored in the memory of the image processing apparatus in step c) may be the entire reference die, or a portion of the reference die which may be tested while it is updated.

While the foregoing description has been made on the algorithms of the array test (cell test) for inspecting periodic structures, and the random test, the cell test and random test can be conducted simultaneously. Specifically, the cell area and random area are separately processed, wherein cells are compared with one another in a die in the cell area, and simultaneously, a comparison is made with adjacent dies, reference die, or CAD data-in the random area. By doing so, the inspection time can be largely reduced to improve the throughput.

In this event, inspection circuits for the cell area are preferably provided independently of one another. Also, if tests are not conducted simultaneously, a single inspection circuit may be provided with programs which can be switched for the cell test and random test, so that the comparison test can be conducted by switching the programs. Specifically, when patterns are tested with a plurality of processing algorithms applied thereto, these algorithms may be executed simultaneously with separate circuits provided therefor, or algorithms corresponding to them may be provided and switched by a single circuit for processing. In any case, this method can be applied as well when there is a plurality of types of cells which are compared with one another, and dies are compared with each other or with CAD data in the random section.

Figure 45:
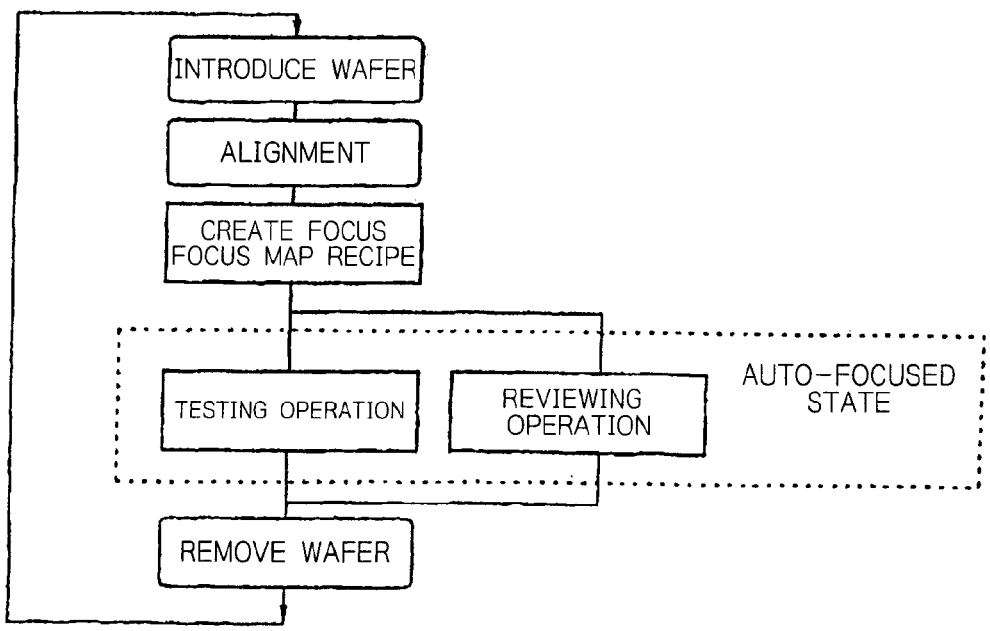

FIG. 45 illustrates a basic flow of a focus function. First, after transferring a wafer including an alignment operation, recipes are created for setting conditions related to the test, and the like. One of the recipes is a focus map recipe which is relied on to perform an auto-focus operation during a inspection operation and a reviewing operation in accordance with focus information set therein. The following description will be made on a procedure of creating the focus map recipe, and a procedure of the auto-focus operation.

In the following example, the focus map recipe has an independent input screen, and the operator executes the following steps to create the focus recipe. Such an input screen may be added to an input screen provided for different purposes.

a) A step of entering focus map coordinate representing the position of a die, a pattern within the die, or the like for which a focus value is entered. A switch 251 in FIG. 46.

b) A step of setting a die pattern which is required for automatically measuring a focus value. This step may be skipped when the focus value is not automatically measured.

c) A step of setting a best focus value at the coordinate on the focus map determined at the foregoing step a).

Among the foregoing steps, while the operator can specify an arbitrary die at step a), other setting can also be made, such as a selection of all dies, a selection of every n die, and the like. In addition, the operator can select the input screen from any of a figure which schematically represents the arrangement of dies within a wafer and an image which uses an actual image.

Figure 46:
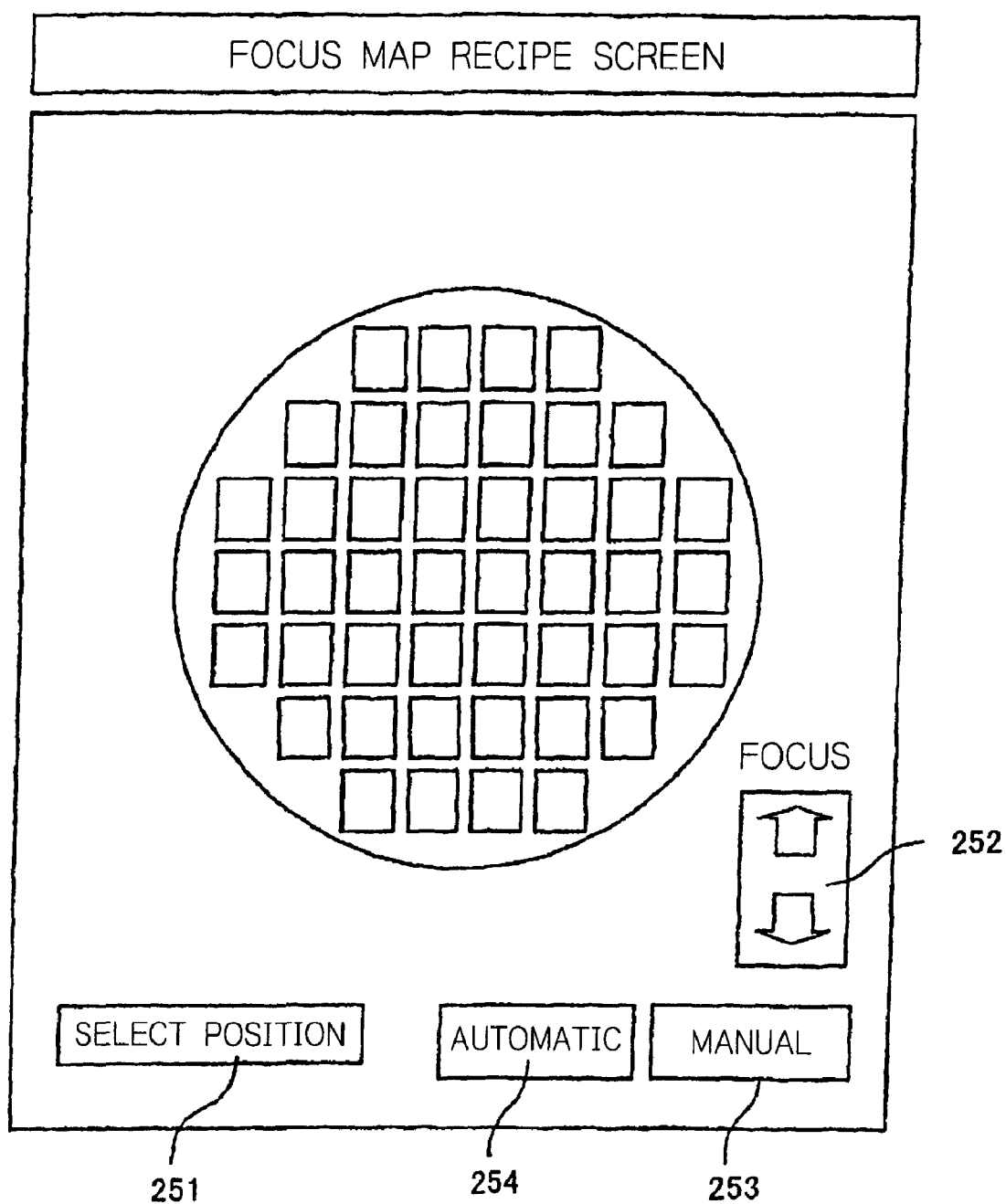
Figure 47:
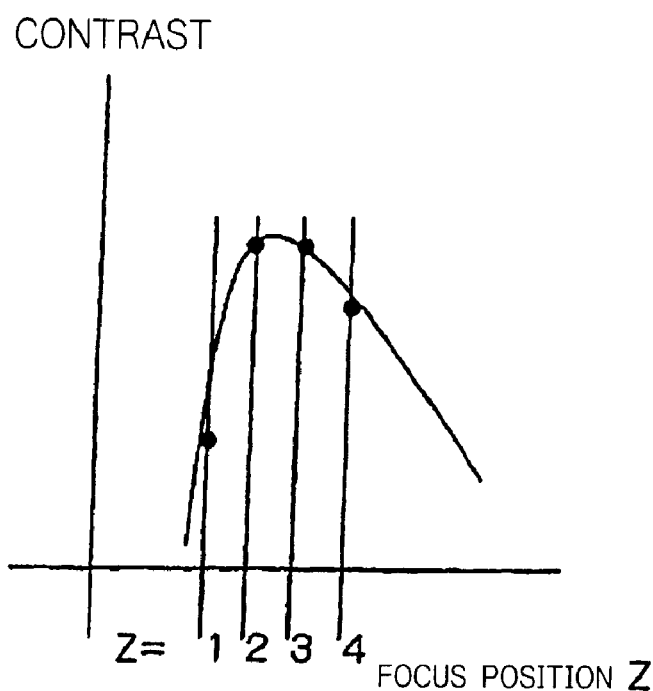

Among them, at step c), the operator manually selects and sets in a mode manually set by a focus switch 252 associated with a voltage value provided to a focusing electrode (switch 253 in FIG. 46). A mode for automatically finding a focus value to be supplied (switch 254 in FIG. 46).

A procedure for automatically finding a focus value at the forgoing step c) involves, for example, the following steps of:

a) finding an image with a focus position Z=1, and calculating the contrast thereof;

b) performing the foregoing step a) while each of focus positions Z=2, 3, and 4;

c) regressing from the contrast values calculated at steps a) and b) to find a contrast function (see FIG. 48); and d) calculating a Z value which results in a maximum value of the contrast function, and choosing it to be the best focus value.

Figure 48:
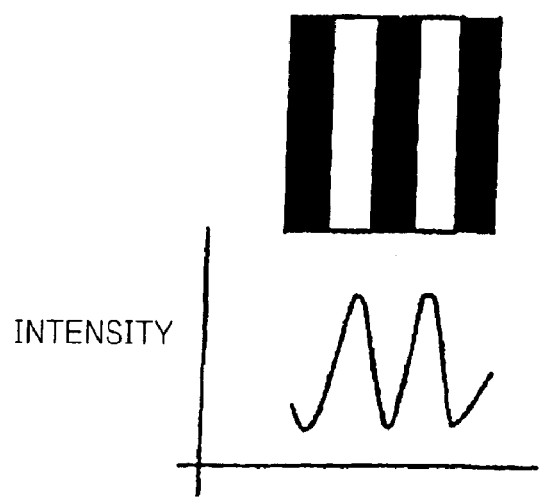

For example, a die pattern required for automatically measuring a focus value presents good results when a selected pattern consists of alternating lines and spaces as illustrated in FIG. 48, the contrast can be measured irrespective of the shape of a black and white pattern, whichever one is selected.

The single best focus value can be found by executing steps a) to d). A data format in this event is (X, Y, Z), which is a combination of a set of the coordinate values X and Y at which the focus is found, and the best focus value Z. Therefore, there exist a number of focus map coordinates (X, Y, Z) determined by the focus map recipe. This is part of the focus map recipe, and is called a "focus map file."

A method of setting a focus to the best focus during a inspection operation for capturing an image and a reviewing operation, is implemented by the following steps.

a) Positional information is further sub-divided based on the focus map file 1 created during the creation of the focus map recipe, and the best focus at this time is calculated to create a sub-divided focus map file 2.

b) The calculation at step a) is performed using an interpolation function.

c) The interpolation function at step b) may be linear interpolation, spline interpolation or the like, and is specified by the operator upon creation of the focus map recipe.

d) The current X-Y position is monitored on the stage, and a voltage at the focus electrode is changed to a focus value described in the focus map file 2 suited to the current X-Y position.

Figure 49:
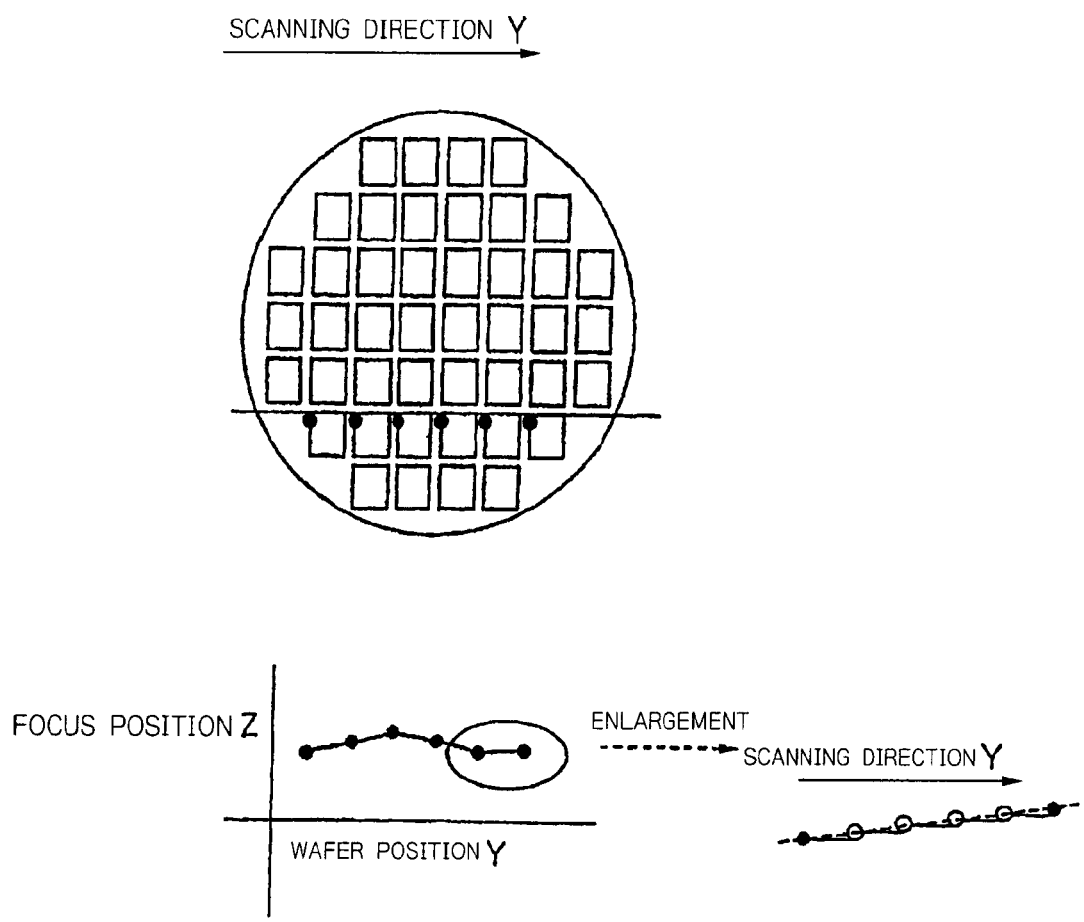

Describing more specifically with reference to FIG. 49, a black circle represents a focus value of the focus map file 1, and a white circle represents a focus value of the focus map file 2, wherein:

1. focus values of the focus map file 2 are inserted between focus values of the focus map file 1; and
2. a focused position Z is varied following the scanning to maintain the best focus. In this event, the value of the preceding focus value is maintained between two white circles until the focus position is varied next time.

FIG. 50 illustrates an exemplary semiconductor manufacturing plant which employs the electron beam apparatus according to the present invention. In FIG. 50, the electron beam apparatus is designated by a reference numeral 261. Information such as a lot number of wafers to be tested by the electron beam apparatus, histories of manufacturing apparatuses, and the like are read from a memory included in SMIF or FOUP 262, or the lot number can be recognized by reading an ID number of the SMIF, FOUP 262 or a wafer cassette. During the transfer of wafers, the amount of moisture is controlled to prevent oxidization of metal wires and the like.

A PC 263 of a defect detector 261 for controlling a defect detection is connected to an information communication network 264 of a production line, so that information such as a lot number of wafers which are objects under inspection, and the result of their tests can be sent to a production line control computer 265, a variety of manufacturing apparatuses 266, and other inspection systems through the network 264. The manufacturing apparatuses 266 include those associated with lithography, for example, an exposure apparatus, a coater, a curing apparatus, a developer, and the like, an etching apparatus, deposition apparatuses such as a sputtering apparatus and a CVD apparatus, a CMP apparatus, a variety of measuring apparatuses, other inspection apparatus, and the like.

Figure 51:
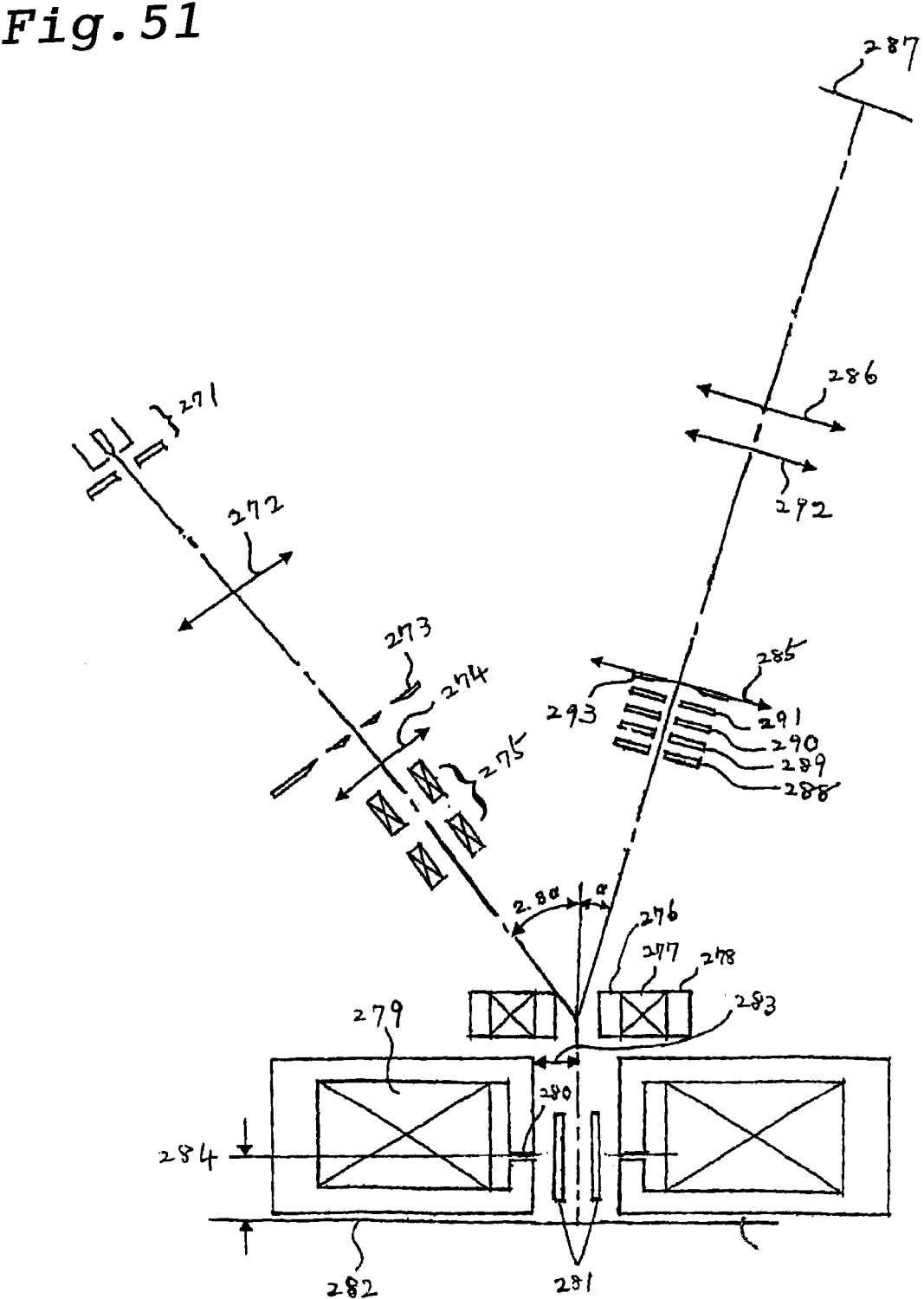

FIG. 51 is a diagram generally illustrating a fourth embodiment of the electron beam apparatus according to the present invention. The present invention will be described with reference to this figure.

An electron gun 271 comprises a cathode made of lanthanum hexaboride (hereinafter called "LaB6") having electron emission capabilities; a Wehnelt electrode having an electrode perpendicular to the optical axis; and an anode. By operating the cathode in a space charge control region, shot noise can be reduced during use.

Electron beams emitted from the electron gun are converged by a condenser lens 272 which comprises an electromagnetic lens, to form a cross-over at a point closer to the electron gun than formation apertures 273. Electron beams diverged from the cross-over can irradiate the formation apertures 273 with a uniform intensity. When the irradiation intensity is too low, the cross-over image can be brought closer to the formation apertures 273, thereby increasing the irradiation intensity. On the other hand, when a uniform irradiation intensity is provided in a small region, the cross-over position may be brought closer to the electron gun.

Electron beams formed into a rectangular shape by the action of the formation apertures 273, are reduced in size by a condenser lens 273 comprising an electromagnetic lens, and an objective lens 279, and focused on the surface of a sample 282 to form a formation image. Under the condenser lens 274, a deflector 275 is provided for adjusting the trajectory of the primary beams.

The cross-over image formed in front of the formation apertures 273 is focused on the main surface of the objective lens 279 by the condenser lens 274 to ensure the separation of the formation image from the cross-over image. A plurality of formation apertures 273 are provided in order to replace one with another when the one gets dirty, and vary a irradiated range in accordance with a change in pixel dimensions.

When the formation apertures are changed in dimensions, the excitation of the condenser lens 274 is also changed. For example, with a small formation aperture, the cross-over image is brought closer to the formation aperture 273 to increase the current density. The adjustment thus made causes the cross-over image to deviate from the main surface of the objective lens 279. However, with the employment of electromagnetic lenses for the condenser lenses 272 and 274 which corrects this deviation by changing the excitation of the lens 274, the supply current need not be largely changed when the energy of primary electron beams is changed, so that a smaller burden is imposed than when electrostatic lenses are employed.

Electromagnetic deflectors 175 are provided at two stages behind the condenser lens 274. As a result, primary electron beams can be adjusted to pass along a shifted trajectory, rather than passing along the same passage as secondary electron beams below an ExB separator which comprises an ExB electrostatic deflector 276, an ExB electromagnetic deflection coil 277, and an ExB deflection core 278.

Secondary electrons from the sample are deflected by $\alpha$ by the electrostatic deflector 276 of the ExB separator by $-2\alpha$ and by an electromagnetic deflector. In this event, since the amount of electrostatic deflection is one-half as much as the amount of electromagnetic deflection and is reverse in direction to the same, the resulting design can substantially eliminate deflection chromatic aberration which is the major aberration of the ExB separator. Since the primary electrons are slightly higher in energy than the secondary electrons, the primary electrons are deflected by $2.8\alpha$ to the left and impinge on the sample 282. It should be noted that in the figure, the deflection to the left is defined as positive.

It is important that a Bohr radius 283 (inner diameter of a cylindrical portion at the center of the objective lens) of the objective lens, and the distance 284 between the sample and the main surface of the objective lens are made larger than the Bohr radius of the objective lens. As a result, the secondary electrons emitted from the sample in the normal can direction intersect with the optical axis and pass through the NA aperture. Even with an objective lens which has a lens gap closer to a sample, a similar effect can also be produced by increasing the distance between the sample and the bottom of the objective lens magnetic pole beyond the Bohr radius of the lens.

A lens gap 280 of the objective lens 279 is as small as 2 mm or less, while the Bohr radius is as large as 20 mm$\phi$. In addition, the objective lens 279 is a normal magnetic lens, i.e., a lens which has the magnetic gap closer to the optical axis. In this event, the Bohr radius is chosen to be 20 mm from the fact that the visual field extends over 200 μm, but by setting the Bohr radius to 80 times or more of the maximum diameter of the visual field, the secondary electrons or reflected electrons emitted from the sample in the normal direction can intersect with the optical axis and pass through the NA aperture. Note, however, that the diameter of the visual field is defined herein to be the length of the diagonal of the image on the surface of the aforementioned rectangular sample.

A Z-direction dimension from the sample 282 to the center of the lens gap 280 is made larger than the Bohr radius so as not to increase chromatic aberration of higher-order magnification and rotation (blur proportional to R3ΔV/V). Also, an axially symmetric cylinder electrode 281 is provided near the lens gap 280, and by applying a positive high voltage to this cylindrical electrode 281, the axial chromatic aberration of the objective lens can be reduced between this cylindrical electrode, which can reduce the axial chromatic aberration and the sample, without ensuring a distance enough to avoid a discharge, and without causing a discharge between the objective lenses.

The secondary electron or reflected electron image is enlarged approximately by a factor of five by the objective lens 279, and further enlarged by a factor of five and by a factor of ten by the electromagnetic lenses 285 and 286, respectively, i.e., totally enlarged by a factor of 250, and creates an enlarged image on a scintillator 287 which is adjusted in magnification by an optical lens system, detected and converted into an electric signal by a TDI detector or a CCD detector, and processed into two-dimensional image data by a signal processing circuit.

Electrodes 288, 289, 290, 291 make up an electrostatic lens, and acts as an auxiliary lens for creating a cross-over image produced by the objective lens substantially on the main surface of the lens 285. This lens can reduce the beam bunch and aberration at the position of the lens 285. Also, the image of the sample by the objective lens 279 is formed on the main surface of this electrostatic lens. This electrostatic lens does not affect the magnification. Likewise, a sample image produced by the lens 285 is formed on the main surface of the auxiliary lens 292, and is focused on the surface of the scintillator 287 by the lens 286. The cross-over image produced on the main surface of the lens 285 is formed on the main surface of the lens 286 by the auxiliary lens 292, and the lens 286 reduces the beam bunch and aberration.

By switching the formation of image between a high-throughput low-accuracy mode and a low-throughput high-accuracy mode, the irradiated area and magnification need be varied. The former may simply involve switching the formation aperture 273 to one having dimensions compatible with the mode. The latter, i.e., variations of the magnification may involve applying a lens voltage to the electrode 290, grounding the electrodes 288, 289, 291, reducing the excitation of the lens 279, and matching a first enlarged image with the position of the electrode 290, thus resulting in a higher magnification. A low-magnification image can be produced by applying a lens voltage to the electrode 289, and matching the first enlarged image with the position of the electrode 289. Since the electrodes 288, 291 are grounded at all times, they need not be insulated.

An NA aperture 293 of the secondary optical system is provided on the main surface of the electromagnetic lens 285. Since the lenses 272, 274, 286, 292 may be electrostatic or electromagnetic, because they are not related to aberration. However, with beam energy of approximately 4 KeV, the electromagnetic lens more easily reduces the focal distance, and can reduce the focal distance of the lens with a practical driving power supply, so that it can reduce the length of the barrel** and a blurred beam due to the space charge effect.

FIG. 52 is a diagram illustrating an electro-optical system in a fifth embodiment of the electron beam apparatus according to the present invention.

An electron gum comprises a cathode 301 made of LaB6; a Wehnelt electrode 302 having an electrode perpendicular to the optical axis; and an anode 303. By operating the cathode in a space charge control region, shot noise is reduced by a factor of five as compared with a Schottky cathode and an FE gun.

Electron beams emitted from the electron gun are aligned by an alignment deflector 304 and enters a condenser lens 305 which comprises an electromagnetic lens. Electron beams converged by the condenser lens 305 forms a cross-over at a position closer to the electron gun than a formation aperture 308. Electron beams diverged from the cross-over can irradiate the formation apertures 308 with a uniform intensity. Electron beams formed into a rectangular shape by the action of the formation apertures 308, are reduced in size by a condenser lens 309 and an objective lens 314, and forms a formation image on the surface of the sample 313. In this event, the cross-over image created in front of the formation apertures 308 is focused on the objective lens 314 by the formation lens 309 to ensure the separation of the formation image from the cross-over image.

A plurality of formation apertures 308 are provided in order to replace one with another when the one gets dirty, and vary a irradiated range in accordance with a change in pixel dimensions. When the formation apertures are changed in dimensions, the excitation of the condenser lens is changed. For example, with a small formation aperture, the cross-over image is brought closer to the formation aperture 273 to increase the current density. The adjustment thus made causes the cross-over image to deviate from the main surface of the objective lens 279, however, without causing any grave problem.

While the lens excitation condition must be changed in order to change the energy of the primary electron beams, with the employment of electromagnetic lenses for the condenser lenses 305 and formation lens 309, the supply current need not be largely changed when the energy of primary electron beams is changed, so that a smaller burden is imposed than when electrostatic lenses are employed.

Deflectors 310, 311 are provided at two stages below the formation lens 309, such that the primary beams of electron beams pass along a trajectory deviated from the main beam of the secondary electrons or reflected electron beams, as indicated by 312. The alignment to the formation apertures 308 and formation lens 309 is performed using the electrostatic deflectors 306, 307 at two stages, so that the two electrostatic deflectors can be set at two different deflection ratios, specifically, (1) a setting which causes deflection fulcrums of the two deflectors to match with formation aperture 308, and (2) a setting which causes the same to match which the main surface of the formation lens 309. By selecting one of the settings, the alignment can be performed without exerting influences on each other. The objective lens 341 will be described with reference to FIG. 55.

Now, a description will be made of two scenarios, where the visual field is divided into sub-visual fields, in each of which a sample image is captured, and where a sample image is collectively captured without deflectors. When a sample image is captured without deflectors, it is necessary to solve a problem that secondary electrons or reflected electrons emitted from a visual field end in the normal direction do not pass through the NA aperture. With the employment of a magnetic lens which has a smaller Bohr radius on the sample side for an objective lens, the secondary electrons or reflected electrons can pass through the NA aperture, and the secondary electrons or reflected electrons can be improved in transmittance. In the present invention, the Bohr radius of the lower magnetic pole is smaller than the Bohr radius of the upper magnetic pole. Ideally, the Bohr radius of the upper magnetic pole should be 1.5 times as large as the Bohr radius of the lower magnetic pole. As a result of a simulation in which the Bohr radius of the lower magnetic pole was chosen to be 8 mm, and the distance between a sample and the main surface of the objective lens was chosen to be 10 mm, it has been found that secondary electrons emitted in a direction inclined by eight degrees with respect to the normal of the surface of the sample intersect with the optical axis. Accordingly, from the cosine rule, components of the secondary electrons centered at eight degrees will pass.

On the other hand, in a division image capture which divides the visual field into sub-visual fields, in each of which a sample image is captured, the visual field is divided into 4-20 sub-visual fields, where electron beams can be corrected for aberrations using deflectors and the like to capture a sample image in a low aberration condition. In this event, the visual fields should be in the shape of a square or a rectangle which is similar to a square and is slightly shorter in the longitudinal direction of the visual field.

A MOL method is known in the field of lithography as an approach for causing electron beams to pass away from the optical axis of a lens, thereby preventing the electron beams from being affected by aberration.

Now, the objective lens will be described with reference to FIG. 55. An upper deflector 342 and a lower deflector 341 are disposed across a lens magnetic field 344, such that a lower deflection magnetic field is generated in an orientation 346 for electron beams which pass to the right of the optical axes, and the upper deflector produces a deflection magnetic field in an orientation 347. Quantitatively, a resulting deflection magnetic field is proportional to a differentiated value in regard to Z of an axial magnetic field distribution of the objective lens 341. The axial magnetic strength distribution of the objective lens 314 presents a maximum value at the position of the objective lens magnetic field 344, positive values in a region above this position, and negative values in a region below this position in regard to Z. The visual field can be expanded with reduced axial chromatic aberration by using a magnetic lens for the objective lens, providing electromagnetic coils at two stages before and after the main surface of the objective lens thereacross, and designing these deflectors to substantially satisfy the MOL condition.

Figure 55:
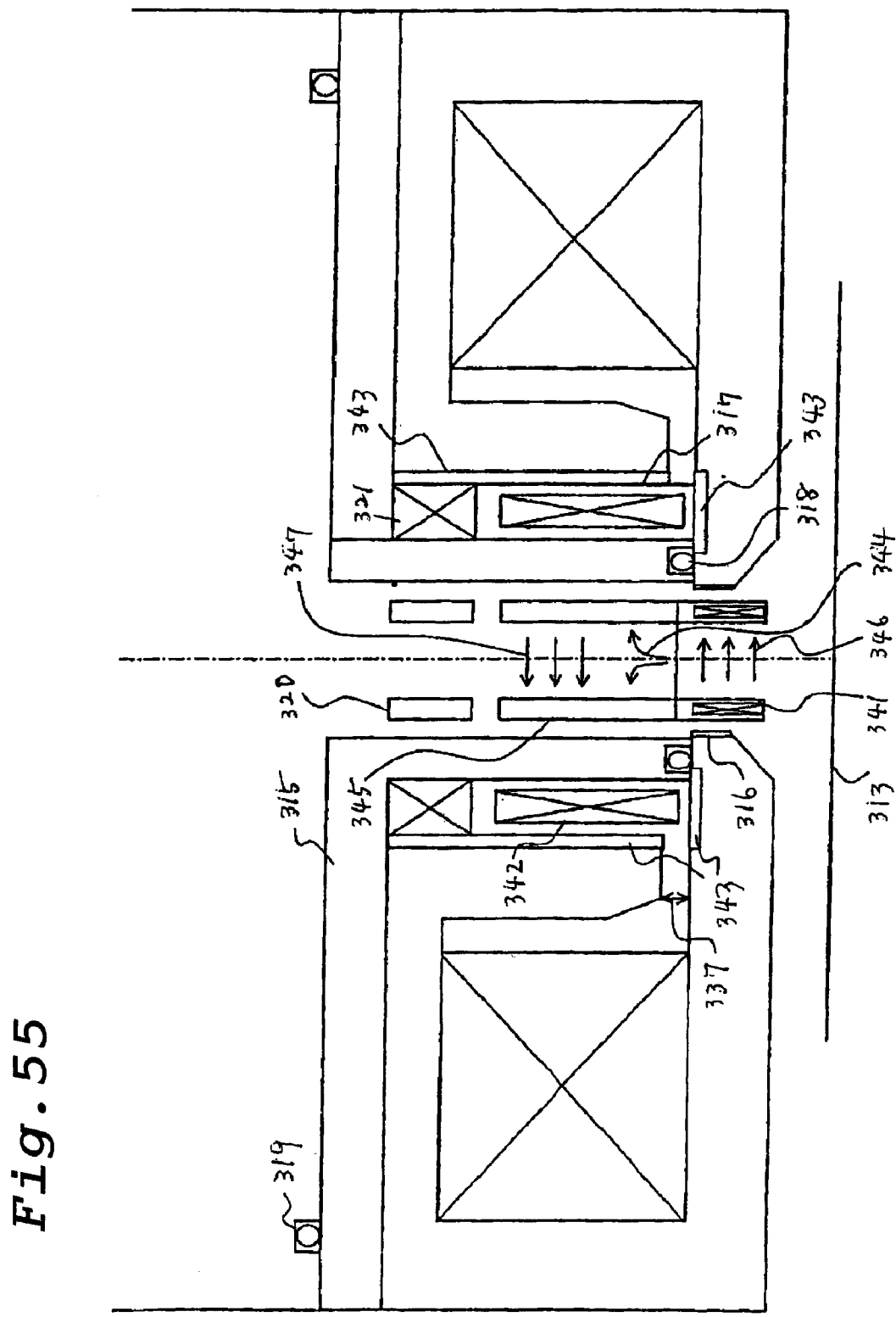

Accordingly, the deflection coil which satisfies the MOL condition may comprise two deflection coils 341, 342 disposed above and below the lens main surface, as illustrated in FIG. 55, where the upper deflection coil 342 may present a small peak value and a large half-value width, while the lower deflection coil may present a large peak value and a small half-value width.

A ferromagnetic material 343 outside the deflection coil is required to respond well at high frequencies with a ferrite adhered at least to the surface thereof. Also, a liner tube (vacuum wall) 315 may be made of an insulating material such as ceramics or the like, the surface of which is coated with a conductive material. The deflection coil 341, which must be contained in vacuum may be contained within a coaxially symmetric electrode 345, the surface of which is coated with a metal. In FIG. 55, as a high negative voltage is applied to the coated surface of the axially symmetric electrode 345, the axial chromatic aberration can be advantageously reduced.

Secondary electrons or reflected electrons from a sample pass through the objective lens, and area deflected by an ExB separator (which comprises the electrostatic deflector 320 of the ExB separator and the electromagnetic deflector 321 of the ExB separator). The optical axis of the secondary optical system is present in a direction inclined by 10 degrees to the right on the figure. The secondary electrons or reflected electrons are deflected by ten degrees to the left by the electrostatic deflector 320, and receives a force from the electromagnetic deflector 321 which deflects the electrons by 20 degrees to the right, and are therefore deflected by 10 degrees to the right in total. Here, since the electrostatic deflection amount is one-half as much as the electromagnetic deflection amount and is reverse in direction to the same, the resulting design can substantially eliminate deflection chromatic aberration which is the major aberration of the ExB separator.

An auxiliary lens 326 acts to converge a cross-over image formed by the secondary electrons or reflected electrons emitted substantially perpendicular from the sample slightly in front of the ExB separator to focus the cross-over image on the main surface of the magnification lens 327.

Three types of enlarged images can be provided by selecting which of three electrodes of the auxiliary lens 326 for the sample image produced by the objective lens 314. For example, when the position of the sample image is formed at the second lowest electrode from below, the resulting magnification is the smallest. In this event, a voltage from a power supply 325 for driving the electrostatic lens is applied from this electrode, while the other electrodes are all grounded through a switch 324. This first image is enlarged by the magnification lens 327 to create an enlarged image at the position of the second electrode of the magnification lens 338 at the final stage, which is further enlarged by a lens action with a negative voltage applied from the fourth electrode from below to create a final image on the surface of a scintillator coated on a flat region of a ball lens 335 made of melted quartz.

The main surface of the magnification lens 327 has an NA aperture 328 and determines a compromise between aberration and secondary electron transmittance. The NA aperture 328 has a dimension of several tens to one hundred μm. The aberration of the auxiliary lens 326 does not at all cause any problem. This is because the position of the electrode serves as an image plane for the sample image so that no lens action develops and no aberration is produced. Accordingly, the power supply 325 supplies a negative voltage. Since the image is focused with a negative voltage of several kV, a simple insulating structure may be employed.

A lens at the final stage may be an electrostatic lens having five electrodes, with a central electrode thereof being applied with a voltage different in sign from voltages applied to electrodes before and after the central electrode, resulting in a maximum magnification. In some cases, the optical distance between the lenses can be shorter than the mechanical dimension, which can be achieved under a low aberration condition. Consequently, the secondary electron or reflected electron image can be improved in magnification.

For achieving the maximum magnification, the fourth electrode from below is applied with a voltage from the switch 323 of the power supply, causing the sample image to be focused at the position of this electrode. In this event, all the other electrodes are grounded. This results in a larger image point of the objective lens and a smaller object point of the magnification lens 327 to provide the maximum magnification.

In designing the final lens 300, the following two aspects should be taken into consideration.

(1) The Bohr radium of the electrode at the position of the auxiliary lens should be sufficiently larger than the diameter of a second image at this position; and (2) the distance between the main surface of the auxiliary lens and the main surface of the magnification lens should be reduced in order not to increase so much the enlarged image at this position and instead to increase the magnification. Of course, the focal distance should be made short in correspondence to this distance between the main surfaces under the foregoing conditions.

For reducing the focal distance of the auxiliary lens and the focal distance of the magnification lens, the present invention applies the third electrode with a voltage 331 which has a reverse sign to voltages applied to the second and fourth electrodes. By doing so, the electric field intensity between the second and third electrodes increases to produce a large lens action, as compared with a normal configuration in which the electrode is grounded. Another advantage is that the optical distance between the two lenses is reduced because the main surfaces of the lenses move toward the electrode simultaneously applied with a positive voltage due to a higher lens action of this electrode.

Also, when the aberration is compared with the magnification lens being driven with a negative voltage and with a positive voltage, no significant difference is found between the two cases. When an electromagnetic lens is employed for the magnification lens, distortion aberration is larger than when an electrostatic lens is employed. However, since the lens 327 is required to have the NA aperture disposed on the main surface, an electromagnetic lens should be employed therefor. Since this lens produces a small image, the value of distortion can be negligible (equal to or less than one tenth of the pixel) though the distortion aberration coefficient is large.

The alignment of the auxiliary lens 326, which is an electrostatic lens, with the electromagnetic lens 327 is performed by the ExB separator and alignment deflector 322 by matching the center of deflection with the auxiliary lens 326 or with the electromagnetic lens 327. The alignment of the magnification lens 330 to a bear is performed by an alignment deflector 329. Alignment 334 is intended for a scintillator 336.

The overall visual field can be reduced in aberration by making adjustments to correct field curvature aberration and anastigmatic, and reduce the difference in beam resolution between the center and periphery of the visual field. A ball lens 335 is designed such that the distance between the center of the sphere and a plane is 1/n (n is the refractive index of the material, and is 2.1 for melted quartz) of the radius of the sphere. Under this condition, a so-called aplanatic hyperhemisphere is established, where, advantageously, there is no spherical aberration, or anastigmatic, or chromatic aberration in the axial direction, the light emission direction is narrowed down to 1/n, and apparent dimensions of the scintillator, viewed from the optical lens 338 is increased by a factor of $n^2$. When the ball lens is corrected for other chromatic aberration and distortion by the optical lens 338, the optical lens system can be increased in transmittance even if the optical lens 338 has a large f-number. Even if the lens exhibits a low resolution, this does not cause any problem because the actual scintillator image is increased by a factor of $n^2$. Also, since the optical lens 338 has a large f-number, a simple lens may be employed therefor.

The electron beam apparatus having the electron-beam based inspection function can be applied to evaluate wafers during a semiconductor device manufacturing process. An exemplary semiconductor device manufacturing process will be described below with reference to a flow chart of FIG. 53.

(1) a wafer manufacturing process for preparing a wafer (or a wafer preparing process for preparing a wafer) (step 401);

(2) a mask manufacturing process for manufacturing masks for use in exposure (or mask preparing process for preparing masks)(step 402);

(3) a wafer processing process for performing processing required to the wafer (step 402);

(4) a chip assembling process for cutting one by one chips formed on the wafer and making them operable (step 403);

(5) a chip testing process for testing complete chips (step 404);

(6) a process for repeating the processes (2) and (3) as required; and (7) cutting the wafer and assembling devices.

The respective main processes are further comprised of several sub-processes. Among these main processes, the wafer fabricating process exerts critical affections to the performance of resulting semiconductor devices. This process involves sequentially laminating designed circuit patterns on the wafer to form a large number of chips which operate as memories, MPUs and so on. The wafer fabricating process includes the following sub-processes:

(A) a thin film forming sub-process for forming dielectric thin films serving as insulating layers, metal thin films for forming wires or electrodes, and so on (using CVD, sputtering and so on);

(B) an oxidation sub-process for oxidizing the thin film layers and the wafer substrate;

(C) a lithography sub-process for forming a resist pattern using masks (reticles) for selectively fabricating the thin film layers and the wafer substrate;

(D) an etching sub-process for fabricating the thin film layers and the substrate in conformity to the resist pattern (using, for example, dry etching techniques);

(E) an ion/impurity implantation/diffusion sub-process;

(F) a resist striping sub-process; and (G) a sub-process for testing the fabricated wafer.

As appreciated, the wafer fabrication process is repeated a number of times equal to the number of required layers to manufacture semiconductor devices which operate as designed.

Figure 54:
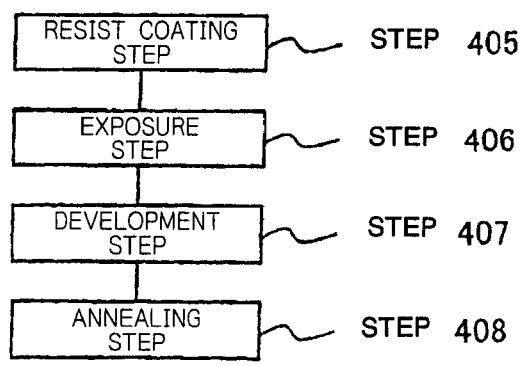

FIG. 54 is a flow chart illustrating the lithography sub-process which forms the core of the wafer processing process. The lithography sub-process includes the following steps:

(a) a resist coating step for coating a resist on the wafer on which circuit patterns have been formed in the previous process (step 405);

(b) a resist exposing step (step 406);

(c) a developing step for developing the exposed resist to produce a resist pattern (step 407); and (d) an annealing step for stabilizing the developed resist pattern (step 408).

Known processes are applied to the foregoing semiconductor device manufacturing process, wafer fabrication process and lithography process. When the electron beam apparatus according to the aforementioned embodiment of the present invention is employed in the wafer testing sub-process (G), the transmittance of secondary electron beams can be improved without causing a discharge between a sample and the objective lens to enable an efficient and highly accurate inspection, thus making it possible to increase the yield rate of products.

Figure 56:
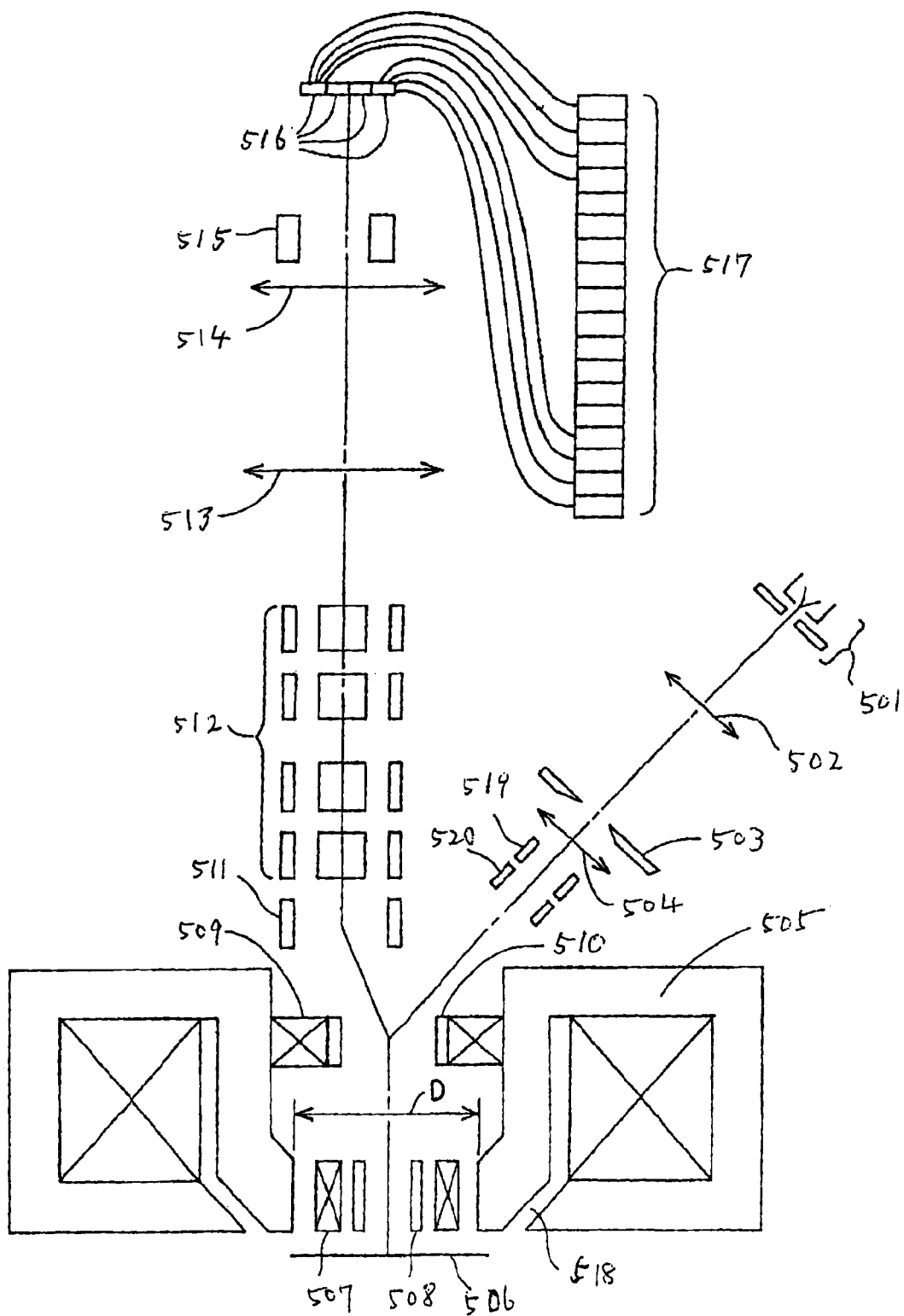

FIG. 56 is an explanatory diagram illustrating an electro-optical system of a sample evaluation apparatus such as a defect inspection apparatus which is a sixth embodiment of the electron beam apparatus according to the present invention. As illustrated in FIG. 56, in the sample evaluation apparatus of the present invention, electron beams emitted from an electron gun 501 are converged by a condenser lens 502, and formed into a rectangular shape through a rectangular aperture 503, such as square. The resulting rectangular electron beams are irradiated to the surface of a sample 506 through an irradiation lens 504 and an objective lens 505. In this event, the rectangular electron beams are deflected by an ExB separator 509 disposed within the objective lens 505, such that the electron beams are irradiated perpendicularly to the surface of the sample. Also, the rectangular electron beams are deflected by deflectors 519 and 520 such that the rectangular electron beams move within the visual field.

On the other hand, secondary electrons emitted from the sample 506 by this irradiation are converged by the objective lens 505 to form an enlarged image near an alignment deflector 511. The image is corrected for chromatic aberration by a chromatic aberration corrector 512, and formed in front of a magnification lens 513. In this embodiment, the chromatic aberration corrector 512 comprises quadrupole lenses stacked one on another at four stages. Then, the magnification lens 513 forms an enlarged image in front of a magnification lens 514, and the magnification lens 514 forms an enlarged image on the surface of a scintillator 516. In this event, a deflector 515 deflects the enlarged image such that it is formed on a corresponding detection plane of the scintillator 516 in synchronism with movements of the rectangular electron beams within the visual field by deflectors 519 and 520.

The scintillator 516 has a plurality of detection plane arranged in matrix, each of which corresponds to a sub-visual field. When primary electron beams are formed into a square shape, the scintillator 516 comprises 16 detection planes arranged, for example, in four rows and four columns. Image data detected by each detection plane of the scintillator 516 is transferred to CCD detectors (or MOS image sensors) associated with 512×512 pixels for conversion into an electric signal.

The objective lens 505 contains a MOL (Moving Objection lens) 7 and an axially symmetric electrode 508. While electron beams present larger aberration as they are further away from the optical axis, they can move in parallel with the axis of the objective lens by an appropriate electric field or magnetic field applied by these deflector and axially symmetric electrode, thus making it possible to provide a wide visual field. The MOL deflector 507 generates a magnetic field for reducing aberration of secondary electrons from the visual field other than the optical axis. Here, since the secondary electrons emitted from the sample 506 have an energy width, large axial chromatic aberration occurs after the secondary electron beam has passed through the objective lens. This axial chromatic aberration is corrected by axial chromatic aberration caused by the chromatic aberration corrector 512. A voltage applied to the axially symmetric electrode 508 is adjusted such that negative chromatic aberration by the chromatic aberration corrector 512 is equal to positive chromatic aberration caused by the objective lens 505 in absolute value.

In the present invention, aberration is reduced near the optical axis by thus correcting the axial chromatic aberration. Also, since off-axis aberration is corrected, CMOS image sensors are made available by dividing the visual field into a plurality of sub-fields and using the MOL deflector, so that the evaluation can be made at a high throughput.

In this regard, the objective lens 505 is configured to have a Bohr radius D which is larger than the diameter of the visual field by a factor of 50 or more, and a magnetic gap 518 is defined near the sample 506 for reducing the axial chromatic aberration.

FIGS. 57(A) and 57(B) are explanatory diagrams illustrating an electro-optical system of an electron beam drawing apparatus which is a seventh embodiment of the electron beam apparatus according to the present invention. In this apparatus, as illustrated in FIG. 57(A), electron beams emitted from an electron gun 531 are adjusted by two condenser lenses 532 and 533 for a uniformly irradiated region, and are irradiated to a rectangular aperture 534 in the shape of square or the like. Rectangular electron beams formed by the rectangular aperture are focused on a character mask 536 by a formation lens 535. The character mask 536 is provided with a plurality of magnification transmission masks for circuit patterns which should be transferred onto desired dies. By deflecting the rectangular electron beams by the deflector 546, a circuit pattern mask is selected on the character mask 536, and by deflecting the rectangular electron beams by the deflector 547, the rectangular electron beams are returned to the original optical axis.

The patterned rectangular electron beams are scaled down by a formation lens 537 and a reducing lens 538 to form a reduced image of the selected circuit pattern in front of a chromatic aberration corrector 539. Then, a reduced image is formed on a sample 545 through an objective lens 540 which comprises an electromagnetic lens. The objective lens 540 contains deflectors 541-544 for moving a circuit pattern image to a position within the visual field, at which a drawing is desired, and for reducing deflection aberration. It should be noted that the off-axis aberration can be reduced by a combination of electromagnetic deflectors 431-544 which are contained in the objective lens 540.

Figure 57:
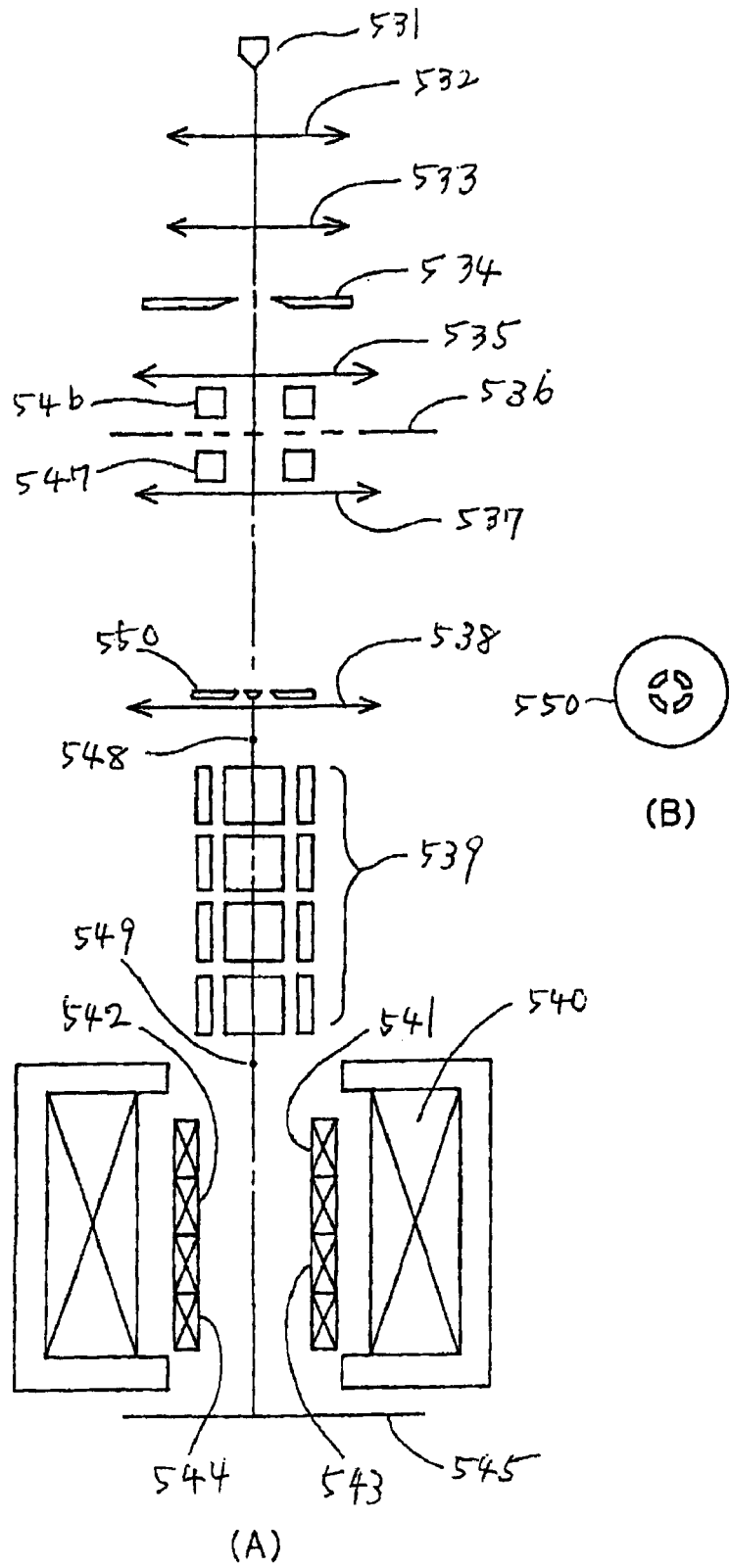

In this way, according to the electron beam drawing apparatus illustrated in FIG. 57, the axial chromatic aberration can be corrected by the chromatic aberration corrector 539, while the off-axis aberration can be corrected by the objective lens 540 and electromagnetic deflectors 541-544. Consequently, the aperture angle of an NA aperture 550 can be increased to reduce the space charge effect. Thus, since a drawing can be made with a large beam current, an LSI pattern and the like can be drawn on the sample at a high throughput.

Preferably, the reduced image formed by the reducing lens 538 is formed in front of the chromatic aberration corrector 539, while the image formed by the chromatic aberration corrector 539 is formed at a position 549 at which the reduction ratio by the objective lens 540 is approximately one.

Also, the NA aperture 550 can be in an annular shape as illustrated in FIG. 57(B) instead of a circular hole as illustrated in FIG. 57(A). Conventionally, an annular aperture is associated with a large aperture angle and large axial chromatic aberration caused thereby, so that the annular aperture has not been used in the past. The present invention can employ an annular NA aperture having a large aperture angle by correcting the axial chromatic aberration by the corrector, and as a result, can reduce the space charge effect and use a large beam current.

FIG. 58 illustrates a sample evaluation apparatus which is an eighth embodiment of the electron beam apparatus according to the present invention. In this apparatus, electron beams emitted from an electron gun 561 are converged by a condenser lens 562 to form a cross-over in front of a multi-aperture pate 563 which is provided with a plurality of apertures. Then, the electron beams diverged from the cross-over are irradiated to the multiple apertures to from a reduced image at a point P by lenses 564 and 565 which can be adjusted in reduction ratio and rotation angle, and the reduced image is formed on a sample 574 through a chromatic aberration corrector 568 and an objective lens 571 which is an electromagnetic lens. In this event, the electron beams are scanned on the sample 574 by electrostatic deflectors 569 and 575. For reducing chromatic aberration when the electron beams are scanned on a position away from the optical axis of the visual field, the Bohr radius D of the objective lens 57 is preferably set to 50 times or more larger than the visual field.

In this eighth embodiment, the electron gun 561 is preferably made of $LaB_6$. Also, for scanning a wider visual field, electromagnetic deflectors 572 and 573 are provided. These electromagnetic deflectors 572 and 573 satisfy the MOL condition. Specifically, an axial magnetic field distribution of the objective lens 571 is represented by a function approximated to a Gaussian distribution which has apeak at the center of a magnetic gap. Therefore, observing its differentiation in the z-axis direction, i.e., optical axis direction, i.e., a changing amount dz, this is represented by a function which reaches zero at the center of the magnetic gap and has opposite signs above and below the center. The deflection magnetic field generated by the deflectors 572 and 573 may be adjusted so as to be proportional to the differentiation function. However, a ferrite pipe 577 must be adhered to the inner surface of the core of the objective lens 571.

Multiple secondary electron beams emitted from the sample 574 are accelerated by an acceleration electric field generated by an axially symmetric electrode 576 applied with a positive voltage and the surface of the sample 574 applied with a negative voltage, and passes through the objective lens 571. Then, immediately before passing through the objective lens 571, the secondary electron beams are deflected in a direction (in the right-hand direction in the figure) orthogonal to a scanning direction by a beam separator 570 disposed at an upper end within the objective lens, and an enlarged image is focused on the surface of an FOP (fiber optical plate) plate 581 on which the scintillator is coated. The FOP plate 581 is not a simple plate but optical fibers which comprise the FOP are connected to PMTs 582 in a one-to-one correspondence, so that the enlarged image is converted into an optical signal by the PMTs 582.

In this way, since the multiple secondary electron beams emitted from the sample are input to the PMTs 582 in a one-to-one correspondence, the problem of cross-talk can be avoided. Also, when a periodic line and space pattern is formed on the sample, a signal generated from each PMT 582 presents a periodic waveform which repeats a high intensity and a low intensity, as indicated by reference numerals 583-585. The PMTs 582 and associated amplifiers are adjusted, while observing diameters 583-585 of the periodic waveform, such that their contrast and offset values are substantially the same.

In the embodiment illustrated in FIG. 58, in regard to deflection chromatic aberration caused by the beam separator 570 for the primary electron beams, no deflection chromatic aberration occurs in the primary electron beams because deflection aberration caused by the electrostatic deflector 569 and electromagnetic deflector 570 are canceled out by each other by setting the distance D1 between an image formed by the chromatic aberration corrector 568 and the electrostatic deflector 569 to be equal to the distance D2 between the electrostatic deflector 569 and electromagnetic deflector 570. Also, by setting a secondary electron beam to be focused near the electromagnetic deflector 570, deflection chromatic aberration to the secondary electron image can also be reduced.

Field curvature which occur when scanning is performed at a position far away from the optical axis can be corrected by adjusting voltages applied to the axially symmetric electrodes 566 and 567 within the rotary lenses 564 and 565. The rotation of electron beam can also be dynamically corrected by changing voltages applied to the axially symmetric electrodes 566 and 567. In this regard, the rotary lenses 564 and 565 are known lenses with axial magnetic fields in directions opposite to each other. The chromatic aberration corrector 568 comprises quadrupole lenses at four stages which are arranged so as not to cause two-time symmetric aberration, four-time symmetric aberration, or coma aberration. A voltage applied to the electrode 576 is adjusted to eliminate chromatic aberration while observing beam aberration.

Figure 59:
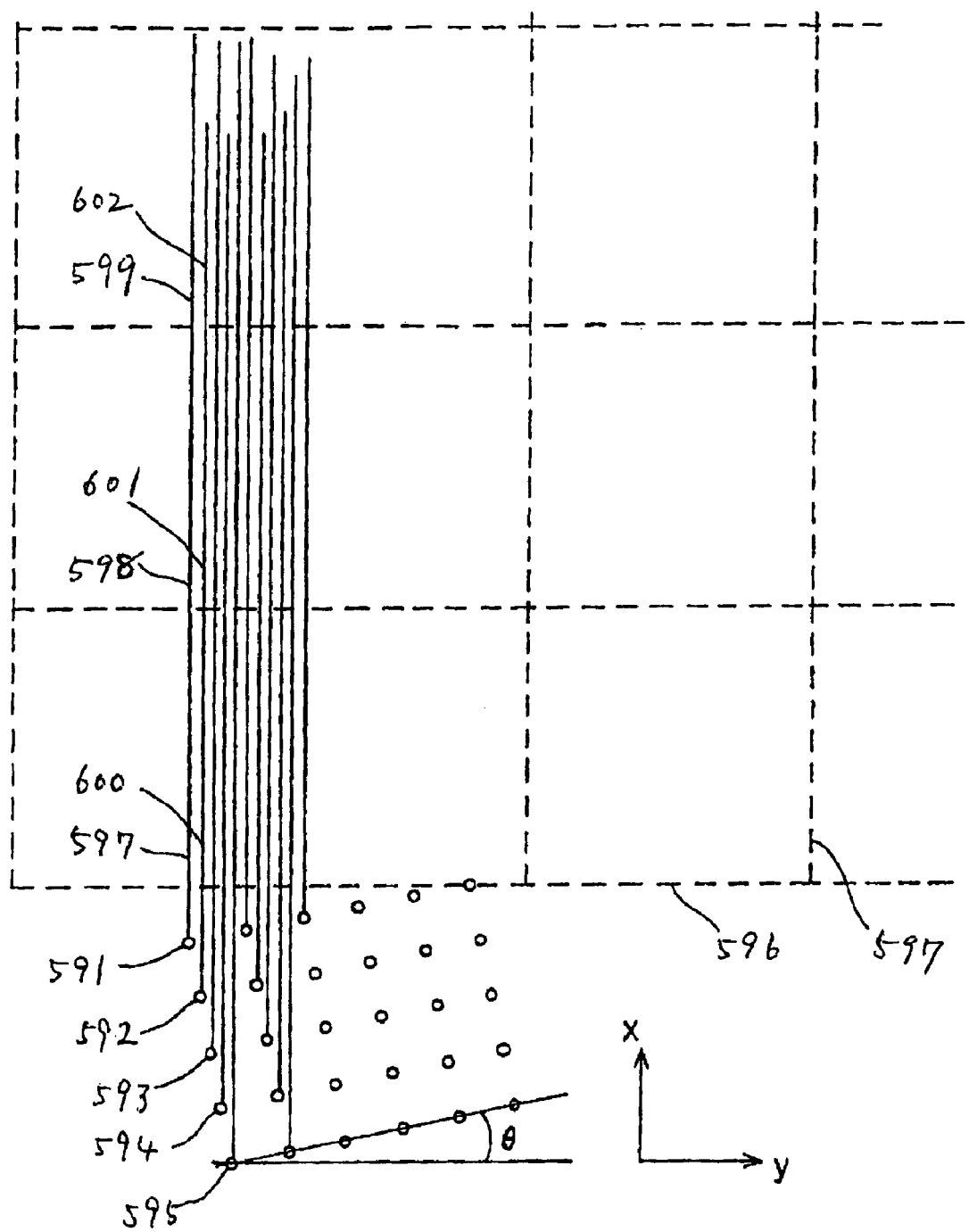

Referring now to FIG. 59, a description will be given of a method of capturing an image of the surface of a sample in the sample evaluation apparatus which uses multiple beams, as illustrated in FIG. 58. FIG. 59 schematically illustrates the surface of a sample, where the stage is continuously moved in the y-axis direction of the x-y coordinate system, and electron beams are scanned in the x-axis direction. Assume also that in this example, multiple beams are formed in six rows and five columns.

When multiple beams are arranged in six rows and five columns, the rows of the multiple beams may be inclined by $\sin^{-1}(1/5)$ with respect to the y-coordinate (therefore, the columns to the x-axis) to equal a raster pitch during multi-beam scanning. In this regard, while the raster pitch may be set to an integer multiple of pixels, but in order to use a largest possible number of multiple beams within a fixed distance from the optical axis, the raster pitch is preferably set to be equal to the pixel dimensions. With n rows and m columns (rows are in close proximity to the y-axis direction, while columns are in close proximity to the x-axis direction), m n is preferred, where the beam interval is calculated by n*pixel dimension/cos $[\sin^{-1}(1/n)]$. When the beams are arranged in an orthogonal matrix, the most beams can be populated in a unit area, however, the beams do not necessarily have to be orthogonally arranged when they are arranged to be at the same raster pitch during scanning.

When raster scanning is performed as illustrated in FIG. 59 for a cell-by-cell inspection, signals at the same positions 597, 598, 599 (or 600, 601, 602) within a cell found by the same scanning of the same beam are compared with each other for evaluation such as a defect inspection or the like.

For conducting a die-by-die inspection, signals at the same y-axis position on different dies may be compared with each other for evaluation. Signals from the same electron beam at the same y-coordinate on different dies may be compared with each other.

Preferably, two-dimensional patterns are created for one scanning session or for one cell, such that the comparison and evaluation are performed with a two-dimensional pattern in the scanning direction, i.e., in the x-axis direction in a cell-by-cell inspection, while die data are compared with each other in the stage moving direction, i.e., in the y-axis direction for evaluation.

Figure 60:
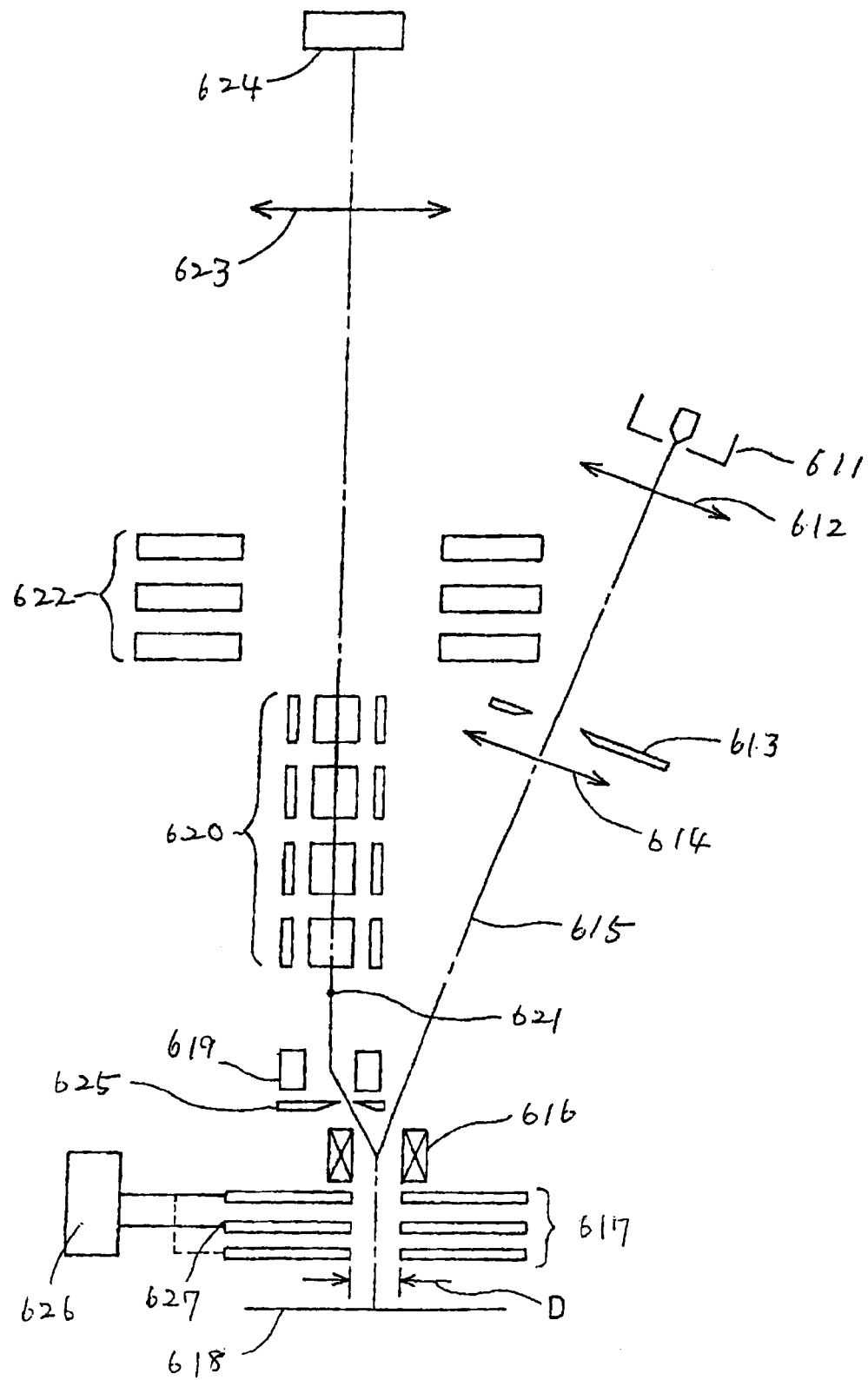

FIG. 60 is an explanatory diagram illustrating an electro-optical system of a sample evaluation apparatus which is a ninth embodiment of the electron beam apparatus according to the present invention. In this apparatus, electron beams emitted from an electron gun 611 are converged by a condenser lens 612, formed into rectangular electron beam by a rectangular aperture formed through an aperture plate 613 in a square shape or the like, and irradiated to a sample 618 through a formation lens 614 and an objective lens 617 which is a unit-potential lens.

Secondary electrons emitted from the sample 618 by the irradiation are accelerated by the objective lens 617, and separated from primary electron beams by a beam separator 616. Then, the secondary electrons are deflected in the vertical direction by an electrostatic deflector 619 and focused at a position 621 in front of a chromatic aberration corrector 620. An image of the chromatic aberration corrector 620 is enlarged by magnification lenses 622, 623 at two stages to focus an image on a detection plane of a detector 624.

Here, the beam separator 616 is a pure electromagnetic deflector, and is set to provide the same deflection amount as the deflection amount of the electrostatic deflector 619 for deflecting the secondary electron beams. In addition, the distance between the position 621 and deflector 619 is set to be equal to the distance between the electrostatic deflector 619 and beam separator 616, thereby eliminating deflection chromatic aberration. Also, even when the objective lens 617 comprises a single lens, off-axis aberration can be reduced to a negligible degree by optimizing the position of an NA aperture 625. Further, the beam separator 616 can be an ExB separator similar to that in the embodiment illustrated in FIG. 56, and the deflector 619 can be an electrostatic deflector.

When the rectangular electron beams are moved within the visual field, field curvature can be corrected by adjusting a voltage applied from a voltage source 626 to an upper electrode or a lower electrode of the objective lens 617. Since the upper electrode is at a voltage close to the ground potential, a lens for correcting the field curvature may be driven with a voltage centered at 0 V, and can therefore be driven at high speeds. Axial chromatic aberration can differ, though slightly, between a value resulting from a simulation and an actually found value. This difference can be reduced to zero by adjusting a voltage applied to aa central electrode 627 of the objective lens 617 and a voltage applied to one of the upper and lower electrode of the same, thereby making it possible to more reliably correct chromatic aberration.

Figure 61:
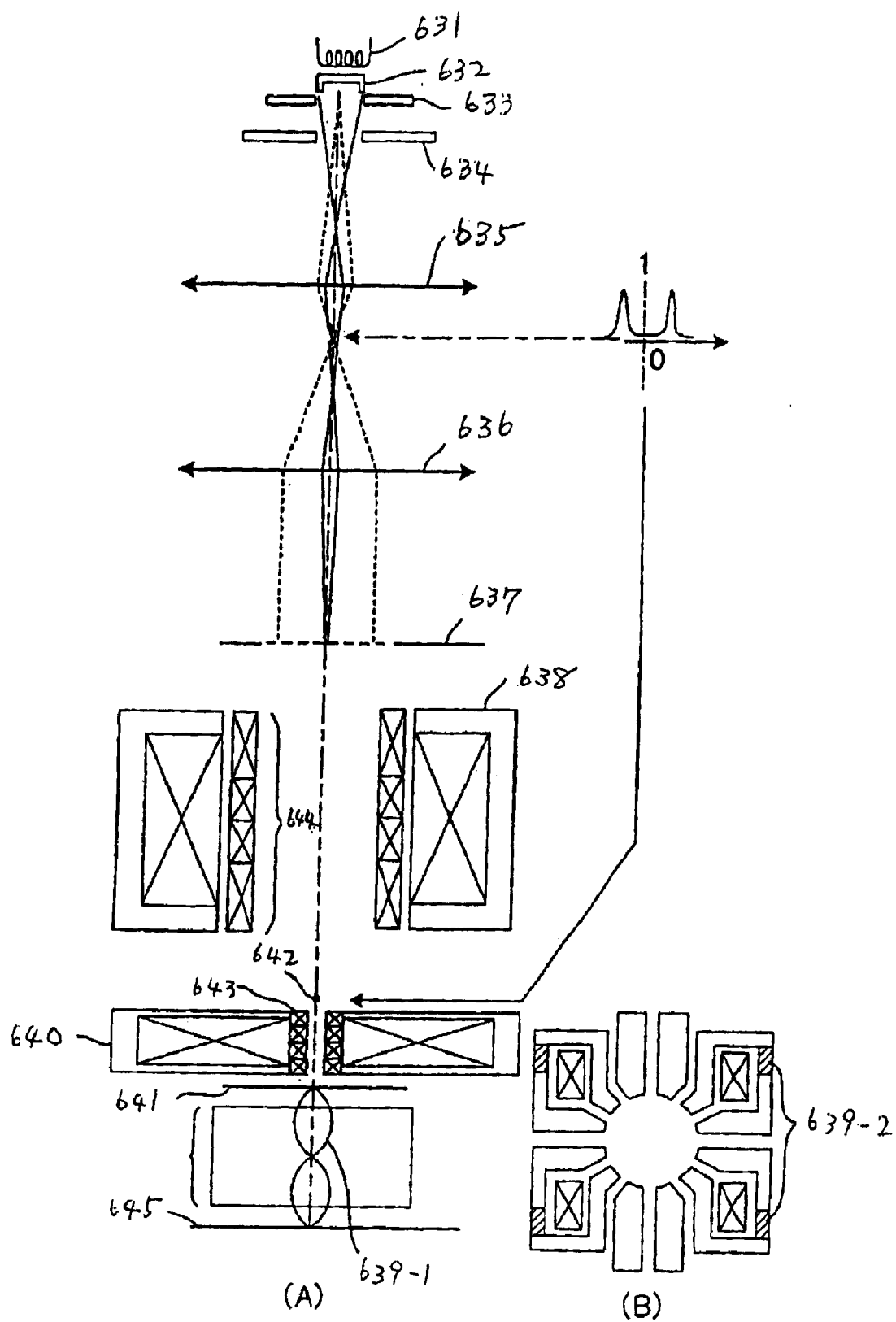

FIG. 61 is an explanatory diagram illustrating an electro-optical system of a transfer apparatus of a tenth embodiment of the electron beam apparatus according to the present invention. An electron gun comprises a heater 631, a ring-shaped cathode 632, a Wehnelt 633, and an anode 634. A cross-over formed by the electron gun is enlarged by condenser lenses 635 and 636 at two stages, and is irradiated to a sub-visual field on a reticle 637. Electron beams formed by the reticle 637 generates a one-quarter reduced image (one quarter of the reticle) on an image plane 641 by axially symmetric magnetic tablet lenses 638 and 640 (640 is an objective lens). A cathode image can be focused on a back focal plane 642 of the objective lens 640 to produce a hollow beam and reduce spherical aberration.

Deflectors 644 and 643 disposed within the lenses 638 and 640 are deflectors for correcting off-axis aberration. These deflectors can extremely reduce the off-axis aberration, and the spherical aberration can be reduced by the hollow beam, so that axial chromatic aberration is major aberration. In this embodiment, this axial chromatic aberration is corrected by the provision of an axial chromatic aberration corrector 639. In this way, an image can be transferred without blur even if the aperture angle is increased, additionally with an improved throughput. Preferably, the hollow beam has the aperture angle of 10-11 mrad. This is because, with a hollow beam having an aperture angle of $\alpha1$-$\alpha2$ (mrad), when $\alpha1 \cdot 10$ mrad and $\alpha2$-$\alpha1 \cdot 1$ mrad are set, the space charge effect is reduced so that a transfer can be performed with a large current density. As illustrated in FIG. 61, the axial chromatic aberration corrector 639 may be disposed below the image plane 641, such that an image on the image plane 641 is focused on the surface of a sample 645 by the aberration correction lens 639.

The correction lens is a Wien filter which has 12 divided electrodes and magnetic poles, as illustrated in FIG. 61(B), and generates negative aberration, without generating excessive aberration, by focusing twice, as indicated by a trajectory 639-1. Reference numeral 639-2 designates a spacer for insulation.

Figure 62:
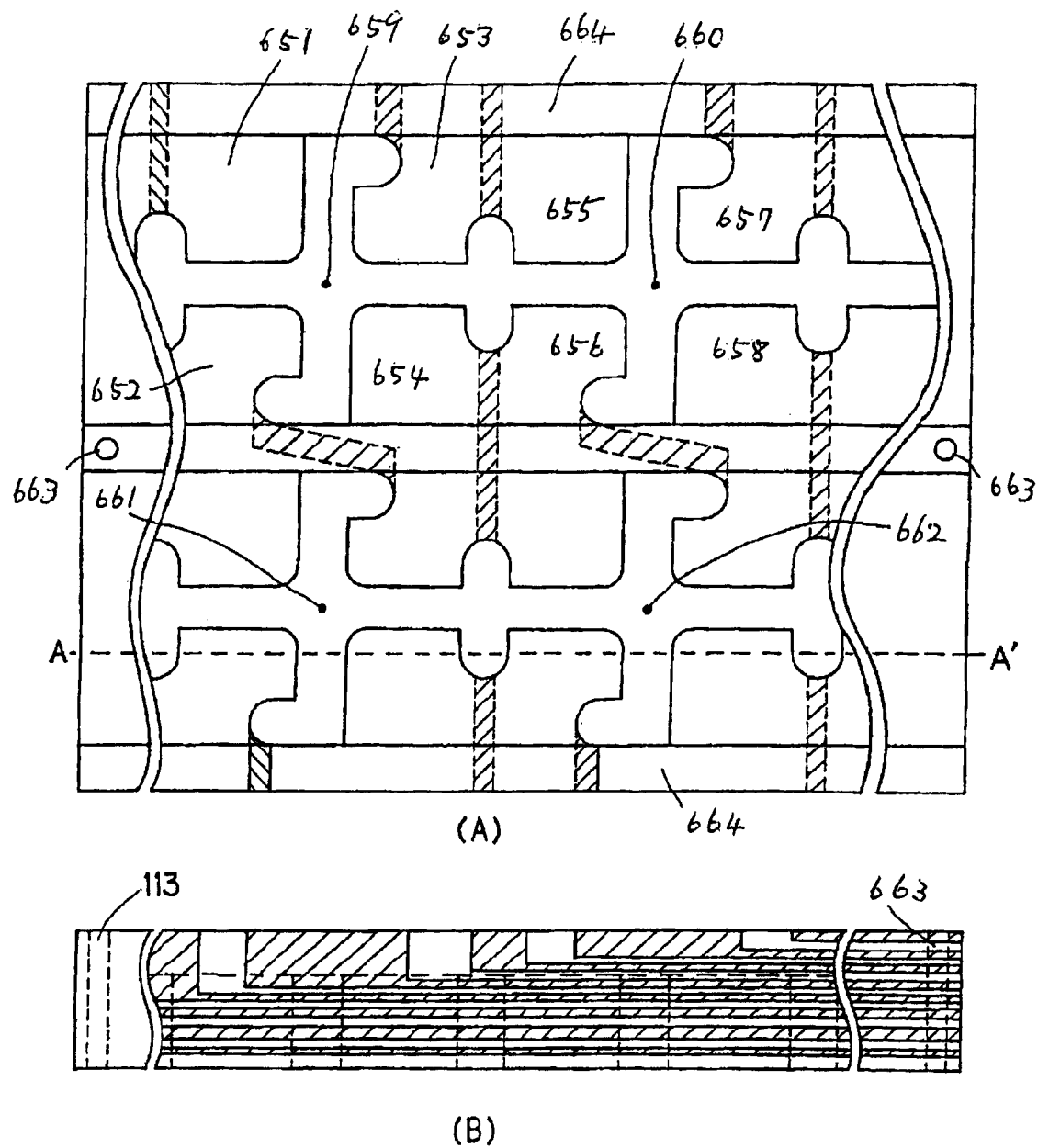

FIG. 62 illustrates the structure of an aberration correction lens system of a chromatic aberration corrector which can be incorporated in an apparatus which comprises a plurality of optical systems, i.e., an electron beam apparatus which has a plurality of optical axes, as illustrated in FIGS. 56-58, FIG. 60, and FIG. 61. FIGS. 62(A) and 62(B) are a plan view and a cross-sectional view, respectively. In this example, optical axes are arranged in two columns and m rows, and one ceramic substrate is formed with a single-stage quadrupole lens. For manufacturing this single-stage quadrupole lens, ribs 664 are formed on two opposing longer edges of the ceramic substrate, four grooves are radially formed around respective optical axes 659-662, and respective electrodes 651-654 are formed. Next, the entirety is non-electrolytically plated, and further plated with Au to form a coating. Then, the coating is removed from a portion indicated by shading in FIG. 62(A), and lead lines are connected to side surfaces of the ribs 664 (in a direction perpendicular to the figure), as illustrated in FIG. 62(B). In addition, holes 663 are formed on two opposing shorter edges. In this way, four quadrupole lenses are formed, and these four lenses are stacked and coupled such that the holes 663 are in alignment to one another, and are assembled such that corresponding optical axes are in alignment. The chromatic aberration corrector thus manufactured can be employed as a chromatic aberration corrector for an electron beam apparatus which comprises a barrel or multiple barrels, as illustrated in FIGS. 56-58 and FIG. 61. Surfaces of the electrodes 651-654 opposing the optical axes 659-662 form part of a hyperbolic plane.

Figure 63:
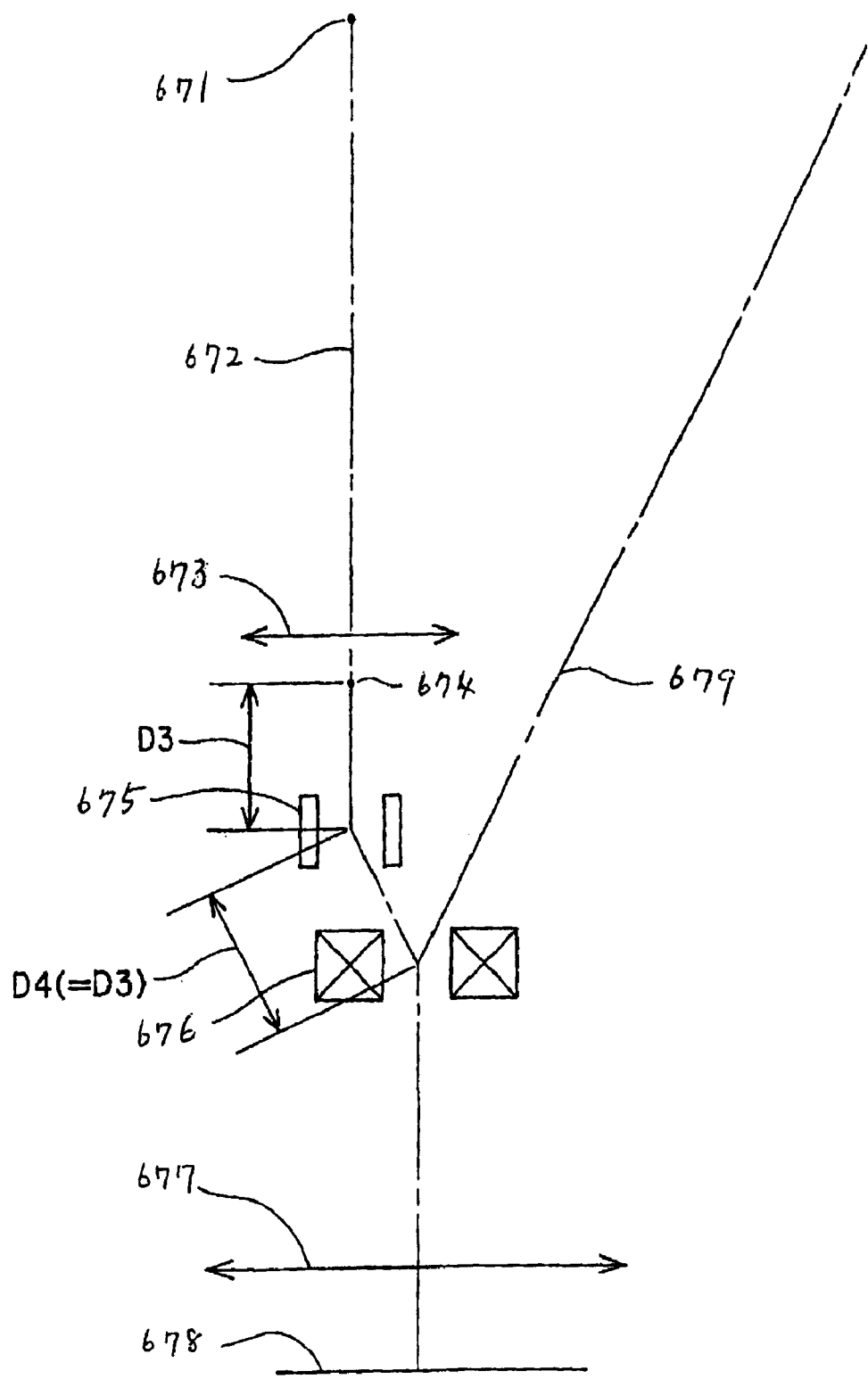

FIG. 63 illustrates an electro-optical system of a sample evaluation apparatus of an eleventh embodiment in the electron beam apparatus according to the present invention. This apparatus is configured to eliminate deflection chromatic aberration. Electron beams from an electron gun 671 are focused at a position 674 by a condenser lens 673 included in a primary optical system 672 to focus an image on a sample 678 by an objective lens 677. In this event, the electron beam is deflected by a deflector 675 and further deflected by an electromagnetic deflector 676 so as to be perpendicular to the surface of the sample 678, where the distance D3 between the focusing position 674 and electrostatic deflector 675 is set to be equal to the distance D4 between the electrostatic deflector 675 and electromagnetic deflector 676. By setting these distances to be equal, deflection aberration caused by the two deflectors can be canceled out by each other to reduce the deflection aberration to zero as a whole. The electromagnetic deflector 676 also functions as a beam separator for directing secondary electron beams to a secondary optical system 679, but can be simplified in structure because the beam separator can be implemented by a single electromagnetic deflector. In this regard, the first embodiment illustrated in FIG. 63 may also comprises an axial chromatic aberration corrector as is the case with the sixth to tenth embodiments.

Figure 64:
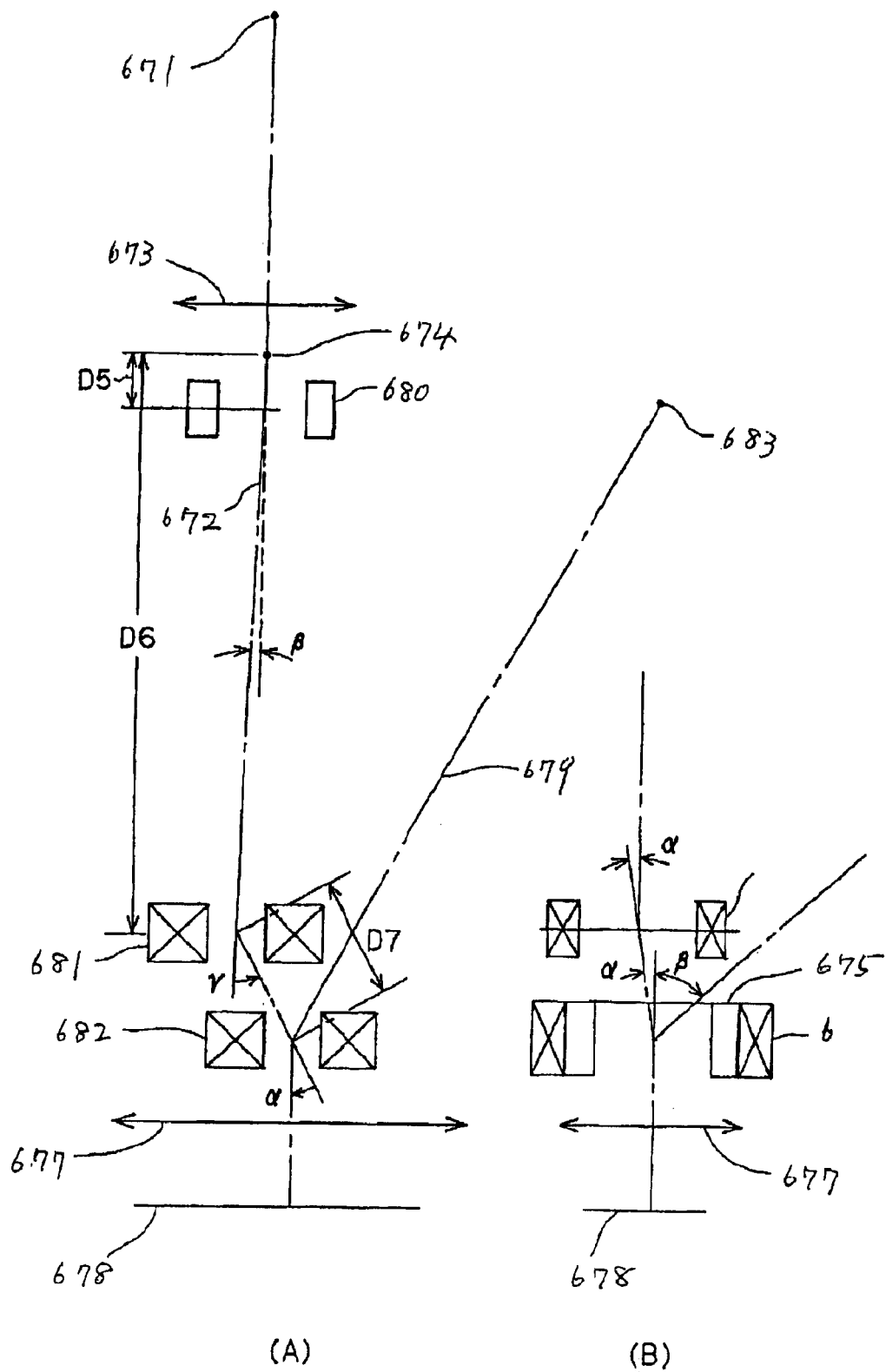

FIG. 64 illustrates an electro-optical system of a sample evaluation apparatus of a twelfth embodiment in the electron beam apparatus according to the present invention. This apparatus employs three deflectors to eliminate deflection chromatic aberration. In FIG. 64, electron beams from an electron gun 671 are focused at a position 674 by a condenser lens 673 included in a primary optical system 672 to focus an image on a sample 678 by an objective lens 677. In this event, the electron beams are deflected by a first to a third deflector 680-682, such that they are perpendicular to the surface of the sample 678. While the first deflector 680 may be an electrostatic deflector or an electromagnetic deflector, the following description will be made on the assumption that it is an electrostatic deflector. The second deflector 681 is an electromagnetic deflector, and the third deflector 682 is an electromagnetic deflector as well.

As illustrated in FIG. 64, deflection amounts provided by the first to third deflectors 680-682 are represented by $\beta$, $\gamma$, $\alpha$, respectively; the distance between the position 674 and first deflector 680 by D5; the distance between the position 674 and second deflector 681 by D6; and the distance between the second deflector 681 and third deflector 683 by D7.

For imposing electron beams emitted perpendicularly from the electron gun 671 to impinge perpendicularly on the surface of the sample 678, the following equation:

$$\alpha = \gamma - \beta \quad (1)$$

must be satisfied.

On the other hand, for eliminating deflection chromatic aberration caused by the three deflectors, the following equation:

$$2\beta \cdot D5 = \gamma \cdot D6 - \alpha \cdot D7 = 0 \quad (2)$$

must be satisfied.

The ratio of $\alpha:\beta:\gamma$ can be calculated from the foregoing Equations (1) and (2). For example, when D5=0, $\gamma \cdot D6 = \alpha \cdot D7$, resulting in:

$$\alpha/\gamma = D6/D7 \quad (3)$$

Substituting Equation (3) into Equation (1) results in:

$$\beta/\gamma = 1 - D6/D7 \quad (4)$$

By thus adjusting the position of the focusing position 674 and deflection angles of the first to third deflectors 680-682, Equations (1) and (2) can be satisfied. Accordingly, primary electron beams can be directed perpendicularly into the sample 678, and the deflection chromatic aberration can be eliminated.

Advantageously, when primary electron beams are slightly deflected and secondary electron beams are largely deflected by a beam separator, aberration does not occur in the primary electron beams except for the deflection chromatic aberration. Such an embodiment is illustrated in FIG. 64(B). When the beam separator 682 is implemented by an ExB separator, and similar equations to the aforementioned Equations (1)-(4) are solved, conditions can be established for small $\alpha$ and large $\beta$, under which the secondary electron beam can be largely deflected without largely deflecting the primary electron beams, and the deflection chromatic aberration can be eliminated.

It should be noted that the twelfth embodiment illustrated in FIG. 64 may also comprise an axial chromatic aberration corrector, as is the case with the sixth to tenth embodiments.

Incidentally, in a electron beam based sample inspection apparatus, the resolution is not always important (may be approximately one fifth to one twentieth of that of a scanning microscope), but importance is placed on an increase in beam current for improving the inspection speed. With the employment of multi-pole lenses at multiple stages as in the present invention, the beam current can be increased approximately by a factor of ten, and accordingly, the inspection speed can be improved approximately by a factor of ten. In the following, the foregoing is described in greater detail.

In the projection electron beam apparatus as those in the sixth to twelfth embodiments, a blur $\delta c$ due to the Coulomb effect can be expressed in the following manner:

$$\delta c = I \cdot L (\alpha \cdot V^{3/2}) \quad (5)$$

where I: Electron Beam Current;
L: Optical Path Length;
$\alpha$: aperture angle; and
V: electron beam energy.

On the other hand, in the projection electron beam apparatus, axial chromatic aberration is predominate among other aberration (larger by an order of magnitude as compared with other aberration), and the other aberration can be kept sufficiently small by devising the configuration of lenses. Accordingly, the elimination of the axial chromatic aberration can result in a reduction in aberration approximately by a factor of ten, and the aperture angle $\alpha$ can be increased approximately by a factor of ten in inverse proportion thereto.

Specifically, the following equation is established:

$$N = I \cdot \eta \cdot t/q$$

where t represents a time taken to scan one pixel with a beam current I; q represents an electron charge; N represents the amount of detected secondary electrons per pixel; and $\eta$ represents a second electron emission ratio. For generating a signal sufficiently larger than shot noise, N must be increased to a certain value or more, but a certain N value can be ensured as the beam current I grows, even if the time t is short. Accordingly, since the scanning time can be shortened, the inspection speed can be improved.

Also, in the eighth embodiment which transforms electron beams emitted from a single electron gun into multiple beams with the aid of a multi-aperture plate, illustrated in FIG. 58, a thermoelectron emission scheme is preferably employed with $LaB_6$ used for an electron gun. However, this type of electron gun suffers from chromatic aberration approximately five times larger as compared with a Schottky type electron gun. This is because the chromatic aberration in the electron gun depends on an energy width of electrons from the electron gun, and the energy width is 0.6 eV in the Schottky type electron gun, and is 3 eV in the $LaB_6$ thermoelectron emission type, which is five times larger than the former.

Accordingly, in the eighth embodiment, the inspection speed can be improved by a factor of five with the ability to eliminate the chromatic aberration, as compared with an apparatus which does not comprise a chromatic aberration correction function. Further, it should be understood that the inspection speed can be largely improved by applying the technical idea of the present invention to an electron beam apparatus which comprises a plurality of single-beam or multi-beam projection barrels.

As described above, when the technical idea of the present invention is applied to a sample evaluation apparatus and a lithography apparatus, the chromatic aberration can be corrected so that the beam diameter can be increased, thus making it possible to perform processing at a high throughput. Also, when the technical idea of the present invention is applied to a sample evaluation apparatus, the space charge effect can be reduced, so that the throughput is further improved.

FIG. 65(A) generally illustrates the configuration of a thirteenth embodiment of the electron beam apparatus according to the present invention. In FIG. 65(A), the electron beam apparatus comprises an electron gun 691, a primary electro-optical system 692, a beam separation system 693, an objective optical system 694, a secondary electro-optical system 695, and a secondary electron detection system 696.

Electron beams emitted from the electron gun 691 are enlarged by a first condenser lens 697 and a second condenser lens 698 in the primary electro-optical system 692, and are irradiated to an aperture plate 699 having a rectangular formation aperture. With this aperture plate, primary beams are formed to have a rectangular cross-section. The primary beams, rectangular in cross-section, is formed by a formation lens 700, and adjusted in magnification by a variable magnification lens 701, before they are directed into the beam separation system 693. The beam separation system 693 is, for example, an ExB separator which comprises an electrostatic deflector 702 and an electromagnetic deflector 703. The primary beams incident on the beam separation system 693 changes their traveling direction in a direction perpendicular to a sample W.

The primary beams, the traveling direction of which has been changed to the direction perpendicular to the sample W by the beam separation system 693 enter the objective optical system 694. The objective optical system 694 comprises an NA aperture plate 704 having a ring-shaped aperture and a rectangular aperture through which the primary beams pass; a dynamic focusing electrode 705; a high voltage application electrode 706; and an objective lens electrode 707. The NA aperture plate 704 has a plurality (four in FIG. 65(B)) of elongated holes 715, 716, 717, 178 which are arranged on the same circumference to create a ring-shaped aperture, and a rectangular hole 719 for passing the primary beams therethrough. The primary beams in rectangular cross-section, which have passed through the beam separation system 693 are deflected to pass through the rectangular hole 719. Subsequently, the primary beams are focused on the sample W by the dynamic focusing electrode 705, high voltage application electrode 706, and objective lens electrode 707, and irradiated to the surface of the sample W.

Secondary electrons emitted from the sample W, which has been irradiated with the primary beams in rectangular cross-section are accelerated and converged by a high voltage generated by the objective lens electrode 707, and intersect with the optical axis of the secondary electrons at the position of the NA aperture plate 704, and form an enlarge image at a position P. The position at which the NA aperture plate 704 is disposed is, as confirmed by a simulation, a position at which a total of coma aberration and magnification chromatic aberration is minimized. While the conventional NA aperture plate is formed with a single circular hole, it has suffered from a problem that an image blurs more due to the space charge effect. Thus, in the present invention, the secondary electrons are transformed into hollow beams by the ring-shaped holes 715-718 of the NA aperture plate 704, and these beams alone are directed toward the detection system 696. Since the holes 715-718 of the NA aperture plate 704 have a small width D, spherical aberration is sufficiently small in the secondary electro-optical system 695. However, since beams with a large aperture angle are used in such an electron beam apparatus, axial chromatic aberration can constitute a grave problem. As such, the hollow secondary electrons separated from the primary electrons by the beam separation system 695 and directed to the detection system 96 are corrected for axial chromatic aberration by an axial chromatic aberration correction lens 708 composed of quadrupole lenses at a plurality (four in this embodiment) of stages in the secondary electro-optical system 695.

The secondary electrons, which have been corrected for the axial chromatic aberration, are enlarged by an auxiliary lens 710 disposed at an image point 709 of the axial aberration correction lens 708, and a magnification lens 711 disposed on the downstream side of the auxiliary lens 710, and is further enlarged by an auxiliary lens 712 and a magnification lens 713 disposed on the downstream side. The auxiliary lens 712 forms reduced images of the ring-shaped holes 715-718 of the NA aperture plate 704 on the main surface of the magnification lens 713. The secondary electron image thus formed is enlarged by the magnification lens 713, and the enlarged image is focused on a MCP (micro-channel plate) 714 of the detection system 696. The detection system 696 is used to evaluate the sample W for defects using the image projected by the magnification lens 713.

FIG. 66(A) is a diagram generally illustrating the configuration of a fourteenth embodiment of the electron beam apparatus according to the present invention, which comprises, like the first embodiment, an electron gun 721, a primary electro-optical system 722, a beam scanning/separation system 723, an objective lens 724, a secondary electro-optical system 725, and a secondary electron detection system 726. In FIG. 66, the electron gun 721 comprises a cathode 731 and a Wehnelt electrode 732, where the cathode 731 comprises a cylindrical material made of an $LaB_6$ single crystal formed with a ring-shaped edge in one end surface thereof, as illustrated. Accordingly, the cathode 731 emits electron beams in hollow cross-section. The Wehnelt electrode 732 surrounds the cathode 731, and is applied with such a voltage that forms a cross-over image C1 between the electrode and a first condenser lens 733 of the primary electro-optical system 2.

The primary electro-optical system 722 comprises a first and a second condenser lens 733, 734, a multi-aperture plate 735, a reducing lens 736, and an axial chromatic aberration correction lens 737. The cross-over image C1 formed by the electron gun 721 is enlarge by the first condenser lens 733 and second condenser lens 734, which are magnification lenses, at two stages, and is uniformly irradiated to the multi-aperture plate 735. It should be noted that the second condenser lens 734 is adjusted in excitation such that the multi-aperture plate 735 is widely and uniformly irradiated, and such that a cross-over image C2 of the condenser lens 734 comes slightly closer to the condenser lens 734 than the multi-aperture plate 735. The multiple primary beams produced by the multi-aperture plate 735 are scaled down by the reducing lens 736, and enters the beam scanning/separation system 723, with negative axial chromatic aberration caused by the axial chromatic aberration correction lens 737.

The beam scanning/separation system 723 comprises a scanning deflector 738, an electromagnetic deflector 739, and an electrostatic deflector 740. The primary beams having the negative axial chromatic aberration are changed in traveling direction by the scanning deflector 738 such that they go to the electromagnetic deflector 739. The traveling direction is again changed by the electromagnetic deflector 739 such that the primary beams impinge vertically on the sample W. In this event, deflection chromatic aberration can occur in the primary beam in the beam scanning/separation system 723. Accordingly, the scanning deflector 738 is positioned at the midpoint between a cross-over image C3 of the axial chromatic aberration lens 737 and the beam scanning/separation system 723, such that the deflection chromatic aberration is corrected by deflecting the primary beams by the scanning deflector 738 and electromagnetic deflector 739 by the same angle in directions opposite to each other. The beams having the negative axial chromatic aberration are canceled out by positive axial chromatic aberration possessed by the objective lens, to correct the axial chromatic aberration. The electrostatic deflector 740 is used to scan the multiple beams on the sample.

Now, the axial chromatic aberration correction lens 737 will be described with reference to FIG. 66(B). This correction lens 737 is also referred to as a "Wien filter" and converges beams emitted from an end surface twice, but causes negative axial chromatic aberration in the cross-over image C3 due to non-dispersion. FIG. 66(B) illustrates one quarter of the cross-section of the correction lens 737. As can be understood from FIG. 66(B), the correction lens 737 has 12 poles, where the Wien condition is satisfied by a dipole field, and the axial chromatic aberration is made negative by quadrupole electric field/magnetic field, and hexipolar electric field/magnetic field is applied to generate negative spherical chromatic aberration, thus making it possible to partially correct spherical aberration which mainly occurs in the objective lens 742. When the spherical aberration is larger, a majority of the spherical aberration and part of the axial chromatic aberration may be corrected.

A 12-pole electrode 746 is made of permalloy B, and generates a dipole, a quadrupole, and a hexipolar magnetic field by applying a current to a coil 747. In the figure, reference numeral 749 designates a core made of permalloy, and 748 designates a spacer for insulating each electrode.

The primary beams which have passed through the beam scanning/separation system focuses an image of the cathode 31 on the NA aperture plate 741 in the objective optical system 724. This is implemented by adjusting the reducing lens 736. For this purpose, the NA aperture plate 741 has a hole large enough to pass hollow beams therethrough. Multiple beams which have been formed by the multi-aperture plate 735 and scaled down by the reducing lens 736 are again scaled down by the objective lens 742, before they are irradiated to the sample W. In this event, the surface of the sample W can be scanned with the primary beams by applying a scanning signal to the scanning deflector 738 and auxiliary deflector 740. The fulcrum of deflection at this time is found at the position of the aperture on the NA aperture plate 41.

Multiple secondary beams are emitted from the sample W irradiated with the primary beams. The emitted secondary beams are accelerated by a high voltage of the objective lens 742, passes through the apertures of the NA aperture plate 741, are separated by the electromagnetic deflector 739 from the primary beams, and travels toward the secondary electro-optical system 725. The secondary electro-optical system 725 comprises a plurality (two in this embodiment) of magnification lenses 743, 744, so that the secondary beams are enlarged by these magnification lenses 743, 744 to focus an image on a multi-detector 7454 in the detection system 726. In this event, zoom lenses may be employed for the magnification lenses 743, 744, whereby the spacings between a plurality of detectors which make up the multi-detector 745 can be precisely matched with the spacing between images of multiple beams which make up the secondary beams, as well as the secondary beams can be detected without changing the spacing between the detectors when the unit area of the sample W irradiated with the secondary beams, i.e., the dimensions of the pixels are increased by a factor of two, four and the like and reduced by a factor of two, four and the like.

Figure 67:
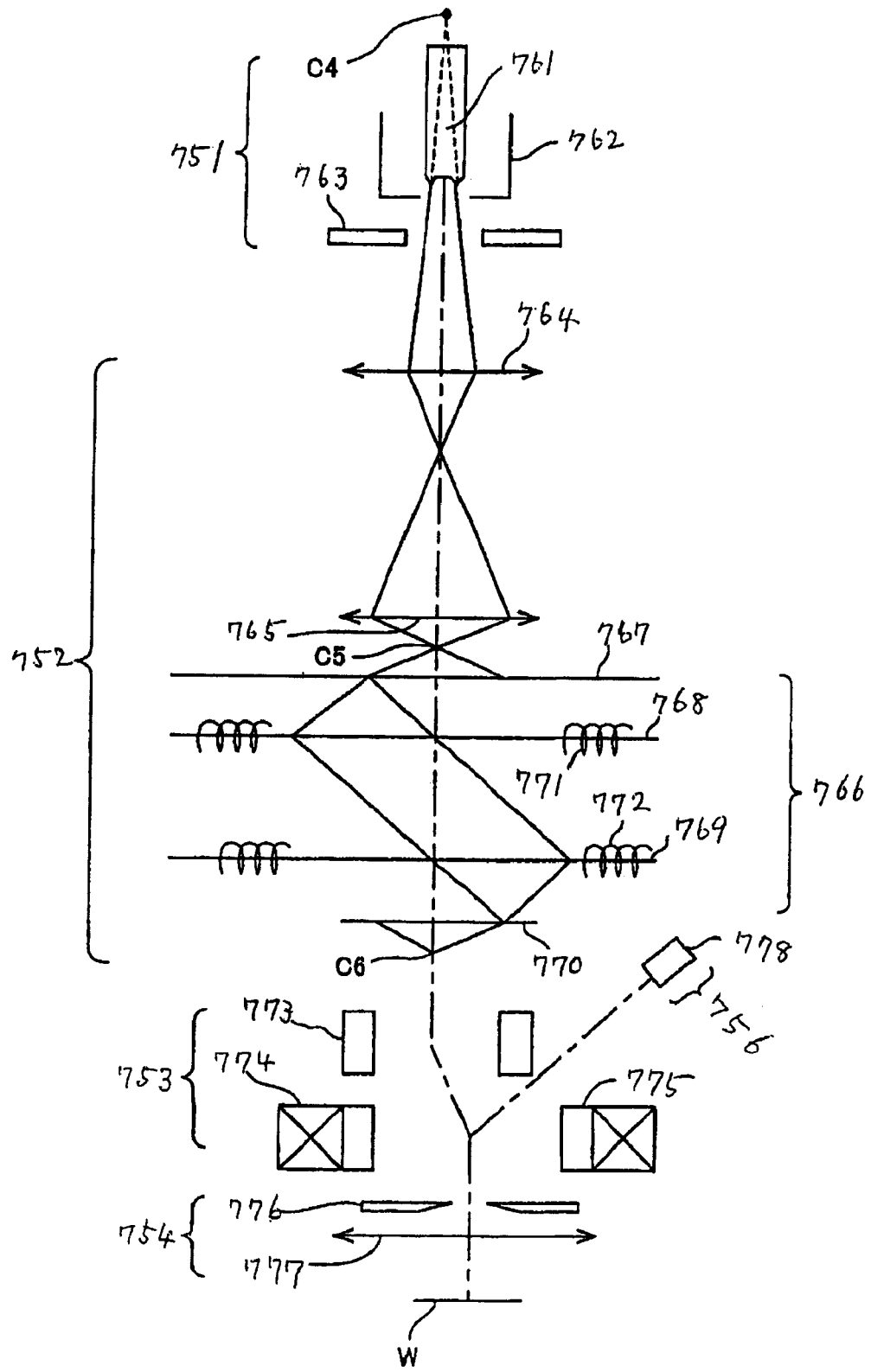

FIG. 67 is a diagram generally illustrating the configuration of a fifteenth embodiment of the electron beam apparatus according to the present invention, where the electron beam apparatus comprises an electron gun 751, a primary electro-optical system 752, a beam scanning/separation system 753, an objective optical system 754, and a secondary electro-optical system 756.

The electron gun 751 comprises a cathode 761, a Wehnelt electrode 762, and an anode 763. The cathode 761 comprises a cylindrical material made of a $LaB_6$ single crystal which has one end surface polished to form a ring-shaped knife edge. A ring formed by the knife edge has a diameter of 0.6 mm, by way of example. Thus, hollow electron beams are emitted from the cathode 761. The periphery of the cathode 761 is surrounded by the Wehnelt electrode 762, and the Wehnelt electrode 762 is biased negatively with respect to the cathode 761 such that a virtual cross-over image C4 is formed behind the cathode 761. The surface of the Wehnelt electrode 762 opposite to the end surface of the cathode 761 formed with the knife edge, is a flat electrode formed with a hole for passing primary beams emitted from the cathode 761 therethrough. The hole has a diameter of 3 mm, by way of example, and the spacing of the leading edge of the cathode 761, i.e., the leading edge of the knife edge, and the flat electrode of the Wehnelt electrode 762 is, for example, 300 µm.

Primary beams emitted from the electron gun 751 are processed by the primary electro-optical system 2 which comprises a first reducing lens 764, a second reducing lens 765, and an axial chromatic aberration correction lens 766, and enters the beam scanning/separation system 753. Describing in greater detail, the virtual cross-over image C4 is scaled down by the first reducing lens 764 and second reducing lens 765, and the second reducing lens 765 forms a cross-over image C5. The axial chromatic aberration correction lens 766 comprises a first quadrupole lens 767, a second quadrupole lens 768, a third quadrupole lens 769, a fourth quadrupole lens 770, a first quadrupole magnetic lens 771, and a second quadrupole magnetic lens 772, and forms a cross-over image C6 which is corrected for axial chromatic aberration of the cross-over image C5. The primary beams which have formed the cross-over image C6 in this way enter the beam scanning/separation system 753.

The beam scanning/separation system 753 comprises an electromagnetic deflector 774 and an electrostatic deflector 775. The primary beams are changed in traveling direction by the scanning deflector 773, and the traveling direction is again changed by the electromagnetic deflector 774 such that the primary beams impinge perpendicularly to the sample W. In this event, deflection chromatic aberration can occur in the primary beams due to the beam scanning/separation system 753. Accordingly, the scanning deflector 773 is positioned at the midpoint between the cross-over image C6 of the axial chromatic aberration lens 766 and the beam scanning/separation system 753, such that the deflection chromatic aberration is corrected by deflecting the primary beams by the scanning deflector 773 and electromagnetic deflector 775 by the same angle in directions opposite to each other.

The primary beams which have passed the beam scanning/separation system 753 focus an image of the cathode 761 on an NA aperture plate 776 of the objective optical system 4. This is implemented by adjusting the reducing lens 765. By focusing the image of the cathode on the NA aperture plate 776, the primary beams are hollow at the position of the NA aperture plate 776. The cross-over having negative axial chromatic aberration appear to be hollow beams at the position of the NA aperture plate, and are scaled down by the objective lens 777, before they are irradiated to the sample W. In this event, the primary electro-optical system is preferably designed such that the aperture angle to the image of the cathode 761, viewed from the sample W, is 100 mrad, by way of example. This aperture angle of 100 mrad can cause a problem of spherical aberration when the primary beams are solid beams, but since the primary beams are hollow beams in the present invention, the spherical aberration can be neglected if the ring has a small width.

The virtual cross-over C4 is scaled down, for example, to approximately $\frac{1}{1000}$ by the reducing lenses 764, 765 at two stages and the objective lens 777. Here, the surface of the sample W can be scanned with the primary beams by applying a scanning signal to the scanning deflector 773 and electrostatic deflector 775. The fulcrum of deflection at this time is located at the position of the aperture on the NA aperture plate 776.

Secondary electrons emitted from the sample W irradiated with the primary beams are accelerated by a high voltage of the objective lens 777, pass through the aperture of the NA aperture plate 776, are separated from the primary beams by the beam scanning/separation system 753, and enter the detection system 756. The detection system 756 may comprise, for example, an SE detector 778.

As will be understood from the foregoing description, in the thirteenth to fifteenth embodiments, the beams on the sample W are corrected for axial chromatic aberration, and the blur due to the space charge effect is insignificant, so that beams of small diameters can be formed with a large beam current.

It should be noted that devices can be manufactured by utilizing the electron beam apparatus described in connection with FIGS. 56 to 70 in the manufacturing process illustrated in FIGS. 53 and 54. Specifically, when the electron beam apparatus according to the present invention is used for the chip testing process at step 403 for performing a defect test, even semiconductor devices having fine patterns can be tested at a high throughput, thus making it possible to enable a total inspection as well as to improve the yield rate of products, and prevents the shipment of defective products.

As will be understood from the foregoing description, the present invention advantageously reduces the influence of the space charge effect, resulting from primary beams which are produced into a hollow by the provision of an aperture plate which has apertures in a ring shape.

FIG. 68 is a diagram generally illustrating the configuration of a sixteenth embodiment of the electron beam apparatus according to the present invention. This electron beam apparatus comprises an electron beam emitter 781, a primary electro-optical system 782, a beam separation system 783, an objective optical system 784, a secondary electro-optical system 785, and a detection system 786. The electron emitter 781 comprises an electron gun 790 which has a cathode made of single crystal $LaB_6$ and operates under a space charge limiting condition.

Primary beams emitted from the electron gun 790 enter the primary electro-optical system 782. The primary electro-optical system 782 comprises a condenser lens 791, a multi-aperture plate 792, a rotation correction lens 793, an NA aperture plate 794, a reducing lens 795, and an axial chromatic aberration correction lens 796. The primary beams from the electron gun 790 are converged by the condenser lens 791, and are uniformly irradiated to the multi-aperture plate 792 which has a plurality of apertures. The electron beams transformed into multiple beams by the multi-aperture plate 792 focus a cross-over on the NA aperture plate 794 by the condenser lens 791 and rotation correction lens 793. With the cross-over fixed on the NA aperture plate 794, the condenser lens 791 and rotation correction lens 793 can adjust an irradiated region of the multi-aperture plate 792, or adjust a current density at which the multi-aperture plate 792 is irradiated.

The multiple beams which have passed through the NA aperture plate 794 are scaled down by the reducing lens 795 to form an image of the multi-aperture plate 792 at a point 797. This image is transformed into an image 798 of the multi-aperture plate 792 having negative axial chromatic aberration by the axial chromatic aberration correction lens 796. The multiple beams which have formed the image 798 is changed in traveling direction to a direction perpendicular to the sample W by the beam separation system 783 which comprises an electromagnetic deflector 800 and an electrostatic deflector 801, and further converged by the objective lens 802 to form a final image on the sample W. It should be noted that the aforementioned negative axial chromatic aberration is canceled out by positive axial chromatic aberration of an objective lens (later described), so that chromatic aberration is eliminated.

The axial chromatic aberration correction lens 796 comprises quadrupole lenses QL1, QL2, QL3, QL4 at a plurality of, for example, four stages, and magnetic quadrupoles 803, 804, and is designed to cancel out axial chromatic aberration caused by the reducing lens 795 and objective lens 802 with the aid of the quadrupole lenses QL1-QL4 and magnetic quadrupoles 803, 804. Also, the scanning of the sample W by the multiple beams is served by electrostatic deflectors 799, 801 at two stages, and particularly, aberration can be reduced during the scanning by optimizing the ratio of a scanning signal applied to the electrostatic deflector 799 to a scanning signal applied to the electrostatic deflector 801 to optimize the fulcrum of deflection. Here, the deflection aberration of the beam separator can be substantially completely corrected by setting the distance between the reduced image 798 of the multi-aperture plate 792 and the electrostatic deflector 799 to one-half of the distance between the image 798 and electromagnetic deflector 800.

Second electrons emitted from a scanned point of the sample W are accelerated by a high voltage of the objective lens 802 and separated from the primary beams by the electromagnetic deflector 800, and enter the secondary electro-optical system 785. The secondary electro-optical system 785 comprises a magnification lens 805 and rotation correction lenses 806, 807. The secondary electron beams separated by the electromagnetic deflector 800 are enlarged by the magnification lens 805, and are again enlarged by the rotation correction lenses 806, 807 to form an enlarged image in the detection system 6. The detection system 786 comprises multiple detectors 808 which are arranged on the same plane, and can thus detect each of multiple beams independently by each detector. The rotation correction lenses 806, 807 are of current control type, and currents are controlled such that axial magnetic fields are generated in opposite directions to each other.

Figure 69:
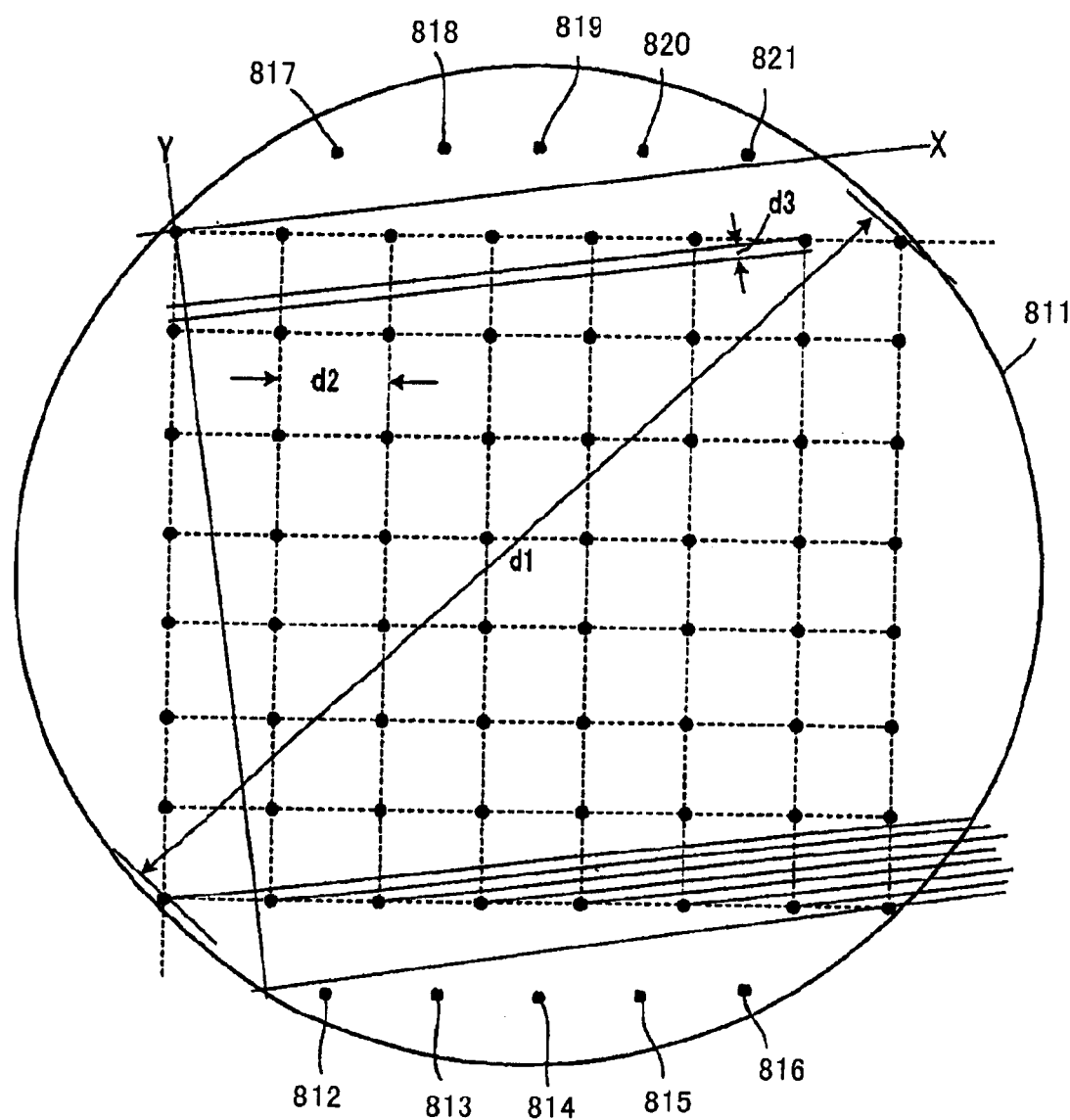

FIG. 69 is a beam arrangement diagram showing how beams are arranged in a region of the sample W irradiated with the multiple beams formed from the primary beams by the multi-aperture plate 792 in FIG. 68, where the position of each beam is indicated by a black circle. In FIG. 69, a region surrounded by a circle 811 indicates a region in which the multi-aperture plate 792 is uniformly irradiated with beams emitted from the electron gun 790, or a region in which aberration of the optical system is equal to or less than a specified value, and its diameter d1 is, for example, 4 μm. Specifically, in this region, 90% or more of beam intensity can be provided with respect to the beam intensity on the optical axis.

The region is irradiated with the intensity of 90% or more because the formation of an image is hindered if the multiple beams are not uniform in intensity. It is further necessary to reduce aberration of the optical system to a predefined value or less in order to narrow down all the multiple beams. While it is known that the axial chromatic aberration can be corrected by a correction lens, the optical system is not axially symmetric and is therefore expected to have much off-axis aberration as well. Accordingly, a circle 811 may represents a region in which the off-axis aberration of the axial chromatic aberration correction lens 796 is smaller than a predetermined threshold. Actually, these conditions must be satisfied.

As illustrated, when coordinates having two orthogonal axes X, Y are defined on the region, the multiple beams are arranged in a matrix of m rows and n columns on the XY-plane (where m and n are positive integers, m represents the number of beams in the X-axis direction, and n represents the number of beams in the Y-axis direction). An interval d2 between the respective columns is, for example, 403 nm. In this way, m*n beams are created in the region 811. Then, when the sample W is scanned in the X-axis direction, the distance d3 between the respective beams, when projected onto the Y-axis, can all be made equal by inclining the scanning direction by $\sin^{-1}(1/m)$ with respect to the X-axis. For example, when m=8, $\sin^{-1}(1/8)=7.18$ degrees, and d3 is, for example, 50 nm. In this way, multi-channel SEM images can be formed without waste by setting the raster pitch when scanning in the X-axis direction, i.e., the distance between adjacent trajectories when one beam scans the sample W to be equal to the dimension of one pixel or an integer multiple thereof.

The beam interval d2 is equal to pixel dimension*m/cos (sin$^{-1}$(1/m)), where larger m causes the denominator to approach to one, and the beam interval to be equal to the pixel dimension multiplied by m. Here, as m is larger, the beam interval is wider, which is disadvantageous for arranging many beams within a circle in which the aberration falls within a certain level. Conversely, with a larger intervals of secondary electron beams, the multi-detector 808 more readily detects the beams. In this sense, when the number of beams is preferred, m<n should be satisfied. Conversely, when the ease of detecting the beams is preferred, m>n should be satisfied.

It should be noted that even when m·n, the raster interval can be made equal when additional beams 812-821 are further arranged outside the matrix of m rows and n columns, as illustrated in FIG. 69.

As described above in detail, in the sixteenth embodiment of the present invention, since the axial chromatic aberration of the primary beams is corrected by the use of the axial chromatic aberration correction lens 796, the S/N ratio can be accomplished as required to perform evaluations at a high resolution even if the throughput is increased. In addition, since the electromagnetic deflector 800 is disposed between the reduced image 798 of the multi-aperture plate 792 and the objective lens 802, the primary beams and secondary electrons commonly pass over a reduced distance, so that the secondary beams exert reduced space charge effects on the primary beams. Consequently, the sample W can be scanned with a large number of narrowed beams.

Next, a seventeenth embodiment of the electron beam apparatus according to the present invention will be described with reference to FIG. 70. Likewise, in this embodiment, the electron beam apparatus comprises an electron beam emitter 831, a primary electro-optical system 832, a beam separation system 833, an objective optical system 834, a secondary electro-optical system 835, and a detection system 836. Electron beams emitted from an electron gun 840 of the electron beam emitter 831 are converged by a condenser lens 841 of the primary electro-optical system 832, and irradiated to a formation aperture plate 842 with a uniform intensity (for example, within 20% of intensity non-uniformity). In this way, the electron beams which have passed through the formation aperture plate 842 are formed into beams having a rectangular cross-section.

The primary beams thus formed to have a rectangular cross-section passes through rotation correction lenses 843, 844, a formation lens 845, and alignment deflectors 846, 847, which also make up the primary electro-optical system 832, and enter the beam separation system 833. The beam separation system 833 comprises an electromagnetic deflector 848. The primary beams which have passed through the primary electro-optical system 832 are changed in traveling direction to a direction perpendicular to the sample W by the electromagnetic deflector 848. The primary beams, the traveling direction of which has been changed by the electromagnetic deflector 848, pass through an aperture for the primary beams provided through an NA aperture plate 849 of the objective lens system 834, and converged and focused on the sample W by an objective lens 850.

The alignment deflectors 846, 847 are provided for shifting the primary beams such that the primary beams and secondary beams emitted from the sample irradiated with the primary beams take different trajectories between the electromagnetic deflector 848 and sample W. In FIG. 70, a dotted line 851 represents the trajectory of the primary beams shifted by these alignment deflectors 846, 847. In FIG. 70, the trajectory of the secondary electrons are enlarged in the lateral direction so that the primary electrons appear to pass within the secondary beams, but actually, the primary beams pass outside the secondary beams. Also, as illustrated in FIG. 70, a plurality of apertures are provided through the formation aperture plate 842 in order to compensate for a change in magnification due to a change in the acceleration voltage intended to change an irradiation voltage. Further, the two rotation correction lenses 843, 844 are used to correct for a rotation amount because the primary beams formed to have a rectangular cross-section by the formation aperture plate 842 change a rotating angle due to a change in the acceleration voltage by a variety of lenses of the primary electro-optical system 832.

The secondary beams emitted from the sample W irradiated with the primary beams pass through the objective lens 850 and NA aperture plate 849, are separated from the primary beams by the electromagnetic deflector 848, and deflected by an electrostatic deflector 852 in the beam separation system 833 to form an enlarged image at a point 853. The electrostatic deflector 852 is provided to deflect by the same angle as and the direction opposite to the electromagnetic deflector 848 in order to correct the deflection chromatic aberration caused by the electromagnetic deflector 848. For correcting the deflection chromatic aberration, the distance between the point 853 and electromagnetic deflector 848 is set to be twice the distance between the point 853 and electrostatic deflector 852.

The secondary beams which have formed the enlarged image at the point 853 by the objective lens 849 are corrected for axial chromatic aberration by an axial chromatic aberration correction lens 854 which comprises a non-dispersion Wien filter, and are focused on a main surface of an auxiliary lens 855. Then, the auxiliary lens 855 focuses the image of the NA aperture plate 849 on a main surface of a magnification lens 856 as an image 857, thereby reducing the divergence of the beams by the magnification lens 856 to reduce distortion aberration caused by the magnification lens 856. The image of the NA aperture plate 849 is enlarged by magnification lenses 856, 858 to form an enlarged image on an MCP (microchannel plate) 859 of the detection system 836. In this way, the image of the sample W is detected. It should be noted that an auxiliary lens 860 is disposed at the image point of the enlarge image by the magnification lens 856. The auxiliary lens 860 has a function of forming the image 857 of the NA aperture plate 849 on a main surface of the magnification lens 858.

Figure 71:
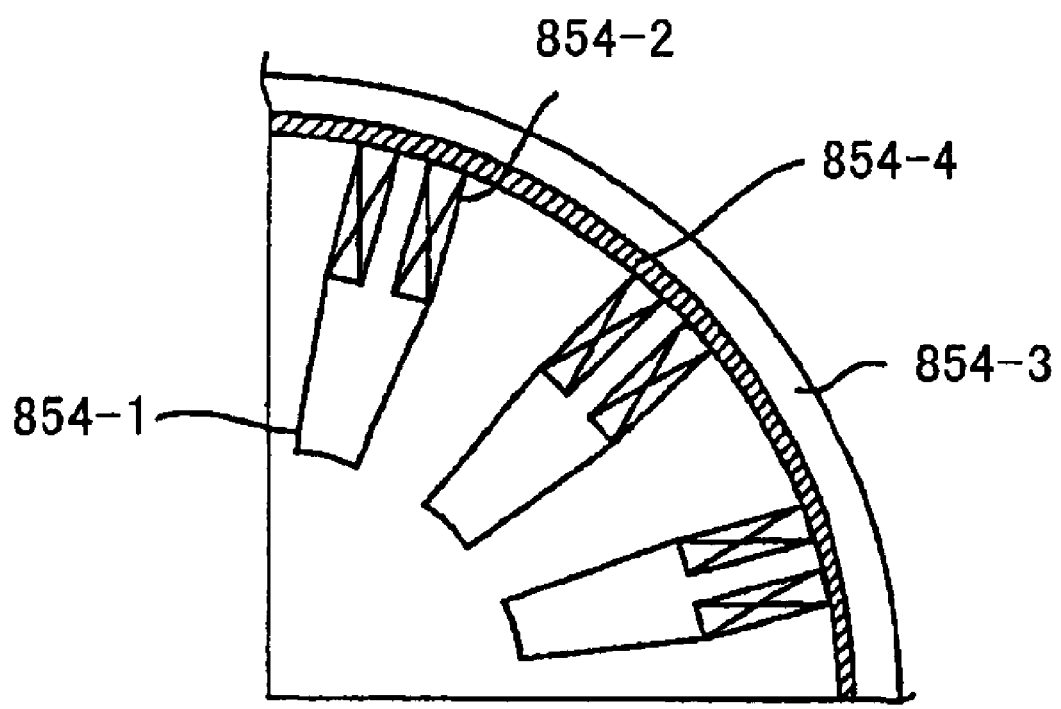

Now, the axial chromatic aberration correction lens 854 will be described. This correction lens 854 is also referred to as a "Wien filter" and converges beams emitted from an end surface twice, but causes negative axial chromatic aberration in the cross-over image C3 due to non-dispersion. FIG. 71 illustrates one quarter of the cross-section of the correction lens 854. As can be understood from FIG. 71, the correction lens 854 has 12 poles, where the Wien condition is satisfied by a dipole field, and the axial chromatic aberration is made negative by quadrupole electric field/magnetic field, and hexipolar electric field/magnetic field is applied to generate negative spherical chromatic aberration, thus making it possible to partially correct spherical aberration which mainly occurs in the objective lens 850. A 12-pole electrode 854-1 is made of permalloy B, and generates a dipole, a quadrupole, and a hexipolar magnetic field by applying a current to a coil 854-2. In the figure, reference numeral 854-3 designates a core made of permalloy, and 854-4 designates a spacer for insulating each electrode.

As described above, since the secondary beams have been corrected for the axial chromatic aberration in the secondary electro-optical system 5, the aberration is reduced even if the NA aperture plate 849 is increased, so that secondary beams having a large aperture angle can pass through the NA aperture plate 849. Consequently, the transmittance of the secondary beams is high and more secondary beams per pixel enter the MCP 859, advantageously making it possible to process images at high speeds.

In FIG. 70, reference numeral 757 designates an image of the NA aperture plate 849 focused on the main surface of the magnification lens 856. The position of an optical conjugate plane 857 of the NA aperture plate 849 can be set at an arbitrary position along the optical axis of the secondary beams by adjusting the focal distance of the auxiliary lens 855. Even if such a setting is made, the image of the secondary beams corrected for the axial chromatic aberration is formed on the main surface of the auxiliary lens 855. The position of the NA aperture plate 849 is designed by taking advantage of the fact that secondary beams emitted from an end of the visual field intersect with the optical axis at a position slightly deviated from a position at which secondary beams emitted from the vicinity of the optical axis intersect with the optical axis. By designing the NA aperture plate 849 such that it is installed at the position at which the secondary beams emitted from an end intersect with the optical axis, a signal based on the secondary beams emitted from an end of the visual field can be enhanced, thereby partially solving a problem that the electron gun cannot increase the beam current density at ends of the visual field.

On the other hand, in regard to the shape of the visual field, the axial chromatic aberration correction lens 854 cannot expand the visual field. For this reason, the surface of the sample W is illuminated by the primary beams in a circular shape, and the MCP 859 preferably has a square detection plane of 2048*2048 pixels, by way of example.

In the two embodiments, when the objective lenses 802, 850 are electromagnetic lenses, secondary electron beams emitted in the normal direction of the sample W do not intersect with the optical axis. However, it has been found from a simulation that secondary electron beams emitted in a direction inclined by 8.5 degrees from the normal direction intersect with the optical axis. Since the secondary electron beams are emitted in accordance with the cosine law, the secondary electron beams emitted in the direction inclined by 8.5 degrees has an intensity equal to cos 8.5=0.9 which is not so different from that of secondary electron beams emitted in the axial axis direction. Accordingly, in the present invention, required operations can be performed taking advantage of the secondary electron beams emitted in the direction inclined by 8.5 degrees from the normal direction of the sample W.

While the electron beam apparatus according to the present invention, and a method of manufacturing a semiconductor device using the apparatus have been described above, the present invention is not limited to their embodiments, but can be modified and altered in various manners, as is obvious to those skilled in the art. For example, as detectors for use in the detection system 6, line sensors may be used instead of plane sensors such as the MCP, multi-detector and the like. In the present invention, since the primary electro-optical system or secondary electro-optical system is provided with an axial chromatic aberration correction lens, a sample can be evaluated at a largely improved throughput and a high resolution. While the axial chromatic aberration correction lens has a relatively narrow visual field, two-dimensional images of a sample can be efficiently captured by employing a visual field having a two-dimensional extent, for example, a square visual field. Also, since the primary beams and secondary beams pass over a short common distance, another effect produced therefrom is that the influence of the space charge effect is mitigated.

While preferred embodiments of the present invention have been described above in detail, it is apparent that these embodiments can be altered and modified without departing from the technical idea of the present invention.

The invention claimed is:

1. An electron beam apparatus having a projection electro-optical system for inspecting a surface of a sample, comprising:
    an electron gun for emitting an electron beam;
    a primary electro-optical system for guiding the emitted electron beam onto a sample for irradiation;
    a detector for detecting electrons; and
    a secondary electro-optical system for guiding an electron beam bearing information on the surface of the sample, emitted from the sample irradiated with the electron beam, to the detector;
    wherein the secondary electro-optical system includes a Wien filter having two focus points.

2. A defect inspection system for inspecting a defect on a surface of a sample, comprising:
    an electron beam apparatus having a projection electro-optical system, as claimed in claim 1;
    an image capturer for generating an image of the surface of the sample based on information on the surface of the sample included in electrons detected by the detector of the electron beam apparatus; and
    a defect evaluator for testing the presence or absence of a defect on the surface of the sample by comparing the captured image with a reference image.

* * * * *

UNITED STATES PATENT AND TRADEMARK OFFICE
CERTIFICATE OF CORRECTION

| | |
|---|---|
| PATENT NO. | : 8,035,082 B2 |
| APPLICATION NO. | : 12/580505 |
| DATED | : October 11, 2011 |
| INVENTOR(S) | : Yuichiro Yamazaki et al. |

Page 1 of 1

It is certified that error appears in the above-identified patent and that said Letters Patent is hereby corrected as shown below:

On the cover page, in Item [62]:
Change

Related U.S. Application Data

"(62) Division of application No. 11/817,763, filed on Dec. 8, 2008."

To be

Related U.S. Application Data

--(62) Division of application No. 11/817,763, filed on Dec. 8, 2008,
which is a national stage of PCT/JP2006/304088 filed on March 3, 2006.--

Signed and Sealed this
Seventh Day of August, 2012

David J. Kappos
*Director of the United States Patent and Trademark Office*